(12) United States Patent
Chen et al.

(10) Patent No.: US 8,642,629 B2
(45) Date of Patent: Feb. 4, 2014

(54) NAPHTHYLACETIC ACIDS

(75) Inventors: Li Chen, Shanghai (CN); Fariborz Firooznia, Florham Park, NJ (US); Paul Gillespie, Westfield, NJ (US); Yun He, Shanghai (CN); Tai-An Lin, Pequannock, NJ (US); Eric Mertz, Fair Lawn, NJ (US); Sung-Sau So, Verona, NJ (US); HongYing Yun, Shanghai (CN); Zhenshan Zhang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 774 days.

(21) Appl. No.: 12/614,485

(22) Filed: Nov. 9, 2009

(65) Prior Publication Data
US 2010/0125058 A1  May 20, 2010

Related U.S. Application Data

(60) Provisional application No. 61/115,133, filed on Nov. 17, 2008, provisional application No. 61/222,182, filed on Jul. 1, 2009.

(51) Int. Cl.
*A61K 31/44* (2006.01)
*C07D 213/02* (2006.01)

(52) U.S. Cl.
USPC .................. 514/345; 546/290; 546/301

(58) Field of Classification Search
USPC ................... 546/290, 301; 514/345
See application file for complete search history.

(56) References Cited

U.S. PATENT DOCUMENTS

| | | |
|---|---|---|
| 3,899,529 A | 8/1975 | Witzel |
| 4,371,537 A | 2/1983 | Markley et al. |
| 4,443,462 A | 4/1984 | Carr et al. |
| 4,868,331 A | 9/1989 | Niewöhner et al. |
| 4,921,998 A | 5/1990 | Niewöhner et al. |
| 5,424,481 A | 6/1995 | Hagen et al. |
| 7,226,951 B2 | 6/2007 | Vasudevan et al. |
| 2005/0014749 A1 | 1/2005 | Chen et al. |
| 2006/0154965 A1 | 7/2006 | Harris et al. |
| 2007/0161698 A1 | 7/2007 | Chien et al. |
| 2010/0016368 A1 | 1/2010 | Chen et al. |
| 2010/0016369 A1 | 1/2010 | Chen et al. |
| 2010/0041713 A1 | 2/2010 | Firooznia et al. |
| 2010/0041714 A1 | 2/2010 | Blanc et al. |
| 2010/0041760 A1 | 2/2010 | Blanc et al. |
| 2010/0125061 A1 | 5/2010 | Firooznia et al. |
| 2010/0137250 A1 | 6/2010 | Firooznia et al. |

FOREIGN PATENT DOCUMENTS

| | | |
|---|---|---|
| DE | 4411856 | 1/1994 |
| EP | 0242518 | 10/1987 |
| EP | 0253257 | 1/1988 |
| EP | 0405602 | 1/1991 |
| EP | 0657422 | 6/1995 |
| EP | 1505061 | 2/2005 |
| EP | 1939175 | 7/2008 |
| EP | 2022793 | 2/2009 |
| WO | 92/01675 | 2/1992 |
| WO | 97/07099 | 2/1997 |
| WO | 00/16798 | 3/2000 |
| WO | 03/087098 | 10/2003 |
| WO | 2004/002992 | 1/2004 |
| WO | 2004/058164 | 7/2004 |
| WO | 2005/040114 | 5/2005 |
| WO | 2005/054232 | 6/2005 |
| WO | 2006/032466 | 3/2006 |
| WO | 2006/034418 | 3/2006 |
| WO | 2006/036664 | 4/2006 |
| WO | 2006/091674 | 8/2006 |
| WO | 2006/136859 | 12/2006 |
| WO | 2007/028132 | 3/2007 |
| WO | 2007/031747 | 3/2007 |
| WO | 2007/138974 | 12/2007 |
| WO | 2007/146136 | 12/2007 |
| WO | 2008/078305 | 7/2008 |

OTHER PUBLICATIONS

Feixas J et al., "Naphthalene Derivatives; a New Series of Selective Cycloxygenase-2 Inhibitors" Bioorganic & Medicinal Chemistry Letters, 11:20 (2001) 2687-2690 XP0029995309.
Nagata et al., FEBS Lett 459: 195-199, 1999.
Hirai et al., J Exp Med 193: 255-261, 2001.
Gervais et al., J Allergy Clin Immunol 108: 982-988 (2001).
Xue et al., J Immunol 175: 6531-6536, 2005.
Yoshimura-Uchiyama et al., Clin Exp Allergy 34:1283-1290, 2004.
Huang et al., Hum Mol Genet 13, 2691-2697, 2004.
Cosmi et al., Eur J. Immunol 30, 2972-2979, 2000.
Lee et al., Tetrahedron Lett., 32 (1991) 5255.

(Continued)

*Primary Examiner* — Golam M M Shameem

(57) ABSTRACT

The invention is concerned with the compounds of formula I:

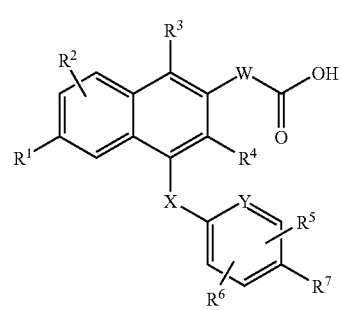

and pharmaceutically acceptable salts and esters thereof, wherein W, X, Y, and $R^1$-$R^7$ are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

47 Claims, No Drawings

(56) References Cited

OTHER PUBLICATIONS

Boger, D. L. et al., J. Org. Chem. 61 (1996) 4894-4912.
Kim, M. et al., J. Org. Chem. 69 (2004) 6945-6948.
Chan W. K., et al., J. Med. Chem. 39 (1996) 3756-3768.
Kozhinov, D. V., et al., J. Org. Chem. 69 (2004) 1378-1379.
Liu, J., et al., Org. Lett. 4 (2002) 3521-3524.
Bloomer, J. L. et al., J. Org. Chem. 58 (1993) 7906-7912.
Fuganti, C. et al., J. Chem. Res (S) 1998, 638-639.
Uno, H., et al., J. Chem. Soc., Perkin Trans. 1, 2001, 229.
Wallace, D. J. et al., Tetrahedron Lett. 43 (2002) 6987-6990.
Zupan M. et al., Bull. Chem. Soc. Jpn., 68 (1995) 1655-1660.
Wu G., et al., Synthesis 11 (2003) 1657-1660.
Thibault, M. E. et al., J. Org. Chem. 68 (2003), 8373-8378.
Schön, U. et al., Tetrahedron Lett. 46 (2005) 7111-7115.
Moseley, J. D. et al., Tetrahedron 62 (2006) 4685-4689.
Baldwin, K. P. et al., Synlett 11 (1993) 853.
Hayashi, N., et al., Org. Lett. 6 (2004) 4981-4983.
Hayashi, N. et al., Org. Lett. 7 (2005) 3093-3096.
Staas, D. D. et al., Bioorg. Med. Chem. 14 (2006) 6900.
Testaferri, L. et al., Tetrahedron 41 (1985) 1373-1384.
Li J. et al., Bioorg. Med. Chem. 13 (2005) 1805-1809.
Bargar, T. M. et al., J. Heterocyclic Chem. 22 (1985) 1583-1592.
Blizzard T. A. et al., Bioorg. Med. Chem. Lett. 14 (2004) 3861-3864.
Arnold et al., Org. Lett, 6 (2004) 3005-3007.
Ulven et al., "Targeting the prostaglandin D2 receptors DP and CRTH2 for treatment of inflammation" Current Topics in Medicinal Chemistry 6:13 (2006) 1427-1444 XP008104082.
Database Registry (online) RN 1026178-75-5 (2008) XP002547292.
Pettipher et al., "Antagonism of the prostaglandin D2 receptors DP1 and CRTH2 as an approach to treat allergic diseases." Nature Reviews Drug Discovery, vol. 6 (Apr. 2007) pp. 313-325, Nature Publishing Group.
Kostenis et al., "Emerging roles of DP and CRTH2 in allergic inflammation" Science Direct, Trends in Molecule Medicine vol. 12 No. 4, Apr. 2006, pp. 148-158, Elsevier.
The English translation of the Japanese Office Action, issued on Jun. 25, 2013, in the corresponding Japanese application No. 2011-535981., pp. 3.
(Translation of Chinese Off Act in Corres Chinese Appl 200980145703.0 Dec. 28, 2012).
The English translation of the Russian Office Action, issued on Aug. 14, 2013, in the corresponding Russian application No. 2011124150.

NAPHTHYLACETIC ACIDS

PRIORITY TO RELATED APPLICATIONS

This application claims the benefit of U.S. Provisional Application No. 61/115,133, filed Nov. 17, 2008 and U.S. Provisional Application No. 61/222,182, filed Jul. 1, 2009. The entire contents of the above-identified applications are hereby incorporated by reference.

BACKGROUND OF THE INVENTION

The present invention relates to novel substituted naphthalene-2-yl acetic acids, their manufacture, pharmaceutical compositions containing them and their use as CRTH2 antagonists or partial agonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention is concerned with the compounds of formula I:

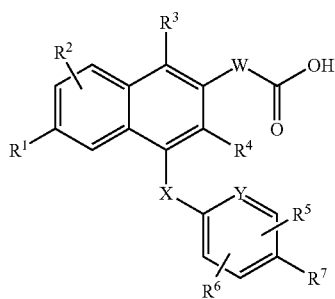

and pharmaceutically acceptable salts and esters thereof, wherein W, X, Y, $R^1$, $R^2$, $R^3$, $R^4$, $R^5$, $R^6$, and $R^7$ are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^7$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower alkoxycarbonyl" refers to the moiety —C(O)—O—R, wherein R is lower alkyl as defined previously. Examples of lower alkoxycarbonyl moieties include methoxycarbonyl and ethoxycarbonyl.

The term "heteroatom" refers to nitrogen, oxygen, or sulfur.

The term "lower heterocycloalkyl" refers to a saturated or partly unsaturated non-aromatic ring moiety having 3 to 7 ring atoms bonded together to form a ring structure wherein one, two or three of the ring atoms is a heteroatom while the remaining ring atoms are carbon atoms. Examples of lower heterocycloalkyls include piperidinyl, piperazinyl, pyrrolidinyl, and morpholinyl.

The term "lower alkylamino" refers to the moiety —N(R), wherein R is lower alkyl as defined previously. An example of a lower alkylamino is methylamino.

The term "lower dialkylamino" refers to the moiety —N(R)(R'), wherein R and R' are lower alkyl as defined previously. An example of a lower dialkylamino is dimethylamino.

The term "lower alkylsulfonyl" refers to the moiety —S(O)$_2$—R, wherein R is lower alkyl as defined previously. Examples of lower alkylsulfonyls include methylsulfonyl and ethylsulfonyl.

The term "halogen" refers to a moiety of fluoro, chloro, bromo or iodo.

Unless otherwise indicated, the term "hydrogen" or "hydro" refers to the moiety of a hydrogen atom (—H) and not H$_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound If not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

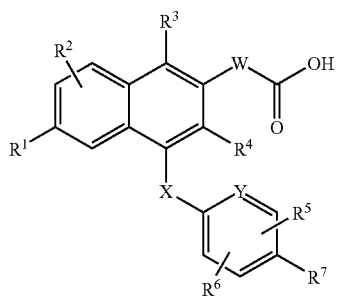

and pharmaceutically acceptable salts and esters thereof, wherein:

W is $CH_2$, $CH_2$—$CH_2$, $C(H)(CH_3)$, $CH_2$—$C(H)(CH_3)$, or $C(H)(CH_3)$—$CH_2$;

X is selected from the group consisting of:
(1) O,
(2) N(H),
(3) $N(CH_3)$,
(4) S,
(5) S(O), and
(6) $S(O)_2$;

Y is carbon or nitrogen;

$R^1$ is selected from the group consisting of:
(1) hydrogen,
(2) halogen,
(3) methyl optionally substituted by fluoro,
(4) lower alkoxy optionally substituted by fluoro,
(5) cyano, and
(6) lower alkylsulfonyl;

$R^2$ is hydrogen, fluoro, chloro, lower alkyl, or lower alkoxy;

$R^3$ is hydrogen, fluoro, chloro, bromo, or methyl;

$R^4$ is selected from the group consisting of:
(1) hydrogen,
(2) halogen,
(3) lower alkyl optionally substituted by fluoro,
(4) lower cycloalkyl, and
(5) ethenyl;

$R^5$ and $R^6$, independently of each other, are selected from the group consisting of:
(1) hydrogen,
(2) halogen,
(3) lower alkyl,
(4) cyano, and
(5) lower cycloalkyl;

$R^7$ is cyano or $S(O)_2$—$R^8$, wherein $R^8$ is selected from the group consisting of:
(1) lower alkyl,
(2) lower cycloalkyl,
(3) phenyl optionally substituted by (a) halogen, (b) lower alkyl optionally substituted by fluoro, or (c) lower alkoxy,
(4) lower alkylamino,
(5) lower dialkylamino,
(6) lower heterocycloalkyl optionally substituted by halogen, lower alkyl, or lower alkoxycarbonyl, and
(7) 2-oxa-6-aza-spiro[3.3]hept-6-yl.

Unless indicated otherwise, the $R^2$ moiety in formula I (or in any subgeneric formula of formula I) is bonded to a carbon atom on the naphthalene core structure at position 5, 7, or 8 in place of a hydrogen atom that would otherwise be bonded to that carbon atom (absent being substituted by $R^2$) where such positions are indicated as follows:

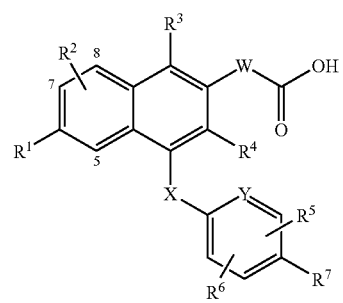

In one particular embodiment the present invention is directed to the compounds of formula I or a subgeneric formula of formula I (and the pharmaceutically acceptable salts and esters thereof), wherein $R^2$ is bonded to the naphthalene core structure at position 5 or 7 (where such positions are as previously indicated).

Unless indicated otherwise, the $R^5$ and $R^6$ moieties (independently of each other) are bonded to one of the ring carbon atoms on the ring containing Y in formula I (or in any subgeneric formula of formula I) at positions 2, 3, 5, or 6 in place of a hydrogen atom that would otherwise be bonded to that carbon atom (absent being substituted by $R^5$ or $R^6$) where such positions are indicated as follows, with the proviso that that $R^5$ and $R^6$ are not simultaneously bonded to the same carbon atom and are not bonded to Y when Y is nitrogen:

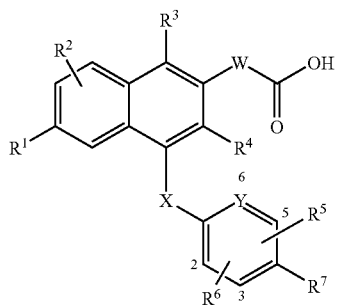

I

Thus, unless indicated otherwise, in reference to formula I or a subgenus of formula I, the terms "Y is carbon or nitrogen" or "Y is carbon" or "Y is nitrogen" indicates that when Y is carbon it is either bonded to a hydrogen atom, $R^5$, or $R^6$; and when Y is nitrogen it is not bonded to a hydrogen atom, $R^5$, or $R^6$.

In one particular embodiment, the present invention is directed to the compounds of formula I or a subgeneric formula of formula I (and the pharmaceutically acceptable salts and esters thereof), wherein at least one of $R^5$ or $R^6$ is bonded to a carbon atom on the ring containing Y at position 2 (where position 2 is as previously indicated).

In another particular embodiment, the present invention is directed to the compounds of formula I or a subgeneric formula of formula I (and the pharmaceutically acceptable salts and esters thereof), wherein at least one of $R^5$ or $R^6$ is bonded to a carbon atom on the ring containing Y at position 2 or 6 when Y is carbon (where positions 2 and 6 are as previously indicated).

In another embodiment, the present invention is directed to the compounds of formula I or a subgeneric formula of formula I (and the pharmaceutically acceptable salts and esters thereof), wherein $R^5$ and $R^6$ are bonded to carbon atoms on the ring containing Y at positions 2 and 6 when Y is carbon (where positions 2 and 6 are as previously indicated).

Unless indicated otherwise, the genus of formula I and any subgenera thereof encompass all possible stereoisomers (i.e., (R)-enantiomers, (S)-enantiomers, diastereomers) as well as racemic and scalemic mixtures thereof.

In one embodiment, the present invention is directed to the compounds of formula I or pharmaceutically acceptable salts or esters thereof wherein W is $C(H)_2$.

In another particular embodiment, the present invention is directed to the compounds of formula I or pharmaceutically acceptable salts or esters thereof wherein W is $C(H)_2$—$C(H)_2$.

In another particular embodiment, the present invention is directed to the compounds of formula I or pharmaceutically acceptable salts or esters thereof wherein X is O.

In another particular embodiment, the present invention is directed to the compounds of formula I or pharmaceutically acceptable salts or esters thereof wherein X is N(H).

In another particular embodiment, the present invention is directed to the compounds of formula I or pharmaceutically acceptable salts or esters thereof wherein X is S.

In another particular embodiment, the present invention is directed to the compounds of formula I or pharmaceutically acceptable salts or esters thereof wherein X is S(O).

In another particular embodiment, the present invention is directed to the compounds of formula I or pharmaceutically acceptable salts or esters thereof wherein X is $S(O)_2$.

In another particular embodiment, the present invention is directed to the compounds of formula I or pharmaceutically acceptable salts or esters thereof wherein Y is carbon as depicted below in formula IA (a subgenus of formula I):

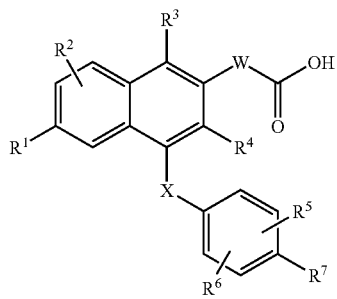

IA wherein W, X, and $R^1$-$R^7$ are defined as in formula I.

In another particular embodiment, the present invention is directed to the compounds of formula I or pharmaceutically acceptable salts or esters thereof wherein Y is nitrogen as depicted below in formula IB (a subgenus of formula I):

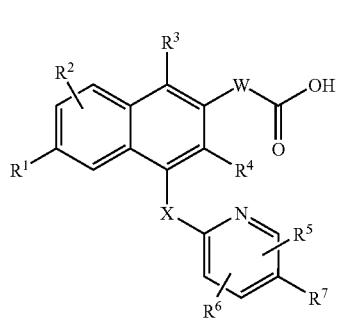

IB wherein W, X, and $R^1$-$R^7$ are defined as in formula I.

In one embodiment the present invention is directed to the compounds of formula I or pharmaceutically acceptable salts or esters thereof wherein $R^1$ is hydrogen, fluoro, chloro, bromo, cyano, methyl, trifluoromethyl, methoxy, trifluoromethoxy or methylsulfonyl.

In another embodiment the present invention is directed to the compounds of formula I or pharmaceutically acceptable salts or esters thereof wherein $R^1$ is halogen, methyl or methoxy.

In a more particular embodiment the present invention is directed to the compounds of formula I or pharmaceutically acceptable salts or esters thereof wherein $R^1$ is halogen.

In another particular embodiment the present invention is directed to the compounds of formula I or pharmaceutically acceptable salts or esters thereof wherein $R^1$ is chloro.

In another particular embodiment the present invention is directed to the compounds of formula I or pharmaceutically acceptable salts or esters thereof wherein $R^1$ is fluoro.

In one embodiment the present invention is directed to the compounds of formula I or pharmaceutically acceptable salts or esters thereof wherein $R^2$ is hydrogen.

In a more particular embodiment the present invention is directed to the compounds of formula I or pharmaceutically acceptable salts or esters thereof wherein $R^2$ is fluoro.

In another particular embodiment the present invention is directed to the compounds of formula I or pharmaceutically acceptable salts or esters thereof wherein $R^2$ is chloro.

In another particular embodiment the present invention is directed to the compounds of formula I or pharmaceutically acceptable salts or esters thereof wherein $R^2$ is methyl.

In another particular embodiment the present invention is directed to the compounds of formula I or pharmaceutically acceptable salts or esters thereof wherein $R^2$ is methoxy.

In another embodiment the present invention is directed to the compounds of formula I or pharmaceutically acceptable salts or esters thereof wherein $R^3$ is hydrogen, fluoro, or methyl.

In a more particular embodiment the present invention is directed to the compounds of formula I or pharmaceutically acceptable salts or esters thereof wherein $R^3$ is hydrogen.

In another particular embodiment the present invention is directed to the compounds of formula I or pharmaceutically acceptable salts or esters thereof wherein $R^3$ is fluoro.

In another particular embodiment the present invention is directed to the compounds of formula I or pharmaceutically acceptable salts or esters thereof wherein $R^3$ is methyl.

In another embodiment the present invention is directed to the compounds of formula I or pharmaceutically acceptable salts or esters thereof wherein $R^4$ is hydrogen, fluoro, methyl, ethyl, ethenyl or cyclopropyl.

In a more particular embodiment the present invention is directed to the compounds of formula I or pharmaceutically acceptable salts or esters thereof wherein $R^4$ is hydrogen.

In another particular embodiment the present invention is directed to the compounds of formula I or pharmaceutically acceptable salts or esters thereof wherein $R^4$ is fluoro.

In another particular embodiment the present invention is directed to the compounds of formula I or pharmaceutically acceptable salts or esters thereof wherein $R^4$ is methyl.

In another embodiment the present invention is directed to the compounds of formula I or pharmaceutically acceptable salts or esters thereof wherein $R^5$ and $R^6$, independently of each other, are selected from the group consisting of: (1) hydrogen, (2) fluoro, (3) chloro, (4) methyl, (5) ethyl, (6) cyclopropyl and (7) cyano.

In a more particular embodiment the present invention is directed to the compounds of formula I or pharmaceutically acceptable salts or esters thereof wherein at least one of $R^5$ or $R^6$ is hydrogen.

In another particular embodiment the present invention is directed to the compounds of formula I or pharmaceutically acceptable salts or esters thereof wherein $R^5$ and $R^6$ are both hydrogen.

In another particular embodiment the present invention is directed to the compounds of formula I or pharmaceutically acceptable salts or esters thereof wherein at least one of $R^5$ or $R^6$ is hydrogen and the other is fluoro, chloro, or bromo.

In another particular embodiment the present invention is directed to the compounds of formula I or pharmaceutically acceptable salts or esters thereof wherein at least one of $R^5$ or $R^6$ is hydrogen and the other is methyl.

In another particular embodiment the present invention is directed to the compounds of formula I or pharmaceutically acceptable salts or esters thereof wherein $R^5$ and $R^6$ are not both cyano.

In another particular embodiment the present invention is directed to the compounds of formula I or pharmaceutically acceptable salts or esters thereof wherein at least one of $R^5$ or $R^6$ is hydrogen and the other is cyano.

In another particular embodiment the present invention is directed to the compounds of formula I or pharmaceutically acceptable salts or esters thereof wherein $R^5$ and $R^6$ are both halogen.

In another embodiment the present invention is directed to the compounds of formula I or pharmaceutically acceptable salts or esters thereof wherein $R^7$ is $S(O)_2$—$R^8$ and $R^8$ is selected from the group consisting of:
(1) methyl,
(2) ethyl,
(3) propyl,
(4) isopropyl,
(5) butyl,
(6) sec-butyl,
(7) tert-butyl,
(8) cyclopropyl,
(9) cyclobutyl,
(10) cyclopentyl,
(11) cyclohexyl,
(12) phenyl optionally substituted by halogen, methyl or methoxy,
(13) dimethylamino,
(14) diethylamino,
(15) pyrrolidin-1-yl,
(16) morpholin-4-yl,
(17) piperidin-1-yl optionally substituted by halogen,
(18) piperazin-1-yl optionally substituted by methyl, and
(19) 2-oxa-6-aza-spiro[3.3]hept-6-yl.

In a more particular embodiment the present invention is directed to the compounds of formula I or pharmaceutically acceptable salts or esters thereof wherein $R^7$ is $S(O)_2$—$R^8$ and $R^8$ is selected from the group consisting of:
(1) methyl,
(2) ethyl,
(3) propyl,
(4) isopropyl,
(5) butyl,
(6) cyclopropyl,
(7) cyclopentyl,
(8) dimethylamino,
(9) diethylamino,
(10) pyrrolidin-1-yl,
(11) morpholin-4-yl,
(12) 4,4-difluoro-piperidin-1-yl,
(13) 4-methyl-piperazin-1-yl, and
(14) 2-oxa-6-aza-spiro[3.3]hept-6-yl.

In a more particular embodiment the present invention is directed to the compounds of formula I or pharmaceutically acceptable salts or esters thereof wherein $R^7$ is $S(O)_2$—$R^8$ and $R^8$ is selected from the group consisting of:
(1) ethyl,
(2) propyl,
(3) isopropyl,
(4) cyclopropyl,
(5) butyl, and
(6) cyclopentyl.

In a more particular embodiment the present invention is directed to the compounds of formula I or pharmaceutically acceptable salts or esters thereof wherein $R^7$ is $S(O)_2$—$R^8$ and $R^8$ is ethyl.

In another particular embodiment the present invention is directed to the compounds of formula I or pharmaceutically acceptable salts or esters thereof wherein W is $C(H)_2$, X is O, $R^2$ is hydrogen and $R^7$ is $S(O)_2$—$R^8$, as depicted below in formula IC (a subgenus of formula I):

IC

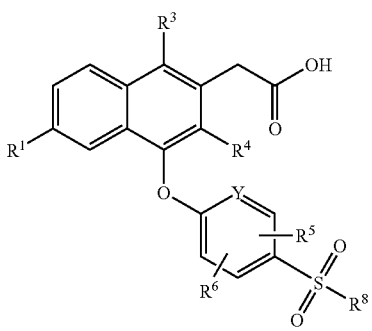

wherein Y, $R^1$, $R^3$-$R^6$ and $R^8$ are defined as in formula I.

In another particular embodiment the present invention is directed to the compounds of formula I or pharmaceutically acceptable salts or esters thereof wherein $R^2$ is hydrogen and $R^7$ is $S(O)_2$—$R^8$, W is $C(H)_2$, and X is $N(R^9)$ wherein $R^9$ is hydrogen or methyl, as depicted below in formula ID (a subgenus of formula I):

ID

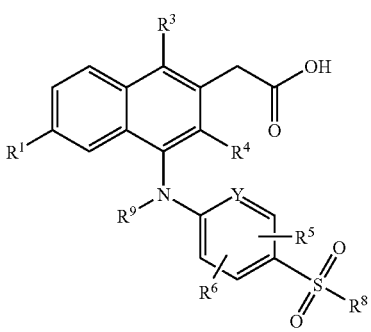

wherein Y, $R^1$, $R^3$-$R^6$ and $R^8$ are defined as in formula I.

In another particular embodiment the present invention is directed to the compounds of formula I or pharmaceutically acceptable salts or esters thereof wherein W is $C(H)_2$, X is S, $R^2$ is hydrogen and $R^7$ is $S(O)_2$—$R^8$, as depicted below in formula IE (a subgenus of formula I):

IE

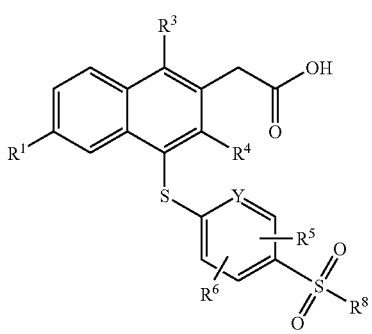

wherein Y, $R^1$, $R^3$-$R^6$ and $R^8$ are defined as in formula I.

In another particular embodiment the present invention is directed to the compounds of formula I or pharmaceutically acceptable salts or esters thereof wherein W is $C(H)_2$, X is S(O), $R^2$ is hydrogen and $R^7$ is $S(O)_2$—$R^8$, as depicted below in formula IF (a subgenus of formula I):

IF

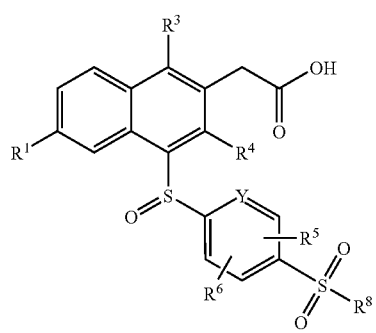

wherein Y, $R^1$, $R^3$-$R^6$ and $R^8$ are defined as in formula I.

In another particular embodiment the present invention is directed to the compounds of formula I or pharmaceutically acceptable salts or esters thereof wherein W is $C(H)_2$, X is $S(O)_2$, $R^2$ is hydrogen and $R^7$ is $S(O)_2$—$R^8$, as depicted below in formula IG (a subgenus of formula I):

IG

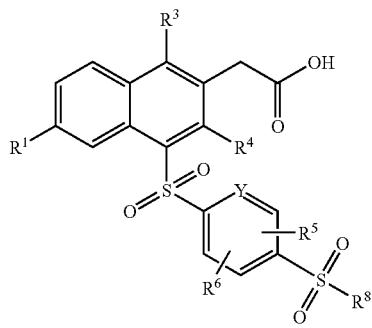

wherein Y, $R^1$, $R^3$-$R^6$ and $R^8$ are defined as in formula I.

In a more specific embodiment, the present invention is directed to a compound of formula I selected from the group consisting of:

[4-(4-ethanesulfonyl-phenoxy)-6-fluoro-naphthalen-2-yl]-acetic acid;

[6-fluoro-4-(4-methanesulfonyl-phenoxy)-naphthalen-2-yl]-acetic acid;

[6-chloro-4-(4-methanesulfonyl-phenoxy)-naphthalen-2-yl]-acetic acid;

{6-fluoro-4-[4-(propane-2-sulfonyl)-phenoxy]-naphthalen-2-yl}-acetic acid;

[4-(4-cyclopropanesulfonyl-phenoxy)-6-fluoro-naphthalen-2-yl]-acetic acid;

[6-fluoro-4-(4-methanesulfonyl-2-methyl-phenoxy)-naphthalen-2-yl]-acetic acid;

[6-fluoro-4-(4-methanesulfonyl-3-methyl-phenoxy)-naphthalen-2-yl]-acetic acid;

[4-(4-ethanesulfonyl-2-methyl-phenoxy)-6-fluoro-naphthalen-2-yl]-acetic acid;

[6-fluoro-4-(5-methanesulfonyl-pyridin-2-yloxy)-naphthalen-2-yl]-acetic acid;

[6-fluoro-4-(5-methanesulfonyl-3-methyl-pyridin-2-yloxy)-naphthalen-2-yl]-acetic acid;

[4-(5-ethanesulfonyl-pyridin-2-yloxy)-6-fluoro-naphthalen-2-yl]-acetic acid;

[4-(5-ethanesulfonyl-3-methyl-pyridin-2-yloxy)-6-fluoro-naphthalen-2-yl]-acetic acid;

[4-(3-bromo-5-ethanesulfonyl-pyridin-2-yloxy)-6-fluoro-naphthalen-2-yl]-acetic acid;
[4-(3-bromo-5-methanesulfonyl-pyridin-2-yloxy)-6-fluoro-naphthalen-2-yl]-acetic acid;
[4-(4-ethanesulfonyl-phenoxy)-6-methoxy-naphthalen-2-yl]-acetic acid;
[4-(5-ethanesulfonyl-pyridin-2-yloxy)-6-trifluoromethyl-naphthalen-2-yl]-acetic acid;
[4-(4-ethanesulfonyl-phenoxy)-6-trifluoromethyl-naphthalen-2-yl]-acetic acid;
[4-(5-ethanesulfonyl-pyridin-2-yloxy)-6-trifluoromethoxy-naphthalen-2-yl]-acetic acid;
[4-(4-ethanesulfonyl-phenoxy)-6-trifluoromethoxy-naphthalen-2-yl]-acetic acid;
[4-(4-ethanesulfonyl-phenoxy)-7-fluoro-naphthalen-2-yl]-acetic acid;
[4-(5-Ethanesulfonyl-pyridin-2-yloxy)-6-methoxy-naphthalen-2-yl]-acetic acid;
[4-(4-Ethanesulfonyl-phenoxy)-5-fluoro-naphthalen-2-yl]-acetic acid;
[4-(4-Ethanesulfonyl-phenoxy)-6,7-dimethoxy-naphthalen-2-yl]-acetic acid;
[4-(4-ethanesulfonyl-phenoxy)-6-fluoro-3-methyl-naphthalen-2-yl]-acetic acid;
[6-fluoro-4-(4-methanesulfonyl-phenoxy)-3-methyl-naphthalen-2-yl]-acetic acid;
[6-fluoro-4-(4-methanesulfonyl-2-methyl-phenoxy)-3-methyl-naphthalen-2-yl]-acetic acid;
{6-fluoro-3-methyl-4-[4-(propane-2-sulfonyl)-phenoxy]-naphthalen-2-yl}-acetic acid;
[4-(4-cyclopropanesulfonyl-phenoxy)-6-fluoro-3-methyl-naphthalen-2-yl]-acetic acid;
[6-fluoro-4-(4-methanesulfonyl-3-methyl-phenoxy)-3-methyl-naphthalen-2-yl]-acetic acid;
[6-chloro-4-(4-methanesulfonyl-phenoxy)-3-methyl-naphthalen-2-yl]-acetic acid;
[6-chloro-4-(4-methanesulfonyl-3-methyl-phenoxy)-3-methyl-naphthalen-2-yl]-acetic acid;
[6-chloro-4-(4-methanesulfonyl-2-methyl-phenoxy)-3-methyl-naphthalen-2-yl]-acetic acid;
[4-(4-ethanesulfonyl-2-methyl-phenoxy)-6-fluoro-3-methyl-naphthalen-2-yl]-acetic acid;
[4-(3-chloro-4-methanesulfonyl-phenoxy)-6-fluoro-3-methyl-naphthalen-2-yl]-acetic acid;
[6-fluoro-4-(2-fluoro-4-methanesulfonyl-phenoxy)-3-methyl-naphthalen-2-yl]-acetic acid;
[4-(4-ethanesulfonyl-2-fluoro-phenoxy)-6-fluoro-3-methyl-naphthalen-2-yl]-acetic acid;
[4-(4-ethanesulfonyl-3-methyl-phenoxy)-6-fluoro-3-methyl-naphthalen-2-yl]-acetic acid;
[4-(2,5-difluoro-4-methanesulfonyl-phenoxy)-6-fluoro-3-methyl-naphthalen-2-yl]-acetic acid;
[6-fluoro-4-(3-fluoro-4-methanesulfonyl-phenoxy)-3-methyl-naphthalen-2-yl]-acetic acid;
[4-(4-ethanesulfonyl-3-fluoro-phenoxy)-6-fluoro-3-methyl-naphthalen-2-yl]-acetic acid;
[4-(2-cyano-4-ethanesulfonyl-phenoxy)-6-fluoro-3-methyl-naphthalen-2-yl]-acetic acid;
[4-(3-chloro-4-ethanesulfonyl-phenoxy)-6-fluoro-3-methyl-naphthalen-2-yl]-acetic acid;
[4-(2-chloro-4-methanesulfonyl-phenoxy)-6-fluoro-3-methyl-naphthalen-2-yl]-acetic acid;
[4-(2-chloro-4-ethanesulfonyl-phenoxy)-6-fluoro-3-methyl-naphthalen-2-yl]-acetic acid;
{6-fluoro-3-methyl-4-[4-(propane-1-sulfonyl)-phenoxy]-naphthalen-2-yl}-acetic acid;
{4-[4-(butane-1-sulfonyl)-phenoxy]-6-fluoro-3-methyl-naphthalen-2-yl}-acetic acid;
[4-(5-chloro-4-ethanesulfonyl-2-fluoro-phenoxy)-6-fluoro-3-methyl-naphthalen-2-yl]-acetic acid;
[4-(2-chloro-4-ethanesulfonyl-5-fluoro-phenoxy)-6-fluoro-3-methyl-naphthalen-2-yl]-acetic acid;
[4-(4-cyclopentanesulfonyl-phenoxy)-6-fluoro-3-methyl-naphthalen-2-yl]-acetic acid;
{6-fluoro-4-[4-(4-fluoro-benzenesulfonyl)-phenoxy]-3-methyl-naphthalen-2-yl}-acetic acid;
[4-(4-benzenesulfonyl-phenoxy)-6-fluoro-3-methyl-naphthalen-2-yl]-acetic acid;
{6-fluoro-3-methyl-4-[4-(toluene-4-sulfonyl)-phenoxy]-naphthalen-2-yl}-acetic acid;
{6-fluoro-4-[4-(4-methoxy-benzenesulfonyl)-phenoxy]-3-methyl-naphthalen-2-yl}-acetic acid;
{4-[4-(4-chloro-benzenesulfonyl)-phenoxy]-6-fluoro-3-methyl-naphthalen-2-yl}-acetic acid;
[6-fluoro-4-(5-methanesulfonyl-pyridin-2-yloxy)-3-methyl-naphthalen-2-yl]-acetic acid;
[4-(5-ethanesulfonyl-pyridin-2-yloxy)-6-fluoro-3-methyl-naphthalen-2-yl]-acetic acid;
[6-fluoro-4-(5-methanesulfonyl-3-methyl-pyridin-2-yloxy)-3-methyl-naphthalen-2-yl]-acetic acid;
[4-(5-ethanesulfonyl-3-methyl-pyridin-2-yloxy)-6-fluoro-3-methyl-naphthalen-2-yl]-acetic acid;
[4-(3-bromo-5-methanesulfonyl-pyridin-2-yloxy)-6-fluoro-3-methyl-naphthalen-2-yl]-acetic acid;
[4-(4-dimethylsulfamoyl-phenoxy)-6-fluoro-3-methyl-naphthalen-2-yl]-acetic acid;
{6-fluoro-3-methyl-4-[4-(pyrrolidine-1-sulfonyl)-phenoxy]-naphthalen-2-yl}-acetic acid;
[4-(4-diethylsulfamoyl-phenoxy)-6-fluoro-3-methyl-naphthalen-2-yl]-acetic acid;
{6-fluoro-3-methyl-4-[4-(morpholine-4-sulfonyl)-phenoxy]-naphthalen-2-yl}-acetic acid;
{6-fluoro-3-methyl-4-[4-(4-methyl-piperazine-1-sulfonyl)-phenoxy]-naphthalen-2-yl}-acetic acid;
{4-[4-(4,4-difluoro-piperidine-1-sulfonyl)-phenoxy]-6-fluoro-3-methyl-naphthalen-2-yl}-acetic acid;
{6-fluoro-3-methyl-4-[4-(2-oxa-6-aza-spiro[3.3]heptane-6-sulfonyl)-phenoxy]-naphthalen-2-yl}-acetic acid;
[4-(4-cyano-phenoxy)-6-fluoro-3-methyl-naphthalen-2-yl]-acetic acid;
[6-chloro-4-(4-cyano-phenoxy)-3-methyl-naphthalen-2-yl]-acetic acid;
[4-(4-methanesulfonyl-phenoxy)-naphthalen-2-yl]-acetic acid;
[4-(4-methanesulfonyl-phenoxy)-3-methyl-naphthalen-2-yl]-acetic acid;
[1,6-difluoro-4-(5-methanesulfonyl-pyridin-2-yloxy)-naphthalen-2-yl]-acetic acid;
[1,6-difluoro-4-(5-ethanesulfonyl-pyridin-2-yloxy)-naphthalen-2-yl]-acetic acid;
[4-(5-ethanesulfonyl-pyridin-2-yloxy)-3,6-difluoro-naphthalen-2-yl]-acetic acid;
[4-(5-ethanesulfonyl-pyridin-2-yloxy)-6-fluoro-1-methyl-naphthalen-2-yl]-acetic acid;
3-[4-(4-ethanesulfonyl-phenoxy)-6-fluoro-3-methyl-naphthalen-2-yl]-propionic acid;
[6-fluoro-4-(4-methanesulfonyl-phenylamino)-naphthalen-2-yl]-acetic acid;
[6-fluoro-4-(4-methanesulfonyl-phenylamino)-3-methyl-naphthalen-2-yl]-acetic acid;
[6-fluoro-4-(4-methanesulfonyl-phenylsulfanyl)-naphthalen-2-yl]-acetic acid;

[6-fluoro-4-(4-methanesulfonyl-benzenesulfinyl)-naphthalen-2-yl]-acetic acid;

[6-fluoro-4-(4-methanesulfonyl-benzenesulfonyl)-naphthalen-2-yl]-acetic acid;

[6-bromo-4-(5-ethanesulfonyl-pyridin-2-yloxy)-naphthalen-2-yl]-acetic acid;

[4-(5-ethanesulfonyl-pyridin-2-yloxy)-6-methyl-naphthalen-2-yl]-acetic acid;

[6-cyano-4-(5-ethanesulfonyl-pyridin-2-yloxy)-naphthalen-2-yl]-acetic acid;

[6-bromo-4-(4-ethanesulfonyl-phenoxy)-naphthalen-2-yl]-acetic acid;

[4-(5-ethanesulfonyl-pyridin-2-yloxy)-6-methyl-naphthalen-2-yl]-acetic acid;

[4-(5-ethanesulfonyl-pyridin-2-yloxy)-6-fluoro-3-vinyl-naphthalen-2-yl]-acetic acid; [3-cyclopropyl-4-(5-ethanesulfonyl-pyridin-2-yloxy)-6-fluoro-naphthalen-2-yl]-acetic acid;

[4-(5-ethanesulfonyl-pyridin-2-yloxy)-3-ethyl-6-fluoro-naphthalen-2-yl]-acetic acid; [4-(5-ethanesulfonyl-3-ethyl-pyridin-2-yloxy)-6-fluoro-3-methyl-naphthalen-2-yl]-acetic acid;

[4-(3-cyclopropyl-5-ethanesulfonyl-pyridin-2-yloxy)-6-fluoro-3-methyl-naphthalen-2-yl]-acetic acid and any pharmaceutically acceptable salt or ester thereof.

General Synthesis of Compounds According to the Invention

The compounds of the present invention can be prepared by any conventional means. Suitable processes for synthesizing these compounds are provided in the examples. Generally, compounds of formula I can be prepared according to the schemes illustrated below. Unless otherwise indicated, the variables W, X, Y, and $R^1$ to $R^8$ are defined in the same manner as defined previously for the genus of formula I.

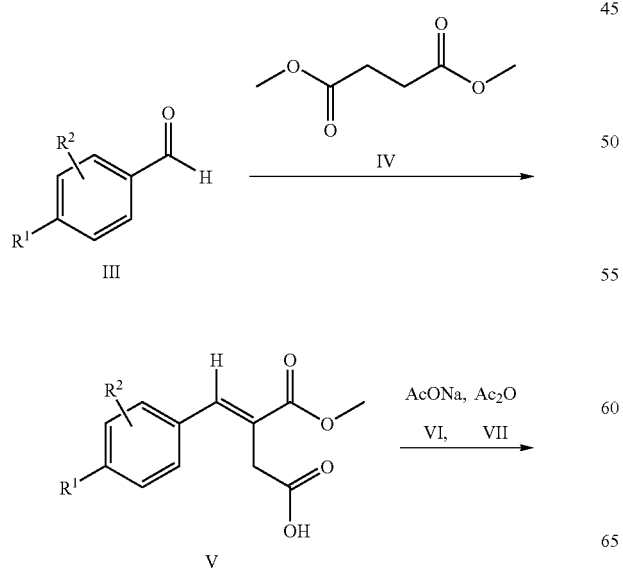

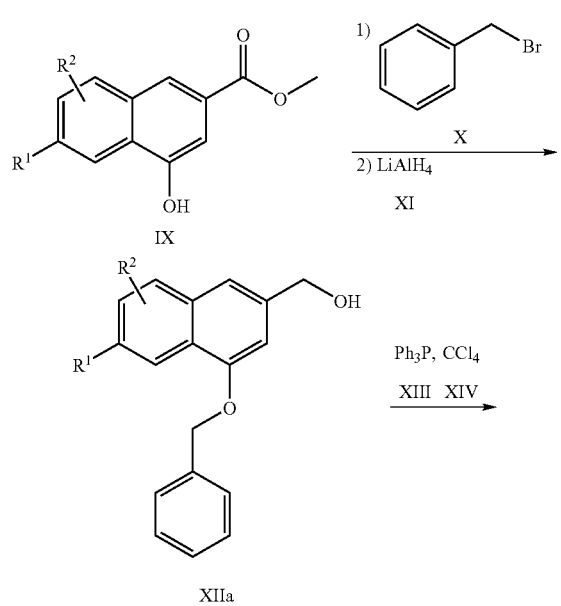

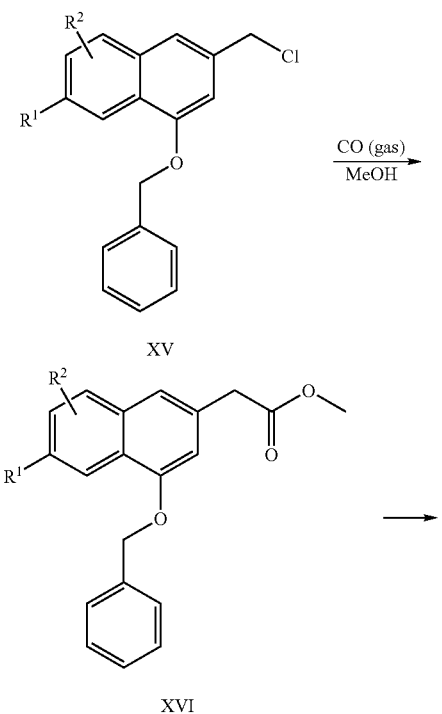

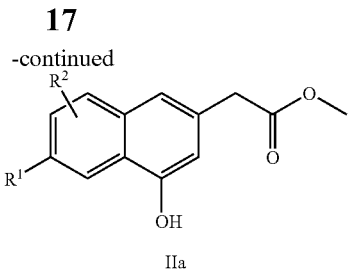

The key intermediates of formula IIa can be prepared according to Scheme 1. In this process, the Stobbe condensation reaction between the benzaldehydes III and dimethyl succinate (IV) gives the unsaturated acids V, which subsequently undergo cyclization in the presence of sodium acetate (VI) and acetic anhydride (VII) to produce compounds VIII. The naphthalene derivatives VIII are then converted to the corresponding hydroxyl analogues IX by a deacetylation reaction. The treatment of the hydroxyl derivatives IX with benzyl bromide (X), followed by reduction using lithium aluminum hydride (XI), affords the alcohols XIIa. Compounds XIIa are then converted to the corresponding chloro intermediates XV by treatment with triphenylphosphine (XIII) and carbon tetrachloride (XIV). Conversion of the chlorides XV to the methyl esters XVI can be accomplished by a palladium-catalyzed carbonylation reaction in methanol. Hydrogenolysis of compounds XVI affords the intermediates IIa.

In the first step outlined in Scheme 1, the unsaturated acids V can be prepared by a condensation reaction between the benzaldehydes III and dimethyl succinate (IV). The reaction can be carried out in the presence of a base such as sodium methoxide, lithium methoxide, sodium tert-butoxide, sodium hydride or potassium tert-butoxide, in an organic solvent such as methanol, tert-butanol, toluene, or mixtures thereof, at a temperature between room temperature and 90° C. for several hours (reference: Dian, Y. L. et al., *Tetrahedron Lett.*, 32 (1991) 5255).

Cyclization of the unsaturated acids V to produce the naphthalene derivatives VIII can be achieved by treatment of the unsaturated acids V with sodium acetate (VI) and acetic anhydride (VII) at a temperature between room temperature and 140° C. for 0.5 to 12 hours (references: Boger, D. L. et al., *J. Org. Chem.* 61 (1996) 4894-4912; Kim, M. et al., *J. Org. Chem.* 69 (2004) 6945-6948).

The acetate derivatives VIII can be converted to the corresponding hydroxyl compounds IX in the presence of a base such as sodium methoxide, potassium tert-butoxide, potassium carbonate or sodium bicarbonate, in a solvent such as methanol, water, or mixtures thereof, at a temperature between room temperature and 80° C. for 10 minutes to several hours (reference: Kim, M. et al., *J. Org. Chem.* 69 (2004) 6945-6948).

Treatment of the hydroxyl compounds IX with benzyl bromide (X) affords the corresponding benzyl ethers. The reaction can be carried out in the presence of a base such as potassium carbonate, or cesium carbonate, in an inert organic solvent such as acetone, acetonitrile, or N,N-dimethylformamide at a temperature between room temperature and 60° C. for several hours.

Reduction of the above benzyl ethers with lithium aluminum hydride (XI) affords the alcohols XIIa. The reaction can be carried out in an inert organic solvent such as tetrahydrofuran, diethyl ether, toluene, or mixtures thereof, at a temperature between room temperature and 80° C. for several hours (reference: Chan W. K., et al., *J. Med. Chem.* 39 (1996) 3756-3768).

The intermediates XV can be prepared by the treatment of the alcohols XIIa with triphenylphosphine (XIII) and carbon tetrachloride (XIV) in an inert organic solvent such as toluene, acetonitrile, dichloromethane, N,N-dimethylformamide, or tetrahydrofuran, at a temperature between 0° C. and 120° C. for several hours (reference: Kozhinov, D. V. et al., *J. Org. Chem.* 69 (2004) 1378-1379).

Conversion of the intermediates XV to the methyl esters XVI can be accomplished by a palladium catalyzed carbonylation reaction under 1 atmospheric pressure of carbon monoxide in methanol. The reaction can be carried out in the presence of a palladium catalyst such as bis(triphenylphosphine)dichloropalladium(II) (Pd(PPh$_3$)$_2$Cl$_2$), palladium(II) acetate (Pd(OAc)$_2$), tetrakis(triphenylphosphine)palladium (0) (Pd(PPh$_3$)$_4$), or tris(dibenzylideneacetone)dipalladium (0) (Pd$_2$(dba)$_3$), in the presence or absence of a phosphine ligand such as tricyclohexylphosphine, or triphenylphosphine, at a temperature between room temperature and 90° C. for 10 minutes to several hours (reference: Kozhinov, D. V. et al., *J. Org. Chem.* 69 (2004) 1378-1379).

Hydrogenolysis of benzyl ethers XVI affords the intermediates IIa. The reaction can be carried out in the presence of 10% palladium on carbon under 1 atmospheric pressure of hydrogen, in an organic solvent such as ethyl acetate, methanol, or ethanol, at room temperature for several hours. Note that hydrogenolysis of benzyl ethers XVI, in which R$^1$ is Cl or Br, can afford IIa, in which R$^1$ is reduced to H, when the hydrogenations are carried out in the presence of 10% palladium on carbon under 1 atmospheric pressure of hydrogen for a longer period of reaction time.

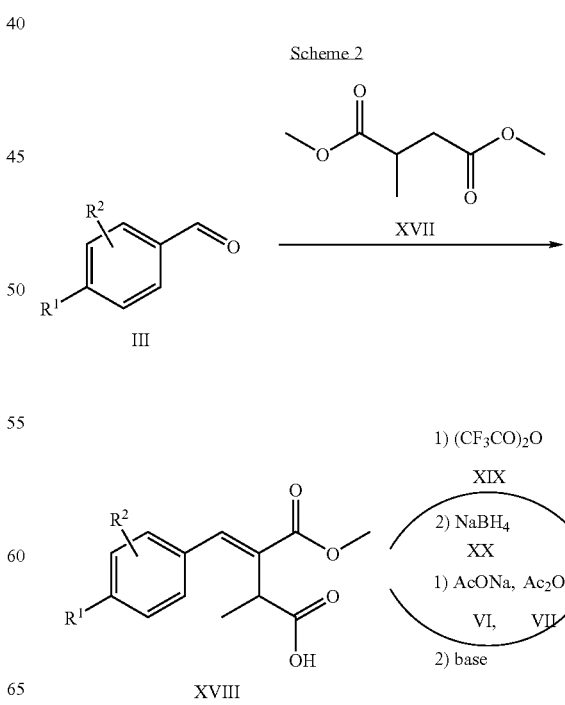

Scheme 2

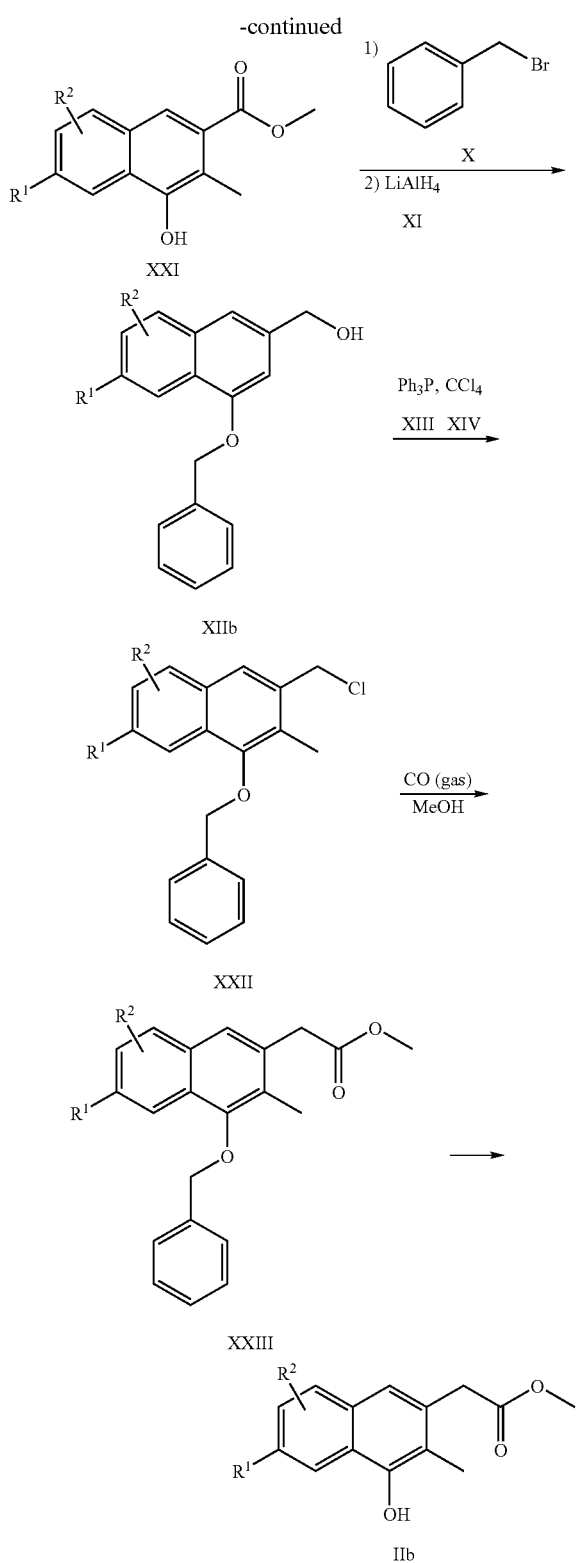

The key intermediates of formula IIb can be prepared according to Scheme 2. In this process, the Stobbe condensation reaction between the benzaldehydes III and dimethyl 2-methyl-succinate (XVII) affords the unsaturated acids XVIII. Cyclization of the unsaturated acids XVIII using trifluoroacetic anhydride (XIX), followed by reduction affords compounds XXI. Alternatively, compounds XXI can be obtained by treatment of the unsaturated acids XVIII with sodium acetate (VI) and acetic anhydride (VII) followed by treatment with a base. Treatment of the hydroxyl derivatives XXI with benzyl bromide (X), followed by reduction affords the alcohols XIIb. The alcohols XIIb are then converted to the corresponding chlorides XXII by treatment with triphenylphosphine (XIII) and carbon tetrachloride (XIV). The chlorides XXII can be converted to the esters XXIII by a palladium catalyzed carbonylation reaction in methanol. Hydrogenolysis of compounds XXIII affords the intermediates IIb.

In the first step outlined in Scheme 2, the unsaturated acids XVIII can be prepared by a condensation reaction between the benzaldehydes III with dimethyl 2-methyl-succinate (XVII). The reaction can be carried out in the presence of a base such as sodium methoxide, lithium methoxide, sodium tert-butoxide, sodium hydride, or potassium tert-butoxide, in an organic solvent such as methanol, tert-butanol, toluene, or mixtures thereof, at a temperature between room temperature and 90° C. for several hours (references: Liu, J. et al., *Org. Lett.* 4 (2002) 3521-3524; Bloomer, J. L. et al., *J. Org. Chem.* 58 (1993) 7906-7912).

The naphthalene derivatives XXI can be prepared by a cyclization reaction, followed by reduction. Cyclization of the unsaturated acids XVIII can be achieved by treatment with trifluoroacetic anhydride (XIX) and triethylamine in an inert organic solvent such as tetrahydrofuran, or dichloromethane at room temperature. The subsequent reduction with sodium borohydride (XX) can be carried out in an alcoholic solvent such as methanol at a temperature between 0° C. and room temperature (reference: Fuganti, C. et al., *J. Chem. Res.* (S) 1998, 638-639).

Alternatively, the naphthalene derivatives XXI can be prepared in a manner analogous to the one described for the intermediates IX in Scheme 1. Cyclization of the unsaturated acids XVIII can be achieved by treatment with sodium acetate (VI) and acetic anhydride (VII) at a temperature between room temperature and 140° C. for 0.5 to 12 hours. The generated acetates can be converted to the corresponding hydroxyl compounds XXI by treatment with a base such as sodium methoxide, potassium tert-butoxide, potassium carbonate, or sodium bicarbonate, in a solvent such as methanol, water or mixtures thereof, at a temperature between room temperature and 80° C. for 10 minutes to several hours (references: Boger, D. L. et al., *J. Org. Chem.* 61 (1996) 4894-4912; Kim, M. et al., *J. Org. Chem.* 69 (2004) 6945-6948).

Treatment of the hydroxyl compounds XXI with benzyl bromide (X) affords the corresponding benzyl ethers. The reaction can be carried out in the presence of a base such as potassium carbonate, or cesium carbonate, in an inert organic solvent such as acetone, acetonitrile, or N,N-dimethylformamide at a temperature between room temperature and 60° C. for several hours.

Reduction of the ester moieties in the above benzyl ethers with lithium aluminum hydride (XI) affords the alcohols XIIb. The reaction can be carried out in an inert organic solvent such as tetrahydrofuran, diethyl ether, toluene or mixtures thereof, at a temperature between room temperature and 80° C. for several hours.

The reaction of the alcohols XIIb with triphenylphosphine (XIII) and carbon tetrachloride (XIV) can be carried out in an inert organic solvent such as tetrahydrofuran, acetonitrile, toluene, N,N-dimethylformamide, or dichloromethane, at a temperature between 0° C. and 120° C. for several hours (reference: Kozhinov, D. V. et al., *J. Org. Chem.* 69 (2004) 1378-1379).

Conversion of the chlorides XXII to the methyl esters XXIII can be accomplished by a palladium catalyzed carbonylation reaction under 1 atmospheric pressure of carbon monoxide in methanol. The reaction can be carried out in the presence of a palladium catalyst such as bis(triphenylphosphine)dichloropalladium(II) (Pd(PPh$_3$)$_2$Cl$_2$), palladium(II) acetate (Pd(OAc)$_2$), tetrakis(triphenylphosphine)palladium (0) (Pd(PPh$_3$)$_4$), or tris(dibenzylideneacetone)dipalladium (0) (Pd$_2$(dba)$_3$), in the presence or absence of a phosphine ligand such as tricyclohexylphosphine, or triphenylphosphine at a temperature between room temperature and 90° C. for 10 minutes to several hours (reference: Kozhinov, D. V. et al., *J. Org. Chem.* 69 (2004) 1378-1379).

Hydrogenolysis of benzyl ethers XXIII affords the intermediates IIb. The reaction can be carried out in the presence of 10% palladium on carbon under 1 atmospheric pressure of hydrogen, in an organic solvent such as ethyl acetate, methanol, or ethanol, at room temperature for several hours.

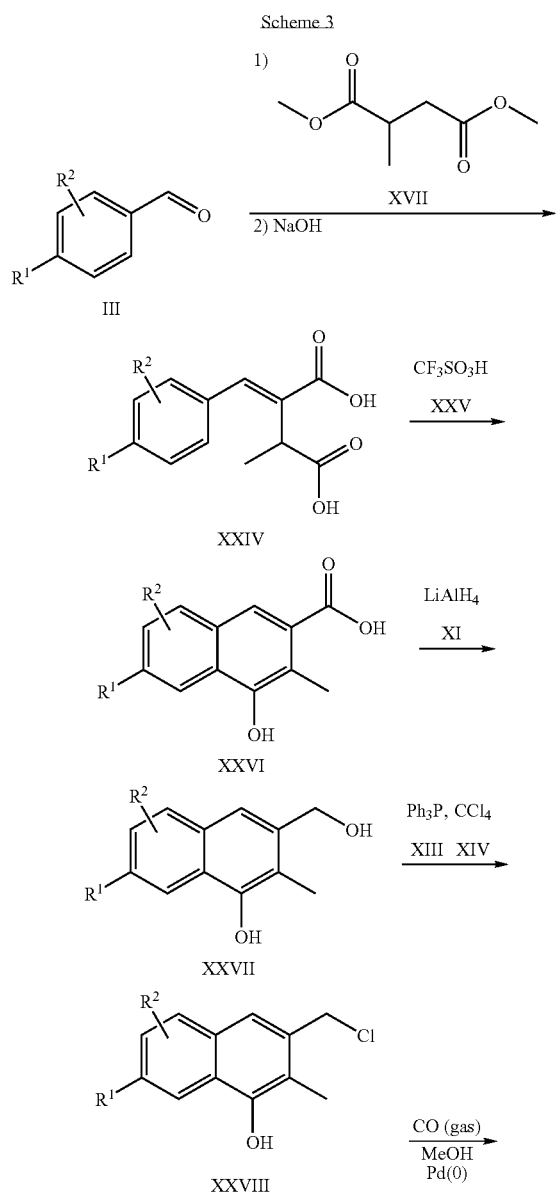

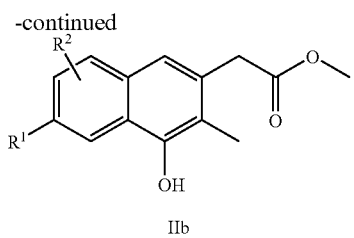

Alternatively, the hydroxyl intermediates IIb can be prepared according to Scheme 3. In this process, the Stobbe condensation reaction between the benzaldehydes III and dimethyl 2-methyl-succinate (XVII) followed by hydrolysis affords the unsaturated diacids XXIV. Cyclization of the unsaturated diacids XXIV followed by reduction affords compounds XXVII. Treatment of compounds XXVII with triphenylphosphine (XIII) and carbon tetrachloride (XIV) affords the corresponding chlorides XXVIII. The chlorides XXVIII can be converted to the methyl esters IIb by a palladium catalyzed carbonylation reaction.

In this process, the Stobbe condensation can be carried out in the presence of a base such as sodium hydride, in an organic solvent such as toluene, at room temperature for several hours. The unsaturated diacids XXIV can be formed by treatment of the products of condensation with an aqueous inorganic base such as sodium hydroxide, in an organic solvent such as toluene, at a temperature between room temperature and 100° C. for several hours.

Cyclization of the diacids XXIV can be achieved by treatment of the diacids with trifluoromethanesulfonic acid (XXV), at room temperature for several hours.

Reduction of the carboxyl moieties in the intermediates XXVI with lithium aluminum hydride (XI) affords the alcohols XXVII. The reaction can be carried out in an inert organic solvent such as tetrahydrofuran, diethyl ether, toluene or mixtures thereof, at a temperature between room temperature and 80° C. for several hours.

The reaction of the alcohols XXVII with carbon tetrachloride (XIV) in the presence of triphenylphosphine (XIII) can be carried out in an inert organic solvent such as tetrahydrofuran, acetonitrile, toluene, N,N-dimethylformamide, or dichloromethane, at a temperature between 0° C. and 120° C. for several hours.

Conversion of the chlorides XXVIII to the intermediates IIb can be accomplished by a carbonylation reaction, in a manner analogous to the one described in Scheme 1 for the preparation of the methyl esters XVI.

Scheme 4

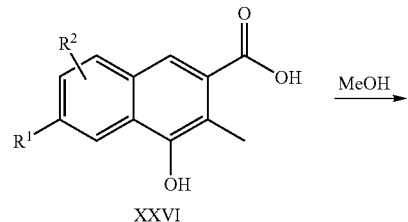

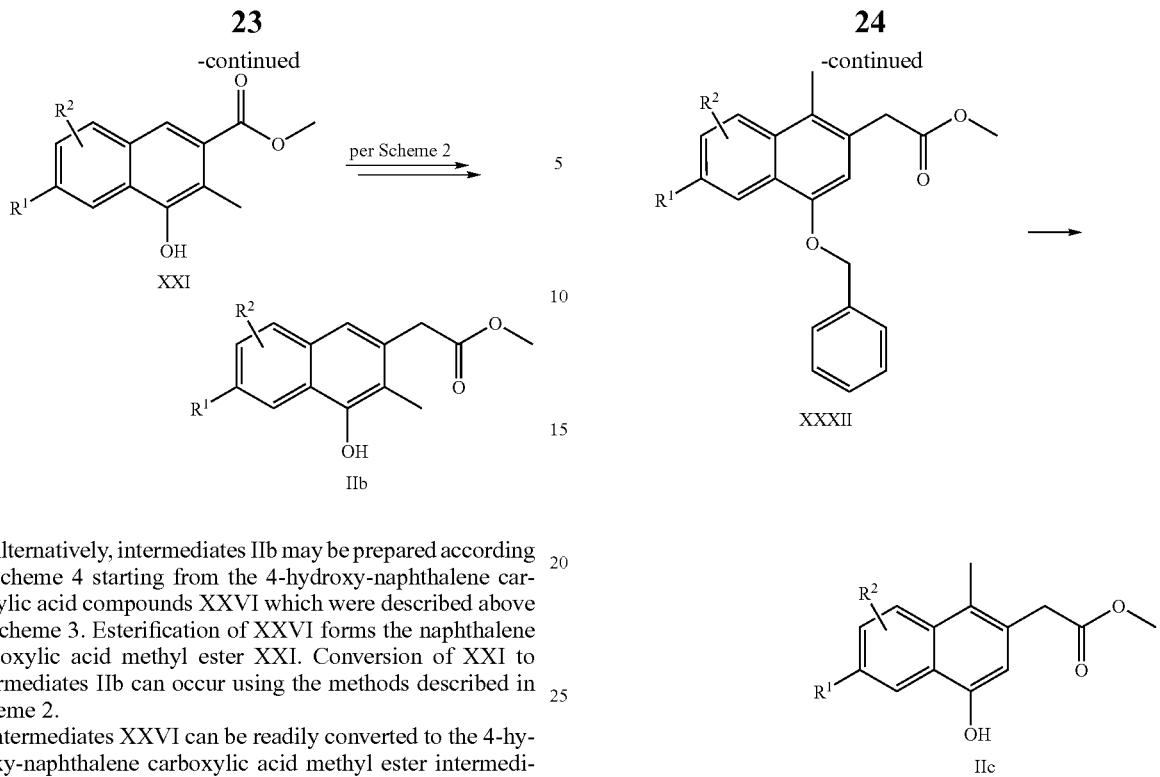

Alternatively, intermediates IIb may be prepared according to Scheme 4 starting from the 4-hydroxy-naphthalene carboxylic acid compounds XXVI which were described above in Scheme 3. Esterification of XXVI forms the naphthalene carboxylic acid methyl ester XXI. Conversion of XXI to intermediates IIb can occur using the methods described in Scheme 2.

Intermediates XXVI can be readily converted to the 4-hydroxy-naphthalene carboxylic acid methyl ester intermediates XXI in the presence of a catalytic amount of concentrated sulfuric acid and an excess of methanol at temperatures between room temperature and 80° C. for several hours. Alternatively, the esterification reaction can be carried out in the presence of thionyl chloride and an excess of methanol at temperatures between 65° C. and 80° C. for several hours. The obtained compounds XXI can be transformed into intermediates IIb using the process described above in Scheme 2.

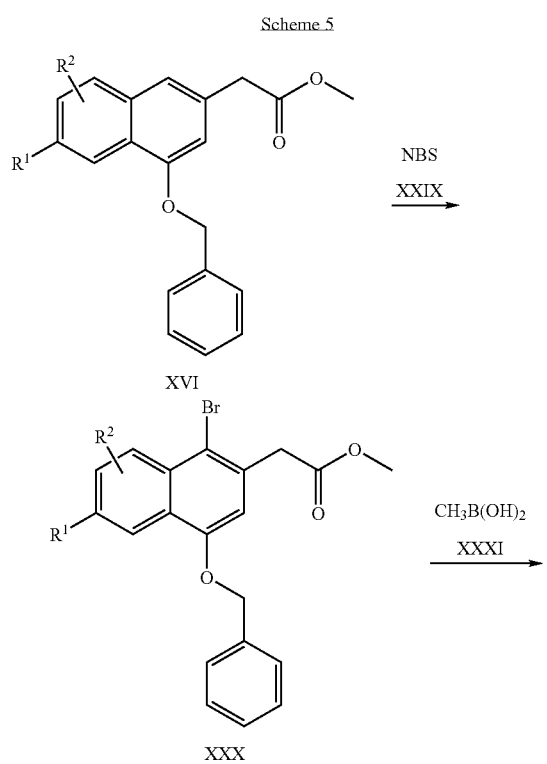

The intermediates of formula IIc can be prepared according to Scheme 5. In this process, bromination of the intermediates XVI, followed by a Suzuki coupling reaction affords the intermediates XXXII. Hydrogenolysis of the intermediates XXXII gives the hydroxyl intermediates IIc.

In this process, bromination can be achieved by treatment of the intermediates XVI with N-bromosuccinimide (NBS, XXIX) in an organic solvent such as acetonitrile, dichloromethane, acetone, N,N-dimethylformamide, tetrahydrofuran, chloroform, or carbon tetrachloride, at room temperature for 30 minutes to several hours (reference: Hidemitsu U., et al., *J. Chem. Soc., Perkin Trans.* 1, 2001, 229).

The Suzuki coupling reaction of the intermediates XXX with methylboronic acid (XXXI) gives compounds XXXII. The reaction can be carried out in the presence of a palladium catalyst such as [1,1'-bis(diphenylphosphino)ferrocene] dichloropalladium(II) ($PdCl_2(dppf)$), palladium acetate (Pd (OAc)$_2$), or tetrakis(triphenylphosphine)palladium(0) (Pd (PPh$_3$)$_4$), in the presence or absence of a ligand such as tricyclohexylphosphine, triphenylphosphine, or tri-2-tolylphosphine, and a base such as potassium tert-butoxide, sodium hydroxide, potassium phosphate, potassium carbonate, or sodium carbonate, in a suitable solvent such as N,N-dimethylformamide, dimethyl sulfoxide, toluene, tetrahydrofuran, 1,4-dioxane, water or mixtures thereof, at a temperature between 130° C. and 180° C. for 15 to 30 minutes under microwave irradiation. Alternatively, the reactions can be carried out at an elevated temperature such as 130° C. without microwave irradiation for a longer reaction time (reference: Wallace, D. J. et al., *Tetrahedron Lett.* 43 (2002) 6987-6990).

Hydrogenolysis of benzyl ethers XXXII affords the intermediates IIc. The reaction can be carried out in the presence of 10% palladium on carbon under 1 atmospheric pressure of hydrogen, in an organic solvent such as ethyl acetate, methanol, or ethanol, at room temperature for several hours.

Scheme 6

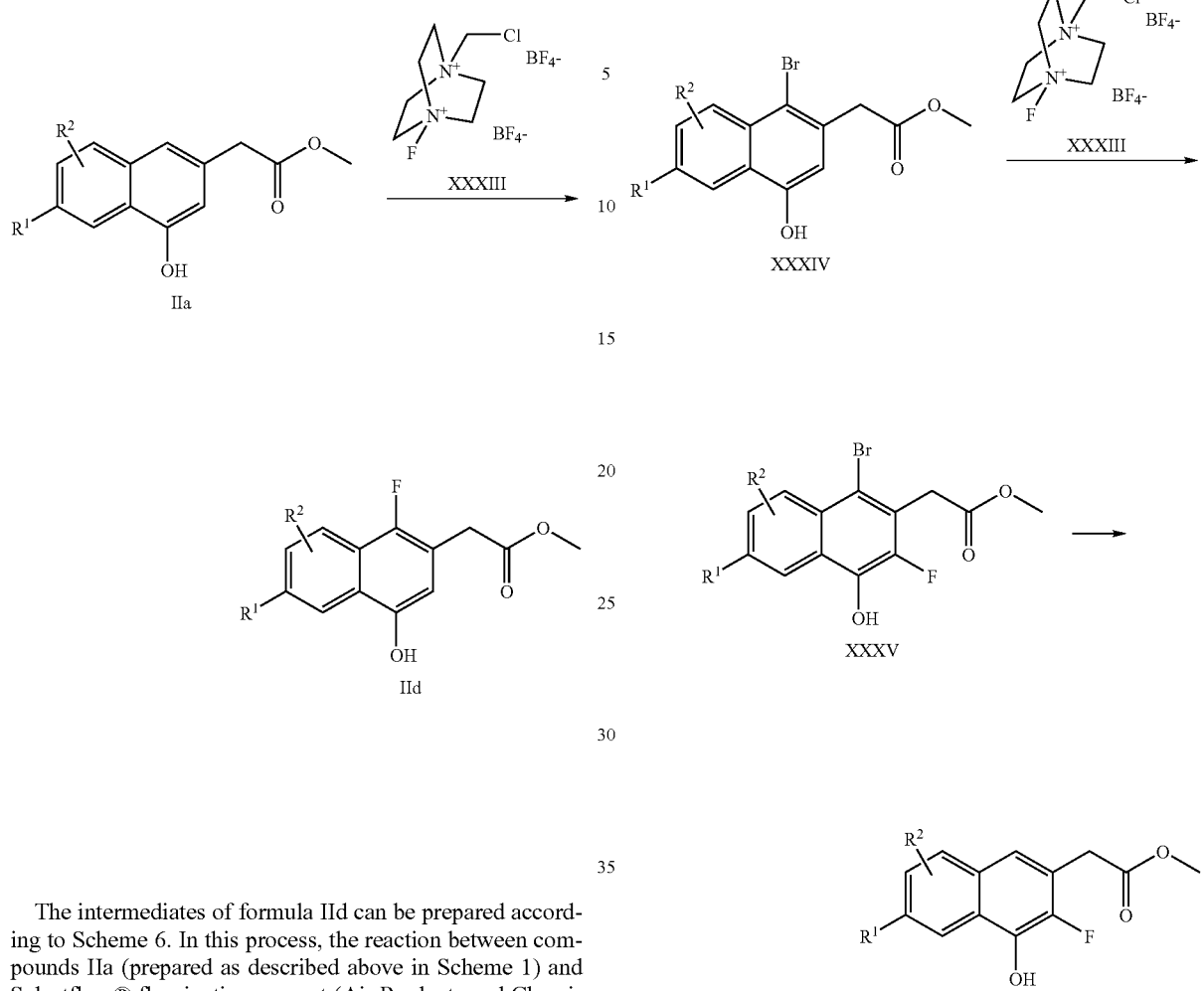

The intermediates of formula IId can be prepared according to Scheme 6. In this process, the reaction between compounds IIa (prepared as described above in Scheme 1) and Selectfluor® fluorinating reagent (Air Products and Chemicals, Inc.) generically shown as XXXIII can be carried out in a suitable solvent such as acetonitrile, methanol, N,N-dimethylformamide, trifluoroacetic acid, water or mixtures thereof, at a temperature between 0° C. and 80° C. for several hours (reference: Zupan M. et al., *Bull. Chem. Soc. Jpn.*, 68 (1995) 1655-1660).

Scheme 7

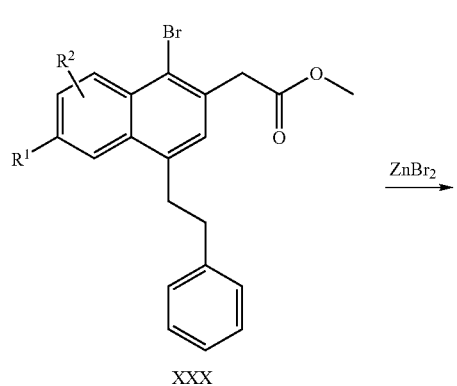

The intermediates IIe can be prepared according to Scheme 7. Debenzylation of compounds XXX followed by a fluorination reaction affords the intermediates XXXV. Hydrogenolysis of compounds XXXV gives the intermediates IIe.

Debenzylation of compounds XXX (prepared as described above in Scheme 5) affords the hydroxyl intermediates XXXIV. The reaction can be accomplished by treatment of the benzyl ethers XXX with zinc bromide in the presence of 10% palladium on carbon under 1 atmospheric pressure of hydrogen, in an organic solvent such as ethyl acetate, methanol, or ethanol, at room temperature for several hours (reference: Wu G. et al., *Synthesis* 11 (2003) 1657-1660).

Conversion of compounds XXXIV to the fluorinated derivatives XXXV can be achieved by using Selectfluor® fluorinating reagent (XXXIII) in a suitable solvent such as N,N-dimethylformamide, acetonitrile, methanol, trifluoroacetic acid, water or mixtures thereof, at a temperature between 0° C. and 80° C. for several hours (reference: Zupan M. et al., *Bull. Chem. Soc. Jpn.*, 68 (1995) 1655-1660).

Hydrogenolysis of the bromo-substituted derivatives XXXV affords the intermediates IIe. The reaction can be carried out in the presence of 10% palladium on carbon under 1 atmospheric pressure of hydrogen, in an organic solvent such as ethyl acetate, methanol, or ethanol, at room temperature for several hours.

Scheme 8

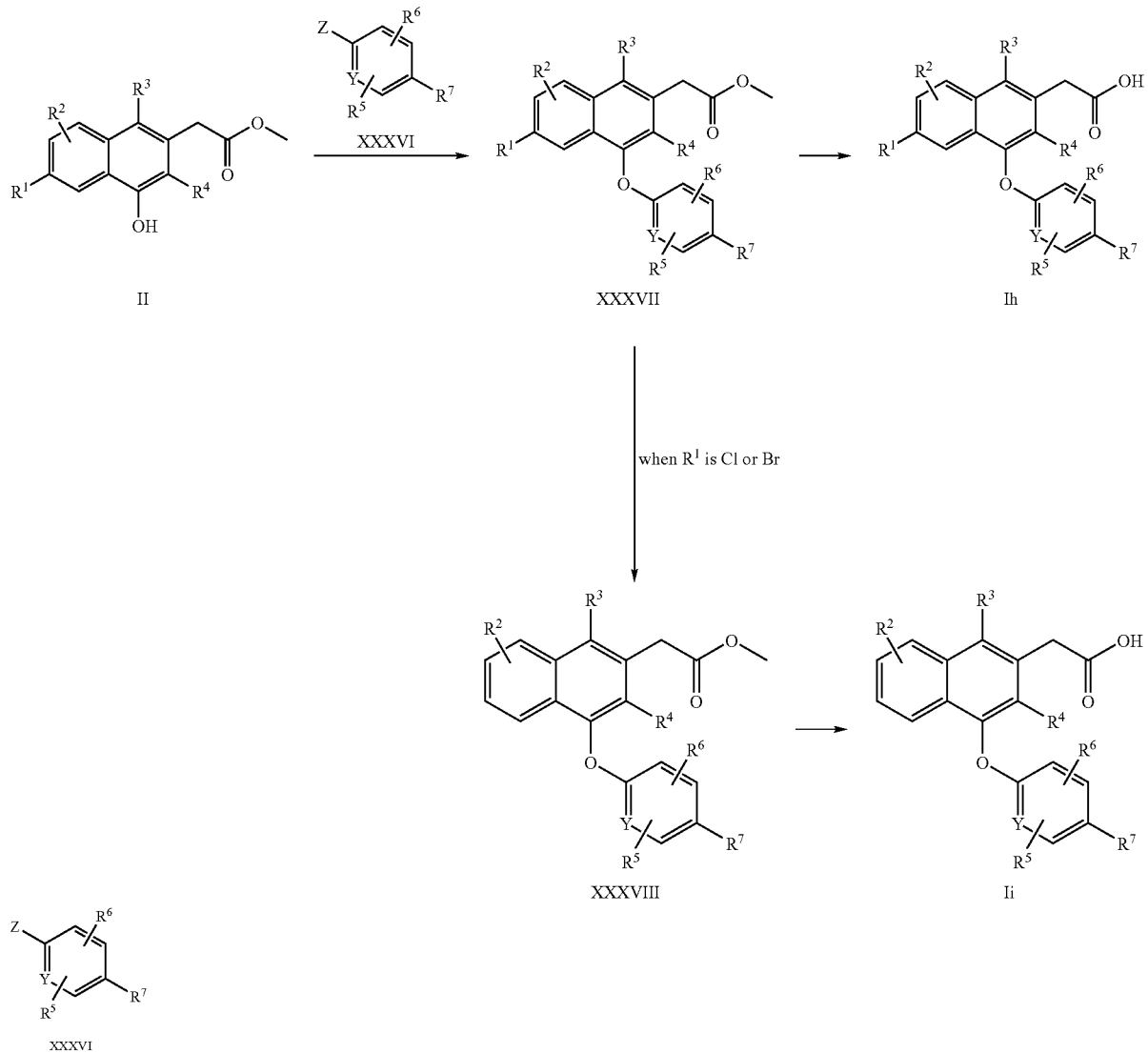

Y is C or N;
when Y is C, Z is F;
when Y is N, Z is Cl, Br or alkylsulfone.

The compounds of interest of formula Ih and Ii can be prepared according to Scheme 8. A reaction between the hydroxyl intermediates II and the aryl derivatives XXXVI followed by ester hydrolysis affords the compounds of interest of formula Ih. Hydrogenolysis of the intermediates XXX-VII when $R^1$ is Cl or Br, followed by ester hydrolysis affords the compounds of interest of formula Ii.

Conversion of the hydroxyl intermediates II (which encompass IIa, IIb, IIc, IId, and IIe from Schemes 1-7) to the ethers XXXVII can be achieved by treating compounds II and the aryl derivatives XXXVI with a base such as sodium carbonate, potassium carbonate, or cesium carbonate, in a suitable organic solvent such as N,N-dimethylformamide, or dimethyl sulfoxide. The reaction can be carried out at a temperature between 100° C. and 150° C. for 30 to 60 minutes under microwave irradiation. Alternatively, the reactions can be carried out at an elevated temperature without microwave irradiation for a longer period of time.

Hydrolysis of the methyl esters XXXVII affords the compounds of interest of formula Ih. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Hydrogenolysis of the intermediates XXXVII can be carried out in the presence of 10% palladium on carbon under 1 atmospheric pressure of hydrogen, in an organic solvent such as ethyl acetate, methanol, or ethanol, at room temperature for several hours.

Hydrolysis of the products of the hydrogenolysis reaction affords the compounds of interest of formula Ii. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Scheme 9

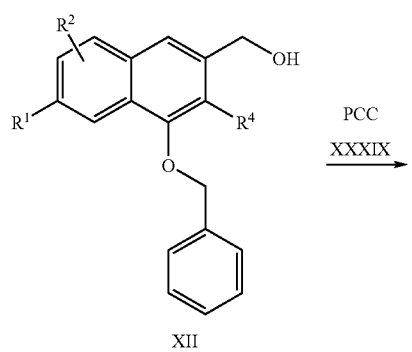

XII

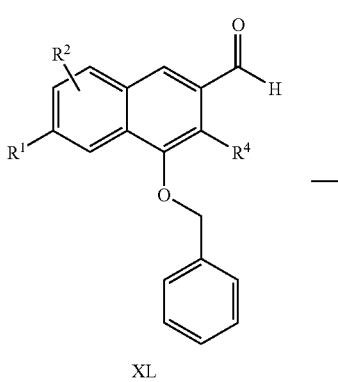

XL

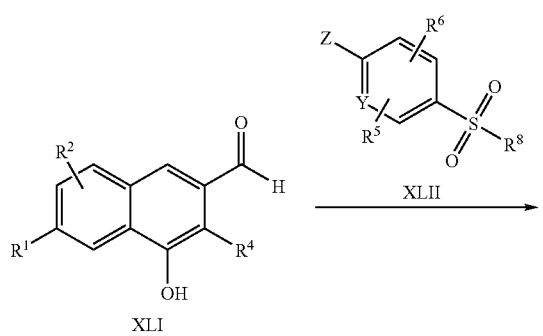

XLI

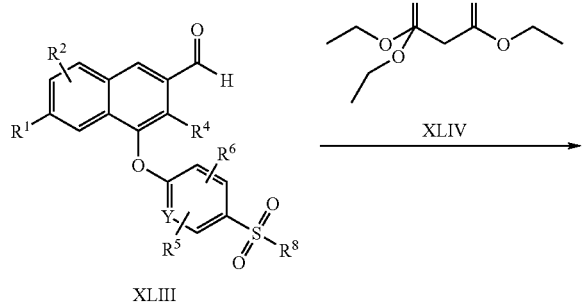

XLIII

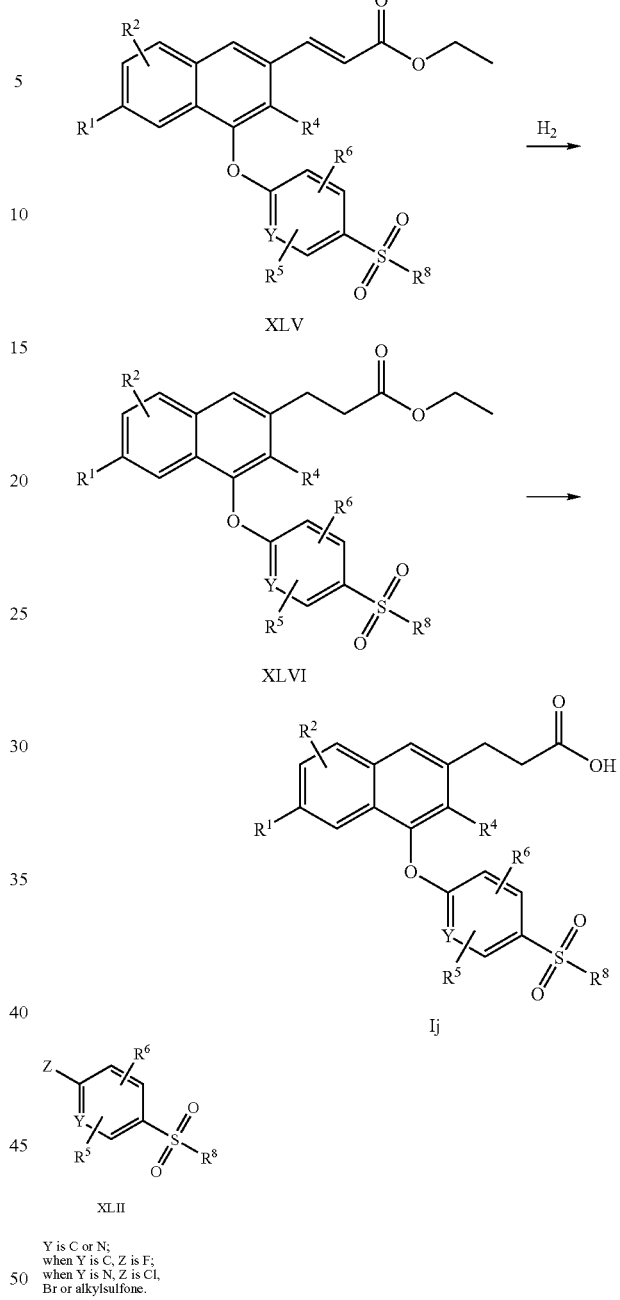

Y is C or N;
when Y is C, Z is F;
when Y is N, Z is Cl,
Br or alkylsulfone.

The compounds of interest of formula Ij can be prepared according to Scheme 9. Oxidation of the alcohols XII (which encompass XIIa and XIIb from Schemes 1 and 2) affords the aldehydes XL. Hydrogenolysis of benzyl ethers XL followed by treatment of the resulting naphthols XLI with the aryl derivatives XLII affords the ether intermediates XLIII. The aldehydes XLIII are converted to the alkenes XLV by the Horner-Wadsworth-Emmons reaction. Hydrogenation of the alkenes XLV followed by ester hydrolysis affords the compounds of interest of formula Ij.

The intermediates XII can be oxidized to the aldehydes XL using pyridinium chlorochromate (PCC) (XXXIX). The reaction can be carried out in a suitable solvent such as dichloromethane, at a temperature between 0° C. and room temperature for several hours (reference: Thibault, M. E. et al., J.

Org. Chem. 68 (2003), 8373-8378). Alternatively, the conversion can also be achieved using manganese oxide, pyridinium dichromate, Dess-Martin periodinane, 2,3-dichloro-5,6-dicyano-1,4-benzoquinone (DDQ), or iron(III) nitrate monohydrate as the oxidizing reagent.

Debenzylation of compounds XL affords the hydroxyl intermediates XLI. The reaction can be accomplished in the presence of 10% palladium on carbon under 1 atmospheric pressure of hydrogen, in an organic solvent such as ethyl acetate, methanol, or ethanol, at room temperature for several hours.

Conversion of the hydroxyl intermediates XLI to the ether compounds XLIII can be achieved by treatment of compounds XLI and compounds XLII with a base such as sodium carbonate, potassium carbonate, or cesium carbonate, in a suitable organic solvent such as N,N-dimethylformamide, or dimethyl sulfoxide, at a temperature between 100° C. and 150° C. for 30 to 60 minutes under microwave irradiation. Alternatively, the reaction can be carried out at an elevated temperature without microwave irradiation for a longer period of time.

The alkenes XLV can be prepared by the Horner-Wadsworth-Emmons reaction between the aldehydes XLIII and triethyl phosphonoacetate (XLIV). The reaction can be carried out in the presence of a base such as sodium hydride, potassium carbonate, cesium carbonate, sodium ethoxide, potassium tert-butoxide, n-butyllithium, triethylamine, 1,8-diazabicyclo[5.4.0]undec-7-ene, sodium hydroxide, potassium hydroxide, or lithium hydroxide, in a suitable solvent such as N,N-dimethylformamide, acetonitrile, benzene, dichloromethane, tetrahydrofuran, 1,4-dioxane, diethyl ether, ethanol, water or mixtures thereof, at a temperature between 0° C. and 60° C. for several hours (reference: Chan W. K. et al., *J. Med. Chem.* 39 (1996) 3756-3768).

Hydrogenation of the alkenes XLV affords the intermediates XLVI. The reaction can be carried out in the presence of 10% palladium on carbon under 1 atmospheric pressure of hydrogen, in an organic solvent such as ethyl acetate, methanol, or ethanol, at room temperature for several hours.

Hydrolysis of the methyl esters XLVI affords the compounds of interest of formula Ij. The reaction can be carried out in the presence of an aqueous inorganic base such as lithium hydroxide, sodium hydroxide, or potassium hydroxide in an organic solvent such as 1,4-dioxane or tetrahydrofuran at room temperature for several hours.

Scheme 10

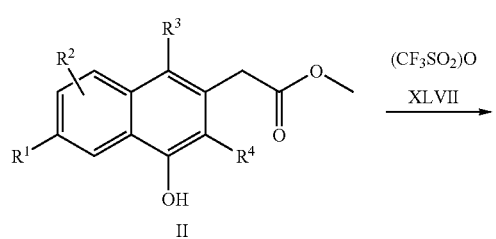

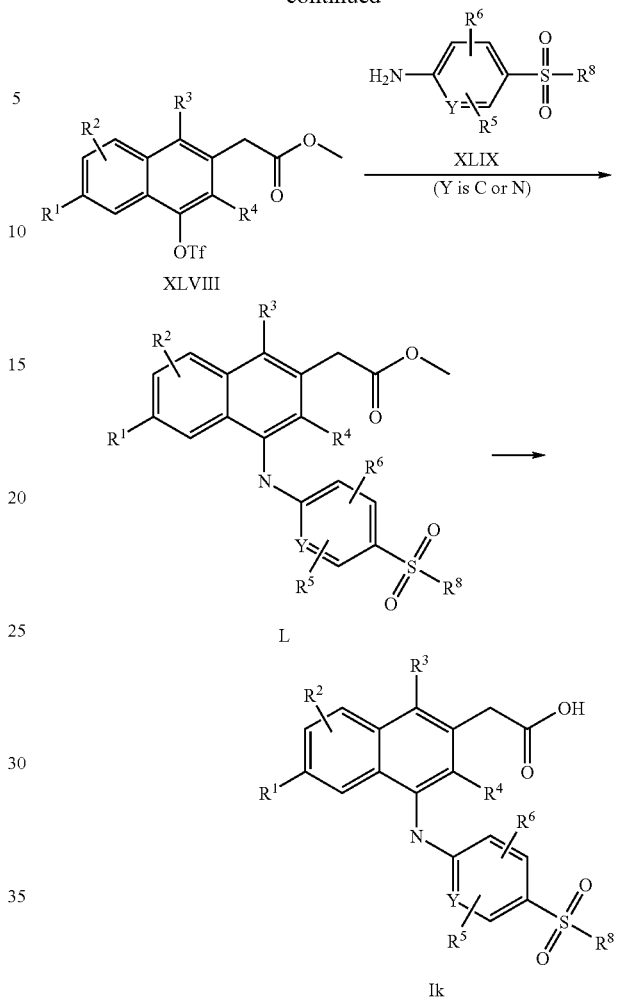

The compounds of interest of formula Ik can be prepared according to Scheme 10. In this process, the hydroxyl compounds II (which encompass IIa, II b, IIc, IId, and IIe from Schemes 1-7) are treated with trifluoromethanesulfonic anhydride (XLVII) to afford the triflates XLVIII. A reaction between the triflates XLVIII and the substituted aryl amine compounds XLIX followed by a hydrolysis reaction affords the compounds of interest of formula Ik.

The hydroxyl compounds II can be converted to the triflates XLVIII by treatment with trifluoromethanesulfonic anhydride (XLVII). The reaction can be carried out in the presence of a base such as pyridine, triethylamine, diisopropylethylamine, N,N-dimethyl-4-pyridinamine, 2,6-dimethylpyridine, 2,4,6-trimethylpyridine, sodium hydride, or potassium carbonate, in a suitable solvent such as dichloromethane, chloroform or acetonitrile, at a temperature between –78° C. and room temperature for 30 minutes to several hours (reference: Chan W. K. et al., *J. Med. Chem.* 39 (1996) 3756-3768).

Reaction of the triflates XLVIII with the aryl amine compounds XLIX can be carried out in the presence of a palladium catalyst such as tetrakis(triphenylphosphine) palladium (0) (Pd(PPh$_3$)$_4$), palladium acetate (Pd(OAc)$_2$), or (tris (dibenzylideneacetone) dipalladium(0) (Pd$_2$(dba)$_3$) in combination with a phosphine ligand such as tricyclohexylphosphine, 1,1'-bis(diphenylphosphino)ferrocene, 2,2'-bis (diphenylphosphino)-1,1'-binaphthalene, or di(tert-butyl)(1,1'-biphenyl-2-yl)phosphine, and a base such as cesium carbonate, potassium carbonate, sodium tert-butoxide, or potassium phosphate, in a suitable solvent such as N,N-dimethylformamide, dimethyl sulfoxide, toluene, or tetrahydrofuran, at a temperature between 130° C. and 180° C. for 15 to 30 minutes under microwave irradiation. Alternatively, the reaction can be carried out at an elevated temperature such as 130° C. without microwave irradiation for a longer reaction time (reference: Uwe S. et al., *Tetrahedron Lett.* 46 (2005) 7111-7115).

Hydrolysis of the methyl esters L affords the compounds of interest of formula Ik. The reaction can be carried out in the presence of an aqueous inorganic base such as lithium hydroxide, sodium hydroxide, or potassium hydroxide in an organic solvent such as 1,4-dioxane or tetrahydrofuran at room temperature for several hours.

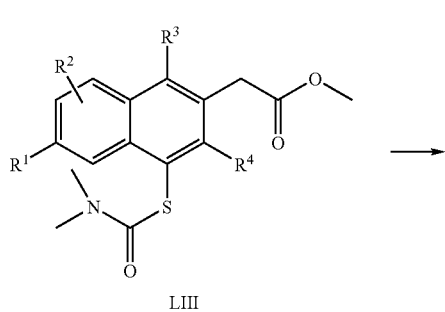

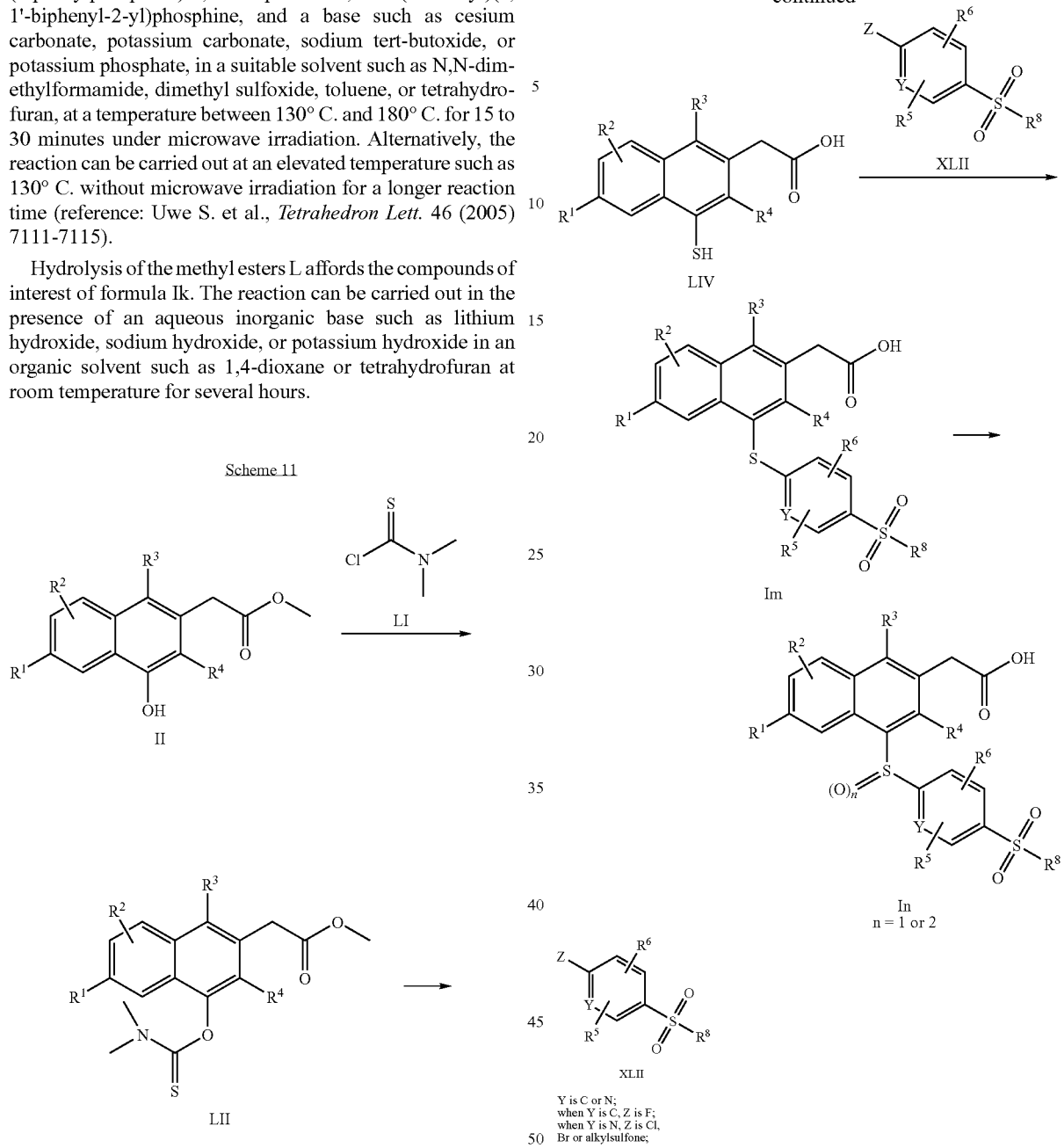

The compounds of interest of formula Im and In can be prepared according to Scheme 11. Treatment of intermediates II (which encompass IIa, IIb, IIc, IId, and IIe from Schemes 1-7) with dimethylthiocarbamoyl chloride (LI) affords the dimethylthiocarbamoyloxy compounds LII. Newman-Kwart rearrangement of the dimethylthiocarbamoyloxy compounds LII affords the intermediates LIII. Hydrolysis of compounds LIII followed by treatment with the aryl derivatives XLII affords the sulfanyl compounds Im. Oxidation of Im gives the sulfinyl or sulfonyl compounds In.

Conversion of the intermediates II to the dimethylthiocarbamoyloxy compounds LII can be achieved by treatment of the intermediates II with dimethylthiocarbamoyl chloride (LI) in the presence of a base such as potassium carbonate, potassium hydroxide, triethylamine, or sodium hydride, in a suitable solvent such as N,N-dimethylformamide, tetrahydrofuran, acetone, water or mixtures thereof, at a temperature between room temperature and 100° C. for several hours.

The Newman-Kwart rearrangement of the dimethylthiocarbamoyloxy compounds LII can be achieved by heating in the presence or absence of an organic solvent such as N-methylpyrrolidone, tetradecane, diphenyl ether, or 1,1-dioxothiolan, at a temperature between 150° C. and 300° C. for 10 minutes to several hours (reference: Moseley, J. D. et al., Tetrahedron 62 (2006) 4685-4689).

Hydrolysis of compounds LIII can afford compounds LIV. The reaction can be carried out in the presence of a base such as potassium hydroxide, sodium hydroxide, or sodium methoxide, in a suitable solvent such as methanol, ethanol, water, or mixtures thereof at a temperature between 60° C. and 100° C. for 30 minutes to several hours.

The sulfonyl compounds Im can be prepared by the reaction of compounds LIV with the aryl derivatives XLII. The reaction can be carried out in the presence of a base such as sodium carbonate, potassium carbonate, or cesium carbonate, in a suitable solvent such as dimethyl sulfoxide, or N,N-dimethylformamide, at a temperature between 100° C. and 150° C. for about 30 to 60 minutes under microwave irradiation. Alternatively, the reaction can be also carried out at an elevated temperature without microwave irradiation for a longer period of time.

Oxidation of the sulfanyl compounds Im to the sulfinyl or sulfonyl analogues In can be achieved using an oxidant such as m-chloroperoxybenzoic acid (m-CPBA), or hydrogen peroxide in an inert solvent such as dichloromethane or 1,2-dichloroethane (or an aqueous solution if hydrogen peroxide is used), at a temperature between 0° C. and room temperature for several hours.

Scheme 12

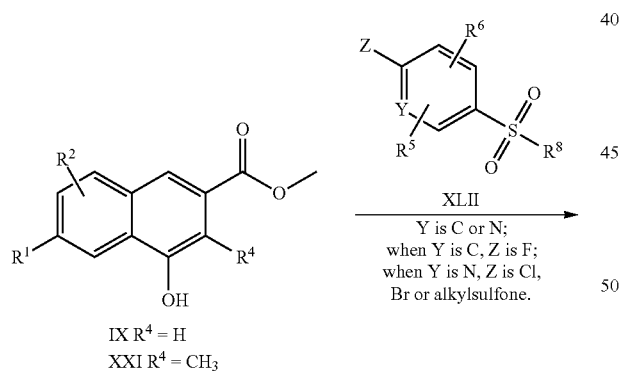

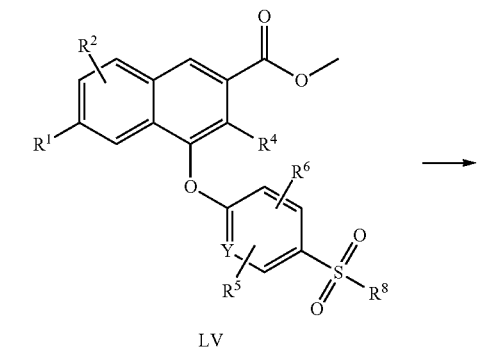

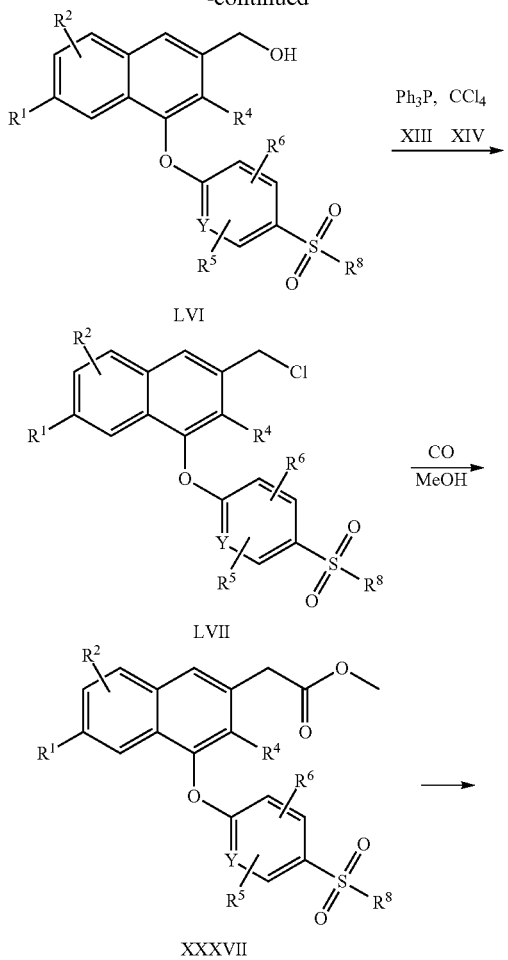

Compounds of interest of formula Ih can alternatively be prepared according to Scheme 12. A substitution reaction between the hydroxyl compounds IX or XXI (prepared as described in Scheme 1 or Scheme 2) and the aryl derivatives XLII followed by reduction gives the alcohols LVI. The alcohols LVI are then transformed to the corresponding chlorides LVII by treatment with carbon tetrachloride (XIV) and triphenylphosphine (XIII). Conversion of the chlorides LVII to the methyl esters XXXVII can be accomplished by a palladium catalyzed carbonylation reaction in methanol. Ester hydrolysis of the methyl esters XXXVII affords the compounds of interest of formula Ih.

Conversion of the hydroxyl intermediates IX or XXI to the ether derivatives LV can be achieved by treatment of compounds IX or XXI and compounds XLII with a base such as sodium carbonate, potassium carbonate, or cesium carbonate, in a suitable organic solvent such as N,N-dimethylformamide, or dimethyl sulfoxide, at a temperature between 100° C. and 150° C. for 30 to 60 minutes under microwave irradiation. Alternatively, the reaction can be carried out at an elevated temperature without microwave irradiation for a longer period of time.

The alcohols LVI can be formed by treatment of the methyl esters LV with diisobutylaluminum hydride in an organic solvent such as toluene, at a temperature between −78° C. and room temperature for several hours.

in methanol, using a method analogous to the one described in Scheme 1 for the preparation of the methyl esters XVI.

As described above in Scheme 8, hydrolysis of the methyl esters XXXVII affords the compounds of interest of formula Ih. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

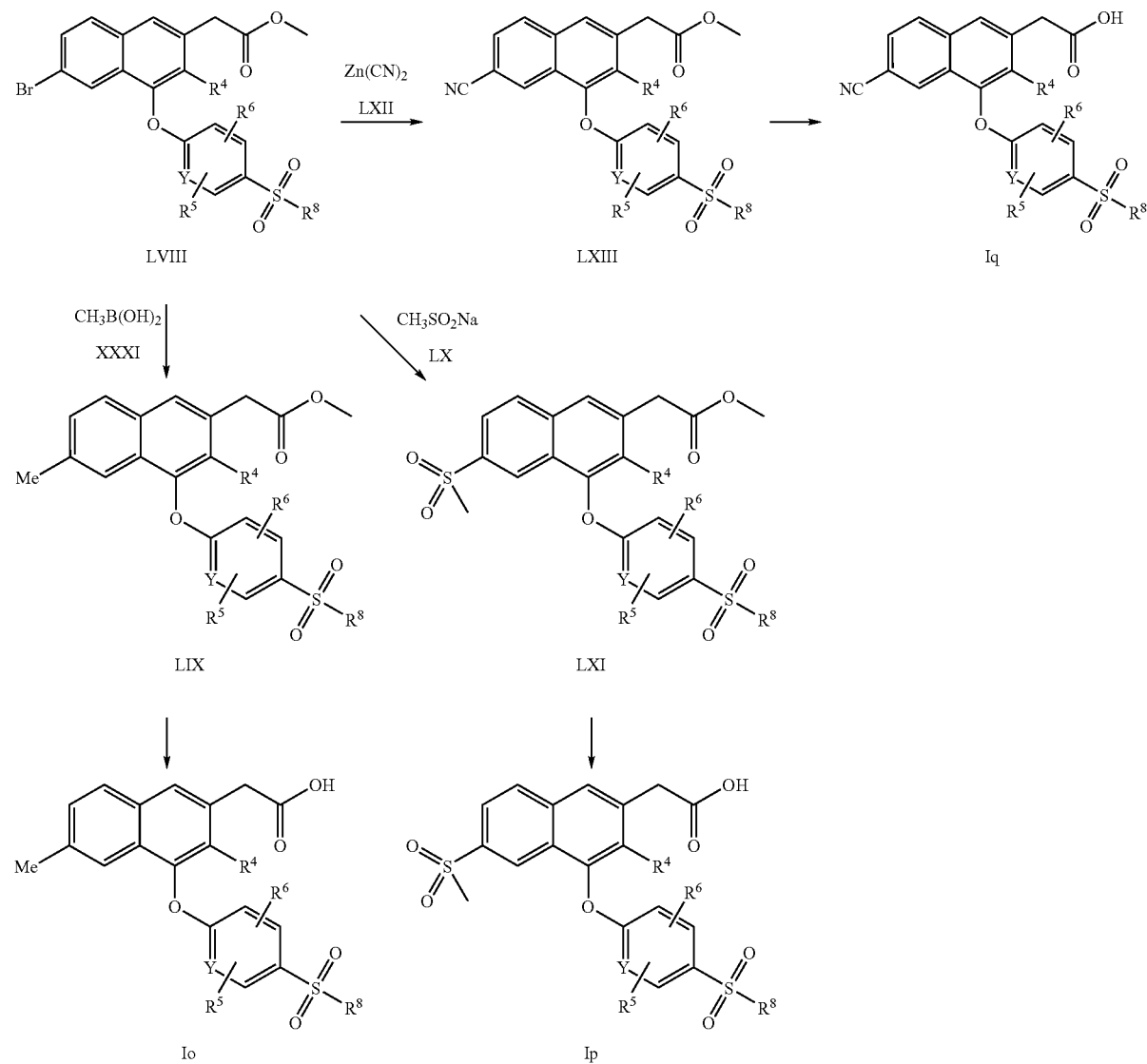

The chlorides LVII can be prepared by the treatment of the alcohols LVI with carbon tetrachloride (XIV) and triphenylphosphine (XIII) in an inert organic solvent such as toluene, acetonitrile, dichloromethane, N,N-dimethylformamide, or tetrahydrofuran, at a temperature between 0° C. and 120° C. for several hours.

Conversion of the chlorides LVII to the methyl esters XXXVII can be accomplished by a palladium catalyzed carbonylation reaction under an atmosphere of carbon monoxide Compounds of interest Io, Ip, and Iq can be prepared according to Scheme 13 starting from the bromo-substituted naphthylacetic acid methyl esters LVIII. A Suzuki coupling reaction between the bromo derivatives LVIII and methylboronic acid (XXXI) followed by an ester hydrolysis affords the compounds of interest of formula Io. A copper (I) iodide catalyzed reaction of the bromo derivatives LVIII with methanesulfinic acid sodium salt (LX) followed by an ester hydrolysis affords the compounds of interest of formula Ip.

Conversion of the bromo derivatives LVIII to the cyano derivatives LXIII followed by an ester hydrolysis affords the compounds of interest of formula Iq.

The Suzuki coupling reactions of the bromo derivatives LVIII with methylboronic acid (XXXI) affords the methyl derivatives LIX. The reaction can be carried out in the presence of a palladium catalyst such as tetrakis(triphenylphosphine)palladium(0) (Pd(PPh$_3$)$_4$), or [1,1'-bis(diphenylphosphino)ferrocene]dichloropalladium(II) (PdCl$_2$(dppf)), and a base such as potassium tert-butoxide, potassium phosphate, or sodium carbonate, in an inert solvent such as N,N-dimethylformamide, dimethyl sulfoxide, toluene, tetrahydrofuran, water or mixtures thereof, at a temperature between 130° C. and 180° C. for 15 to 30 minutes under microwave irradiation. Alternatively, the reactions can be carried out at a heated temperature such as 130° C. without microwave irradiation for a longer reaction time.

The sulfonyl compounds LXI can be formed via a copper (I) iodide catalyzed reaction of the bromo derivative LVIII with methanesulfinic acid sodium salt (LX). The reaction can be carried out in the presence of catalysts copper(I) iodide and L-proline in a polar solvent such as N,N-dimethylformamide, dimethyl sulfoxide, or 1,4-dioxane at 150° C. for 30 minutes under microwave irradiation. Alternatively, the reaction can be carried out at a heated temperature such as 110° C. without microwave irradiation for a longer reaction time.

Conversion of the bromo derivatives LVIII to the cyano derivatives LXIII can be achieved by treatment of the bromo derivatives with zinc cyanide (LXII) in the presence of a catalyst such as tetrakis(triphenylphosphine)palladium(0) (Pd(PPh$_3$)$_4$), in an inert organic solvent such as N,N-dimethylacetamide, at a heated temperature such as 150° C. for several hours.

Hydrolysis of the methyl esters LIX, LXI or LXIII in a manner analogous to the one described above for the preparation of Ih affords the compounds of interest of formula Io, Ip and Iq, respectively.

Scheme 14
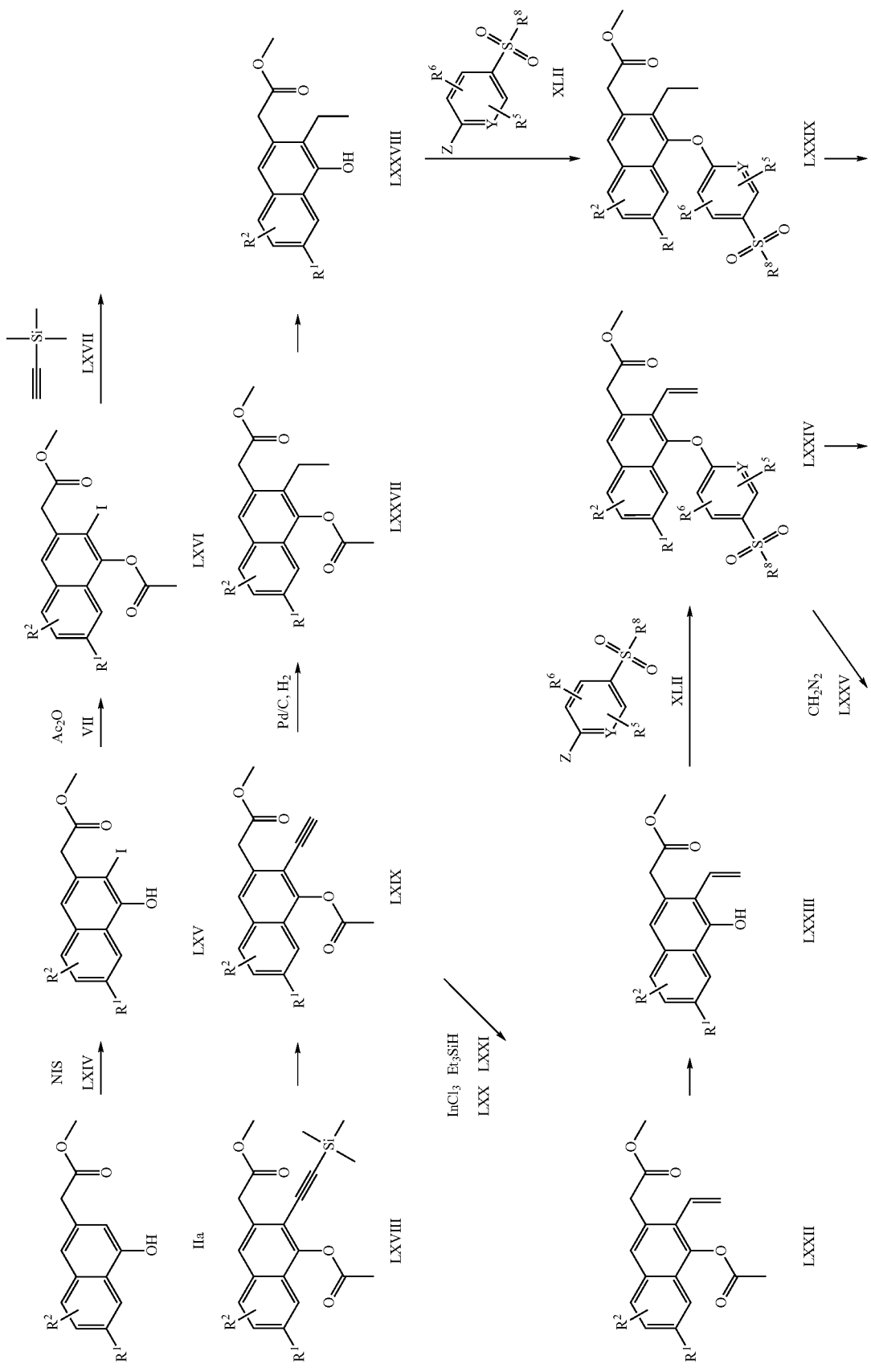

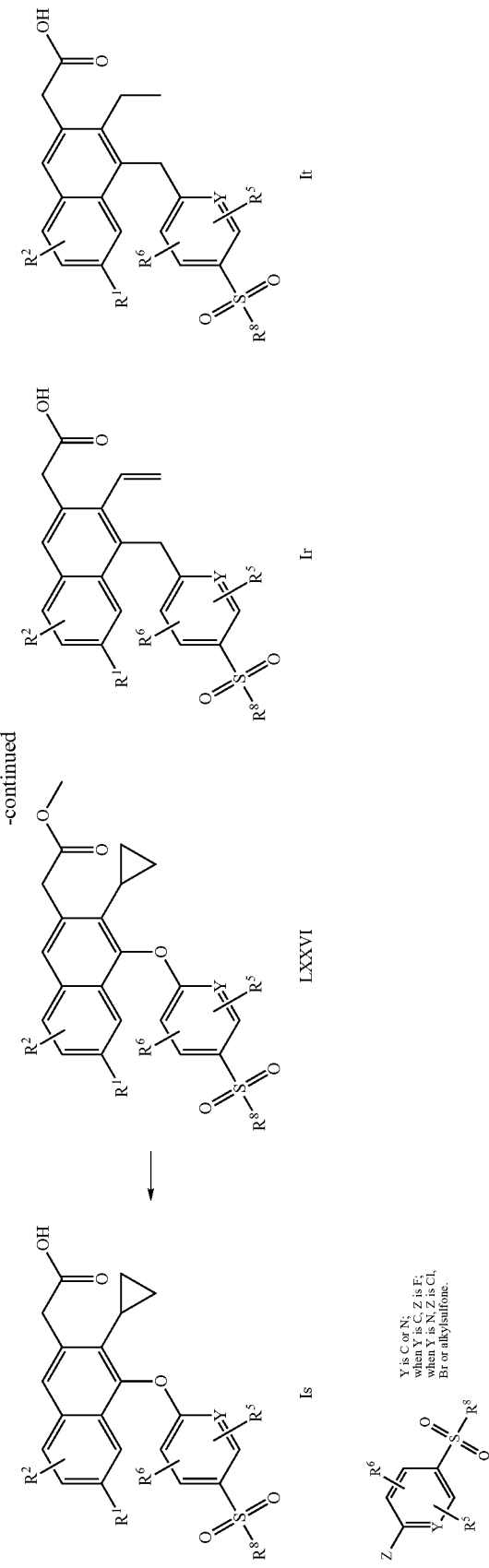

The compounds of interest of formula Ir, Is and It can be prepared according to Scheme 14. In this process, iodination of the intermediates IIa followed by acylation affords the iodo derivatives LXVI. The acetylene derivatives LXIX can be formed by a Sonogashira coupling reaction between the iodo derivatives LXVI and trimethylsilylacetylene (LXVII), followed by a potassium fluoride-mediated trimethylsilanyl removal. Reduction of the acetylene derivatives LXIX to the olefins LXXII followed by treatment of the olefins LXXII with a base affords the corresponding hydroxyl compounds LXXIII. The ether intermediates LXXIV can be obtained by treatment of the hydroxyl intermediates LXXIII with the aryl derivatives XLII. Hydrolysis of the ether intermediates LXXIV affords the final compounds Ir. The cyclopropyl derivatives Is can be formed by treating the intermediates LXXIV with diazomethane (DOW) followed by a hydrolysis reaction. Hydrogenation of the acetylene derivatives LXIX, followed by treatment with a base affords the hydroxyl intermediates LXXVIII. The ethyl derivatives It can be obtained by a reaction between the hydroxyl intermediates LXXVIII and the aryl derivatives XLII followed by a hydrolysis reaction.

In the first step, iodination can be achieved by treatment of the intermediates IIa with N-iodosuccinimide (NIS, LXIV) in an organic solvent such as chloroform, acetonitrile, dichloromethane, acetone, N,N-dimethylformamide, tetrahydrofuran, or carbon tetrachloride, at a temperature between 0° C. and room temperature for 30 minutes to several hours.

The acetates LXVI can be formed by a reaction of the intermediates LXV with acetic anhydride (VII). The reaction can be carried out in the presence of a base such as 4-dimethylaminopyridine, in an organic solvent such as pyridine, at room temperature for several hours.

The intermediates LXVIII can be generated by a coupling reaction between the iodo derivatives LXVI and trimethylsilylacetylene (LXVII) in the presence of a palladium catalyst such as bis(triphenylphosphine)dichloropalladium(II), or tetrakis(triphenylphosphine) palladium(0), and a copper(I) catalyst such as copper(I) iodide. The reaction can be carried out in the presence of a base such as triethylamine, or diisopropylethylamine in an inert solvent such as tetrahydrofuran, N,N-dimethylformamide or toluene at 150° C. for about 6 minutes under microwave irradiation (Baldwin, K. P. et al., *Synlett* 11 (1993) 853).

Removal of the trimethylsilanyl group of the compounds LXVIII to give the acetylenes LXIX can be achieved by treating with potassium fluoride or tetrabutylammonium fluoride in a suitable solvent such as water, tetrahydrofuran, dimethyl sulfoxide, N,N-dimethylformamide, methanol, or mixtures thereof, at room temperature for several hours. Alternatively, a base such as potassium carbonate or potassium hydroxide can be used for the trimethylsilanyl group removal. The reaction can be carried out in a suitable solvent such as methanol, tetrahydrofuran, water or the mixtures thereof at room temperature for several hours.

Reduction of the acetylene derivatives LXIX affords the olefins LXXII. The reduction can be achieved by treatment of the acetylene derivatives LXIX with indium trichloride (LXX) and triethylsilane (LXXI) in the presence of triethylborane in an inert organic solvent such as acetonitrile, tetrahydrofuran, hexane, or mixtures thereof, at a temperature between −15° C. and room temperature for several hours (Hayashi, N.; et al., *Org. Lett.* 6 (2004) 4981-4983). Alternatively, diphenylsilane can be used as the hydride source (Hayashi, N.; et al., *Org. Lett.* 7 (2005) 3093-3096).

Compounds LXXII can be converted to the corresponding hydroxyl compounds LXXIII by treatment with a base such as sodium methoxide, potassium tert-butoxide, potassium carbonate, or sodium bicarbonate, in a solvent such as methanol, water or mixtures thereof, at a temperature between room temperature and 80° C. for 10 minutes to several hours (references: Boger, D. L. et al., *J. Org. Chem.* 61 (1996) 4894-4912; Kim, M. et al., *J. Org. Chem.* 69 (2004) 6945-6948).

Conversion of the hydroxyl intermediates LXXIII to the ethers LXXIV can be achieved by treating the hydroxyl intermediates LXXIII and the aryl derivatives XLII with a base such as sodium carbonate, potassium carbonate, or cesium carbonate, in the presence of potassium iodide, in a suitable organic solvent such as N,N-dimethylformamide, acetone, dimethyl sulfoxide or mixtures thereof. The reaction can be carried out at a temperature between 100° C. and 150° C. for 30 to 60 minutes under microwave irradiation. Alternatively, the reactions can be carried out at an elevated temperature without microwave irradiation for a longer period of time.

Hydrolysis of the methyl ester moieties of the olefins LXXIV affords the final compounds Ir.

The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Transformation of the olefins LXXIV to the corresponding cyclopropyl derivatives LXXVI can be done by treatment of compounds LXXIV with diazomethane (DOW) in the presence of a palladium catalyst such as palladium(II) acetylacetone, palladium acetate, or palladium dichloride bis(benzonitrile), in a solvent such as dichloromethane, diethyl ether, tetrahydrofuran, or mixtures thereof, at a temperature between 0° C. and room temperature for several hours (reference: Staas, D. D. et al. *Bioorg. Med. Chem.* 14 (2006) 6900).

Further hydrolysis of the generated ether derivatives LXXVI in a manner analogous to the one described for the ether derivatives LXXIV affords the final compounds Is.

Hydrogenation of the acetylene derivatives LXIX can be carried out in the presence of 10% palladium on carbon under 40 psi of hydrogen, in an organic solvent such as ethyl acetate, methanol, or ethanol, at room temperature for several hours.

In a manner analogous to the one described above for the transformation of the acetates LXXII to the ether derivatives LXXIV, compounds LXXVII can be converted to the corresponding ethers LXXIX. Hydrolysis of the generated ether derivatives LXXIX in a manner analogous to the one described for the ether derivatives LXXIV affords the final compounds It.

Scheme 15

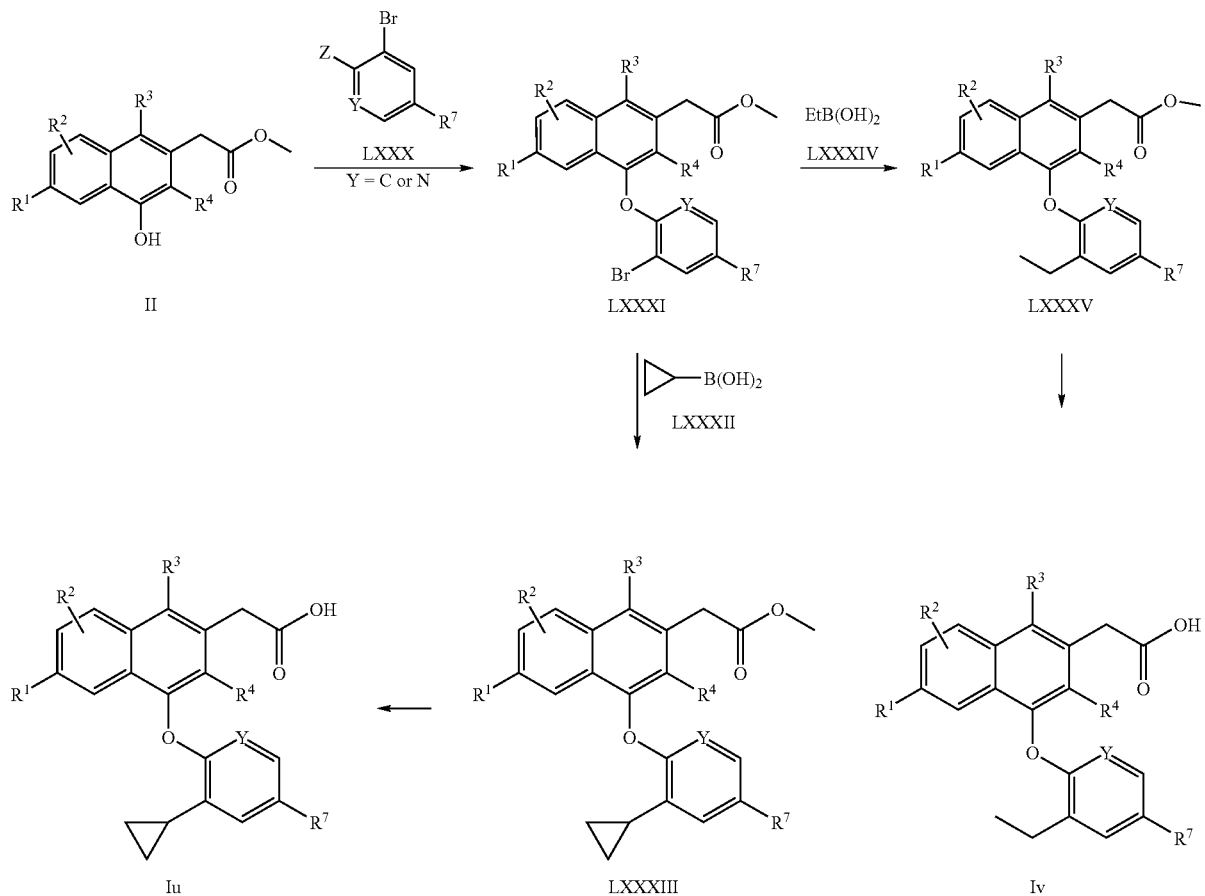

The compounds of interest of formula Iu and Iv can be prepared according to Scheme 15. In this process, the bromo derivatives LXXXI can be generated by a reaction between the hydroxyl intermediates II (which encompass IIa, IIb, IIc, IId, and IIe from Schemes 1-7) and the aryl derivatives LXXX. A Suzuki coupling reaction between the bromo derivatives and cyclopropyl boronic acid (LXXXII) followed by a hydrolysis reaction affords the final compounds Iu. A Suzuki coupling reaction between the bromo derivatives and ethyl boronic acid (LXXXIV) followed by a hydrolysis reaction affords the final compounds Iv.

In a manner analogous to the one described in Scheme 8 for the preparation of the intermediates XXXVII, the ethers LXXXI can be generated by a reaction between the hydroxyl intermediates II and the aryl derivatives LXXX.

The bromo group of the generated ethers LXXXI can be converted to ethyl or cyclopropyl by a Suzuki coupling reaction between compounds LXXXI and ethyl boronic acid (LXXXIV), or cyclopropyl boronic acid (LXXXII), in a manner analogous to the one described in Scheme 13 for the preparation of the methyl intermediates LIX. In a method analogous to the hydrolysis step described in Scheme 8, hydrolysis of compounds LXXXIII and compounds LXXXIV affords the final compounds of interest Iu and Iv, respectively.

Scheme 16

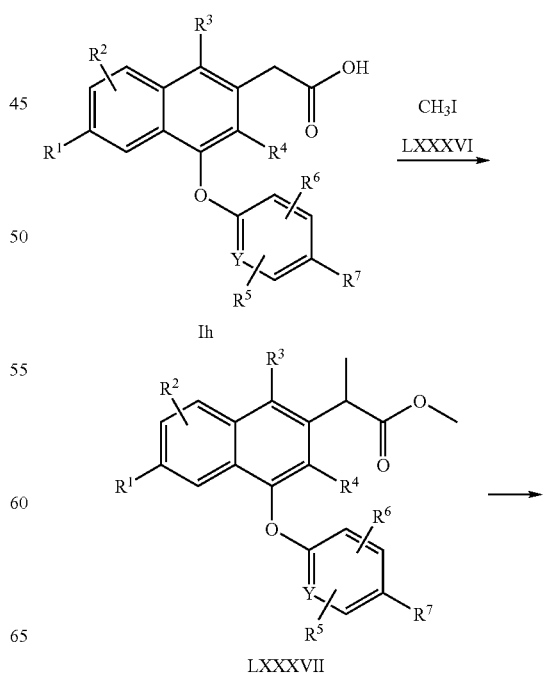

-continued

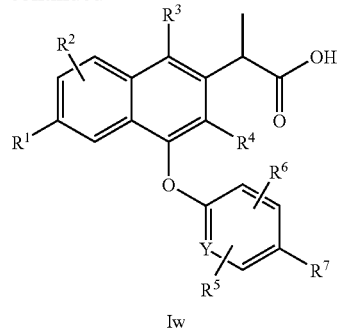

Iw

The compounds of interest of formula Iw can be prepared according to Scheme 16. In this process, treatment of compounds Ih with iodomethane (LXXXVI) followed by hydrolysis affords the final compounds Iw.

In the first step of this process, the intermediates LXXXVII can be formed by treatment of compounds Ih with iodomethane (LXXXVI) in the presence of a base such as sodium hydride, in an inert organic solvent such as N,N-dimethylformamide, at a temperature between −30° C. and −15° C. for several hours.

In a manner analogous to the hydrolysis step described in Scheme 8, hydrolysis of the intermediates LXXXVII affords the final compounds Iw.

Scheme 17

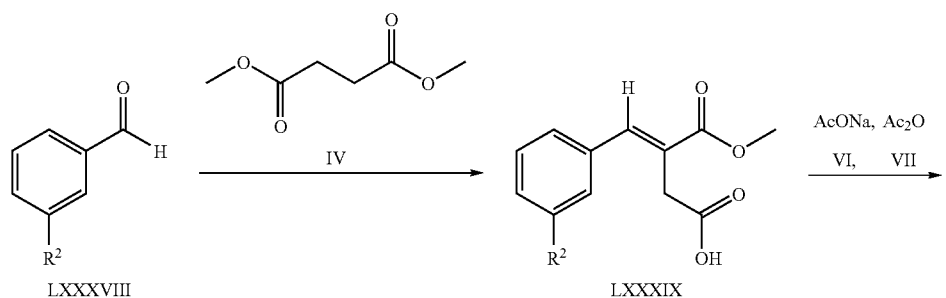

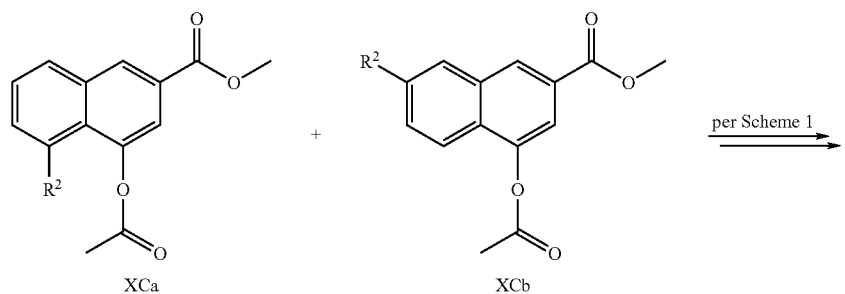

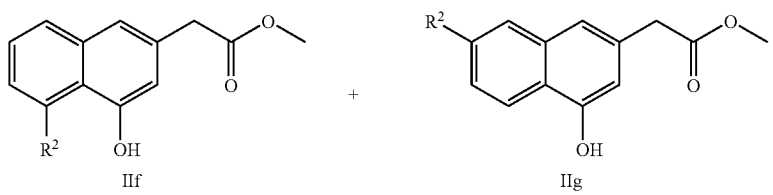

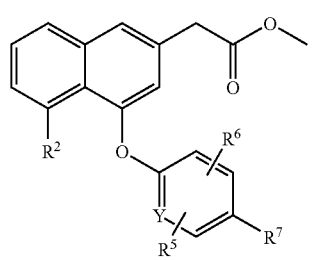

XCIa

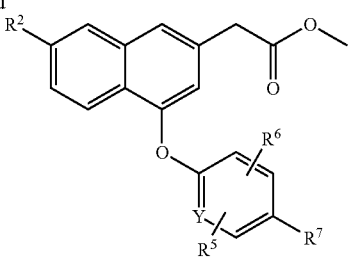

XCIb

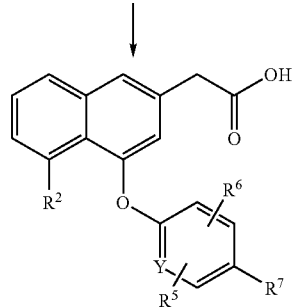

Ix

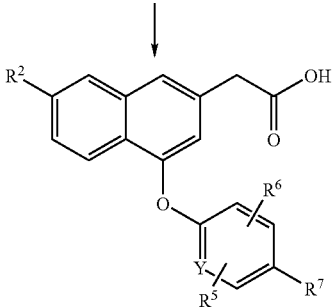

Iy

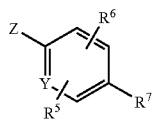

XXXVI

Y is C or N;
when Y is C, Z is F;
when Y is N, Z is Cl,
Br or alkylsulfone.

The compounds of interest of formula Ix and Iy can be prepared according to Scheme 17. In this process, the Stobbe condensation reaction between the meta-substituted-benzaldehydes LXXXVIII and dimethyl succinate (IV) gives the unsaturated acids LXXXIX, which subsequently undergo cyclization in the presence of sodium acetate (VI) and acetic anhydride (VII) to produce the mixture of compounds XCa and XCb. Using the method described in Scheme 1, the mixtures of the naphthalene derivatives XCa and XCb are then converted to the mixture of the corresponding intermediates IIf and IIg, which are separated by column chromatography to afford the intermediates IIf and IIg. A reaction between the hydroxyl intermediates IIf and the aryl derivatives XXXVI followed by ester hydrolysis affords the compounds of interest of formula Ix. A reaction between the hydroxyl intermediates IIg and the aryl derivatives XXXVI followed by ester hydrolysis affords the compounds of interest of formula Iy.

In the first step outlined in Scheme 17, the unsaturated acids LXXXIX can be prepared by a condensation reaction between the meta-substituted-benzaldehydes LXXXVIII and dimethyl succinate (IV). The reaction can be carried out in the presence of a base such as sodium methoxide, lithium methoxide, sodium tert-butoxide, sodium hydride or potassium tert-butoxide, in an organic solvent such as methanol, tert-butanol, toluene, or mixtures thereof, at a temperature between room temperature and 90° C. for several hours (reference: Dian, Y. L. et al., *Tetrahedron Lett.*, 32 (1991) 5255).

Cyclization of the unsaturated acids LXXXIX to produce the mixture of naphthalene derivatives XCa and XCb can be achieved by treatment of the unsaturated acids LXXXIX with sodium acetate (VI) and acetic anhydride (VII) at a temperature between room temperature and 140° C. for 0.5 to 12 hours (references: Boger, D. L. et al., *J. Org. Chem.* 61 (1996) 4894-4912; Kim, M. et al., *J. Org. Chem.* 69 (2004) 6945-6948). Using the process described above in scheme 1, the mixture of naphthalene derivatives XCa and XCb can be transformed into the mixture of the hydroxyl intermediates IIf and IIg, which are separated by column chromatography to afford the intermediates IIf and IIg.

Conversion of the hydroxyl intermediates IIf to the ethers XCIa can be achieved by treating compounds IIf and the aryl derivatives XXXVI with a base such as sodium carbonate, potassium carbonate, or cesium carbonate, in a suitable organic solvent such as N,N-dimethylformamide, or dimethyl sulfoxide. The reaction can be carried out at a temperature between 100° C. and 150° C. for 30 to 60 minutes under microwave irradiation.

Alternatively, the reactions can be carried out at an elevated temperature without microwave irradiation for a longer period of time.

Hydrolysis of the methyl esters XCIa affords the compounds of interest of formula Ix. The reaction can be carried out in the presence of an aqueous inorganic base such as lithium hydroxide, sodium hydroxide, or potassium hydroxide in an inert solvent such as 1,4-dioxane or tetrahydrofuran at room temperature for several hours.

Conversion of the hydroxyl intermediates IIg to the compounds of interest of formula Iy can be accomplished in a manner analogous to the one described above for the preparation of the compounds of interest of formula Ix.

Scheme 18

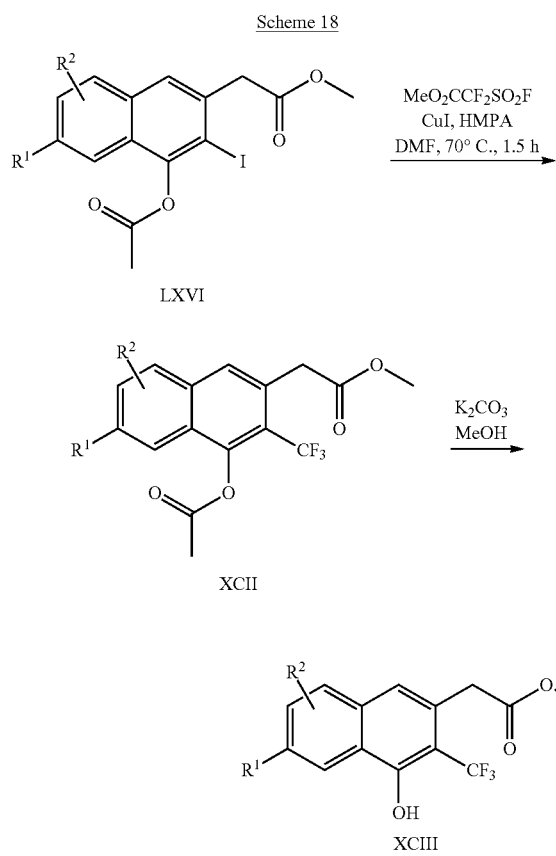

Scheme 19

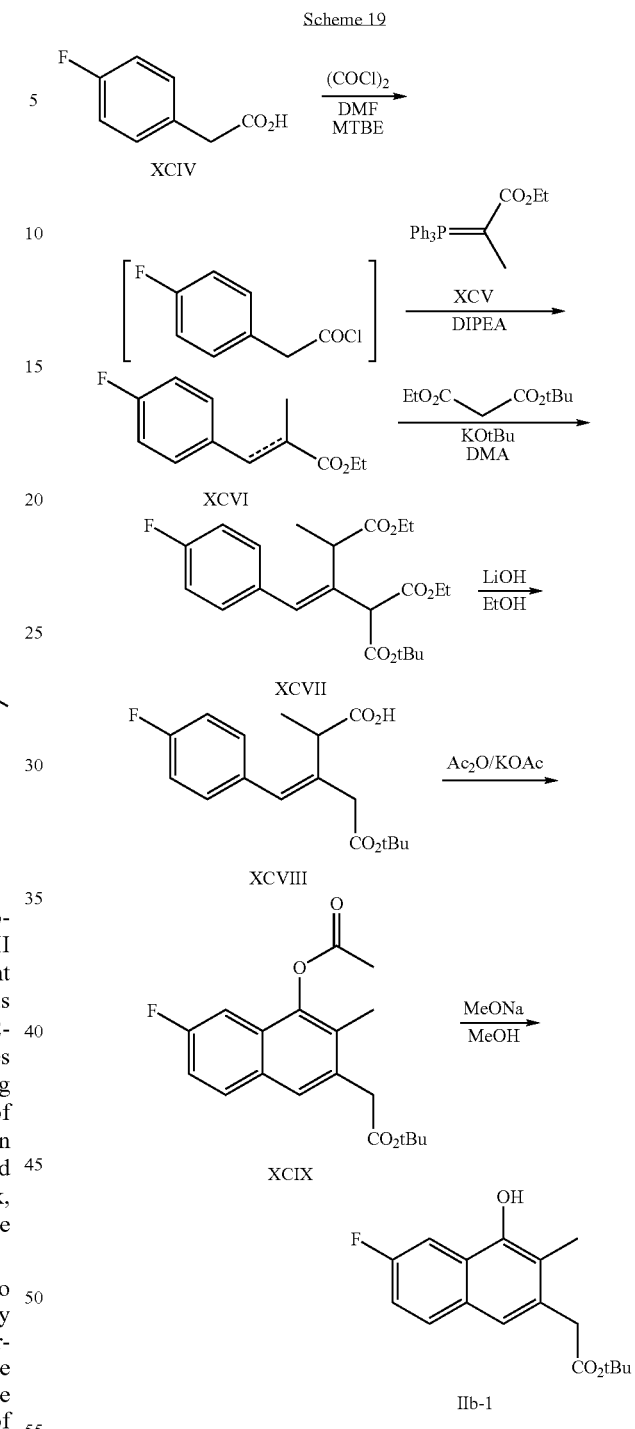

Compounds of the invention when $R^4$ represents trifluoromethyl can be prepared using the intermediates XCIII which can be prepared as described in Scheme 18. Treatment of the intermediate iodides of formula LXVI (prepared as described above in Scheme 14) with methyl 2,2-difluoro-2-(fluorosulfonyl)acetate under copper(I) iodide catalysis gives the intermediates of formula XCII. The acetyl protecting groups in XCII can then be removed to give the phenols of formula XCIII which correspond to the starting materials in Schemes 8, 10, 11, when $R^4$ represents trifluoromethyl, and can be used to prepare compounds of interest of formula Ii, Ik, Im, and In (when $R^4$ represents trifluoromethyl), using the reactions described in these schemes.

The conversion of the intermediates of formula LXVI to intermediates of formula XCII can be effected using any conventional means. For example, the intermediates of formula LXVI may be treated with the commercially available reagent methyl 2,2-difluoro-2-(fluorosulfonyl)acetate in the presence of copper(I) iodide and in the additional presence of hexamethylphosphoramide in an inert solvent such as N,N-dimethylformamide at a temperature about 70° C. for several hours to give the corresponding trifluormethyl derivatives of formula XCII (reference: Briner, K. et al. WO 2007028132).

The acetate derivatives XCII can be converted to the corresponding hydroxyl compounds XCIII in the presence of a base such as sodium methoxide, potassium tert-butoxide, potassium carbonate or sodium bicarbonate, in a solvent such as methanol, water, or mixtures thereof, at a temperature between room temperature and 80° C. for 10 minutes to several hours (reference: Kim, M. et al., *J. Org. Chem.* 69 (2004) 6945-6948).

The key intermediate IIb-1 (which can be used as a replacement for intermediate II in scheme 8 to make the compounds of formula Ih and Ii) can be prepared as described in Scheme 19. Treatment of (4-fluoro-phenyl)-acetic acid (XCIV) with oxalyl chloride generates the corresponding acid chloride in situ, which is not isolated, but treated with the Wittig-type reagent XCV in the presence of a base to produce the allene derivative XCVI. A conjugate addition reaction of the allene with malonic acid tert-butyl ester ethyl ester produces the tri-ester derivative XCVII, which upon hydrolysis and subsequent decarboxylation generates the acid derivative XCVIII.

Acetic anhydride-promoted cyclization of XCVIII furnishes the naphthalene derivative XCIX, which upon hydrolysis of the acetyl group produces the key intermediate IIb-1.

The conversion of (4-fluorophenyl)-acetic acid to its corresponding acid chloride derivatives can be accomplished by methods known in the art. For example, the reaction can be carried out with oxalyl chloride and a catalytic amount of N,N-dimethylformamide (DMF), in an ether solvent, at room temperature. Subsequent treatment of the in situ generated acid chloride with a base such as N,N-diisopropylethylamine will lead to the generation of the corresponding ketene, which upon treatment with a Wittig type reagent such as XCV in an ether solvent at a temperature between 0-10° C. produces the allene derivative XCVI.

The conjugate addition reaction between the allene derivative XCVI and malonic acid tert-butyl ester ethyl ester to produce the tri-ester derivative XCVII is conducted in the presence of a base such as potassium tert-butoxide, in a solvent such as N,N-dimethyl acetamide at room temperature.

The ester hydrolysis of the two ethyl esters in XCVII can be accomplished using methods known in the art. For example, the reaction can be conducted using an aqueous base such as lithium hydroxide, in the presence of a solvent such as ethanol, at room temperature overnight. The subsequent decarboxylation reaction can then be carried out by heating the solution of the resulting diacid at reflux for several hours, to produce XCVIII.

The cyclization of the unsaturated acid derivative XCVIII to the naphthalene XCIX is accomplished as previously described (similar to Scheme 2), in the presence of acetic anhydride and potassium acetate or sodium acetate, at a temperature of about 85° C., for several hours.

The acetate derivative XCIX then undergoes a hydrolysis, upon treatment with a base such as sodium methoxide, in a solvent such as methanol, at room temperature, to produce the desired key intermediate IIb-1.

EXAMPLES

Although certain exemplary embodiments are depicted and described herein, the compounds of the present invention can be prepared using appropriate starting materials according to the methods described generally herein and/or by methods available to one of ordinary skill in the art.

Materials and Instrumentation In General

Intermediates and final compounds were purified by either flash chromatography and/or preparative HPLC (high performance liquid chromatography). Flash chromatography was performed using (1) the Biotage SP1™ system and the Quad 12/25 Cartridge module from Biotage AB) or (2) the ISCO CombiFlash® chromatography instrument (from Teledyne Isco, Inc.); unless otherwise noted. The silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Preparative HPLC was performed on a reversed phase column using an Xbridge™ Prep $C_{18}$ (5 μm, OBD™ 30×100 mm) column (from Waters Corporation), or a SunFire™ Prep $C_{18}$ (5 μm, OBD™ 30×100 mm) column (from Waters Corporation).

Mass spectrometry (MS) was performed using a Waters® Alliance® 2795-ZQ™2000 (from Waters Corporation). Mass spectra data generally only indicates the parent ions unless otherwise stated. MS data is provided for a particular intermediate or compound where indicated.

Nuclear magnetic resonance spectroscopy (NMR) was performed using a Bruker Avance™ 400 MHZ Digital NMR Spectrometer (for the $^1$H NMR spectrum acquired at 400 MHz) (from Bruker BioSpin AG Ltd.). NMR data is provided for a particular intermediate or compound where indicated.

The microwave assisted reactions were carried out in a Biotage Initiator™ Sixty (from Biotage AB).

All reactions involving air-sensitive reagents were performed under an inert atmosphere. Reagents were used as received from commercial suppliers unless otherwise noted.

Part I: Preparation of Preferred Intermediates

Preparation of
2,5-bis-methanesulfonyl-3-methyl-pyridine

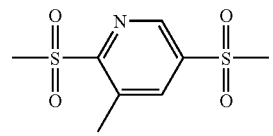

3-Methyl-2,5-bis-methylsulfanyl-pyridine

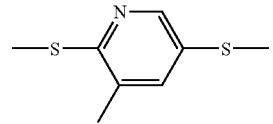

To a cooled (ice-water bath) solution of 5-bromo-2-fluoro-3-methyl-pyridine (1.0 g, 5.3 mmol) in anhydrous N,N-dimethylformamide (50 mL) was added sodium methanethiolate (775 mg, 11.1 mmol) portion-wise under a nitrogen atmosphere. The resulting mixture was stirred at room temperature for 15 minutes, then at 100° C. overnight. The reaction mixture was cooled to room temperature, poured into water, and extracted with diethyl ether (50 mL×2). The combined organic layers were dried over sodium sulfate and concentrated in vacuo to afford 3-methyl-2,5-bis-methylsulfanyl-pyridine, which was used in the next step without purification (reference: Testaferri, L. et al., *Tetrahedron* 41 (1985) 1373-1384).

2,5-Bis-methanesulfonyl-3-methyl-pyridine

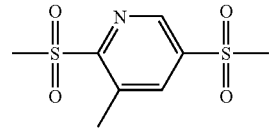

To a cooled (ice-water bath) solution of 3-methyl-2,5-bis-methylsulfanyl-pyridine in dichloromethane (50 mL) was added m-chloroperoxybenzoic acid (5.3 g, 80% purity, 24.6 mmol). After being stirred at room temperature for 2 hours, the mixture was treated with a saturated aqueous solution of sodium sulfite (20 mL), and stirred for 15 minutes. The organic layer was separated, washed with a saturated aqueous solution of sodium carbonate and brine, then dried over sodium sulfate, and concentrated in vacuo. The residue was crystallized from ethyl acetate to give 2,5-bis-methanesulfonyl-3-methyl-pyridine (1.2 g, 91% yield for two steps) as a white solid (reference: Testaferri, L. et al., *Tetrahedron* 41 (1985) 1373-1384). ¹H NMR (400 MHz, CD₃OD) δ ppm 9.00 (d, J=1.6 Hz, 1H), 8.52 (d, J=1.6 Hz, 1H), 3.48 (s, 3H), 3.41 (s, 3H), 2.72 (s, 3H).

Preparation of 2-bromo-5-methanesulfonyl-pyridine

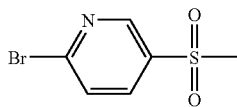

Starting with 2-bromo-5-fluoro-pyridine, sodium methanethiolate and m-chloroperoxybenzoic acid, using a method analogous to the one described for 2,5-bis-methanesulfonyl-3-methyl-pyridine, 2-bromo-5-methanesulfonyl-pyridine was obtained as a white solid.

Preparation of 2-bromo-5-ethanesulfonyl-pyridine

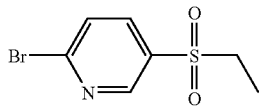

To a solution of 2,5-dibromopyridine (2 g, 8.4 mmol) in diethyl ether (50 mL) was added n-butyl lithium (1.6 M in hexanes, 9.24 mmol) dropwise at −78° C. under a nitrogen atmosphere. After the mixture was stirred at this temperature for 1 hour, diethyldisulfide (1.15 mL, 9.24 mmol) was added slowly at −78° C., and the mixture was stirred at this temperature for 1 hour and at 0° C. for an additional 1 hour. The reaction mixture was then quenched with 1 N hydrochloric acid (20 mL). The aqueous layer was separated and extracted with diethyl ether (20 mL). The combined organic layers were dried over sodium sulfate and concentrated in vacuo. The residue was dissolved in dichloromethane (50 mL). To the solution, m-chloroperoxybenzoic acid (4.3 g, 80% purity, 16.8 mmol) was added portion-wise at 0° C. After being stirred at room temperature for 2 hours, the mixture was treated with a saturated aqueous solution of sodium sulfite (20 mL), and stirred for 15 minutes. The organic layer was separated and washed with a saturated aqueous solution of sodium bicarbonate (20 mL), then dried over sodium sulfate, and concentrated in vacuo. The residue was purified by flash column chromatography (elution with 30% ethyl acetate in petroleum ether) to give 2-bromo-5-ethanesulfonyl-pyridine (400 mg, 19%) as a white solid (reference: Li J. et al., *Bioorg. Med. Chem.* 13 (2005) 1805-1809).

Preparation of 3-bromo-2-chloro-5-methanesulfonyl-pyridine

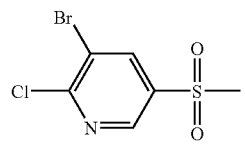

A stirred solution of sodium sulfite (4.80 g, 38.1 mmol) and sodium bicarbonate (6.10 g, 72.6 mmol) in water (100 mL) was cooled to 15° C., and 5-bromo-6-chloropyridine-3-sulfonyl chloride (10.00 g, 34.4 mmol) was added. After being stirred at 15° C. for 3 hours and then at room temperature overnight under a nitrogen atmosphere, the mixture was heated to 40° C., and a solution of 2-chloroacetic acid (3.80 g, 40.2 mmol) and sodium hydroxide (1.90 g. 47.5 mmol) in water (20 mL) was added. The resulting mixture was stirred at reflux for 48 hours and then cooled to room temperature. The precipitated product was collected by filtration, washed with water (50 mL) and purified by column chromatography (gradient elution with 15-20% ethyl acetate in petroleum ether) to afford 3-bromo-2-chloro-5-methanesulfonyl-pyridine (1.80 g, 6.65 mmol) as a white solid. A solution of 2-chloroacetic acid (1.90 g, 20.1 mmol) and sodium hydroxide (0.80 g, 20.0 mmol) in water (10 mL) was added to the filtrate. The mixture was heated at reflux overnight, and then evaporated to remove most of the water (about 100 mL). The residue was cooled to room temperature, and then extracted with dichloromethane (80 mL×3). The combined organic layers were dried over sodium sulfate and concentrated in vacuo. The residue was purified by flash column chromatography (gradient elution with 15-20% ethyl acetate in petroleum ether) to afford another batch of 3-bromo-2-chloro-5-methanesulfonyl-pyridine (1.30 g, 4.8 mmol, yield of two batches 35.5%) as a white solid (reference: U.S. Pat. No. 5,424,481).

Preparation of 2,5-bis-ethanesulfonyl-pyridine

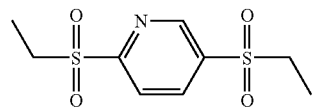 [SMILES: CCS(=O)(=O)c1ccc(S(=O)(=O)CC)nc1]

2,5-bis-ethylsulfanyl-pyridine

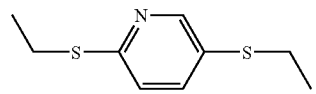

To a solution of sodium hydroxide (16.0 g, 400 mmol) in dimethyl sulfoxide (200 mL), was added ethanethiol (49.6 g, 798 mmol) followed by 2,5-dibromopyridine (23.7 g, 100 mmol) between −5° C. and 0° C. under a nitrogen atmosphere. After being heated at 180° C. for 5 hours, the reaction mixture was cooled to room temperature, poured into water (340 mL) and extracted with diethyl ether (400 mL×2). The combined organic layers were dried over sodium sulfate and concentrated in vacuo. The residue (21.0 g) was directly used in the next step without further purification (reference: Testaferri, L. et al., *Tetrahedron* 41 (1985) 1373-1384).

2,5-bis-ethanesulfonyl-pyridine

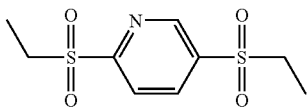

To a solution of the crude 2,5-bis-ethylsulfanyl-pyridine (prepared above) in 6 N hydrochloric acid (100 mL) was added an aqueous solution of sodium hypochlorite (8.0%, 500 mL) at 0° C. The resulting precipitate was collected by filtration, washed with water, dried in vacuo and then recrystallized from diethyl ether to afford 2,5-bis-ethanesulfonyl-pyridine (18.0 g, 70%) as a white solid (reference: U.S. Pat. No. 4,371,537).

Preparation of 3-bromo-2-chloro-5-ethanesulfonyl-pyridine

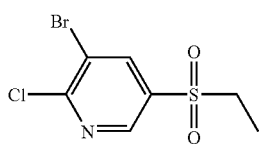

5-ethanesulfonyl-pyridin-2-ol

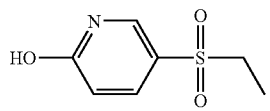

A solution of potassium hydroxide (11.0 g, 196 mmol, 50%) in water was added to a suspension of 2,5-bis-ethanesulfonyl-pyridine (12.0 g, 45.6 mmol, prepared using the method described above) in water and tetrahydrofuran (100 mL, 1:1, v/v). After being heated at reflux for 1 hour, the mixture was acidified with 0.5 N hydrochloric acid to pH 3 and concentrated in vacuo to remove the solvent. The residue was triturated with boiling ethanol (150 mL) and filtered. The filtrates were concentrated in vacuo to afford the crude product which was used in the next step without further purification.

3-bromo-5-ethanesulfonyl-pyridin-2-ol

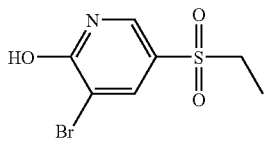

To a solution crude of 5-ethanesulfonyl-pyridin-2-ol prepared above, and sodium acetate (3.74 g, 45.6 mmol) in acetic acid (50 mL) was added a solution of bromine (7.3 g, 46.0 mmol) in acetic acid (10 mL) dropwise over a period of 1 hour. After being stirred at room temperature overnight, additional bromine (7.3 g, 46.0 mmol) in acetic acid (10 mL) was added dropwise to the reaction mixture over a period of 1 hour. After being stirred overnight, the reaction mixture was warmed to 30° C. and stirred for 2 hours. The mixture was concentrated in vacuo to remove the solvent. The residue was triturated with water (100 mL). The solid was collected by filtration, washed with a dilute solution of sodium thiosulfate and dried in vacuo to afford 3-bromo-5-ethanesulfonyl-pyridin-2-ol (9.1 g, 75%, two steps) as a white solid (reference: Bargar, T. M. et al., *J. Heterocyclic Chem.* 22 (1985) 1583-1592).

3-bromo-2-chloro-5-ethanesulfonyl-pyridine

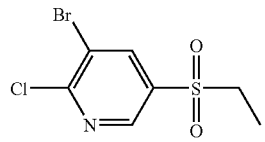

A suspension of 3-bromo-5-ethanesulfonyl-pyridin-2-ol (6.0 g, 22.5 mmol) in phosphorus oxychloride (30 mL) was heated at reflux for 4 hours under a nitrogen atmosphere. After removal of the excess of phosphorus oxychloride in vacuo, the white solid residue was triturated with cooled water (200 mL). The mixture was stirred for 1 hour.

The solid was collected by filtration, and dried in vacuo to afford 3-bromo-2-chloro-5-ethanesulfonyl-pyridine (5.5 g, 85.7%) as a white solid (reference: Bargar, T. M. et al., *J. Heterocyclic Chem.* 22 (1985) 1583-1592).

Preparation of 2-(4-fluoro-benzenesulfonyl)-2-azaspiro[3.3]heptane

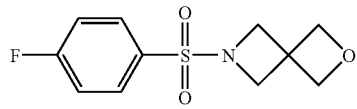

To a cooled (ice-water bath) solution of 4-fluoro-benzenesulfonamide (320 mg, 1.83 mmol) in N,N-dimethylformamide (5 mL), was added sodium hydride (150 mg, 60% dispersion, 3.75 mmol) portion-wise. After the mixture was stirred at 0° C. for 10 minutes, a solution of 3,3-bis-bromomethyl-oxetane (440 mg, 1.8 mmol) in N,N-dimethylformamide (3 mL) was added. The resulting mixture was stirred at room temperature overnight, then neutralized with 1 N hydrochloric acid, and extracted with ethyl acetate (20 mL×3). The combined organic layers were washed with brine (20 mL×3), dried over sodium sulfate, and concentrated in vacuo. The residue was purified by flash column chromatography (elution with 20% ethyl acetate in petroleum ether) to afford 2-(4-fluoro-benzenesulfonyl)-2-aza-spiro[3.3]heptane (120 mg, 26%) as a white solid (reference: Blizzard T. A. et al., *Bioorg. Med. Chem. Lett.* 14 (2004) 3861-3864), MS cald. for $C_{12}H_{14}FNO_2S$ 255, obsd. (ESI$^+$) [(M+H)$^+$] 256.

Preparation of
4-fluoro-N,N-dimethyl-benzenesulfonamide

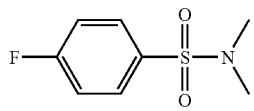

A solution of 4-fluorobenzenesulfonyl chloride (1.95 g, 10 mmol) and dimethylamine hydrochloric acid salt (978 mg, 12 mmol) in tetrahydrofuran (10 mL) was added to a solution of 4-dimethylaminopyridine (3.05 g, 25 mmol) in tetrahydrofuran (10 mL) dropwise at room temperature. The resulting mixture was stirred at room temperature overnight and concentrated in vacuo. The residue was purified by flash column (elution with 20% ethyl acetate in petroleum ether) to afford 4-fluoro-N,N-dimethyl-benzenesulfonamide (1.02 g, 50%) as a white solid.

The following sulfonamides were prepared in an analogous manner as described for 4-fluoro-N,N-dimethyl-benzenesulfonamide by the reaction of 4-fluorobenzenesulfonyl chloride with commercially available amines.

| Starting benzenesulfonyl chloride | Starting amine | Sulfonamide |
|---|---|---|
| 4-fluoro-benzenesulfonyl chloride | pyrrolidine | 1-(4-fluoro-benzenesulfonyl)-pyrrolidine |
| 4-fluoro-benzenesulfonyl chloride | diethylamine | N,N-diethyl-4-fluoro-benzenesulfonamide |
| 4-fluoro-benzenesulfonyl chloride | morpholine | 4-(4-fluoro-benzenesulfonyl)-morpholine |
| 4-fluoro-benzenesulfonyl chloride | 1-methyl-piperazine | 1-(4-fluoro-benzenesulfonyl)-4-methyl-piperazine |
| 4-fluoro-benzenesulfonyl chloride | 4,4-difluoro-piperidine | 4,4-difluoro-1-(4-fluoro-benzenesulfonyl)-piperidine |

Preparation of 1-ethanesulfonyl-4-fluoro-benzene

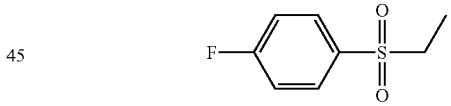

To a solution of sodium hydrogen phosphate (14.2 g, 0.1 mol) and sodium sulfite (25.2 g, 0.2 mol) in water (200 mL) was added 4-fluoro-benzenesulfonyl chloride (19.5 g, 0.1 mol). After the mixture was stirred at 60° C. overnight, a solution of bromoethane (32.7 g, 0.3 mol) in acetone (20 mL) was added dropwise, followed by the addition of tetrabutylammonium iodide (3.7 g, 0.01 mol) in one portion. The resulting reaction mixture was stirred at room temperature for 5 days, then diluted with water (50 mL), and extracted with ethyl acetate (100 mL×3). The combined organic layers were washed with brine, dried over sodium sulfate, and concentrated in vacuo. The residue was purified by flash column chromatography (elution with 20% ethyl acetate in petroleum ether) to afford 1-ethanesulfonyl-4-fluoro-benzene (11.9 g, 63%) as a yellow oil (reference: Arnold, Leggy A. A., et al., *Org. Lett,* 6 (2004), 3005-3007).

The following sulfone-substituted fluoro-benzenes were prepared in an analogous manner as described for 1-ethanesulfonyl-4-fluoro-benzene starting with commercially available alkyl halides and substituted benzenesulfonyl chlorides.

| Starting benzenesulfonyl chloride | Starting alkyl halide | Sulfone substituted fluoro-benzene |
| --- | --- | --- |
| 4-fluoro-benzenesulfonyl chloride | bromoethane | 1-ethanesulfonyl-4-fluoro-benzene |
| 4-fluoro-benzenesulfonyl chloride | n-propyl iodide | 1-fluoro-4-(propane-1-sulfonyl)-benzene |
| 4-fluoro-benzenesulfonyl chloride | 2-bromo-propane | 1-fluoro-4-(propane-2-sulfonyl)-benzene |
| 4-fluoro-benzenesulfonyl chloride | cyclopropyl bromide | 1-cyclopropanesulfonyl-4-fluoro-benzene |
| 4-fluoro-benzenesulfonyl chloride | 1-bromo-butane | 1-(butane-1-sulfonyl)-4-fluoro-benzene |
| 4-fluoro-benzenesulfonyl chloride | bromo-cyclopentane | 1-cyclopentanesulfonyl-4-fluoro-benzene |
| 4-fluoro-3-methyl-benzenesulfonyl chloride | methyl iodide | 1-fluoro-4-methanesulfonyl-2-methyl-benzene |
| 4-fluoro-3-methyl-benzenesulfonyl chloride | bromoethane | 4-ethanesulfonyl-1-fluoro-2-methyl-benzene |
| 4-fluoro-2-methyl-benzenesulfonyl chloride | methyl iodide | 4-fluoro-1-methanesulfonyl-2-methyl-benzene |
| 4-fluoro-2-methyl-benzenesulfonyl chloride | bromoethane | 1-ethanesulfonyl-4-fluoro-2-methyl-benzene |
| 3-chloro-4-fluoro-benzenesulfonyl chloride | methyl iodide | 2-chloro-1-fluoro-4-methanesulfonyl-benzene |
| 3-chloro-4-fluoro-benzenesulfonyl chloride | bromoethane | 2-chloro-4-ethanesulfonyl-1-fluoro-benzene |
| 3,4-difluoro-benzenesulfonyl chloride | methyl iodide | 1,2-difluoro-4-methanesulfonyl-benzene |
| 3,4-difluoro-benzenesulfonyl chloride | bromoethane | 4-ethanesulfonyl-1,2-difluoro-benzene |
| 3-cyano-4-fluoro-benzenesulfonyl chloride | bromoethane | 5-ethanesulfonyl-2-fluoro-benzonitrile |
| 2-chloro-4-fluoro-benzenesulfonyl chloride | methyl iodide | 2-chloro-4-fluoro-1-methanesulfonyl-benzene |
| 2-chloro-4-fluoro-benzenesulfonyl chloride | bromoethane | 2-chloro-1-ethanesulfonyl-4-fluoro-benzene |
| 2,4-difluoro-benzenesulfonyl chloride | methyl iodide | 2,4-difluoro-1-methanesulfonyl-benzene |
| 2,4-difluoro-benzenesulfonyl chloride | bromoethane | 1-ethanesulfonyl-2,4-difluoro-benzene |
| 2,4,5-trifluoro-benzenesulfonyl chloride | methyl iodide | 1,2,4-trifluoro-5-methanesulfonyl-benzene |
| 2-chloro-4,5-difluoro-benzenesulfonyl chloride | bromoethane | 1-chloro-2-ethanesulfonyl-4,5-difluoro-benzene |
| 5-chloro-2,4-difluoro-benzenesulfonyl chloride | bromoethane | 1-chloro-5-ethanesulfonyl-2,4-difluoro-benzene |

Preparation of (6-fluoro-4-hydroxy-3-methyl-naphthalen-2-yl)-acetic acid tert-butyl ester

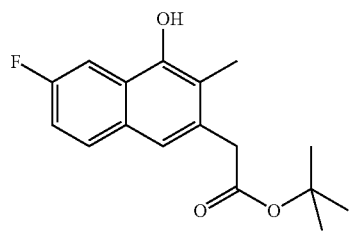 [SMILES: Cc1c(CC(=O)OC(C)(C)C)cc2ccc(F)cc2c1O]

4-(4-Fluoro-phenyl)-2-methyl-buta-2,3-dienoic acid ethyl ester

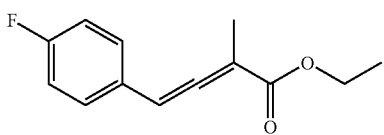 [SMILES: CCOC(=O)C(C)=C=Cc1ccc(F)cc1]

To a solution of (4-fluoro-phenyl)-acetic acid (22.33 g, 144.9 mmol) in 100 mL of methyl tert-butyl ether and 250 μL of DMF was added 13.02 mL (146.3 mmol) of oxalyl chloride at room temperature dropwise over 30 minutes. The resulting mixture was stirred at room temperature for an additional 20 minutes (HPLC indicated completed reaction), and then the entire solution was added dropwise over 1 hour to a solution of N,N-diisopropylethylamine (50.48 mL, 289.8 mmol) and ethyl 2-(triphenylphosphoranylidene)propionate (50.0 g, 138.0 mmol) in 100 mL of methyl tert-butyl ether, while maintaining the internal temperature between 0-15° C. After the addition was complete, the reaction mixture was stirred for an additional 10 minutes at 0-10° C., when HPLC indicated a completed reaction. The reaction mixture was then diluted with 100 mL of heptane, and stirred for 30 minutes at 0-10° C. The resulting solid was filtered and washed with 2×100 mL of 1:1 methyl tert-butyl ether:heptane. The filtrate and the washings were combined and washed with 100 mL of water, 100 mL of 1M citric acid, 2×100 mL of water, then concentrated azeotropically at 25° C./60 mmHg to a total volume of ~40 mL. The residue was diluted with 60 mL of methyl tert-butyl ether. This solution was then directly used for the next step.

2-Ethoxycarbonyl-3-[1-(4-fluoro-phenyl)-meth-(E)-ylidene]-4-methyl-pentanedioic acid 1-tert-butyl ester 5-ethyl ester

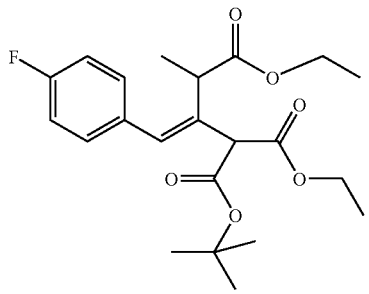 [SMILES: CCOC(=O)C(C)/C(=C\c1ccc(F)cc1)C(C(=O)OCC)C(=O)OC(C)(C)C]

Malonic acid tert-butyl ester ethyl ester (30.08 g, 151.8 mmol) was added to a solution of potassium tert-butoxide (16.30 g, 138.0 mmol) in 200 mL of N,N-dimethylacetamide, while the reaction temperature was maintained at ~25° C. To the resulting mixture was then added the solution of 4-(4-fluoro-phenyl)-2-methyl-buta-2,3-dienoic acid ethyl ester prepared above, at such a rate that the reaction temperature was maintained between 20-28° C. After the addition was complete, the reaction mixture was stirred at room temperature for 20 minutes, when HPLC indicated completed reaction. The mixture was then treated with 100 mL of 1M citric acid and 150 mL of ice-water, and then extracted with 400 mL of methyl tert-butyl ether. The organic extract was separated and washed with 2×200 mL of water, and then concentrated to produce 56.36 g of a yellow oil, which was used in the next step without further purification.

3-[1-(4-Fluoro-phenyl)-meth-(Z)-ylidene]-2-methyl-pentanedioic acid 5-tert-butyl ester

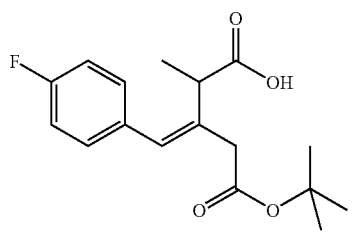 [SMILES: CC(C(=O)O)/C(=C\c1ccc(F)cc1)CC(=O)OC(C)(C)C]

The malonate ester derivative prepared above (56.36 g, 138 mmol) was dissolved in 280 mL of absolute ethanol. Lithium hydroxide (1M solution, 414.0 mL, 414.0 mmol) was added slowly over 15 minutes, and the resulting reaction mixture was stirred at room temperature overnight. The solution was then heated at reflux for 3 hours (HPLC analysis indicated completed decarboxylation). At this time, the solution was concentrated at 30° C./30 mmHg to remove ~350 mL of solvent. The residue was cooled to 10° C., and treated with concentrated hydrochloric acid (32.0 mL, 389.7 mmol) dropwise, in order to adjust the pH to 2.75. The reaction mixture was then extracted with methyl tert-butyl ether (400 mL). The organic phase was separated and washed with 200 mL of water, then treated with 17.00 mL of 1M sodium carbonate in 150 mL of water, washed with an additional 200 mL of water, and then concentrated azeotropically at 30° C./80 mmHg to produce an oil. Methyl tert-butyl ether (200 mL) was added, and the residue was concentrated azeotropically at 30° C./80 mmHg to produce 38.3 g of a yellow oil, which was used in the next step without further purification.

(4-Acetoxy-6-fluoro-3-methyl-naphthalen-2-yl)-acetic acid tert-butyl ester

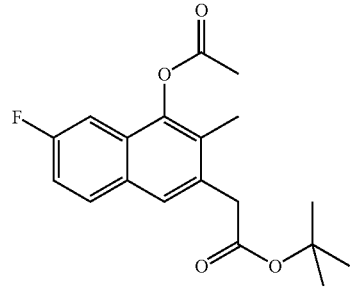 [SMILES: CC(=O)Oc1c(C)c(CC(=O)OC(C)(C)C)cc2ccc(F)cc12]

The above prepared 3-[1-(4-fluoro-phenyl)-meth-(Z)-ylidene]-2-methyl-pentanedioic acid 5-tert-butyl ester (38.3 g, 124.2 mmol) was dissolved in acetic anhydride (96.00 mL, 995.3 mmol). To this solution was added potassium acetate (18.66 g, 186.3 mmol), and the reaction mixture was stirred at 85±2° C. for 10 hours, when HPLC analysis showed completed reaction. The reaction mixture was then cooled to room temperature and diluted with 96 mL of heptane. To this solution, 270 mL of water was added over 1 hour, while maintaining the internal temperature at ~23° C. The mixture was then cooled to 0-5° C., and stirred for 2 hours. The solid formed was filtered, and then washed with water (2×40 mL), heptane (2×40 mL), and then dried under vacuum to furnish 28.5 g of a yellow solid, which was used in the next step without further purification.

(6-Fluoro-4-hydroxy-3-methyl-naphthalen-2-yl)-acetic acid tert-butyl ester (IIb-1)

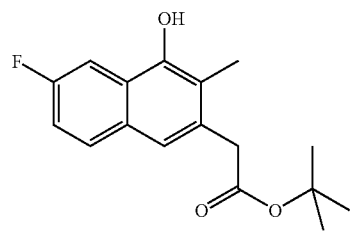 [SMILES: Cc1c(CC(=O)OC(C)(C)C)cc2ccc(F)cc2c1O]

To a mixture of the above prepared (4-acetoxy-6-fluoro-3-methyl-naphthalen-2-yl)-acetic acid tert-butyl ester (28.4 g, 85.44 mmol) in 140 mL of methanol was added sodium methoxide (25% solution in methanol, 23.44 mL, 102.5 mmol) rapidly dropwise. The resulting reaction mixture was stirred at room temperature for 20 minutes, when HPLC analysis indicated a completed reaction. The mixture was cooled to 0° C., and then acidified to pH 2 with 1N hydrochloric acid solution (111.1 mL, 111.1 mmol). The mixture was then stirred at 0-5° C. for an additional 30 minutes. The resulting solid was filtered, and washed with water (2×40 mL), then dried under vacuum overnight (40° C.), to produce 23.7 g of a light yellow solid. $^1$H NMR (300 MHz, DMSO-$d_6$)

δ ppm 9.09 (s, 1H), 7.76-7.86 (m, 2H), 7.26-7.35 (m, 2H), 3.71 (s, 2H), 2.23 (s, 3H), 1.41 (s, 9H).

Part II: Preparation of Specific Compounds

Example 1-1

[4-(4-ethanesulfonyl-phenoxy)-6-fluoro-naphthalen-2-yl]-acetic acid

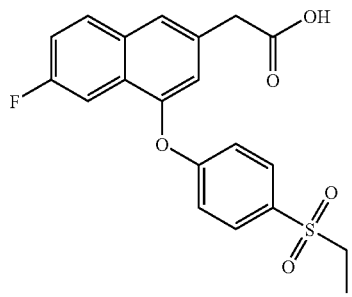 [SMILES: CCS(=O)(=O)c1ccc(Oc2cc(CC(=O)O)cc3ccc(F)cc23)cc1]

2-(4-fluoro-benzylidene)-succinic acid 1-methyl ester

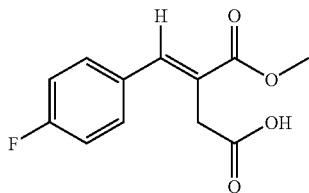 [SMILES: COC(=O)/C(=C/c1ccc(F)cc1)CC(=O)O]

To a refluxing mixture of potassium tert-butoxide (27 g, 242 mmol) and tert-butanol (150 mL) was added a solution of 4-fluoro-benzaldehyde (20 g, 161 mmol) and dimethyl succinate (28 g, 193.2 mmol) in tert-butanol (100 mL) dropwise. After being heated at reflux for 3 hours, the mixture was concentrated in vacuo to remove tert-butanol. The residue was dissolved in 1 N hydrochloric acid (180 mL). The resulting aqueous solution was extracted with ethyl acetate (100 mL×3). The combined organic layers were dried over sodium sulfate, and concentrated in vacuo. The residue was purified by column chromatography (elution with 30% ethyl acetate in petroleum ether) to afford 2-(4-fluoro-benzylidene)-succinic acid 1-methyl ester (25.5 g, 66%) as a light yellow solid. $^1$H NMR (400 MHz, CD$_3$OD) δ ppm 7.84 (s, 1H), 7.41-7.46 (m, 2H), 7.13-7.20 (m, 2H), 3.81 (s, 3H), 3.49 (s, 2H).

4-acetoxy-6-fluoro-naphthalene-2-carboxylic acid methyl ester

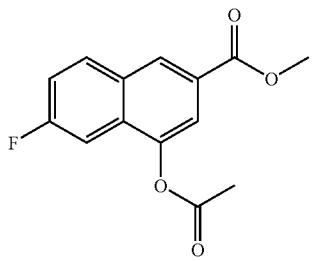 [SMILES: COC(=O)c1cc(OC(C)=O)c2cc(F)ccc2c1]

To a solution of 2-(4-fluoro-benzylidene)-succinic acid 1-methyl ester (2 g, 8.4 mmol) in acetic anhydride (10 mL) was added sodium acetate (0.83 g, 10.1 mmol). After being heated at reflux for 6 hours, the mixture was concentrated in vacuo. The residue was dissolved in 1 N hydrochloric acid (20 mL). The aqueous solution was extracted with ethyl acetate (15 mL×3). The combined organic layers were dried over sodium sulfate, and concentrated in vacuo. The residue was purified by column chromatography (10-20% ethyl acetate in petroleum ether) to afford 4-acetoxy-6-fluoro-naphthalene-2-carboxylic acid methyl ester (1.1 g, 50%) as a white solid. $^1$H NMR (400 MHz, CDCl$_3$) δ ppm 8.52 (s, 1H), 8.00 (dd, J=9.09, 5.56 Hz, 1H), 7.89 (s, 1H), 7.50 (dd, J=9.85, 2.53 Hz, 1H), 7.37 (td, J=8.59, 2.53 Hz, 1H), 3.99 (s, 3H), 2.49 (s, 3H).

6-fluoro-4-hydroxy-naphthalene-2-carboxylic acid methyl ester

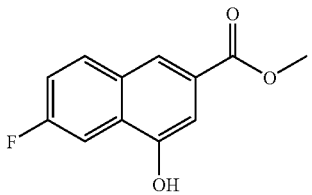 [SMILES: COC(=O)c1cc(O)c2cc(F)ccc2c1]

To a solution of 4-acetoxy-6-fluoro-naphthalene-2-carboxylic acid methyl ester (1 g, 3.8 mmol) in methanol (20 mL) was added sodium methoxide (309 mg, 5.7 mmol). After being stirred at room temperature for 1 hour, the reaction mixture was acidified with 1 N hydrochloric acid to pH 3. The resulting precipitate was collected by filtration and dissolved in ethyl acetate. The organic solution was dried over sodium sulfate, and concentrated in vacuo to afford 900 mg of crude 6-fluoro-4-hydroxy-naphthalene-2-carboxylic acid methyl ester as a pale yellow solid, which was used in the next step without further purification.

4-benzyloxy-6-fluoro-naphthalene-2-carboxylic acid methyl ester

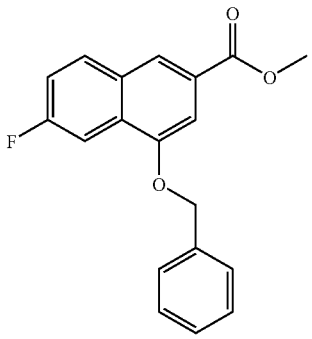 [SMILES: COC(=O)c1cc(OCc2ccccc2)c2cc(F)ccc2c1]

To a mixture of 6-fluoro-4-hydroxy-naphthalene-2-carboxylic acid methyl ester (4.6 g, 21 mmol), potassium carbonate (5.8 g, 42 mmol) and acetone (100 mL) was added benzyl bromide (5.47 g, 32 mmol). After being stirred vigorously at reflux for 4 hours under a nitrogen atmosphere, the resulting mixture was cooled to room temperature, and filtered. The organic solution was concentrated in vacuo to give 4-benzyloxy-6-fluoro-naphthalene-2-carboxylic acid methyl ester (5.85 g, 90%) as a white solid.

69

(4-benzyloxy-6-fluoro-naphthalen-2-yl)-methanol

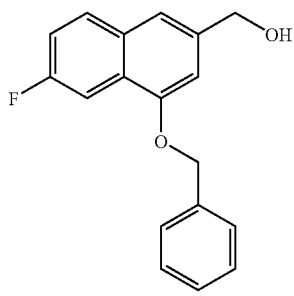 [SMILES: OCc1cc(OCc2ccccc2)c2cc(F)ccc2c1]

To the slurry of lithium aluminum hydride (1.4 g, 36.9 mmol) in tetrahydrofuran (30 mL) was added a solution of 4-benzyloxy-6-fluoro-naphthalene-2-carboxylic acid methyl ester (5.8 g, 18.7 mmol) in tetrahydrofuran (30 mL) at 0° C. under a nitrogen atmosphere. After being heated at 60° C. for 1 hour under a nitrogen atmosphere, the resulting mixture was cooled to 0° C. and 1 N hydrochloric acid was added to quench the reaction. The aqueous layer was extracted with diethyl ether (50 mL×4). The combined organic layers were dried over sodium sulfate and concentrated in vacuo to give (4-benzyloxy-6-fluoro-naphthalen-2-yl)-methanol (4.9 g, 93%) as a white solid.

1-benzyloxy-3-chloromethyl-7-fluoro-naphthalene

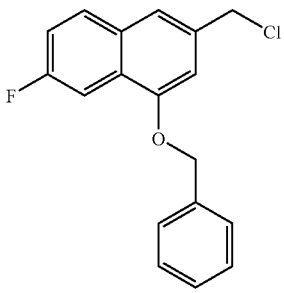 [SMILES: Fc1ccc2cc(CCl)cc(OCc3ccccc3)c2c1]

To a solution of triphenylphosphine (2.8 g, 10.6 mmol) in anhydrous tetrahydrofuran (16 mL) was added carbon tetrachloride (5 mL). After the mixture was stirred at room temperature for 10 minutes, (4-benzyloxy-6-fluoro-naphthalen-2-yl)-methanol (1.5 g, 5.3 mmol) was added as a solid under a nitrogen atmosphere. After being stirred at reflux for 2 hours, the resulting mixture was cooled to room temperature, diluted with water, and extracted with ethyl acetate (100 mL). The organic layer was washed with water (50 mL×2). The combined aqueous layers were extracted with ethyl acetate (100 mL). The combined organic layers were dried over sodium sulfate and concentrated in vacuo. The residue was purified by column chromatography (elution with 5% ethyl acetate in petroleum ether) to afford 1-benzyloxy-3-chloromethyl-7-fluoro-naphthalene (1.4 g, 87.5%) as a white solid.

70

(4-benzyloxy-6-fluoro-naphthalen-2-yl)-acetic acid methyl ester

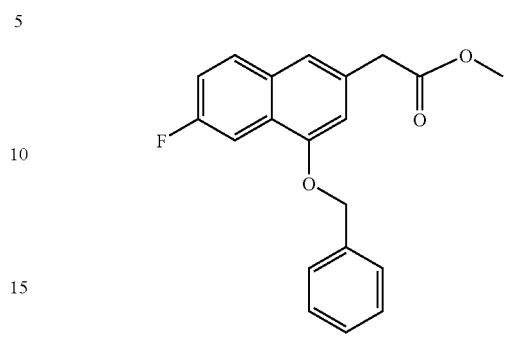

To a flask containing 1-benzyloxy-3-chloromethyl-7-fluoro-naphthalene (5.4 g, 18 mmol), bis(triphenylphosphine)dichloropalladium(II) (630 mg, 0.9 mmol) and potassium carbonate (2.6 g, 18.9 mmol), which was evacuated and then filled with carbon monoxide (balloon), methanol (25 mL) and tetrahydrofuran (50 mL) were added by means of a syringe. After being stirred at room temperature under a carbon monoxide atmosphere overnight, the resulting mixture was diluted with water (100 mL), and extracted with ethyl acetate (100 mL). The organic layer was washed with water (50 mL×2). The combined aqueous layers were extracted with ethyl acetate (150 mL), and the combined organic layers were dried over sodium sulfate and concentrated in vacuo. The residue was purified by column chromatography (elution with 20% ethyl acetate in petroleum ether) to afford (4-benzyloxy-6-fluoro-naphthalen-2-yl)-acetic acid methyl ester (5.3 g, 91%) as a white solid.

(6-fluoro-4-hydroxy-naphthalen-2-yl)-acetic acid methyl ester

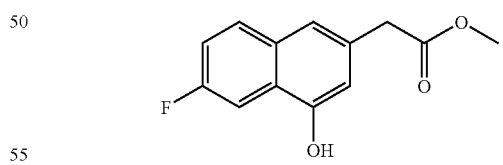

To a solution of (4-benzyloxy-6-fluoro-naphthalen-2-yl)-acetic acid methyl ester (876 mg, 2.7 mmol) in methanol (20 mL) was added 10% palladium on carbon (132 mg). The resulting mixture was stirred vigorously under a hydrogen atmosphere (balloon) overnight and then filtered. The filtrate was concentrated in vacuo to give (6-fluoro-4-hydroxy-naphthalen-2-yl)-acetic acid methyl ester (601 mg, 95%) as a white solid. $^1$H NMR (400 MHz, CDCl$_3$) δ ppm 7.69-7.76 (m, 2H), 7.30 (s, 1H), 7.22-7.26 (m, 1H), 6.82 (s, 1H), 3.74 (s, 3H), 3.72 (s, 2H).

[4-(4-ethanesulfonyl-phenoxy)-6-fluoro-naphthalen-2-yl]acetic acid methyl ester

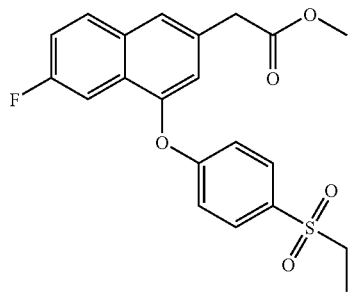 [SMILES: CCS(=O)(=O)c1ccc(Oc2cc(CC(=O)OC)cc3ccc(F)cc23)cc1]

A sealed tube containing (6-fluoro-4-hydroxy-naphthalen-2-yl)-acetic acid methyl ester (49 mg, 0.21 mmol), 1-ethanesulfonyl-4-fluoro-benzene (87 mg, 0.427 mmol), and potassium carbonate (73 mg, 0.53 mmol) was evacuated and filled with nitrogen. Anhydrous N,N-dimethylformamide (2 mL) was added. After being stirred at 100° C. overnight, the mixture was cooled to room temperature, then diluted with water (10 mL), and extracted with ethyl acetate (10 mL×2). The combined organic layers were washed with brine (10 mL×3), dried over sodium sulfate and concentrated in vacuo. The residue was purified by column chromatography (elution with 30% ethyl acetate in petroleum ether) to give [4-(4-ethanesulfonyl-phenoxy)-6-fluoro-naphthalen-2-yl]-acetic acid methyl ester (67.6 mg, 80%) as a white solid.

[4-(4-ethanesulfonyl-phenoxy)-6-fluoro-naphthalen-2-yl]acetic acid

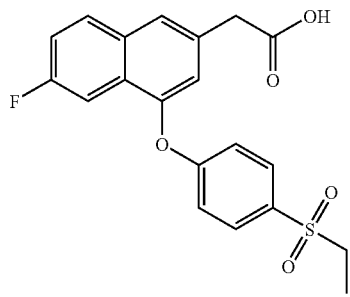

5 N lithium hydroxide (6 mL) was added to a solution of [4-(4-ethanesulfonyl-phenoxy)-6-fluoro-naphthalen-2-yl]-acetic acid methyl ester (64 mg, 0.16 mmol) in tetrahydrofuran (4 mL). After being stirred at room temperature overnight, the resulting mixture was acidified to pH 3 with 5 N hydrochloric acid, and then extracted with ethyl acetate (10 mL×2). The organic layers were dried over sodium sulfate and concentrated in vacuo. The residue was precipitated from ethyl ester/petroleum ether (1:10) to give [4-(4-ethanesulfonyl-phenoxy)-6-fluoro-naphthalen-2-yl]-acetic acid (25 mg) as a white solid. $^1$H NMR (400 MHz, CDCl$_3$) δ ppm 7.84-7.90 (m, 3H), 7.65 (s, 1H), 7.57 (dd, J=9.85, 2.53 Hz, 1H), 7.33 (td, J=8.65, 2.65 Hz, 1H), 7.09-7.14 (m, 3H), 3.80 (s, 2H), 3.13 (q, J=7.33 Hz, 2H), 1.30 (t, J=7.45 Hz, 3H); MS cald. for C$_{20}$H$_{17}$FO$_5$S 388, obsd. (ESI$^+$) [(M+H)$^+$] 389.

Examples 1-2 to 1-23

The following examples 1-2 to 1-23 were prepared in an analogous manner to example 1-1 starting with 4-fluoro-benzaldehyde, 4-chloro-benzaldehyde, 4-methoxy-benzaldehyde, 4-trifluoromethyl-benzaldehyde, 4-trifluoromethoxy-benzenaldehyde, 3,4-dimethoxy-benzaldehyde, and 3-fluoro-benzaldehyde, to derive (6-fluoro-4-hydroxy-naphthalen-2-yl)-acetic acid methyl ester, (6-chloro-4-hydroxy-naphthalen-2-yl)-acetic acid methyl ester, (4-hydroxy-6-methoxy-naphthalen-2-yl)-acetic acid methyl ester, (4-hydroxy-6-trifluoromethyl-naphthalen-2-yl)-acetic acid methyl ester, (4-hydroxy-6-trifluoromethoxy-naphthalen-2-yl)-acetic acid methyl ester, (4-hydroxy-6,7-dimethoxy-naphthalen-2-yl)-acetic acid methyl ester, and derive (5-fluoro-4-hydroxy-naphthalen-2-yl)-acetic acid methyl ester and (7-fluoro-4-hydroxy-naphthalen-2-yl)-acetic acid methyl ester (Note: Starting with 3-fluoro-benzaldehyde, both of (5-fluoro-4-hydroxy-naphthalen-2-yl)-acetic acid methyl ester and (7-fluoro-4-hydroxy-naphthalen-2-yl)-acetic acid methyl ester can be obtained. See Scheme 17) respectively, which were then further treated with the appropriate commercially available or prepared sulfonylaryl derivatives in accordance with the procedure described for example 1-1.

| Example No. | Systematic Name | $^1$H NMR (400 MHz, CDCl$_3$) δ ppm | MS (ESI$^+$, [(M + H)$^+$] | Structure |
|---|---|---|---|---|
| 1-2 | [6-fluoro-4-(4-methanesulfonyl-phenoxy)-naphthalen-2-yl]-acetic acid | 7.82-7.89 (m, 1H), 7.86 (d, J = 8.84 Hz, 2H), 7.61 (s, 1H), 7.53 (dd, J = 9.98, 2.40 Hz, 1H), 7.26-7.32 (m, 1H), 7.07 (d, J = 9.09 Hz, 2H), 7.10 (s, 1H), 3.76 (s, 2H), 3.03 (s, 3H) | 375 | 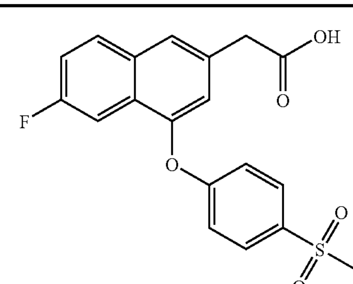 |

| Example No. | Systematic Name | $^1$H NMR (400 MHz, CDCl$_3$) δ ppm | MS (ESI$^+$, [(M + H)$^+$] | Structure |
|---|---|---|---|---|
| 1-3* | [6-chloro-4-(4-methanesulfonyl-phenoxy)-naphthalen-2-yl]-acetic acid | 7.90-7.96 (m, 4H), 7.72 (s, 1H), 7.52 (dd, J = 8.84, 2.02 Hz, 1H), 7.18-7.22 (m, 3H), 3.79 (s, 2H), 3.12 (s, 3H) | 391 | 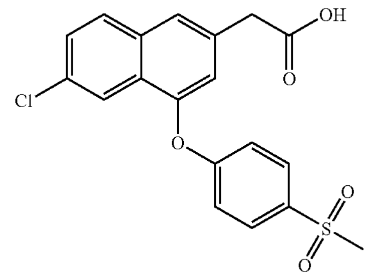 [SMILES: CS(=O)(=O)c1ccc(Oc2cc(CC(=O)O)cc3ccc(Cl)cc23)cc1] |
| 1-4 | {6-fluoro-4-[4-(propane-2-sulfonyl)-phenoxy]-naphthalen-2-yl}-acetic acid | 7.83-7.92 (m, 3H), 7.67 (s, 1H), 7.60 (dd, J = 9.85, 2.53 Hz, 1H), 7.35 (td, J = 8.65, 2.65 Hz, 1H), 7.13 (s, 3H), 3.82 (s, 2H), 3.17-3.25 (m, 1H), 1.34 (d, J = 7.07 Hz, 6H) | 403 | 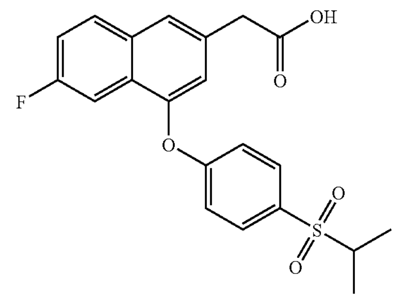 [SMILES: CC(C)S(=O)(=O)c1ccc(Oc2cc(CC(=O)O)cc3ccc(F)cc23)cc1] |
| 1-5 | [4-(4-cyclopropanesulfonyl-phenoxy)-6-fluoro-naphthalen-2-yl]-acetic acid | 7.86-7.92 (m, 3H), 7.65-7.69 (m, 1H), 7.61 (dd, J = 9.98, 2.65 Hz, 1H), 7.35 (td, J = 8.59, 2.53 Hz, 1H), 7.10-7.16 (m, 3H), 3.79 (br. s, 2H), 2.45-2.53 (m, 1H), 1.37 (dd, J = 4.80, 1.77 Hz, 2H), 1.07 (dd, J = 7.96, 1.89 Hz, 2H) | 401 | 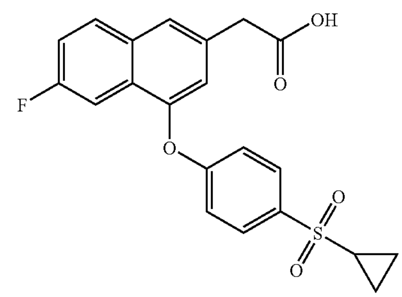 [SMILES: O=C(O)Cc1cc(Oc2ccc(S(=O)(=O)C3CC3)cc2)c2cc(F)ccc2c1] |
| 1 1-6 | [6-fluoro-4-(4-methanesulfonyl-2-methyl-phenoxy)-naphthalen-2-yl]-acetic acid | 7.91 (br. s, 1H), 7.88 (t, 1H), 7.68 (dd, J = 8.46, 1.89 Hz, 1H), 7.60-7.64 (m, 2H), 7.35 (td, J = 8.72, 2.53 Hz, 1H), 6.98 (s, 1H), 6.82 (d, J = 8.59 Hz, 1H), 3.79 (s, 2H), 3.09 (s, 3H), 2.50 (s, 3H) | 389 | 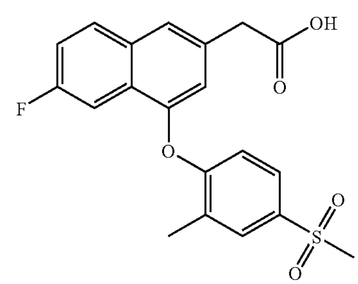 [SMILES: Cc1cc(S(C)(=O)=O)ccc1Oc1cc(CC(=O)O)cc2ccc(F)cc12] |
| 1-7 | [6-fluoro-4-(4-methanesulfonyl-3-methyl-phenoxy)-naphthalen-2-yl]-acetic acid | 7.99 (d, J = 8.59 Hz, 1H), 7.87 (dd, J = 9.09, 5.31 Hz, 1H), 7.64 (s, 1H), 7.58 (dd, J= 10.11, 2.53 Hz, 1H), 7.33 (td, J = 8.65, 2.40 Hz, 1H), 7.12 (s, 1H), 6.95 (d, J = 2.27 Hz, 1H), 6.89 (dd, J = 8.72, 2.40 Hz, 1H), 3.80 (s, 2H), 3.09 (s, 3H), 2.66 (s, 3H) | 389 | 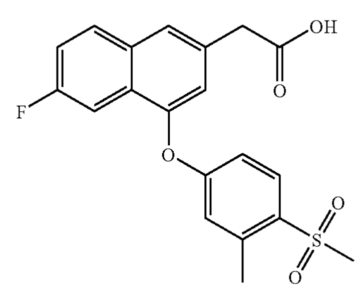 [SMILES: Cc1cc(Oc2cc(CC(=O)O)cc3ccc(F)cc23)ccc1S(C)(=O)=O] |

-continued

| Example No. | Systematic Name | ¹H NMR (400 MHz, CDCl₃) δ ppm | MS (ESI⁺, [(M + H)⁺] | Structure |
|---|---|---|---|---|
| 1-8 | [4-(4-ethanesulfonyl-2-methyl-phenoxy)-6-fluoro-naphthalen-2-yl]-acetic acid | 7.98 (dd, J = 8.97, 5.43 Hz, 1H), 7.88 (d, J = 1.52 Hz, 1H), 7.68 (s, 1H), 7.65 (dd, J = 8.46, 2.15 Hz, 1H), 7.57 (dd, J = 10.23, 2.65 Hz, 1H), 7.37 (td, J = 8.78, 2.65 Hz, 1H), 7.05 (s, 1H), 6.87 (d, J = 8.59 Hz, 1H), 3.75 (s, 2H), 3.21 (q, J = 7.49 Hz, 2H), 2.50 (s, 3H), 1.23 (t, J = 7.45 Hz, 3H) | 403 | 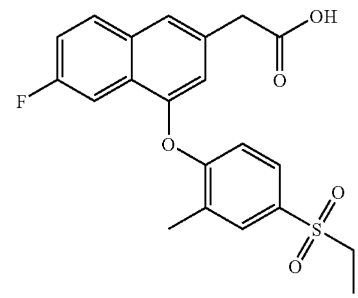 [SMILES: CCS(=O)(=O)c1ccc(Oc2cc(CC(=O)O)cc3ccc(F)cc23)c(C)c1] |
| 1-9** | [6-fluoro-4-(5-methanesulfonyl-pyridin-2-yloxy)-naphthalen-2-yl]-acetic acid | 8.56 (d, J = 2.53 Hz, 1H), 8.38 (dd, J = 8.59, 2.53 Hz, 1H), 8.09 (dd, J = 8.84, 5.56 Hz, 1H), 7.82 (s, 1H), 7.44-7.51 (m, 2H), 7.42 (s, 1H), 7.38 (s, 1H), 3.76 (s, 2H), 3.28 (s, 3H) | 376 | 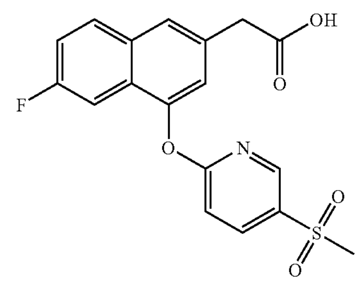 [SMILES: CS(=O)(=O)c1ccc(Oc2cc(CC(=O)O)cc3ccc(F)cc23)nc1] |
| 1-10** | [6-fluoro-4-(5-methanesulfonyl-3-methyl-pyridin-2-yloxy)-naphthalen-2-yl]-acetic acid | 12.45 (s, 1H), 8.31 (br. s, 2H), 8.08 (br. s, 1H), 7.81 (s, 1H), 7.42-7.51 (m, 2H), 7.34 (s, 1H), 3.77 (s, 2H), 3.26 (s, 3H), 2.56 (s, 3H) | 390 | 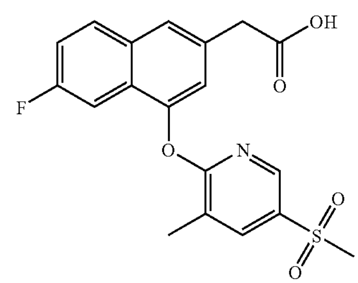 [SMILES: Cc1cc(S(C)(=O)=O)cnc1Oc1cc(CC(=O)O)cc2ccc(F)cc12] |
| 1-11** | [4-(5-ethanesulfonyl-pyridin-2-yloxy)-6-fluoro-naphthalen-2-yl]-acetic acid | 8.53 (d, J = 2.02 Hz, 1H), 8.34 (dd, J = 8.72, 2.40 Hz, 1H), 8.10 (dd, J = 8.97, 5.68 Hz, 1H), 7.83 (s, 1H), 7.35-7.55 (m, 4H), 3.78 (s, 2H), 3.35-3.40 (m, 2H), 1.14 (t, J = 7.45 Hz, 3H) | 390 | 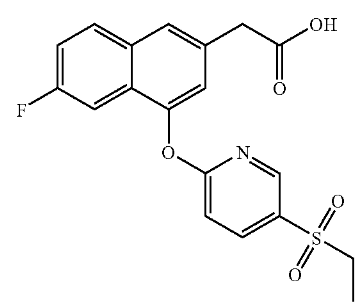 [SMILES: CCS(=O)(=O)c1ccc(Oc2cc(CC(=O)O)cc3ccc(F)cc23)nc1] |
| 1-12* | [4-(5-ethanesulfonyl-3-methyl-pyridin-2-yloxy)-6-fluoro-naphthalen-2-yl]-acetic acid | 8.27 (s, 1H), 8.17 (s, 1H), 7.97 (dd, J = 8.08, 6.06 Hz, 1H), 7.75 (s, 1H), 7.30-7.38 (m, 3H), 3.79 (s, 2H), 3.24 (t, 2H), 2.60 (s, 3H), 1.25 (t, J = 6.95 Hz, 3H) | 404 | 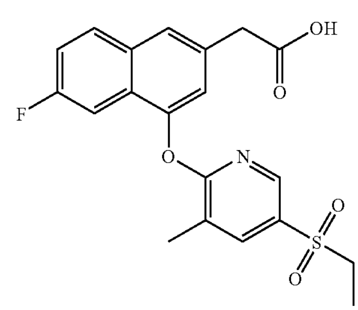 [SMILES: CCS(=O)(=O)c1cnc(Oc2cc(CC(=O)O)cc3ccc(F)cc23)c(C)c1] |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 1-13* | [4-(3-bromo-5-ethanesulfonyl-pyridin-2-yloxy)-6-fluoro-naphthalen-2-yl]-acetic acid | 8.60 (d, J = 2.27 Hz, 1H), 8.42 (d, J = 2.27 Hz, 1H), 7.99 (dd, J= 8.97, 5.18 Hz, 1H), 7.79 (s, 1H), 7.32-7.43 (m, 3H), 3.81 (s, 2H), 3.26-3.29 (m, 2H), 1.26 (t, J = 7.33 Hz, 3H) | 468 | 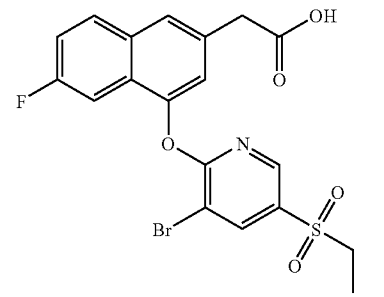 [SMILES: CCS(=O)(=O)c1cnc(Oc2cc(CC(=O)O)cc3ccc(F)cc23)c(Br)c1] |
| 1-14* | [4-(3-bromo-5-methanesulfonyl-pyridin-2-yloxy)-6-fluoro-naphthalen-2-yl]-acetic acid | 8.65 (d, J = 2.27 Hz, 1H), 8.46 (d, J = 2.02 Hz, 1H), 7.99 (dd, J = 9.73, 5.43 Hz, 1H), 7.79 (s, 1H), 7.32-7.40 (m, 3H), 3.81 (s, 2H), 3.20 (s, 3H) | 454 | 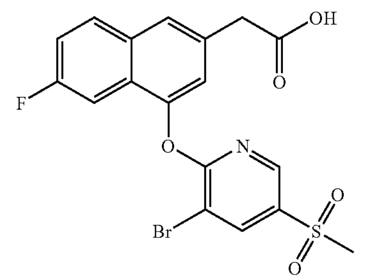 |
| 1-15 | [4-(4-Ethanesulfonyl-phenoxy)-6-methoxy-naphthalen-2-yl]-acetic acid | 7.87 (d, J = 8.59 Hz, 2H), 7.79 (d, J = 8.84 Hz, 1H), 7.60 (s, 1H), 7.19-7.24 (m, 2H), 7.14 (d, J = 8.59 Hz, 2H), 7.10 (d, J = 1.26 Hz, 1H), 3.84 (s, 3H) 3.79 (s, 2H), 3.14 (q, J = 7.49 Hz, 2H), 1.32 (t, J = 7.45 Hz, 3H) | 401 | 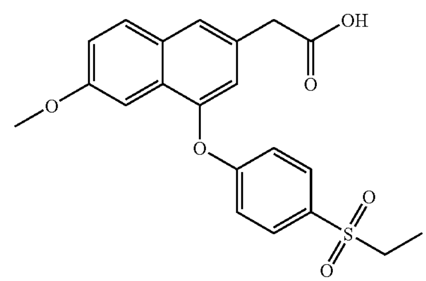 [SMILES: CCS(=O)(=O)c1ccc(Oc2cc(CC(=O)O)cc3ccc(OC)cc23)cc1] |
| 1-16* | [4-(5-Ethanesulfonyl-pyridin-2-yloxy)-6-trifluoromethyl-naphthalen-2-yl]-acetic acid | 8.55 (d, J = 2.53 Hz, 1H), 8.34 (dd, J = 8.59, 2.27 Hz, 1H), 8.10-8.15 (m, 2H), 7.86 (s, 1H), 7.73 (d, J = 9.09 Hz, 1H), 7.46 (s, 1H), 7.40 (d, J = 8.84 Hz, 1H), 3.86 (s, 2H), 3.27 (dd, 2H) 1.26 (t, J = 7.33 Hz, 3H) | 440 | 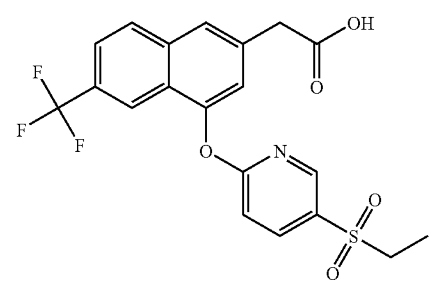 [SMILES: CCS(=O)(=O)c1ccc(Oc2cc(CC(=O)O)cc3ccc(C(F)(F)F)cc23)nc1] |
| 1-17** | [4-(4-Ethanesulfonyl-phenoxy)-6-trifluoromethyl-naphthalen-2-yl]-acetic acid | 8.30 (s, 1H) 8.13 (d, J = 8.59 Hz, 1H) 7.93 (d, J = 8.84 Hz, 2H) 7.80 (s, 1H) 7.76 (dd, J = 8.34, 1.26 Hz, 1H) 7.23-7.31 (m, 3H) 3.84 (s, 2H) 3.22 (q, J = 7.33 Hz, 2H) 1.24 (t, J = 7.33 Hz, 3H) | 439 | 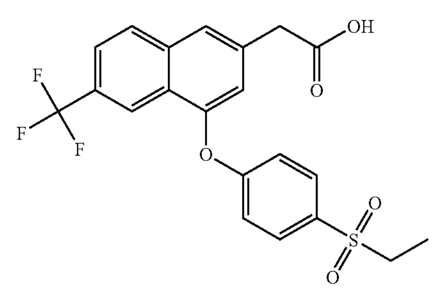 [SMILES: CCS(=O)(=O)c1ccc(Oc2cc(CC(=O)O)cc3ccc(C(F)(F)F)cc23)cc1] |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 1-18* | [4-(5-Ethanesulfonyl-pyridin-2-yloxy)-6-trifluoromethoxy-naphthalen-2-yl]-acetic acid | 8.55 (d, J = 2.27 Hz, 1H), 8.32 (dd, J = 8.84, 2.53 Hz, 1H), 8.06 (d, J = 8.84 Hz, 1H), 7.82 (s, 1H), 7.62 (s, 1H), 7.46 (d, J = 1.52 Hz, 1H), 7.42 (s, 1H), 7.36 (d, J = 8.59 Hz, 1H), 3.84 (s, 2H), 3.26 (q, J = 7.33 Hz, 2H), 1.25 (t, J = 7.33 Hz, 3H) | 456 | 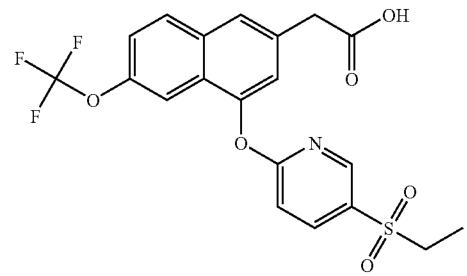 [SMILES: CCS(=O)(=O)c1ccc(Oc2cc(CC(=O)O)cc3ccc(OC(F)(F)F)cc23)nc1] |
| 1-19* | [4-(4-Ethanesulfonyl-phenoxy)-6-trifluoromethoxy-naphthalen-2-yl]-acetic acid | 8.05 (d, J = 9.09 Hz, 1H), 7.91 (d, J = 8.84 Hz, 2H), 7.77 (s, 2H), 7.46 (d, J = 8.84 Hz, 1H), 7.27 (s, 1H), 7.25 (d, J = 8.84 Hz, 2H), 3.81 (s, 2H), 3.20 (q, J = 7.33 Hz, 2H), 1.25 (d, J = 7.33 Hz, 3H) | 455 | 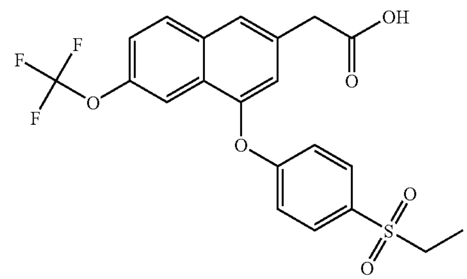 [SMILES: CCS(=O)(=O)c1ccc(Oc2cc(CC(=O)O)cc3ccc(OC(F)(F)F)cc23)cc1] |
| 1-20* | [4-(4-Ethanesulfonyl-phenoxy)-7-fluoro-naphthalen-2-yl]-acetic acid | 8.02 (dd, J = 9.09, 5.56 Hz, 1H), 7.90 (d, J = 8.84 Hz, 2H), 7.69 (s, 1H), 7.62 (dd, J = 10.11, 2.53 Hz, 1H), 7.32 (td, J = 8.78, 2.40 Hz, 1H), 7.22 (d, J = 8.59 Hz, 2H), 7.15 (s, 1H), 3.80 (s, 2H), 3.22 (q, J = 7.41 Hz, 2H), 1.25 (t, J = 7.45 Hz, 3H) | 389 | 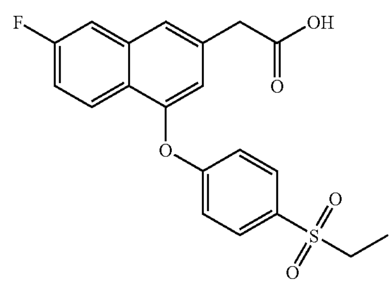 [SMILES: CCS(=O)(=O)c1ccc(Oc2cc(CC(=O)O)cc3cc(F)ccc23)cc1] |
| 1-21* | [4-(5-Ethanesulfonyl-pyridin-2-yloxy)-6-methoxy-naphthalen-2-yl]-acetic acid | 8.60 (d, J = 2.80 Hz, 1H), 8.30 (dd, J = 8.84, 2.40 Hz, 1H), 7.85 (d, J = 9.20 Hz, 1H), 7.69 (s, 1H), 7.28-7.25 (m, 2H), 7.21 (dd, J = 9.20, 2.40 Hz, 1H), 7.10 (d, J = 2.40 Hz, 1H), 3.80 (s, 5H), 3.20 (q, J = 7.45 Hz, 2H), 1.28 (t, J = 7.45 Hz, 3H) | 402 | 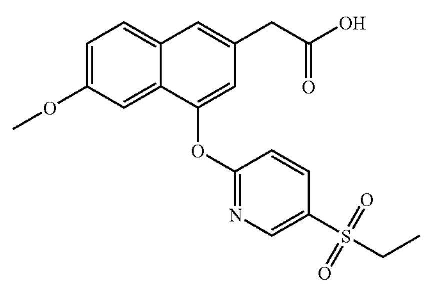 [SMILES: CCS(=O)(=O)c1ccc(Oc2cc(CC(=O)O)cc3ccc(OC)cc23)nc1] |
| 1-22* | [4-(4-Ethanesulfonyl-phenoxy)-5-fluoro-naphthalen-2-yl]-acetic acid | 7.87 (d, J = 8.84 Hz, 2H), 7.81 (s, 1H), 7.77 (d, J = 8.84 Hz, 1H), 7.50 (td, 1H), 7.30 (s, 1H), 7.14 (dd, 1H), 7.08 (d, J = 8.84 Hz, 2H), 3.81 (s, 2H), 3.20 (q, J = 7.45 Hz, 2H), 1.26 (t, J = 7.45 Hz, 3H) | 389 | 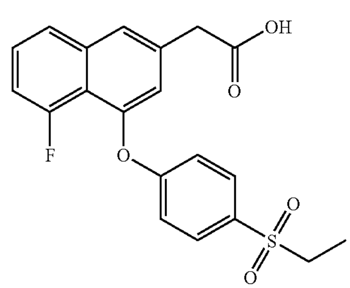 [SMILES: CCS(=O)(=O)c1ccc(Oc2cc(CC(=O)O)cc3cccc(F)c23)cc1] |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 1-23* | [4-(4-Ethanesulfonyl-phenoxy)-6,7-dimethoxy-naphthalen-2-yl]-acetic acid | 7.89 (d, J = 8.84 Hz, 2H), 7.59 (s, 1H), 7.34 (s, 1H), 7.22-7.19 (m, 3H), 7.04 (s, 1H), 3.99 (s, 3H), 3.83 (s, 3H), 3.75 (s, 2H), 3.23 (q, J = 7.45 Hz, 2H), 1.25 (t, J = 7.45 Hz, 3H) | 431 | 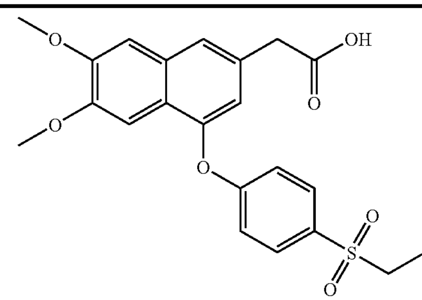 |

*CD$_3$OD was used as the solvent;
**DMSO-d$_6$ was used as the solvent.

Example 2-1

[4-(4-ethanesulfonyl-phenoxy)-6-fluoro-3-methyl-naphthalen-2-yl]-acetic acid

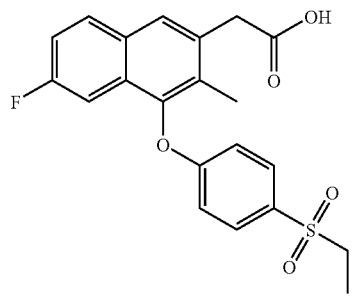

2-(4-fluoro-benzylidene)-3-methyl-succinic acid 1-methyl ester

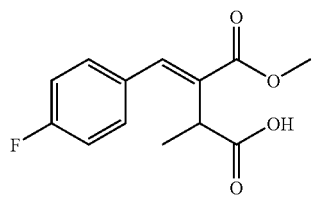 [SMILES: COC(=O)/C(=C/c1ccc(F)cc1)C(C)C(=O)O]

After careful addition of absolute methanol (0.1 mL) to a suspension of sodium hydride (60% in mineral oil, 20 g, 0.5 mol) in anhydrous toluene (200 mL), a solution of 4-fluoro-benzaldehyde (31 g, 0.25 mol) and 2-methyl-succinic acid dimethyl ester (60 g, 0.38 mol) in anhydrous toluene (100 mL) was added at room temperature under a stream of nitrogen. The resulting mixture was stirred at room temperature for 30 minutes and then quenched by the slow addition of water (20 mL). The mixture was acidified by the addition of concentrated hydrochloric acid, and extracted with ethyl acetate (200 mL×3). The combined organic layers were dried over sodium sulfate, and concentrated in vacuo. The residue was purified by column chromatography (elution with 30% ethyl acetate in petroleum ether) to afford 2-(4-fluoro-benzylidene)-3-methyl-succinic acid 1-methyl ester (20 g, 33%) as a white solid. $^1$H NMR (400 MHz, acetone-d$_6$) δ ppm 7.77 (s, 1H), 7.54 (d, J=8.8 Hz, 2H), 7.25 (d, J=8.8 Hz, 2H), 3.82 (q, 7.2 Hz, 1H), 1.40 (d, J=6.8 Hz, 3H).

6-fluoro-4-hydroxy-3-methyl-naphthalene-2-carboxylic acid methyl ester

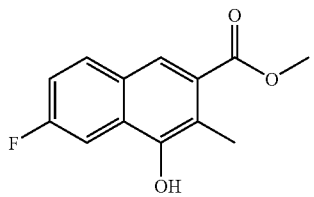 [SMILES: COC(=O)c1cc2ccc(F)cc2c(O)c1C]

To a solution of 2-(4-fluoro-benzylidene)-3-methyl-succinic acid 1-methyl ester (1 g, 4 mmol) in anhydrous tetrahydrofuran (10 mL), trifluoroacetic anhydride (3.3 g, 15.7 mmol) was added in one portion followed by the addition of triethylamine (3.3 mL, 24 mmol) dropwise. After being stirred at room temperature for 4 hours, the mixture was acidified to pH 3 with 5% aqueous hydrochloric acid and extracted with ethyl acetate (30 mL). The organic layer was concentrated in vacuo. The residue was dissolved in methanol (15 mL). The resulting solution was cooled to 0° C., then treated with sodium borohydride (380 mg, 10 mmol), and stirred for 1 hour. The reaction mixture was diluted with ethyl acetate (20 mL) and 5% aqueous hydrochloric acid (20 mL). The aqueous phase was separated and extracted with ethyl acetate (15 mL×3). The combined organic layers were washed with brine (40 mL), dried over sodium sulfate, filtered, and concentrated in vacuo. The residue was purified by column chromatography (elution with 10% ethyl acetate in hexanes) to afford 6-fluoro-4-hydroxy-3-methyl-naphthalene-2-carboxylic acid methyl ester (740 mg, 80%) as a pale solid.

Alternatively, 6-fluoro-4-hydroxy-3-methyl-naphthalene-2-carboxylic acid methyl ester was obtained by treating 2-(4-fluoro-benzylidene)-3-methyl-succinic acid 1-methyl ester with acetic anhydride and sodium acetate followed by sodium methoxide, in a manner analogous to the one described above for the preparation of 6-fluoro-4-hydroxy-naphthalene-2-carboxylic acid methyl ester.

4-benzyloxy-6-fluoro-3-methyl-naphthalene-2-carboxylic acid methyl ester

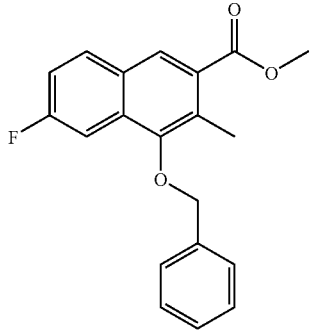 [SMILES: COC(=O)c1cc2ccc(F)cc2c(OCc2ccccc2)c1C]

To a mixture of 6-fluoro-4-hydroxy-3-methyl-naphthalene-2-carboxylic acid methyl ester (8.0 g, 34.2 mmol) and potassium carbonate (9.45 g, 68.4 mmol) was added benzyl bromide (4.5 mL, 37.6 mmol) in acetone (100 mL). The resulting mixture was vigorously stirred at reflux for 10 hours under a nitrogen atmosphere. The mixture was cooled and filtered. The combined organic solution was concentrated in vacuo to give 4-benzyloxy-6-fluoro-3-methyl-naphthalene-2-carboxylic acid methyl ester (10.4 g, 94%) as a white solid.

(4-benzyloxy-6-fluoro-3-methyl-naphthalen-2-yl)-methanol

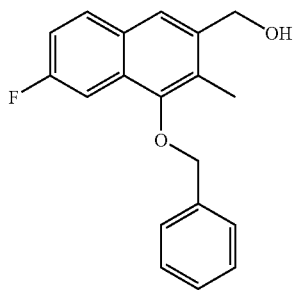 [SMILES: Cc1c(CO)cc2ccc(F)cc2c1OCc1ccccc1]

To the slurry of lithium aluminum hydride (1.8 g, 47.5 mmol) in tetrahydrofuran (50 mL) was added a solution of 4-benzyloxy-6-fluoro-3-methyl-naphthalene-2-carboxylic acid methyl ester (10 g, 30.8 mmol) in tetrahydrofuran (50 mL) at 0° C. under a nitrogen atmosphere. After being heated at 60° C. for 2 hours, the resulting mixture was cooled to 0° C. and treated with 1 N hydrochloric acid to quench the reaction. The aqueous layer was extracted with diethyl ether (100 mL×5). The combined organic layers were dried over sodium sulfate and concentrated in vacuo to give (4-benzyloxy-6-fluoro-3-methyl-naphthalen-2-yl)-methanol (8.4 g, 92%) as a white solid. $^1$H NMR (400 MHz, CDCl$_3$) δ ppm 7.84 (dd, J=5.6, 9.2 Hz, 1H), 7.70 (dd, J=2.4, 10.0 Hz, 1H), 7.69 (s, 1H), 7.40-7.50 (m, 5H), 7.24 (td, J=2.4, 8.4 Hz, 1H), 4.99 (s, 2H), 4.87 (s, 2H), 2.47 (s, 3H).

1-benzyloxy-3-chloromethyl-7-fluoro-2-methyl-naphthalene

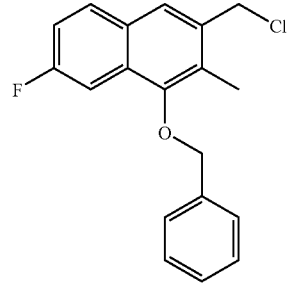

To a solution of triphenylphosphine (7.1 g, 27.2 mmol) in anhydrous tetrahydrofuran (32 mL) was added carbon tetrachloride (10 mL). The mixture was stirred for 10 minutes and 4-benzyloxy-6-fluoro-3-methyl-naphthalen-2-yl)-methanol (4 g, 13.6 mmol) was introduced as a solid under a nitrogen atmosphere. After being stirred at reflux for 2 hours, the resulting mixture was diluted with water, extracted with ethyl acetate (150 mL) and washed with water (50 mL×2). The combined aqueous layers were then extracted with ethyl acetate (150 mL) and the combined organic layers were dried over sodium sulfate and concentrated in vacuo. The residue was purified by column chromatography (5% ethyl acetate in petroleum ether) to afford 1-benzyloxy-3-chloromethyl-7-fluoro-2-methyl-naphthalene (3.5 g, 83%) as a white solid. $^1$H NMR (400 MHz, CDCl$_3$) δ ppm 7.83 (dd, J=5.6, 9.3 Hz, 1H), 7.71 (d, J=2.4 Hz, 1H), 7.68 (s, 1H), 7.40-7.58 (m, 5H), 7.25 (td, J=2.4, 8.8 Hz, 1H), 5.01 (s, 2H), 4.79 (s, 2H), 2.54 (s, 3H); MS cald. for C$_{19}$H$_{16}$ClFO 314, obsd. (ESI$^+$) [(M+H)$^+$] 315.

(4-benzyloxy-6-fluoro-3-methyl-naphthalen-2-yl)-acetic acid methyl ester

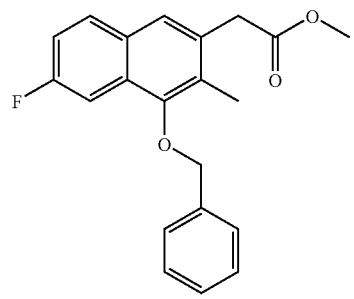 [SMILES: COC(=O)Cc1cc2ccc(F)cc2c(OCc2ccccc2)c1C]

A flask containing 1-benzyloxy-3-chloromethyl-7-fluoro-2-methyl-naphthalene (3.3 g, 10.4 mmol), bis(triphenylphosphine)dichloropalladium(II) (360 mg, 0.5 mmol) and potassium carbonate (1.52 g, 11.0 mmol) was evacuated and then filled with carbon monoxide (balloon). Methanol (18 mL) and tetrahydrofuran (35 mL) were added by means of a syringe. After being stirred at room temperature under a carbon monoxide atmosphere overnight, the resulting mixture was diluted with water (50 mL), and extracted with ethyl acetate (100 mL). The organic layer was washed with water (50 mL×2). The combined aqueous layers were extracted with ethyl acetate (150 mL) and the combined organic layers were dried over sodium sulfate and concentrated in vacuo. The residue was purified by column chromatography (20% ethyl acetate in petroleum ether) to afford (4-benzyloxy-6-fluoro-3-methyl-naphthalen-2-yl)-acetic acid methyl ester (3.4 g, 96%) as a white solid. ¹H NMR (400 MHz, CDCl₃) δ ppm 7.80 (dd, J=5.2, 8.4 Hz, 1H), 7.70 (d, J=10.4 Hz, 1H), 7.40-7.59 (m, 6H), 7.25 (td, J=2.0, 8.8 Hz, 1H), 5.00 (s, 2H), 3.84 (s, 2H), 3.75 (s, 3H), 2.42 (s, 3H); MS calcd. for C₂₁H₁₉FO₃ 338, obsd. (ESI⁺) [(M+H)⁺] 339.

(6-fluoro-4-hydroxy-3-methyl-naphthalen-2-yl)-acetic acid methyl ester

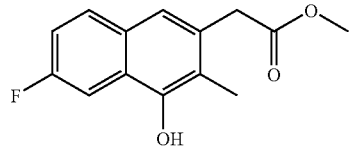

To a solution of (4-benzyloxy-6-fluoro-3-methyl-naphthalen-2-yl)-acetic acid methyl ester (3.4 g, 10.0 mmol) in methanol (50 mL) was added 10% palladium on carbon (0.5 g). The resulting mixture was vigorously stirred under a hydrogen (balloon) atmosphere overnight. The filtrate was concentrated in vacuo to give (6-fluoro-4-hydroxy-3-methyl-naphthalen-2-yl)-acetic acid methyl ester (2.44 g, 98%) as a white solid. ¹H NMR (400 MHz, CDCl₃) δ ppm 7.69-7.74 (m, 2H), 7.34 (s, 1H), 7.21 (td, J=2.4, 8.4 Hz, 1H), 5.16 (s, 1H), 3.82 (s, 2H), 3.74 (s, 3H), 2.35 (s, 3H); MS calcd. for C₁₄H₁₃FO₃ 248, obsd. (ESI⁺) [(M+H)⁺] 249.

[4-(4-ethanesulfonyl-phenoxy)-6-fluoro-3-methyl-naphthalen-2-yl]-acetic acid methyl ester

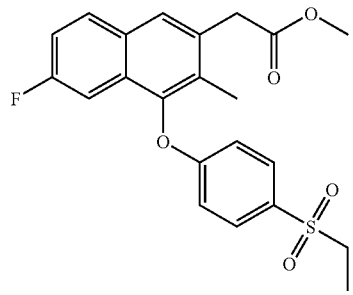 [SMILES: CCS(=O)(=O)c1ccc(Oc2c(C)c(CC(=O)OC)cc3ccc(F)cc23)cc1]

A sealed tube containing 6-fluoro-4-hydroxy-3-methyl-naphthalen-2-yl)-acetic acid methyl ester (100 mg, 0.4 mmol), 1-ethanesulfonyl-4-fluoro-benzene (152 mg, 0.8 mmol), and potassium carbonate (111 mg, 0.8 mmol) was evacuated and filled with nitrogen. Anhydrous N,N-dimethylformamide (2 mL) was added. After being stirred at 100° C. overnight, the mixture was cooled to room temperature, then diluted with water (10 mL), and extracted with ethyl acetate (10 mL×2). The combined organic layers were washed with brine (10 mL×3), dried over sodium sulfate and concentrated in vacuo. The residue was purified by column chromatography (30% ethyl acetate in petroleum ether) to give [4-(4-ethanesulfonyl-phenoxy)-6-fluoro-3-methyl-naphthalen-2-yl]-acetic acid methyl ester (160 mg, 96%). MS calcd. for C₂₂H₂₁FO₅S 416, obsd. (ESI⁺) [(M+H)⁺] 417.

[4-(4-ethanesulfonyl-phenoxy)-6-fluoro-3-methyl-naphthalen-2-yl]-acetic acid

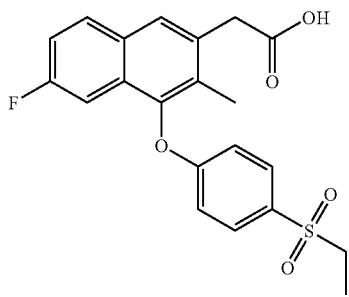 [SMILES: CCS(=O)(=O)c1ccc(Oc2c(C)c(CC(=O)O)cc3ccc(F)cc23)cc1]

Starting with [4-(4-ethanesulfonyl-phenoxy)-6-fluoro-3-methyl-naphthalen-2-yl]-acetic acid methyl ester (150 mg, 0.36 mmol), using a method analogous to the one described for example 1-1, final step, [4-(4-ethanesulfonyl-phenoxy)-6-fluoro-3-methyl-naphthalen-2-yl]-acetic acid (116 mg, 80%) was obtained as a white solid. ¹H NMR (400 MHz, CDCl₃) δ ppm 7.82 (d, J=8.84 Hz, 2H), 7.80-7.86 (m, 1H), 7.70 (s, 1H), 7.34 (dd, J=9.98, 2.40 Hz, 1H), 6.92 (d, J=8.84 Hz, 2H), 3.90 (s, 2H), 3.11 (q, J=7.33 Hz, 2H), 2.25 (s, 3H), 1.30 (t, J=7.45 Hz, 3H); MS calcd. for C₂₁H₁₉FO₅S 402, obsd. (ESI⁺) [(M+H)⁺] 403.

Examples 2-2 to 2-45

The following examples 2-2 to 2-45 were prepared in an analogous manner to example 2-1 starting with 4-fluoro-benzaldehyde or 4-chloro-benzaldehyde to derive (6-fluoro-4-hydroxy-3-methyl-naphthalen-2-yl)-acetic acid methyl ester or (6-chloro-4-hydroxy-3-methyl-naphthalen-2-yl)-acetic acid methyl ester, respectively, which were then further treated with the appropriate commercially available or prepared aryl derivatives in accordance with the procedure described for example 2-1.

| Example No. | Systematic Name | ¹H NMR (400 MHz, CDCl₃) δ ppm | MS (ESI⁺, [(M + H)⁺] | Structure |
|---|---|---|---|---|
| 2-2 | [6-fluoro-4-(4-methanesulfonyl-phenoxy)-3-methyl-naphthalen-2-yl]-acetic acid | 7.82-7.88 (m, 1H), 7.86 (d, J = 9.09 Hz, 2H), 7.70 (s, 1H), 7.33 (dd, J = 10.11, 2.53 Hz, 1H), 7.25 (dd, J = 10.11, 2.53 Hz, 1 H), 6.92 (d, J = 8.84 Hz, 2 H), 3.89 (s, 2H), 3.06 (s, 3 H), 2.25 (s, 3H) | 389 | 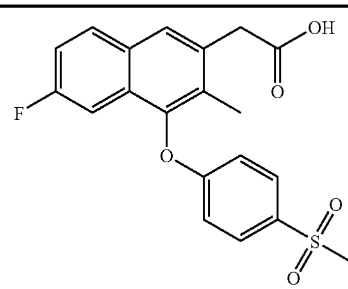 |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 2-3 | [6-fluoro-4-(4-methanesulfonyl-2-methyl-phenoxy)-3-methyl-naphthalen-2-yl]-acetic acid | 7.88 (d, J = 2.27 Hz, 1H), 7.84 (dd, J = 9.73, 5.43 Hz, 1H), 7.70 (s, 1H), 7.52 (dd, J = 8.21, 2.40 Hz, 1H), 7.23-7.26 (m, 1H), 6.26 (d, J = 8.84 Hz, 1H), 3.90 (s, 2H), 3.05 (s, 3H), 2.63 (s, 3H), 2.22 (s, 3H) | 403 | 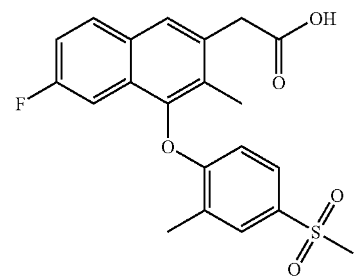 |
| 2-4 | {6-fluoro-3-methyl-4-[4-(propane-2-sulfonyl)-phenoxy]-naphthalen-2-yl}-acetic acid | 7.84 (dd, J = 8.97, 5.43 Hz, 1H), 7.79 (d, J = 8.84 Hz, 2H), 7.70 (s, 1H), 7.35 (dd, J = 10.11, 2.27 Hz, 1H), 6.90-6.94 (m, 2H), 3.90 (s, 2H), 3.14-3.22 (m, 1H), 2.24 (s, 3H), 1.31 (d, J = 6.82 Hz, 6H) | 417 | 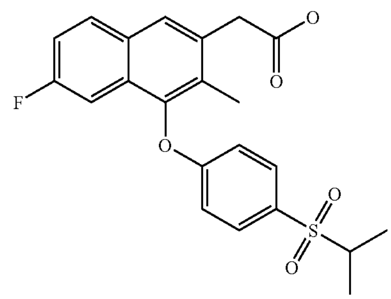 [SMILES: Cc1c(CC(=O)O)cc2ccc(F)cc2c1Oc1ccc(S(=O)(=O)C(C)C)cc1] |
| 2-5 | [4-(4-cyclopropanesulfonyl-phenoxy)-6-fluoro-3-methyl-naphthalen-2-yl]-acetic acid | 7.81 (d, J = 9.09 Hz, 2H), 7.79-7.86 (m, 1H), 7.70 (s, 1H), 7.35 (dd, J = 9.98, 2.40 Hz, 1H), 6.91 (d, J = 8.84 Hz, 2H), 3.90 (s, 2H) 2.43-2.50 (m, 1H), 2.25 (s, 3H), 1.31-1.36 (m, 2H), 1.04 (m, 1H) | 415 | 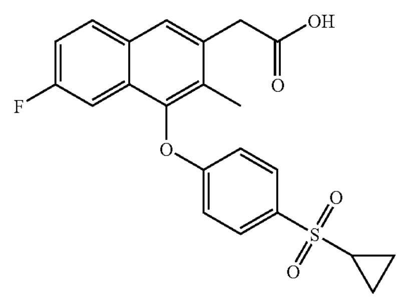 [SMILES: Cc1c(CC(=O)O)cc2ccc(F)cc2c1Oc1ccc(S(=O)(=O)C2CC2)cc1] |
| 2-6 | [6-fluoro-4-(4-methanesulfonyl-3-methyl-phenoxy)-3-methyl-naphthalen-2-yl]-acetic acid | 7.92 (d, J = 8.84 Hz, 1H), 7.84 (dd, J = 8.97, 5.68 Hz, 1H), 7.69 (s, 1H) 7.34 (dd, J = 10.23, 2.40 Hz, 1H), 7.22-7.26 (m, 1H), 6.80 (d, J = 2.02 Hz, 1H), 6.64 (dd, J = 8.72, 2.40 Hz, 1H), 3.90 (s, 2H), 3.07 (s, 3H), 2.64 (s, 3H), 2.25 (s, 3H) | 403 | 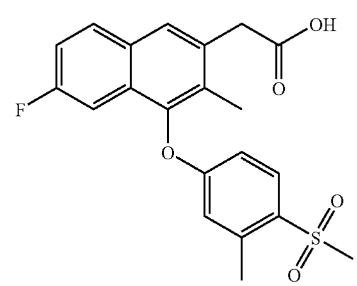 |
| 2-7 | [6-Chloro-4-(4-methanesulfonyl-phenoxy)-3-methyl-naphthalen-2-yl]-acetic acid | 7.86 (d, J = 8.84 Hz, 2H), 7.79 (d, J = 8.59 Hz, 1H), 7.72 (s, 1H), 7.69 (s, 1H), 7.42 (d, J = 7.07 Hz, 1H), 6.93 (d, J = 8.59 Hz, 2H), 3.90 (s, 2H), 3.07 (s, 3H), 2.24 (s, 3H) | 405 | 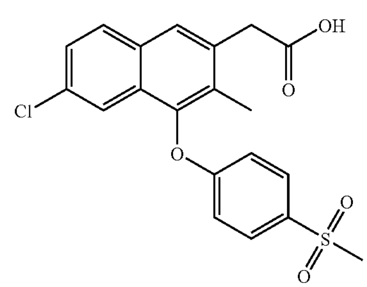 [SMILES: Cc1c(CC(=O)O)cc2ccc(Cl)cc2c1Oc1ccc(S(C)(=O)=O)cc1] |

| Example No. | Systematic Name | ¹H NMR (400 MHz, CDCl₃) δ ppm | MS (ESI⁺, [(M + H)⁺] | Structure |
|---|---|---|---|---|
| 2-8* | [6-chloro-4-(4-methanesulfonyl-3-methyl-phenoxy)-3-methyl-naphthalen-2-yl]-acetic acid | 7.91 (d, J = 8.84 Hz, 1H), 7.86 (d, J = 8.84 Hz, 1H), 7.72 (s, 1H), 7.62 (d, = 1.52 Hz, 1H), 7.39 (dd, J = 8.59, 2.02 Hz, 1H), 6.91 (d, J = 2.27 Hz, 1H), 6.77-6.82 (m, 1H), 3.74 (s, 2H), 3.11 (s, 3H), 2.62 (s, 3H), 2.26 (s, 3H) | 419 | 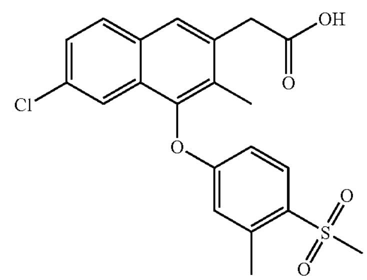 [SMILES: Cc1cc(Oc2c(C)c(CC(=O)O)cc3ccc(Cl)cc23)ccc1S(C)(=O)=O] |
| 2-9 | [6-chloro-4-(4-methanesulfonyl-2-methyl-phenoxy)-3-methyl-naphthalen-2-yl]-acetic acid | 7.89 (s, 1H), 7.79 (d, J = 8.34 Hz, 1H), 7.69 (s, 1H), 7.65 (s, 1H), 7.53 (br. s, 1H), 7.43 (dd, 1H), 6.25 (d, J = 8.59 Hz, 1H), 3.90 (s, 2H), 3.05 (s, 3H), 2.64 (s, 3H), 2.21 (s, 3H) | 419 | 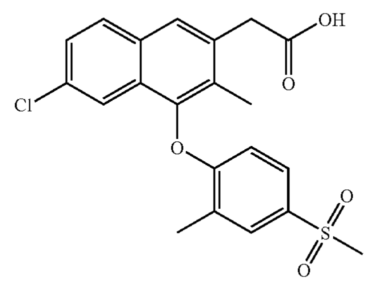 [SMILES: Cc1cc(S(C)(=O)=O)ccc1Oc1c(C)c(CC(=O)O)cc2ccc(Cl)cc12] |
| 2-10 | [4-(4-ethanesulfonyl-2-methyl-phenoxy)-6-fluoro-3-methyl-naphthalen-2-yl]-acetic acid | 7.85 (br. s, 2H), 7.70 (s, 1H), 7.48 (d, J = 8.08 Hz, 1H), 7.24 (br. s, 2H), 6.25 (d, J = 8.08 Hz, 1H), 3.90 (s, 2H), 3.11 (q, J = 7.49 Hz, 2H), 2.62 (s, 3H), 2.22 (s, 3H), 1.29 (t, J = 6.82 Hz, 3H) | 417 | 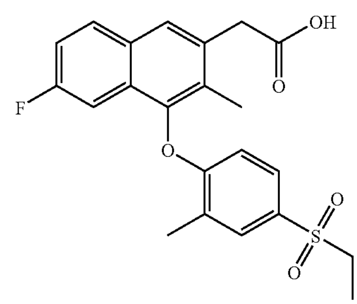 |
| 2-11 | [4-(3-chloro-4-methanesulfonyl-phenoxy)-6-fluoro-3-methyl-naphthalen-2-yl]-acetic acid | (d, J = 8.84 Hz, 1H), 7.86 (dd, J = 8.72, 5.43 Hz, 1H), 7.72 (s, 1H), 7.29 (br. s, 1H), 7.24-7.26 (m, 1H), 6.99 (d, J = 1.77 Hz, 1H), 6.80 (dd, J = 9.09, 2.02 Hz, 2H), 3.91 (s, 2H), 3.26 (s, 3H), 2.26 (s, 3H) | 423 | 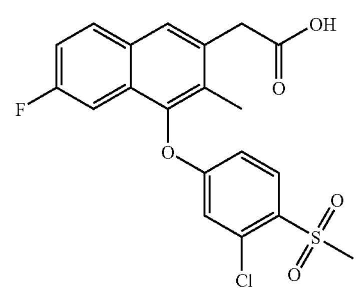 [SMILES: Cc1c(CC(=O)O)cc2ccc(F)cc2c1Oc1ccc(S(C)(=O)=O)c(Cl)c1] |
| 2-12 | [6-fluoro-4-(2-fluoro-4-methanesulfonyl-phenoxy)-3-methyl-naphthalen-2-yl]-acetic acid | 7.85 (t, J = 8.34 Hz, 2H), 7.72 (s, 1H), 7.49 (d, J = 8.34 Hz, 1H), 7.35 (d, J = 9.85 Hz, 1H), 7.29 (br. s, 1H), 6.45 (t, J = 8.21 Hz, 1H), 3.91 (s, 2H), 3.07 (s, 3H), 2.28 (s, 3H), | 407 | 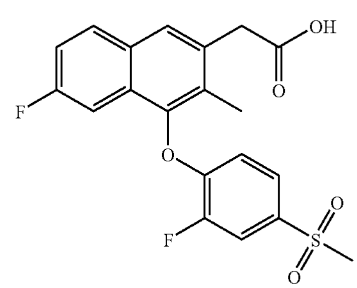 |

-continued

| Example No. | Systematic Name | 1H NMR (400 MHz, CDCl3) δ ppm | MS (ESI+, [(M + H)+] | Structure |
|---|---|---|---|---|
| 2-13 | [4-(4-ethanesulfonyl-2-fluoro-phenoxy)-6-fluoro-3-methyl-naphthalen-2-yl]-acetic acid | 7.86 (dd, J = 8.97, 5.43 Hz, 1H), 7.80 (dd, J = 9.73, 2.15 Hz, 1H), 7.72 (s, 1H), 7.45 (dd, J = 8.59, 1.26 Hz, 1H), 7.36 (dd, J = 9.85, 2.27 Hz, 1H), 7.29 (br. s, 1 H), 6.45 (t, 1H), 3.91 (s, 2 H), 3.13 (q, J = 7.41 Hz, 2 H), 2.27 (s, 3H), 1.31 (t, J = 7.33 Hz, 3H) | 421 | 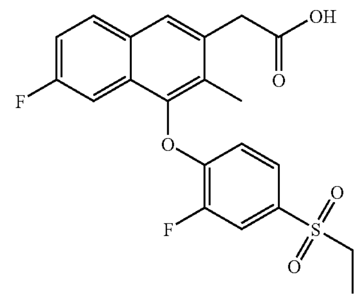 |
| 2-14 | [4-(4-ethanesulfonyl-3-methyl-phenoxy)-6-fluoro-3-methyl-naphthalen-2-yl]-acetic acid | 7.88 (d, J = 8.84 Hz, 1H), 7.84 (dd, J = 8.97, 5.18 Hz, 1H), 7.70 (s, 1H), 7.35 (dd, J = 10.11, 2.53 Hz, 1 H), 7.24 (dd, J = 10.11, 2.53 Hz, 1H), 6.80 (d, J = 2.27 Hz, 1H), 6.65 (dd, J = 8.72, 2.40 Hz, 1H), 3.90 (s, 2H), 3.14 (q, J = 7.49 Hz, 2 H), 2.62 (s, 3H), 2.25 (s, 3 H), 1.29 (t, J = 7.45 Hz, 3 H) | 417 | 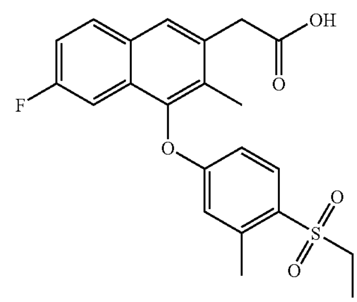 [SMILES: CCS(=O)(=O)c1ccc(Oc2c(C)c(CC(=O)O)cc3ccc(F)cc23)cc1C] |
| 2-15 | [4-(2,5-difluoro-4-methanesulfonyl-phenoxy)-6-fluoro-3-methyl-naphthalen-2-yl]-acetic acid | 7.86 (ddd, J = 9.73, 5.43, 5.05 Hz, 2H), 7.74 (s, 1H), 7.31 (ddd, J = 9.35, 7.07, 2.53 Hz, 2H), 6.17 (dd, J = 10.36, 6.32 Hz, 1H), 3.91 (s, 2H), 3.20 (s, 3H), 2.29 (s, 3H) | 425 | 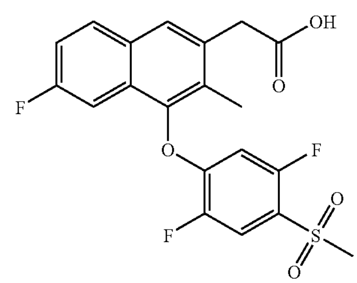 [SMILES: Cc1c(CC(=O)O)cc2ccc(F)cc2c1Oc1cc(F)c(S(C)(=O)=O)cc1F] |
| 2-16 | [6-fluoro-4-(3-fluoro-4-methanesulfonyl-phenoxy)-3-methyl-naphthalen-2-yl]-acetic acid | 7.83-7.90 (m, 2H), 7.72 (s, 1H), 7.30 (br. s, 1H), 7.25 (br. s, 1H), 6.75 (dd, J = 8.97, 1.89 Hz, 1H), 6.62 (dd, J = 11.49, 2.15 Hz, 1 H), 3.91 (s, 2H), 3.21 (s, 3 H), 2.26 (s, 3H) | 407 | 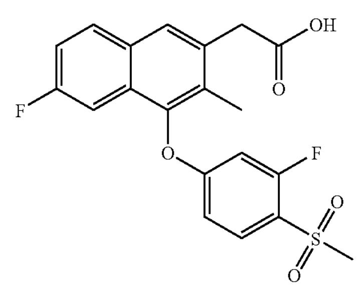 [SMILES: Cc1c(CC(=O)O)cc2ccc(F)cc2c1Oc1ccc(S(C)(=O)=O)c(F)c1] |
| 2-17 | [4-(4-ethanesulfonyl-3-fluoro-phenoxy)-6-fluoro-3-methyl-naphthalen-2-yl]-acetic acid | 7.85 (ddd, J = 8.65, 4.23, 4.04 Hz, 2H), 7.71 (s, 1H), 7.31 (br. s, 1H), 7.25 (br. s, 1H), 6.75 (dd, J = 8.72, 2.15 Hz, 1H), 6.61 (dd, J = 11.12, 2.27 Hz, 1H), 3.90 (s, 2H), 3.29 (q, J = 7.49 Hz, 2H), 2.25 (s, 3H), 1.33 (t, J = 7.45 Hz, 3H) | 421 | 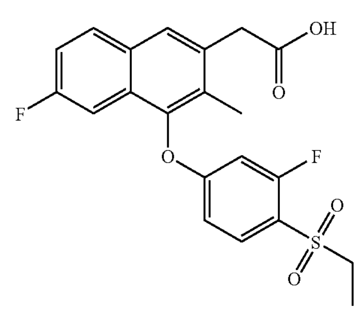 [SMILES: CCS(=O)(=O)c1ccc(Oc2c(C)c(CC(=O)O)cc3ccc(F)cc23)cc1F] |

-continued

| Example No. | Systematic Name | $^1$H NMR (400 MHz, CDCl$_3$) δ ppm | MS (ESI$^+$, [(M + H)$^+$]) | Structure |
|---|---|---|---|---|
| 2-18 | [4-(2-cyano-4-ethanesulfonyl-phenoxy)-6-fluoro-3-methyl-naphthalen-2-yl]-acetic acid | 8.29 (d, J = 2.27 Hz, 1H), 7.85 (ddd, J = 8.97, 2.15 Hz, 2H), 7.88 (dd, 1H), 7.74 (s, 1H), 7.31 (br. s, 2H), 6.49 (d, J = 8.84 Hz, 1H), 3.91 (s, 2H), 3.15 (q, J = 7.41 Hz, 2H), 2.26 (s, 3H), 1.33 (t, J = 7.45 Hz, 3H) | 428 | 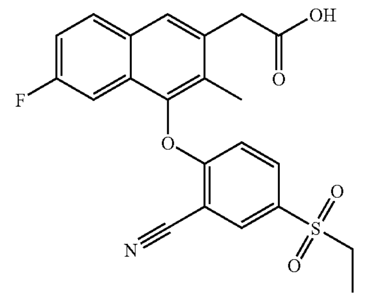 [SMILES: CCS(=O)(=O)c1ccc(Oc2c(C)c(CC(=O)O)cc3ccc(F)cc23)c(C#N)c1] |
| 2-19 | [4-(3-chloro-4-ethanesulfonyl-phenoxy)-6-fluoro-3-methyl-naphthalen-2-yl]-acetic acid | 8.02 (d, J = 8.84 Hz, 1H), 7.85 (dd, J = 8.97, 5.43 Hz, 1H), 7.71 (s, 1H), 7.31 (br. s, 1H), 7.25 (br. s, 1H), 6.98 (d, J = 2.27 Hz, 1H), 6.79 (dd, J = 8.84, 2.27 Hz, 1H), 3.90 (s, 2H), 3.41 (q, J = 7.58 Hz, 2H), 2.25 (s, 3H), 1.30 (t, J = 7.45 Hz, 3H) | 437 | 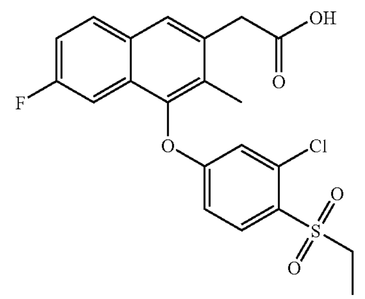 [SMILES: CCS(=O)(=O)c1ccc(Oc2c(C)c(CC(=O)O)cc3ccc(F)cc23)cc1Cl] |
| 2-20 | [4-(2-chloro-4-methanesulfonyl-phenoxy)-6-fluoro-3-methyl-naphthalen-2-yl]-acetic acid | 8.12 (d, J = 2.27 Hz, 1H), 7.86 (dd, J = 8.84, 5.31 Hz, 1H), 7.73 (s, 1H), 7.59 (dd, J = 8.72, 2.40 Hz, 1H), 7.28-7.32 (m, 1H), 7.25 (br. s, 1H), 6.41 (d, J = 8.84 Hz, 1H), 3.91 (s, 2H), 3.07 (s, 3H), 2.26 (s, 3H) | 423 | 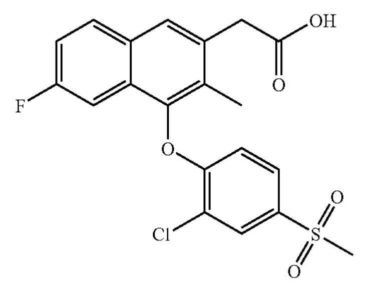 |
| 2-21 | [4-(2-chloro-4-ethanesulfonyl-phenoxy)-6-fluoro-3-methyl-naphthalen-2-yl]-acetic acid | 8.08 (d, J = 2.27 Hz, 1H), 7.86 (dd, J = 9.09, 5.31 Hz, 1H), 7.72 (s, 1H), 7.55 (dd, J = 8.72, 2.15 Hz, 1H), 7.30 (br. s, 1H), 7.25 (br. s, 1H), 6.41 (d, J = 8.84 Hz, 1H), 3.91 (s, 2H), 3.13 (q, J = 7.58 Hz, 2H), 2.26 (s, 3H), 1.32 (t, J = 7.45 Hz, 3H) | 437 | 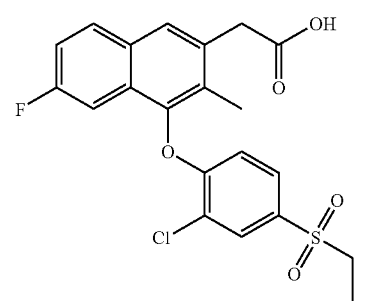 |
| 2-22 | {6-fluoro-3-methyl-4-[4-(propane-1-sulfonyl)-phenoxy]-naphthalen-2-yl}-acetic acid | 7.85 (t, 1H), 7.81 (d, J = 8.84 Hz, 2H), 7.70 (s, 1H), 7.34 (dd, J = 10.11, 2.53 Hz, 1H), 7.25 (dd, 1H), 6.92 (d, J = 8.84 Hz, 2H), 3.90 (s, 2H), 3.03-3.09 (m, 2H), 2.25 (s, 3H), 1.71-1.81 (m, 2H), 1.02 (t, J = 7.45 Hz, 3H) | 417 | 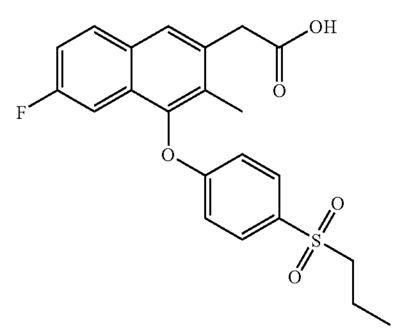 [SMILES: CCCS(=O)(=O)c1ccc(Oc2c(C)c(CC(=O)O)cc3ccc(F)cc23)cc1] |

-continued

| Example No. | Systematic Name | $^1$H NMR (400 MHz, CDCl$_3$) δ ppm | MS (ESI$^+$, [(M + H)$^+$] | Structure |
| --- | --- | --- | --- | --- |
| 2-23 | {4-[4-(butane-1-sulfonyl)-phenoxy]-6-fluoro-3-methyl-naphthalen-2-yl}-acetic acid | 7.83-7.87 (m, 1H), 7.81 (d, J = 8.84 Hz, 2H), 7.70 (s, 1H), 7.34 (dd, J = 10.23, 2.40 Hz, 1H), 7.22-7.26 (m, 1H), 6.92 (d, J = 8.84 Hz, 2H), 3.90 (s, 2H), 3.04-3.11 (m, 2H), 2.25 (s, 3H), 1.68-1.76 (m, 2H), 1.36-1.46 (m, 2H), 0.91 (t, J = 7.33 Hz, 3H) | 431 | 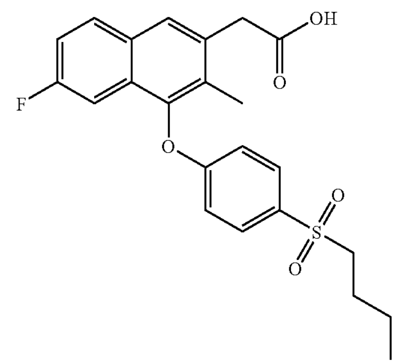 [SMILES: CCCCS(=O)(=O)c1ccc(Oc2c(C)c(CC(=O)O)cc3ccc(F)cc23)cc1] |
| 2-24 | [4-(5-chloro-4-ethanesulfonyl-2-fluoro-phenoxy)-6-fluoro-3-methyl-naphthalen-2-yl]-acetic acid | 8.03 (d, J = 10.36 Hz, 1H), 7.87 (dd, J = 8.84, 5.31 Hz, 1H), 7.74 (s, 1H), 7.28-7.36 (m, 2H), 6.43 (d, J = 7.07 Hz, 1H), 3.91 (s, 2H), 3.39 (q, J = 7.33 Hz, 2H), 2.28 (s, 3H), 1.32 (t, J = 7.45 Hz, 3H) | 455 | 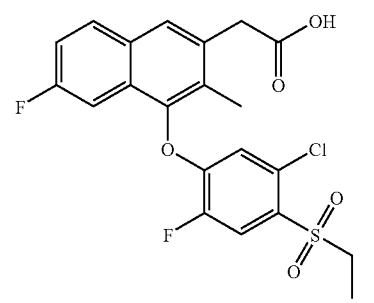 [SMILES: CCS(=O)(=O)c1cc(F)c(Oc2c(C)c(CC(=O)O)cc3ccc(F)cc23)cc1Cl] |
| 2-25 | [4-(2-chloro-4-ethanesulfonyl-5-fluoro-phenoxy)-6-fluoro-3-methyl-naphthalen-2-yl]-acetic acid | 8.10 (d, J = 6.82 Hz, 1H), 7.87 (dd, J = 9.47, 5.68 Hz, 1H), 7.74 (s, 1H), 7.28-7.32 (m, 2H), 6.09-6.16 (m, 1H), 3.91 (s, 2H), 3.27 (q, J = 7.41 Hz, 2H), 2.27 (s, 3H), 1.34 (t, J = 7.45 Hz, 3H) | 455 | 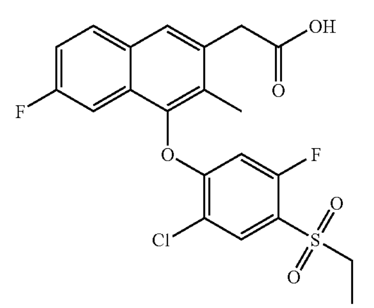 [SMILES: CCS(=O)(=O)c1cc(Cl)c(Oc2c(C)c(CC(=O)O)cc3ccc(F)cc23)cc1F] |
| 2-26 | [4-(4-cyclopentanesulfonyl-phenoxy)-6-fluoro-3-methyl-naphthalen-2-yl]-acetic acid | 7.83-7.87 (m, 1H), 7.81 (d, J = 8.84 Hz, 2H), 7.70 (s, 1H), 7.35 (dd, J = 10.11, 2.27 Hz, 1H), 7.24 (dd, J = 10.11, 2.27 Hz, 1H), 6.91 (d, J = 8.84 Hz, 2H), 3.90 (s, 2H), 2.21-2.26 (m, 3H), 2.01-2.11 (m, 2H), 1.85-1.95 (m, 2H), 1.73-1.81 (m, 2H), 1.56-1.67 (m, 2H) | 443 | 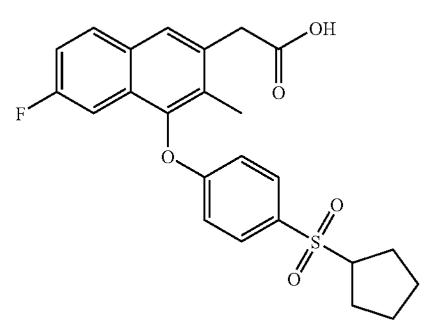 |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 2-27 | {6-fluoro-4-[4-(4-fluoro-benzenesulfonyl)-phenoxy]-3-methyl-naphthalen-2-yl}-acetic acid | 7.92-7.98 (m, 2H), 7.80-7.87 (m, 3H), 7.69 (s, 1H), 7.28-7.32 (m, 1H), 7.14-7.25 (m, 3H), 6.87 (d, J = 8.84 Hz, 2H), 3.89 (s, 2H), 2.22 (s, 3H) | 469 | 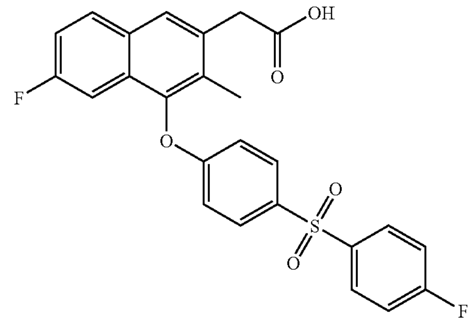 [SMILES: Cc1c(CC(=O)O)cc2ccc(F)cc2c1Oc1ccc(S(=O)(=O)c2ccc(F)cc2)cc1] |
| 2-28 | [4-(4-benzenesulfonyl-phenoxy)-6-fluoro-3-methyl-naphthalen-2-yl]-acetic acid | 7.94 (d, J = 7.07 Hz, 1H), 7.80-7.89 (m, 3H) 7.68 (s, 1H), 7.49-7.59 (m, 3H), 7.29-7.32 (m, 1H), 7.20-7.26 (m, 1H), 6.86 (d, J = 8.84 Hz, 2H), 3.89 (s, 2H), 2.22 (s, 3H) | 451 | 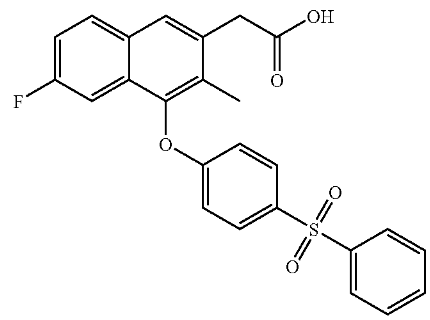 [SMILES: Cc1c(CC(=O)O)cc2ccc(F)cc2c1Oc1ccc(S(=O)(=O)c2ccccc2)cc1] |
| 2-29 | {6-fluoro-3-methyl-4-[4-(toluene-4-sulfonyl)-phenoxy]-naphthalen-2-yl}-acetic acid | 7.82 (t, J = 8.21 Hz, 5H), 7.68 (s, 1H), 7.30 (d, = 8.08 Hz, 2H), 7.26 (br. s, 2 H), 6.84 (d, J = 8.84 Hz, 2 H), 3.89 (s, 2H), 2.41 (s, 3 H), 2.22 (s, 3H) | 465 | 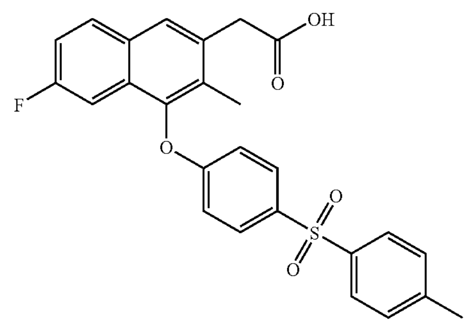 [SMILES: Cc1ccc(S(=O)(=O)c2ccc(Oc3c(C)c(CC(=O)O)cc4ccc(F)cc34)cc2)cc1] |
| 2-30 | {6-fluoro-4-[4-(4-methoxy-benzenesulfonyl)-phenoxy]-3-methyl-naphthalen-2-yl}-acetic acid | 7.78-7.91 (m, 5H), 7.70 (s, 1H), 7.30-7.34 (m, 1 H), 7.21-7.27 (m, 1H), 6.98 (d, J = 8.84 Hz, 2H), 6.85 (d, J = 8.84 Hz, 2H), 3.90 (s, 2H), 3.86 (s, 3H), 2.23 (s, 3H) | 481 | 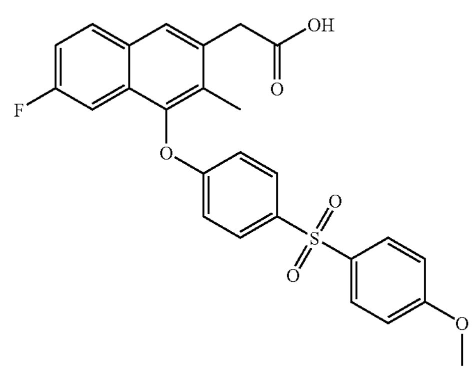 [SMILES: COc1ccc(S(=O)(=O)c2ccc(Oc3c(C)c(CC(=O)O)cc4ccc(F)cc34)cc2)cc1] |

| Example No. | Systematic Name | $^1$H NMR (400 MHz, CDCl$_3$) δ ppm | MS (ESI$^+$, [(M + H)$^+$]) | Structure |
|---|---|---|---|---|
| 2-31 | {4-[4-(4-chloro-benzenesulfonyl)-phenoxy]-6-fluoro-3-methyl-naphthalen-2-yl}-acetic acid | 7.82-7.89 (m, 5H), 7.70 (s, 1H), 7.50 (d, J = 8.84 Hz, 2H), 7.32 (m, 1H), 7.24 (m, 1H), 6.88 (d, J = 8.84 Hz, 2H), 3.90 (s, 2H), 2.23 (s, 3H) | 485 | 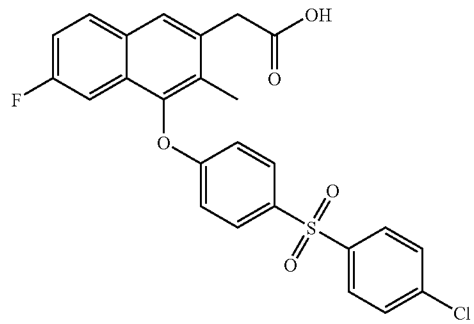 [SMILES: Cc1c(CC(=O)O)cc2ccc(F)cc2c1Oc1ccc(S(=O)(=O)c2ccc(Cl)cc2)cc1] |
| 2-32** | [6-fluoro-4-(5-methanesulfonyl-pyridin-2-yloxy)-3-methyl-naphthalen-2-yl]-acetic acid | 12.50 (s, 1H), 8.52 (d, J = 2.53 Hz, 1H), 8.39 (dd, J = 8.59, 2.53 Hz, 1H), 8.03 (dd, J = 9.09, 5.56 Hz, 1H), 7.82 (s, 1H), 7.38-7.46 (m, 2H), 7.30 (dd, J = 10.36, 2.27 Hz, 1H), 3.84 (s, 2H), 3.29 (s, 3H), 2.14 (s, 3H) | 390 | 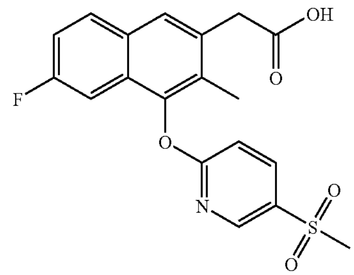 |
| 2-33** | [4-(5-ethanesulfonyl-pyridin-2-yloxy)-6-fluoro-3-methyl-naphthalen-2-yl]-acetic acid | 8.48 (br. s, 1H), 8.34 (d, J = 8.34 Hz, 1H), 8.02 (ddd, J = 6.63, 3.79, 3.47 Hz, 1H), 7.81 (s, 1H), 7.43 (br. s, 2H), 7.31 (d, J = 10.11 Hz, 1 H), 3.84 (s, 2 H), 3.36 (br. s, 2H), 2.14 (s, 3H), 1.13 (t, J = 6.95 Hz, 3H) | 404 | 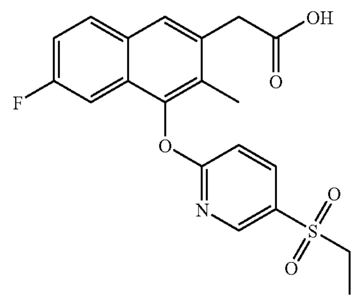 [SMILES: CCS(=O)(=O)c1ccc(Oc2c(C)c(CC(=O)O)cc3ccc(F)cc23)nc1] |
| 2-34** | [6-fluoro-4-(5-methanesulfonyl-3-methyl-pyridin-2-yloxy)-3-methyl-naphthalen-2-yl]-acetic acid | 8.29 (dd, J = 10.86, 2.02 Hz, 2H), 8.01 (dd, J = 8.97, 5.68 Hz, 1H), 7.79 (s, 1H), 7.39 (td, J = 8.84, 2.53 Hz, 1H), 7.28 (dd, J = 10.48, 2.65 Hz, 1H), 3.83 (s, 2H), 3.25 (s, 3H), 2.60 (s, 3H), 2.11 (s, 3H) | 404 | 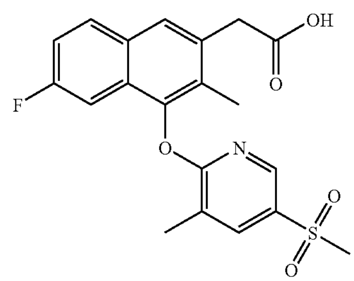 |
| 2-35** | [4-(5-ethanesulfonyl-3-methyl-pyridin-2-yloxy)-6-fluoro-3-methyl-naphthalen-2-yl]-acetic acid | 8.24 (d, J = 9.35 Hz, 5H), 8.22-8.27 (m, 5H), 8.01 (dd, J = 9.09, 5.81 Hz, 5H), 7.79 (s, 5H), 7.40 (td, J = 8.84, 2.53 Hz, 5H), 7.31 (dd, J = 10.48, 2.40 Hz, 5 H), 3.83 (s, 2H), 3.31 (t, 2 H), 2.59 (s, 3 H), 2.10 (s, 3 H), 1.12 (t, J = 7.45 Hz, 3 H) | 418 | 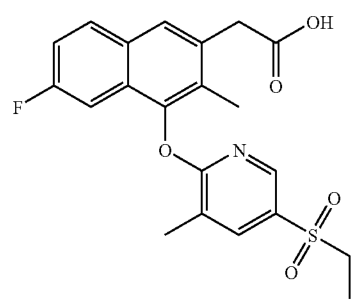 [SMILES: CCS(=O)(=O)c1cnc(Oc2c(C)c(CC(=O)O)cc3ccc(F)cc23)c(C)c1] |

-continued

| Example No. | Systematic Name | ¹H NMR (400 MHz, CDCl₃) δ ppm | MS (ESI⁺, [(M + H)⁺] | Structure |
|---|---|---|---|---|
| 2-36* | [4-(3-bromo-5-methanesulfonyl-pyridin-2-yloxy)-6-fluoro-3-methyl-naphthalen-2-yl]-acetic acid | 8.67 (d, J = 2.02 Hz, 1H), 8.41 (d, J = 2.27 Hz, 1H), 7.94 (dd, J = 8.97, 5.43 Hz, 1H), 7.77 (s, 1H), 7.28 (td, J = 8.84, 2.27 Hz, 1H), 7.20 (dd, J = 10.23, 2.40 Hz, 1H), 3.88 (s, 2H), 3.20 (s, 3H), 2.22 (s, 3H) | 468 | 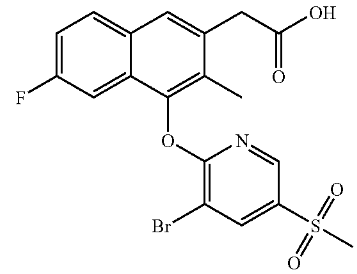 [SMILES: Cc1c(CC(=O)O)cc2ccc(F)cc2c1Oc1ncc(S(C)(=O)=O)cc1Br] |
| 2-37 | [4-(4-dimethylsulfamoyl-phenoxy)-6-fluoro-3-methyl-naphthalen-2-yl]-acetic acid | 7.84 (dd, J= 8.84, 5.56 Hz, 1H), 7.70 (br. s, 3H), 7.36 (dd, J = 10.23, 2.40 Hz, 1H), 7.25 (dd, J = 10.23, 2.40 Hz, 1H), 6.90 (d, J = 8.84 Hz, 2H), 3.90 (s, 2H), 2.72 (s, 6H), 2.25 (s, 3H) | 418 | 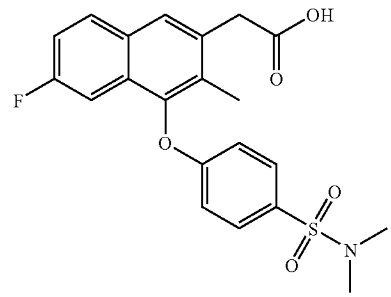 [SMILES: Cc1c(CC(=O)O)cc2ccc(F)cc2c1Oc1ccc(S(=O)(=O)N(C)C)cc1] |
| 2-38** | {6-fluoro-3-methyl-4-[4-(pyrrolidine-1-sulfonyl)-phenoxy]-naphthalen-2-yl}-acetic acid | 12.51 (s, 1H), 8.05 (dd, J = 9.09, 5.56 Hz, 1H), 7.85 (s, 1H), 7.77 (d, J = 9.09 Hz, 2H), 7.43 (td, J = 8.84, 2.53 Hz, 1H), 7.31 (dd, J = 10.61, 2.53 Hz, 1H), 3.86 (s, 2H), 3.11 (br. s, 4H), 2.17 (s, 3H), 1.64 (ddd, J = 6.38, 3.66, 3.35 Hz, 4H) | 444 | 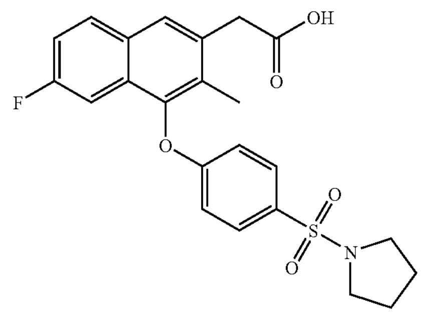 [SMILES: Cc1c(CC(=O)O)cc2ccc(F)cc2c1Oc1ccc(S(=O)(=O)N2CCCC2)cc1] |
| 2-39** | [4-(4-diethylsulfamoyl-phenoxy)-6-fluoro-3-methyl-naphthalen-2-yl]-acetic acid | 12.51 (s, 1H), 8.05 (dd, J = 8.97, 5.68 Hz, 1H), 7.84 (s, 1H), 7.74 (d, J = 9.09 Hz, 2H), 7.43 (td, J = 8.84, 2.53 Hz, 1H), 7.30 (dd, J = 10.36, 2.53 Hz, 1H), 6.94 (d, J = 9.09 Hz, 2H), 3.86 (s, 2H) 3.13 (q, J = 7.07 Hz, 4H), 2.17 (s, 3H), 1.02 (t, J = 7.07 Hz, 6H) | 446 | 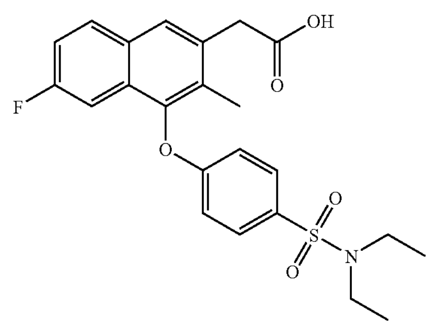 [SMILES: CCN(CC)S(=O)(=O)c1ccc(Oc2c(C)c(CC(=O)O)cc3ccc(F)cc23)cc1] |
| 2-40** | {6-fluoro-3-methyl-4-[4-(morpholine-4-sulfonyl)-phenoxy]-naphthalen-2-yl}-acetic acid | 12.53 (br. s, 1H), 8.06 (dd, J = 8.97, 5.68 Hz, 1H), 7.85 (s, 1H), 7.70 (d, J = 8.84 Hz, 2H), 7.44 (td, J = 8.84, 2.78 Hz, 1H), 7.33 (dd, J = 10.23, 2.65 Hz, 1H), 7.00 (d, J = 8.59 Hz, 2H), 3.87 (s, 2H), 3.59-3.65 (m, 4H), 2.84 (t, 4H), 2.18 (s, 3H) | 460 | 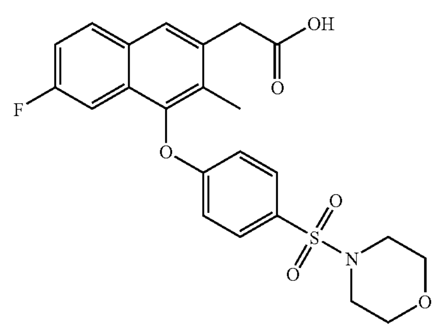 [SMILES: Cc1c(CC(=O)O)cc2ccc(F)cc2c1Oc1ccc(S(=O)(=O)N2CCOCC2)cc1] |

-continued

| Example No. | Systematic Name | $^1$H NMR (400 MHz, CDCl$_3$) δ ppm | MS (ESI$^+$, [(M + H)$^+$] | Structure |
|---|---|---|---|---|
| 2-41** | {6-fluoro-3-methyl-4-[4-(4-methyl-piperazine-1-sulfonyl)-phenoxy]-naphthalen-2-yl}-acetic acid | 12.53 (br. s, 1H), 8.07 (dd, J = 9.09, 5.56 Hz, 1H), 7.87 (s, 1H), 7.76 (d, J = 8.84 Hz, 2H), 7.45 (td, J= 8.84, 2.53 Hz, 1H), 7.31 (dd J = 10.23 2.40 Hz 1 H), 7.04 (d, J = 9.09 Hz, 2 H), 3.86 (s, 2H), 3.44 (br. s, 8H), 2.77 (s, 3H), 2.18 (s, 3H) | 473 | 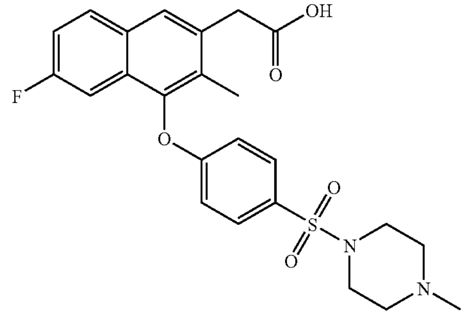 [SMILES: Cc1c(CC(=O)O)cc2ccc(F)cc2c1Oc1ccc(S(=O)(=O)N2CCN(C)CC2)cc1] |
| 2-42** | {4-[4-(4,4-difluoro-piperidine-1-sulfonyl)-phenoxy]-6-fluoro-3-methyl-naphthalen-2-yl}-acetic acid | 12.53 (s, 1H), 8.05 (dd, J = 9.09, 5.56 Hz, 1H), 7.85 (s, 1H) 7.75 (d, J = 8.84 Hz, 2 H), 7.43 (td, J = 8.72, 2.53 Hz, 1H), 7.32 (dd, J = 10.36, 2.53 Hz, 1H), 7.00 (d, J = 8.84 Hz, 2H), 3.86 (s, 2H), 3.04-3.11 (m, 4 H), 2.18 (s, 3H), 1.98-2.10 (m, 4H) | 494 | 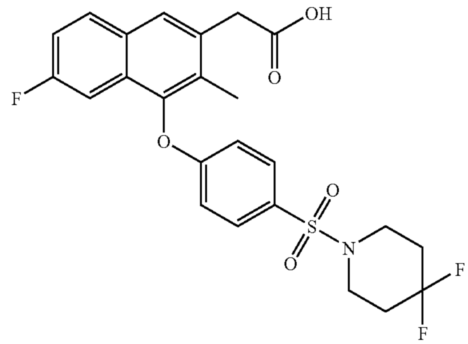 [SMILES: Cc1c(CC(=O)O)cc2ccc(F)cc2c1Oc1ccc(S(=O)(=O)N2CCC(F)(F)CC2)cc1] |
| 2-43 | {6-fluoro-3-methyl-4-[4-(2-oxa-6-aza-spiro[3.3]heptane-6-sulfonyl)-phenoxy]-naphthalen-2-yl}-acetic acid | 7.85 (dd, J = 8.97, 5.43 Hz, 1H), 7.75 (d, J = 8.84 Hz, 2 H), 7.70 (s, 1H), 7.33 (dd, J = 9.98, 2.15 Hz, 1H), 6.93 (d, J = 8.84 Hz, 2H), 4.64 (s, 4H), 3.95 (s, 4H), 3.90 (s, 2H), 2.25 (s, 3H) | 472 | 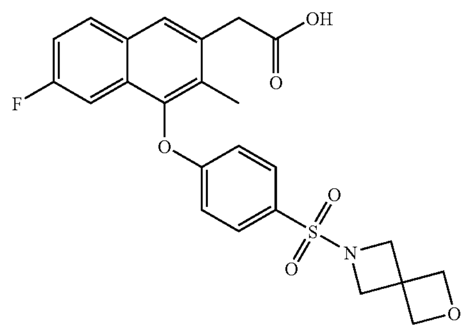 [SMILES: Cc1c(CC(=O)O)cc2ccc(F)cc2c1Oc1ccc(S(=O)(=O)N2CC3(COC3)C2)cc1] |
| 2-44 | [4-(4-cyano-phenoxy)-6-fluoro-3-methyl-naphthalen-2-yl]-acetic acid | 7.83 (dd, J = 9.09, 5.56 Hz, 1H), 7.69 (s, 1H), 7.58 (d, J = 8.84 Hz, 2H), 7.32 (dd, J = 10.11, 2.27 Hz, 1H), 7.24 (dd., J = 10.11, 2.27 Hz, 1H), 6.86 (d, J = 8.84 Hz, 2H), 3.89 (s, 2H), 2.24 (s, 3H) | 336 | 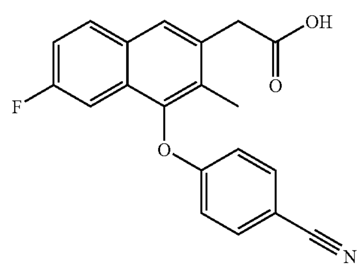 [SMILES: Cc1c(CC(=O)O)cc2ccc(F)cc2c1Oc1ccc(C#N)cc1] |
| 2-45 | [6-chloro-4-(4-cyano-phenoxy)-3-methyl-naphthalen-2-yl]-acetic acid | 7.78 (d, J = 8.84 Hz, 1H), 7.70 (d, J = 1.77 Hz, 1H), 7.67 (s, 1H), 7.58 (d, J = 8.84 Hz, 2H), 7.42 (dd, J = 8.84, 2.02 Hz, 1H), 6.85 (d, J = 8.84 Hz, 2H), 3.89 (s, 2 H) 2.23 (s, 3H) | 352 | 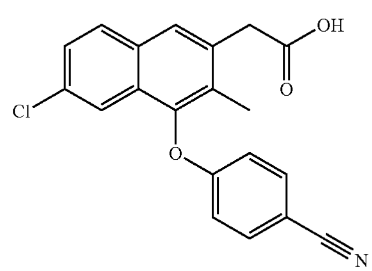 [SMILES: Cc1c(CC(=O)O)cc2ccc(Cl)cc2c1Oc1ccc(C#N)cc1] |

*CD$_3$OD was used as the solvent for $^1$H NMR;
**DMSO-d$_6$ was used as the solvent for $^1$H NMR.

Example 3-1

[4-(4-methanesulfonyl-phenoxy)-naphthalen-2-yl]-acetic acid

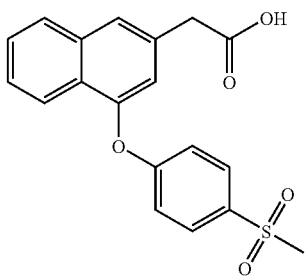 [SMILES: CS(=O)(=O)c1ccc(Oc2cc(CC(=O)O)cc3ccccc23)cc1]

(4-Hydroxy-naphthalen-2-yl)-acetic acid methyl ester

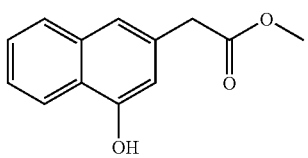 [SMILES: COC(=O)Cc1cc(O)c2ccccc2c1]

To a solution of (4-benzyloxy-6-chloro-naphthalen-2-yl)-acetic acid methyl ester (340 mg, 1.0 mmol, prepared using a method analogous to the one described above for the preparation of 4-benzyloxy-6-fluoro-naphthalene-2-carboxylic acid methyl ester, $1^{st}$-$7^{th}$ step for example 1-1) in methanol was added 10% palladium on carbon (10 mg). The resulting mixture was vigorously stirred at room temperature overnight under a hydrogen atmosphere (balloon) and then filtered. The filtrate was concentrated in vacuo to give (4-hydroxy-naphthalen-2-yl)-acetic acid methyl ester (200 mg, 92.6%) as a white solid.

[4-(4-methanesulfonyl-phenoxy)-naphthalen-2-yl]-acetic acid

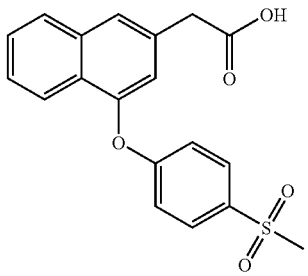 [SMILES: CS(=O)(=O)c1ccc(Oc2cc(CC(=O)O)cc3ccccc23)cc1]

Starting with (4-hydroxy-naphthalen-2-yl)-acetic acid methyl ester (108 mg, 0.5 mmol) and 1-fluoro-4-methanesulfonyl-benzene (174 mg, 1.0 mmol), using a method analogous to the one described for example 1-1, the final two steps), 4-(4-methanesulfonyl-phenoxy)-naphthalen-2-yl]-acetic acid (65.8 mg, 37%) was obtained as a white solid. $^1$H NMR (400 MHz, CD$_3$OD) δ ppm 7.89-7.94 (m, 4H), 7.71 (s, 1H), 7.54 (dt, J=8.08, 4.04 Hz, 1H), 7.48 (s, 2H), 7.14-7.19 (m, 3H), 3.80 (s, 2H), 3.11 (s, 3H); MS cald. for C$_{19}$H$_{16}$O$_5$S 356, obsd. (ESI$^+$) [(M+H)$^+$] 357.

Example 3-2

[4-(4-methanesulfonyl-phenoxy)-3-methyl-naphthalen-2-yl]-acetic acid

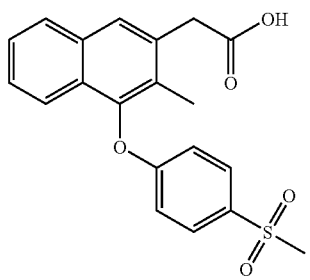 [SMILES: Cc1c(CC(=O)O)cc2ccccc2c1Oc1ccc(S(C)(=O)=O)cc1]

2-(4-Chloro-benzylidene)-3-methyl-succinic acid

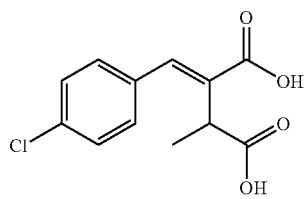 [SMILES: CC(C(=O)O)/C(=C\c1ccc(Cl)cc1)C(=O)O]

After careful addition of absolute methanol (0.1 mL) to a suspension of sodium hydride (60% in mineral oil, 16 g, 0.40 mol) in anhydrous toluene (200 mL), a solution of 4-chloro-benzaldehyde (28 g, 0.20 mol) and 2-methyl-succinic acid dimethyl ester (48 g, 0.30 mol) in anhydrous toluene (100 mL) was added dropwise at room temperature under a stream of nitrogen. After being stirred at room temperature for 2 hours, the resulting mixture was diluted by adding 2 N sodium hydroxide (200 mL) dropwise, then heated to 80° C., and stirred at the same temperature for 2 hours. After being cooled to room temperature naturally, the aqueous layer was separated, washed with ethyl acetate (100 mL×3), then acidified with 2 N hydrochloric acid to pH 2, and extracted with ethyl acetate (150 mL×3). The combined organic layers were dried over sodium sulfate, and concentrated in vacuo. The residue was precipitated from ethyl acetate/petroleum ether (10:1) to give 2-(4-chloro-benzylidene)-3-methyl-succinic acid (13.4 g, 26%) as a yellow solid.

6-Chloro-4-hydroxy-3-methyl-naphthalene-2-carboxylic acid

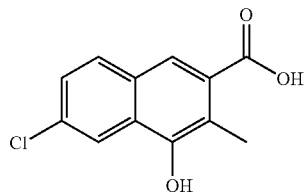 [SMILES: Cc1c(C(=O)O)cc2ccc(Cl)cc2c1O]

To a flask containing trifluoromethanesulfonic acid (40 mL), 2-(4-chloro-benzylidene)-3-methyl-succinic acid (14.0 g) was added in portions. After being stirred at room temperature for 18 hours, the resulting mixture was poured onto ice-water, and stirred for 15 minutes. The formed precipitate was collected by filtration, and dissolved in ethyl acetate (150 mL). The solution was dried over sodium sulfate, and concentrated in vacuo. The residue was precipitated from ethyl acetate/petroleum ether (1:10) to afford 6-chloro-4-hydroxy-3-methyl-naphthalene-2-carboxylic acid (12.7 g, 97.6%) as a pink solid.

7-Chloro-3-hydroxymethyl-2-methyl-naphthalen-1-ol

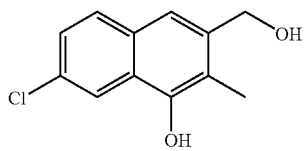

To a slurry of lithium aluminum hydride (4.1 g) in tetrahydrofuran (80 mL) was added a solution of 6-chloro-4-hydroxy-3-methyl-naphthalene-2-carboxylic acid (12.7 g, 54 mmol) in tetrahydrofuran (80 mL) at 0° C. under a nitrogen atmosphere. After being heated at 60° C. for 5 hours, the resulting mixture was cooled to 0° C. and treated with 1 N hydrochloric acid to quench the reaction. The aqueous layer was extracted with ethyl acetate (100 mL×4). The combined organic layers were washed with brine (200 mL×2), dried over sodium sulfate and concentrated in vacuo to give 7-chloro-3-hydroxymethyl-2-methyl-naphthalen-1-ol (8.5 g, 71%) as a white solid.

7-Chloro-3-chloromethyl-2-methyl-naphthalen-1-ol

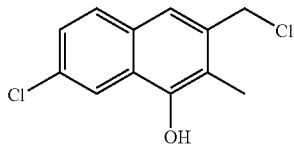

To a solution of triphenylphosphine (20 g, 75.6 mmol) in anhydrous tetrahydrofuran (165 mL) was added carbon tetrachloride (50 mL). After the mixture was stirred at room temperature for 20 minutes, 7-chloro-3-hydroxymethyl-2-methyl-naphthalen-1-ol (8.4 g, 37.8 mmol) was added as a solid under a nitrogen atmosphere. After being stirred at reflux for 2 hours, the resulting mixture was cooled to room temperature, and concentrated in vacuo. The residue was purified by column chromatography (elution with 5% ethyl acetate in petroleum ether) to afford 7-chloro-3-chloromethyl-2-methyl-naphthalen-1-ol (8.7 g, 96%) as a white solid.

(6-Chloro-4-hydroxy-3-methyl-naphthalen-2-yl)-acetic acid methyl ester

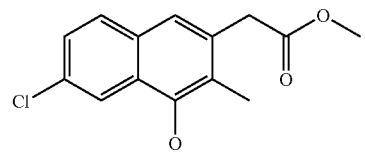 [SMILES: COC(=O)Cc1cc2ccc(Cl)cc2c(O)c1C]

To a flask containing 7-chloro-3-chloromethyl-2-methyl-naphthalen-1-ol (8.64 g, 36 mmol), bis(triphenylphosphine)dichloropalladium(II) (1.26 g, 1.8 mmol) and potassium carbonate (5.2 g, 37.8 mmol), which was evacuated and then filled with carbon monoxide (balloon), methanol (30 mL) and tetrahydrofuran (60 mL) were added by means of a syringe. After being stirred at room temperature under a carbon monoxide atmosphere overnight, the resulting mixture was diluted with water (100 mL), and extracted with ethyl acetate (100 mL). The organic layer was washed with water (50 mL×2). The combined aqueous layers were extracted with ethyl acetate (150 mL), and the combined organic layers were dried over sodium sulfate and concentrated in vacuo. The residue was purified by column chromatography (elution with 20% ethyl acetate in petroleum ether) to afford (6-chloro-4-hydroxy-3-methyl-naphthalen-2-yl)-acetic acid methyl ester (7.0 g, 74%) as an orange solid.

[6-Chloro-4-(4-methanesulfonyl-phenoxy)-3-methyl-naphthalen-2-yl]-acetic acid methyl ester

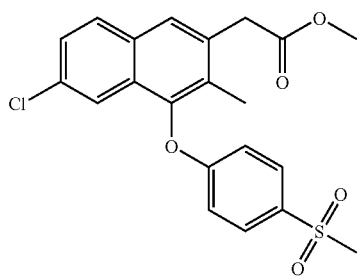 [SMILES: COC(=O)Cc1cc2ccc(Cl)cc2c(Oc2ccc(S(C)(=O)=O)cc2)c1C]

Starting with (6-chloro-4-hydroxy-3-methyl-naphthalen-2-yl)-acetic acid methyl ester (132 mg, 0.5 mmol) and 1-fluoro-4-methanesulfonyl-benzene (174 mg, 1.0 mmol), using a method analogous to the one described for the methyl ester of example 1-1, [6-chloro-4-(4-methanesulfonyl-phenoxy)-3-methyl-naphthalen-2-yl]-acetic acid methyl ester (70 mg, 33%) was obtained as a yellow oil.

[4-(4-methanesulfonyl-phenoxy)-3-methyl-naphthalen-2-yl]-acetic acid methyl ester

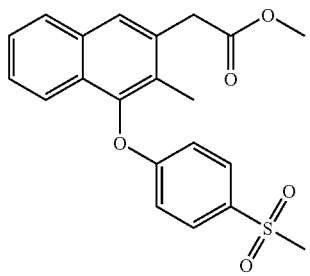 [SMILES: COC(=O)Cc1cc2ccccc2c(Oc2ccc(S(C)(=O)=O)cc2)c1C]

To a solution of [6-chloro-4-(4-methanesulfonyl-phenoxy)-3-methyl-naphthalen-2-yl]-acetic acid methyl ester (110 mg, 0.26 mmol) in methanol (3 mL) was added 10% palladium on carbon (10 mg). The resulting mixture was vigorously stirred at room temperature overnight under a hydrogen atmosphere (balloon) and then filtered. The filtrate was concentrated in vacuo to give [4-(4-methanesulfonyl-phenoxy)-3-methyl-naphthalen-2-yl]-acetic acid methyl ester (68 mg, 67%) as a colorless oil which was directly used in the next step without further purification.

[4-(4-methanesulfonyl-phenoxy)-3-methyl-naphthalen-2-yl]-acetic acid

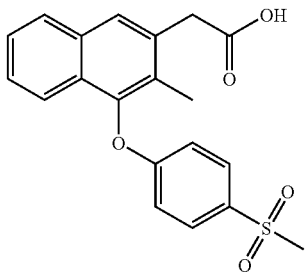 [SMILES: Cc1c(CC(=O)O)cc2ccccc2c1Oc1ccc(S(C)(=O)=O)cc1]

Starting with [6-chloro-4-(4-methanesulfonyl-phenoxy)-3-methyl-naphthalen-2-yl]-acetic acid methyl ester (68 mg), using a method analogous to the one described for example 1-1, final step, [4-(4-methanesulfonyl-phenoxy)-3-methyl-naphthalen-2-yl]-acetic acid (24 mg, 37%) was obtained as a white solid. $^1$H NMR (400 MHz, CDCl$_3$) δ ppm 7.84 (d, J=8.84 Hz, 3H), 7.70-7.75 (m, 2H), 7.45 (ddd, J=23.43, 7.26, 6.69 Hz, 2H), 6.94 (d, J=8.84 Hz, 2H), 3.92 (s, 2H), 3.04 (s, 3H), 2.26 (s, 3H); MS cald. for C$_{20}$H$_{18}$O$_5$S 370, obsd. (ESI$^+$) [(M+H)$^+$] 371.

Example 4-1

[1,6-difluoro-4-(5-methanesulfonyl-pyridin-2-yloxy)-naphthalen-2-yl]-acetic acid

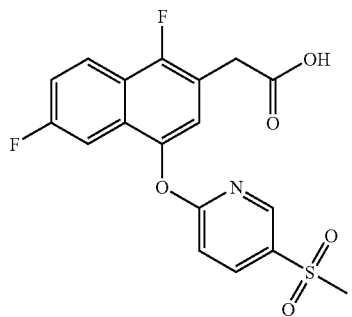 [SMILES: CS(=O)(=O)c1ccc(Oc2cc(CC(=O)O)c(F)c3ccc(F)cc23)nc1]

(1,6-difluoro-4-hydroxy-naphthalen-2-yl)-acetic acid methyl ester

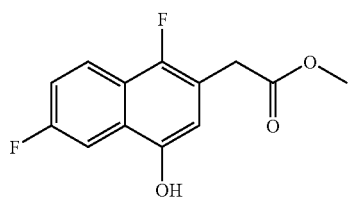 [SMILES: COC(=O)Cc1cc(O)c2cc(F)ccc2c1F]

To a solution of (6-fluoro-4-hydroxy-naphthalen-2-yl)-acetic acid methyl ester (100 mg, 0.277 mmol) in acetonitrile (3 mL) was added 1-chloromethyl-4-fluoro-1,4-diazoniabicyclo[2.2.2]octane bis(tetrafluoroborate) (255 mg, 0.72 mmol) at 0° C. The resulting mixture was stirred at room temperature overnight, and diluted with water, then extracted with ethyl acetate (20 mL×3). The combined organic layers were washed with brine (20 mL×3), dried over sodium sulfate, and concentrated in vacuo. The residue was purified by flash column chromatography (30% ethyl acetate in petroleum ether) to give (1,6-difluoro-4-hydroxy-naphthalen-2-yl)acetic acid methyl ester (60 mg, 86%) as a yellow solid. MS cald. for C$_{13}$H$_{10}$F$_2$O$_3$ 252, obsd. (ESI$^+$) [(M+H)$^+$] 253.

[1,6-difluoro-4-(5-methanesulfonyl-pyridin-2-yloxy)-naphthalen-2-yl]-acetic acid methyl ester

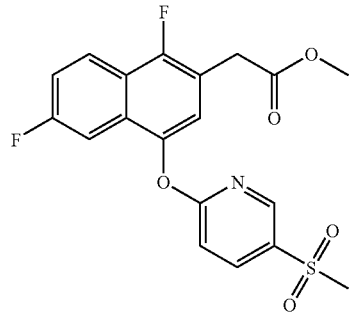 [SMILES: COC(=O)Cc1cc(Oc2ccc(S(C)(=O)=O)cn2)c2cc(F)ccc2c1F]

A mixture of (1,6-difluoro-4-hydroxy-naphthalen-2-yl) acetic acid methyl ester (50 mg, 0.198 mmol), 2-bromo-5-methanesulfonyl-pyridin (52 mg, 0.22 mmol), potassium carbonate (60 mg, 0.434 mmol) and N,N-dimethylformamide (2.0 mL) was heated at 70° C. for 3 hours. The resulting mixture was cooled to room temperature, acidified with 1 N hydrochloric acid to pH 3, and extracted with ethyl acetate (20 mL×3). The combined organic layers were washed with brine (20 mL×3), dried over sodium sulfate, and concentrated in vacuo to afford [1,6-difluoro-4-(5-methanesulfonyl-pyridin-2-yloxy)-naphthalen-2-yl]-acetic acid methyl ester (70 mg, 87%) as a white solid which was used in the next step without further purification.

[1,6-difluoro-4-(5-methanesulfonyl-pyridin-2-yloxy)-naphthalen-2-yl]-acetic acid

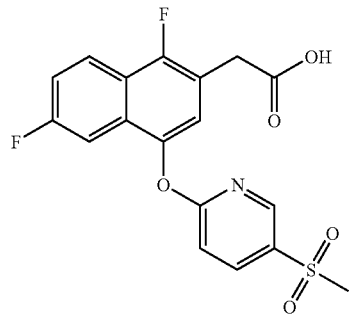 [SMILES: CS(=O)(=O)c1ccc(Oc2cc(CC(=O)O)c(F)c3ccc(F)cc23)nc1]

Starting with [1,6-difluoro-4-(5-methanesulfonyl-pyridin-2-yloxy)-naphthalen-2-yl]-acetic acid methyl ester (70 mg, 0.172 mmol), using a method analogous to the one described for example 1-1, final step, [1,6-difluoro-4-(5-methanesulfonyl-pyridin-2-yloxy)-naphthalen-2-yl]-acetic acid (10 mg, 15%) was obtained as a white solid. $^1$H NMR (400 MHz, DMSO-d$_6$) δ ppm 8.56 (d, J=2.53 Hz, 1H), 8.39 (dd, J=8.84, 2.53 Hz, 1H), 8.19 (dd, J=9.35, 5.31 Hz, 1H), 7.60 (td, J=8.97, 2.53 Hz, 1H), 7.49-7.54 (m, 1H), 7.43-7.48 (m, 2H), 3.82 (s, 2H), 3.28 (s, 3H); MS cald. for $C_{18}H_{13}F_2NO_5S$ 393, obsd. (ESI⁺) [(M+H)⁺] 394.

Example 4-2

[1,6-difluoro-4-(5-ethanesulfonyl-pyridin-2-yloxy)-naphthalen-2-yl]-acetic acid

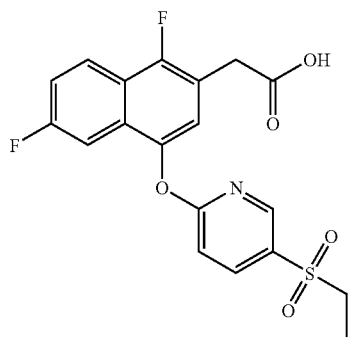 [SMILES: CCS(=O)(=O)c1ccc(Oc2cc(CC(=O)O)c(F)c3ccc(F)cc23)nc1]

Starting with (1,6-difluoro-4-hydroxy-naphthalen-2-yl) acetic acid methyl ester (50 mg, 0.198 mmol) and 2-bromo-5-ethanesulfonyl-pyridine (52 mg, 0.208 mmol), using a method analogous to the one described for example 4-1, [1,6-difluoro-4-(5-ethanesulfonyl-pyridin-2-yloxy)-naphthalen-2-yl]-acetic acid (10 mg, 12%) was obtained as a white solid. ¹H NMR (400 MHz, DMSO-d₆) δ ppm 8.52 (d, 1H), 8.34 (dd, 1H), 8.19 (dd, 1H), 7.42-7.76 (m, 4H), 3.78-3.86 (m, 2H), 3.37-3.40 (m, 2H), 1.12 (t, 3H); MS cald. for $C_{19}H_{15}F_2NO_5S$ 407, obsd. (ESI⁺) [(M+H)⁺] 408.

Example 5-1

[4-(5-ethanesulfonyl-pyridin-2-yloxy)-3,6-difluoro-naphthalen-2-yl]-acetic acid

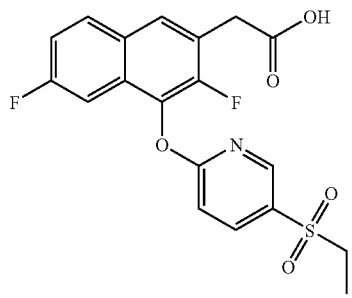 [SMILES: CCS(=O)(=O)c1ccc(Oc2c(F)c(CC(=O)O)cc3ccc(F)cc23)nc1]

(4-benzyloxy-1-bromo-6-fluoro-naphthalen-2-yl)-acetic acid methyl ester

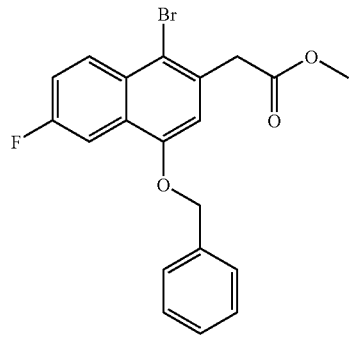 [SMILES: COC(=O)Cc1cc(OCc2ccccc2)c2cc(F)ccc2c1Br]

To a stirred solution of (4-benzyloxy-6-fluoro-naphthalen-2-yl)-acetic acid methyl ester (350 mg, 1.08 mmol) in acetonitrile (10 mL) was added N-bromosuccinimide (385 mg, 2.16 mmol). After being stirred at room temperature for 1 hour, the resulting mixture was diluted with water (20 mL), and extracted with ethyl acetate (20 mL×2). The combined organic layers were washed with water (15 mL) and brine (20 mL), dried over sodium sulfate and concentrated in vacuo. The residue was purified by column chromatography (gradient elution with 0-20% ethyl acetate in hexanes) to afford (4-benzyloxy-1-bromo-6-fluoro-naphthalen-2-yl)-acetic acid methyl ester (400 mg, 92%) as a white solid.

(1-bromo-6-fluoro-4-hydroxy-naphthalen-2-yl)-acetic acid methyl ester

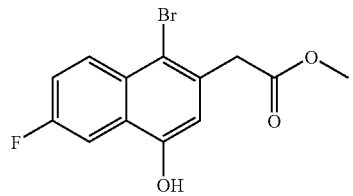 [SMILES: COC(=O)Cc1cc(O)c2cc(F)ccc2c1Br]

To a solution of (4-benzyloxy-1-bromo-6-fluoro-naphthalen-2-yl)-acetic acid methyl ester (400 mg, 0.992 mmol) in ethyl acetate (10 mL) was added zinc bromide (670 mg, 2.978 mmol) and 10% palladium on carbon (40 mg) under a hydrogen atmosphere (balloon). After being stirred at room temperature for 1 hour, the resulting mixture was filtered. The filtrate was concentrated in vacuo. The residue was purified by preparative HPLC (gradient elution with 50-80% 0.1% trifluoroacetic acid in water in acetonitrile, 8 minutes) to afford (1-bromo-6-fluoro-4-hydroxy-naphthalen-2-yl)acetic acid methyl ester (200 mg, 64.4%) as a white solid.

(1-bromo-3,6-difluoro-4-hydroxy-naphthalen-2-yl)-acetic acid methyl ester

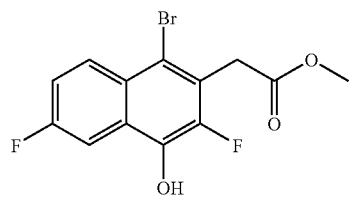 [SMILES: COC(=O)Cc1c(F)c(O)c2cc(F)ccc2c1Br]

To a solution of (1-bromo-6-fluoro-4-hydroxy-naphthalen-2-yl)-acetic acid methyl ester (135 mg, 0.433 mmol) in acetonitrile (4 mL) was added 1-chloromethyl-4-fluoro-1,4-diazoniabicyclo[2.2.2]octane bis(tetrafluoroborate) (230 mg, 0.650 mmol) at 0° C. The resulting mixture was stirred at room temperature overnight, then diluted with water (10 mL), and extracted with ethyl acetate (20 mL×3). The combined organic layers were washed with brine (20 mL×3), dried over sodium sulfate, and concentrated in vacuo. The residue was purified by flash column chromatography (30% ethyl acetate in petroleum ether) to give (1-bromo-3,6-difluoro-4-hydroxy-naphthalen-2-yl)-acetic acid methyl ester (60 mg, 42%) as a yellow solid. MS cald. for $C_{13}H_9BrF_2O_3$ 330, obsd. (ESI$^+$) [(M+H)$^+$] 331.

(3,6-difluoro-4-hydroxy-naphthalen-2-yl)-acetic acid methyl ester

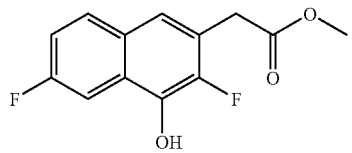 [SMILES: COC(=O)Cc1cc2ccc(F)cc2c(O)c1F]

To a solution of (1-bromo-3,6-difluoro-4-hydroxy-naphthalen-2-yl)-acetic acid methyl ester (50 mg, 0.152 mmol) in methanol was added 10% palladium on carbon (10 mg). After being stirred at room temperature under a hydrogen atmosphere overnight, the resulting mixture was filtered. The filtrate was concentrated in vacuo to afford (3,6-difluoro-4-hydroxy-naphthalen-2-yl)-acetic acid methyl ester (25 mg, 65%) as a white solid.

[4-(5-ethanesulfonyl-pyridin-2-yloxy)-3,6-difluoro-naphthalen-2-yl]-acetic acid methyl ester

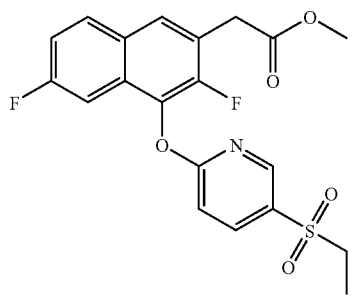 [SMILES: CCS(=O)(=O)c1ccc(Oc2c(F)c(CC(=O)OC)cc3ccc(F)cc23)nc1]

Starting with (3,6-difluoro-4-hydroxy-naphthalen-2-yl)-acetic acid methyl ester (25 mg, 0.099 mmol) and 2-bromo-5-ethanesulfonyl-pyridine (28 mg, 0.112 mmol), using a method analogous to the one described for the methyl ester of example 1-1, [4-(5-ethanesulfonyl-pyridin-2-yloxy)-3,6-difluoro-naphthalen-2-yl]-acetic acid methyl ester (20 mg, 48%) was obtained as a white solid, which was used in the next step without further purification.

[4-(5-ethanesulfonyl-pyridin-2-yloxy)-3,6-difluoro-naphthalen-2-yl]-acetic acid

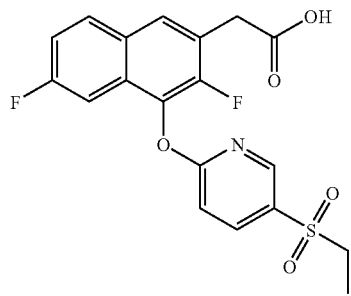

Starting with [4-(5-ethanesulfonyl-pyridin-2-yloxy)-3,6-difluoro-naphthalen-2-yl]-acetic acid methyl ester (20 mg, 0.475 mmol), using a method analogous to the one described for example 1-1, final step, [4-(5-ethanesulfonyl-pyridin-2-yloxy)-3,6-difluoro-naphthalen-2-yl]-acetic acid (1.9 mg) was obtained as a white solid. $^1$H NMR (400 MHz, DMSO-d$_6$) δ ppm 8.51 (d, J=2.02 Hz, 1H), 8.37 (dd, J=8.72, 2.65 Hz, 1H), 8.09 (dd, J=9.09, 5.56 Hz, 1H), 7.92 (d, J=6.82 Hz, 1H), 7.55 (d, J=8.59 Hz, 1H), 7.51 (dd, J=10.23, 2.65 Hz, 1H), 7.42-7.48 (m, 1H), 3.74 (s, 2H), 3.37 (t, 2H), 1.14 (t, J=7.33 Hz, 3H); MS cald. for $C_{19}H_{15}F_2NO_5S$ 407, obsd. (ESI$^+$) [(M+H)$^+$] 408.

Example 6-1

[4-(5-ethanesulfonyl-pyridin-2-yloxy)-6-fluoro-1-methyl-naphthalen-2-yl]-acetic acid

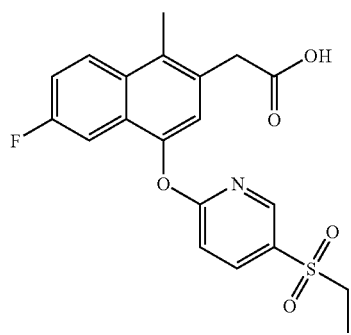 [SMILES: CCS(=O)(=O)c1ccc(Oc2cc(CC(=O)O)c(C)c3ccc(F)cc23)nc1]

(4-benzyloxy-6-fluoro-1-methyl-naphthalen-2-yl)-acetic acid methyl ester

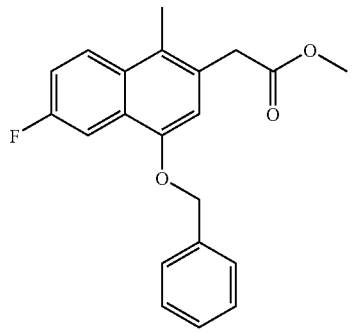 [SMILES: COC(=O)Cc1cc(OCc2ccccc2)c2cc(F)ccc2c1C]

To a solution of (4-benzyloxy-1-bromo-6-fluoro-naphthalen-2-yl)-acetic acid methyl ester (100 mg, 0.248 mmol, prepared using an analogous procedure to the first step of example 5-1), methylboronic acid (19.3 mg, 0.322 mmol), potassium phosphate (184 mg, 0.868 mmol) and tricyclohexylphosphine (69.4 mg, 0.248 mmol) in toluene (4.0 mL) and water (2 drops) was added palladium acetate (3 mg, 0.0124 mmol) under a nitrogen atmosphere. After being heated under microwave conditions (150° C., 30 minutes), the mixture was cooled to room temperature, then diluted with water (10 mL), and extracted with ethyl acetate (15 mL×2). The combined organic layers were washed with brine (10 mL), dried over sodium sulfate and concentrated in vacuo. The residue was purified by column chromatography (10% ethyl acetate in hexanes) to afford (4-benzyloxy-6-fluoro-1-methyl-naphthalen-2-yl)-acetic acid methyl ester (50 mg, 59.5%) as a light yellow solid.

(6-fluoro-4-hydroxy-1-methyl-naphthalen-2-yl)-acetic acid methyl ester

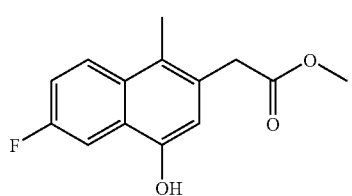 [SMILES: COC(=O)Cc1cc(O)c2cc(F)ccc2c1C]

To a solution of (4-benzyloxy-6-fluoro-1-methyl-naphthalen-2-yl)-acetic acid methyl ester (50 mg) in methanol was added 10% palladium on carbon (10 mg). After being stirred at room temperature under a hydrogen atmosphere overnight, the resulting mixture was filtered. The filtrate was concentrated in vacuo to afford (6-fluoro-4-hydroxy-1-methyl-naphthalen-2-yl)-acetic acid methyl ester (30 mg) as a white solid.

[4-(5-ethanesulfonyl-pyridin-2-yloxy)-6-fluoro-1-methyl-naphthalen-2-yl]-acetic acid methyl ester

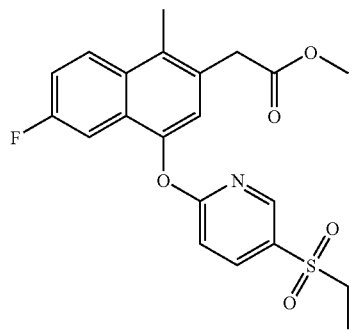 [SMILES: CCS(=O)(=O)c1ccc(Oc2cc(CC(=O)OC)c(C)c3ccc(F)cc23)nc1]

Starting with (6-fluoro-4-hydroxy-1-methyl-naphthalen-2-yl)acetic acid methyl ester (18 mg, 0.073 mmol) and 2-bromo-5-ethanesulfonyl-pyridine (27 mg, 0.109 mmol), using a method analogous to the one described for the methyl ester of example 1-1, [4-(5-ethanesulfonyl-pyridin-2-yloxy)-6-fluoro-1-methyl-naphthalen-2-yl]-acetic acid methyl ester (22.7 mg, 75%) was obtained as a light yellow solid.

[4-(5-ethanesulfonyl-pyridin-2-yloxy)-6-fluoro-1-methyl-naphthalen-2-yl]-acetic acid Starting with [4-(5-ethanesulfonyl-pyridin-2-yloxy)-6-fluoro-1-methyl-naphthalen-2-yl]-acetic acid methyl ester (22.7 mg, 0.054 mmol), using a method analogous to the one described for example 1-1, final step, [4-(5-ethanesulfonyl-pyridin-2-yloxy)-6-fluoro-1-methyl-naphthalen-2-yl]-acetic acid was obtained (10 mg) as a white solid. $^1$H NMR (400 MHz, CD$_3$OD) δ ppm 8.54 (d, J=2.53 Hz, 1H), 8.20-8.30 (m, 2H), 7.35-7.45 (m, 2H), 7.28 (t, J=4.42 Hz, 2H), 3.88 (s, 2H), 3.26 (q, J=7.33 Hz, 2H), 2.67 (s, 3H), 1.25 (t, J=7.45 Hz, 3H); MS cald. for C$_{20}$H$_{18}$FNO$_5$S 403, obsd. (ESI$^+$) [(M+H)$^+$] 404.

Example 7-1

3-[4-(4-ethanesulfonyl-phenoxy)-6-fluoro-3-methyl-naphthalen-2-yl]-propionic acid

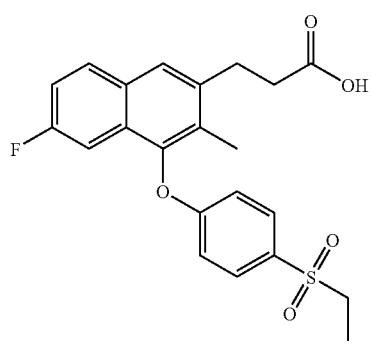 [SMILES: CCS(=O)(=O)c1ccc(Oc2c(C)c(CCC(=O)O)cc3ccc(F)cc23)cc1]

4-benzyloxy-6-fluoro-3-methyl-naphthalene-2-carbaldehyde

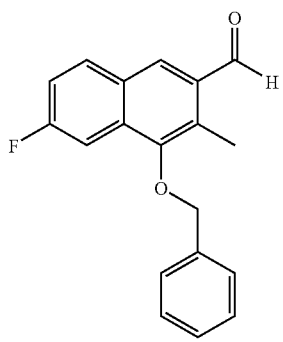 [SMILES: Cc1c(C=O)cc2ccc(F)cc2c1OCc1ccccc1]

To a solution of (4-benzyloxy-6-fluoro-3-methyl-naphthalen-2-yl)-methanol (180 mg, 0.6 mmol) in dichloromethane (10 mL) was added pyridinium chlorochromate (260 mg, 1.2 mmol) in portions. After being stirred at room temperature for 3 hours, the resulting dark mixture was diluted with diethyl ether, and stirred at room temperature for 10 minutes. The mixture was filtered through a short silica gel column. The filtrate was concentrated in vacuo to give 4-benzyloxy-6-fluoro-3-methyl-naphthalene-2-carbaldehyde (165 mg, 93%) as a white solid, which was used in the next step without further purification. $^1$H NMR (400 MHz, CDCl$_3$) δ ppm 10.31 (s, 1H), 8.16 (s, 1H), 8.00 (dd, J=8.84, 5.56 Hz, 1H), 7.73 (dd, J=10.48, 2.40 Hz, 1H), 7.55 (d, J=6.82 Hz, 2H), 7.39-7.49 (m, 2H), 7.32 (td, J=8.65, 2.65 Hz, 1H), 4.99 (s, 2H), 2.75 (s, 3H).

6-fluoro-4-hydroxy-3-methyl-naphthalene-2-carbaldehyde

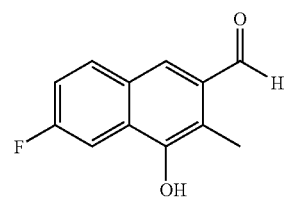

To a solution of 4-benzyloxy-6-fluoro-3-methyl-naphthalene-2-carbaldehyde (165 mg, 0.56 mmol) in ethyl acetate (5 mL) was added 10% palladium on carbon (7 mg). The resulting mixture was stirred vigorously under a hydrogen atmosphere (balloon) for 4 hours, and then filtered. The filtrate was concentrated in vacuo to give 6-fluoro-4-hydroxy-3-methyl-naphthalene-2-carbaldehyde (115 mg, 99%) as a yellow solid which was directly used in the next step without further purification.

4-(4-ethanesulfonyl-phenoxy)-6-fluoro-3-methyl-naphthalene-2-carbaldehyde

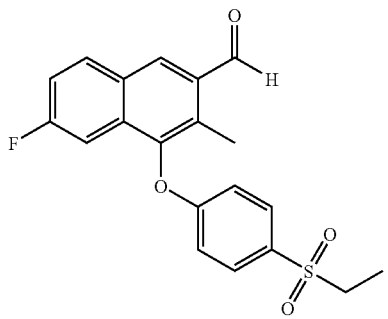 [SMILES: CCS(=O)(=O)c1ccc(Oc2c(C)c(C=O)cc3ccc(F)cc23)cc1]

Starting with 6-fluoro-4-hydroxy-3-methyl-naphthalene-2-carbaldehyde (115 mg, 0.6 mmol) and 1-ethanesulfonyl-4-fluoro-benzene (226 mg, 1.2 mmol), using a method analogous to the one described for the methyl ester of example 1-1,4-(4-ethanesulfonyl-phenoxy)-6-fluoro-3-methyl-naphthalene-2-carbaldehyde (120 mg, 57%) was obtained as a yellow solid which was used in the next step without further purification. $^1$H NMR (400 MHz, CDCl$_3$) δ ppm 10.35 (s, 1H), 8.32 (s, 1H), 8.07 (dd, J=8.97, 5.68 Hz, 1H), 7.84 (d, J=9.09 Hz, 2H), 7.33-7.45 (m, 2H), 6.94 (d, J=8.84 Hz, 2H), 3.12 (q, J=7.41 Hz, 2H), 2.59 (s, 3H), 1.31 (t, J=7.45 Hz, 3H).

3-[4-(4-ethanesulfonyl-phenoxy)-6-fluoro-3-methyl-naphthalen-2-yl]-acrylic acid ethyl ester

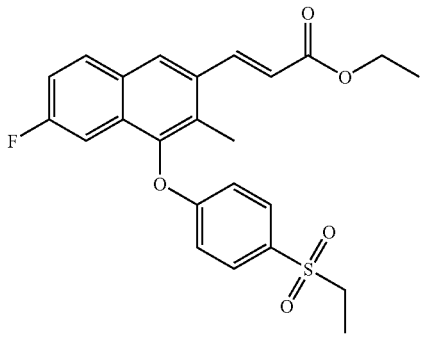 [SMILES: CCOC(=O)/C=C/c1cc2ccc(F)cc2c(Oc2ccc(S(=O)(=O)CC)cc2)c1C]

To a suspension of sodium hydride (15 mg, 0.37 mmol, 60% in mineral oil) in anhydrous tetrahydrofuran (1 mL) was added triethyl phosphonoacetate (83 mg, 0.37 mmol) in anhydrous tetrahydrofuran (2 mL) dropwise at 0° C. After the mixture was warmed naturally to room temperature and stirred at room temperature for 30 minutes, a solution of 4-(4-ethanesulfonyl-phenoxy)-6-fluoro-3-methyl-naphthalene-2-carbaldehyde (120 mg, 0.33 mmol) in anhydrous tetrahydrofuran (2 mL) was added dropwise. The reaction mixture was stirred at room temperature for 5 hours. The resulting mixture was diluted with water (10 mL), and extracted with ethyl acetate (10 mL×3). The combined organic layers were washed with brine, dried over sodium sulfate, and concentrated in vacuo. The residue was purified by column chromatography (20% ethyl acetate in petroleum ether) to afford 3-[4-(4-ethanesulfonyl-phenoxy)-6-fluoro-3-methyl-naphthalen-2-yl]-acrylic acid ethyl ester (80 mg, 56%) as a white solid. $^1$H NMR (400 MHz, CDCl$_3$) δ ppm 8.02-8.08 (m, 2H), 7.90 (dd, J=9.22, 5.43 Hz, 1H), 7.83 (d, J=8.84 Hz, 2H), 7.34 (dd, J=10.23, 2.15 Hz, 1H), 7.28-7.31 (m, 1H), 6.94 (d, J=8.59 Hz, 2H), 6.53 (d, J=15.66 Hz, 1H), 4.32 (q, J=7.07 Hz, 2H), 3.11 (q, J=7.58 Hz, 2H), 1.38 (t, J=7.20 Hz, 3H), 1.30 (t, J=7.45 Hz, 3H).

3-[4-(4-ethanesulfonyl-phenoxy)-6-fluoro-3-methyl-naphthalen-2-yl]-propionic acid ethyl ester

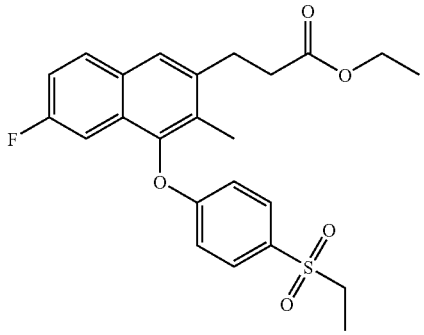 [SMILES: CCOC(=O)CCc1cc2ccc(F)cc2c(Oc2ccc(S(=O)(=O)CC)cc2)c1C]

To a solution of 3-[4-(4-ethanesulfonyl-phenoxy)-6-fluoro-3-methyl-naphthalen-2-yl]-acrylic acid ethyl ester (40 mg, 0.09 mmol) in ethyl acetate (3 mL) was added 10% palladium on carbon (4 mg). The resulting mixture was stirred vigorously under a hydrogen (balloon) atmosphere overnight, and then filtered. The filtrate was concentrated in vacuo to give 3-[4-(4-ethanesulfonyl-phenoxy)-6-fluoro-3-methyl-naphthalen-2-yl]-propionic acid ethyl ester (30 mg, 75%) as a yellow solid, which was used for the next step without any further purification.

3-[4-(4-ethanesulfonyl-phenoxy)-6-fluoro-3-methyl-naphthalen-2-yl]-propionic acid

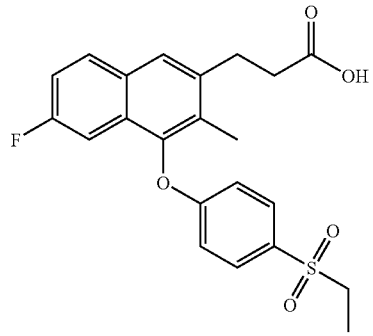 [SMILES: CCS(=O)(=O)c1ccc(Oc2c(C)c(CCC(=O)O)cc3ccc(F)cc23)cc1]

Starting with 3-[4-(4-ethanesulfonyl-phenoxy)-6-fluoro-3-methyl-naphthalen-2-yl]-propionic acid ethyl ester (30 mg, 0.068 mmol), using a method analogous to the one described for example 1-1, final step, 3-[4-(4-ethanesulfonyl-phenoxy)-6-fluoro-3-methyl-naphthalen-2-yl]-propionic acid (19 mg, 68%) was obtained as a yellow solid. $^1$H NMR (400 MHz, CDCl$_3$) δ ppm 7.78-7.85 (m, 3H), 7.63 (s, 1H), 7.32 (dd, J=10.11, 2.27 Hz, 1H), 7.24 (dd, 1H), 6.91 (d, J=8.84 Hz, 2H), 3.08-3.19 (m, 4H), 2.80 (t, J=7.83 Hz, 2H), 2.27 (s, 3H), 1.30 (t, J=7.45 Hz, 3H); MS cald. for C$_{22}$H$_{21}$FO$_5$S 416, obsd. (ESI$^+$) [(M+H)$^+$] 417.

Example 8-1

[6-fluoro-4-(4-methanesulfonyl-phenylamino)-naphthalen-2-yl]-acetic acid

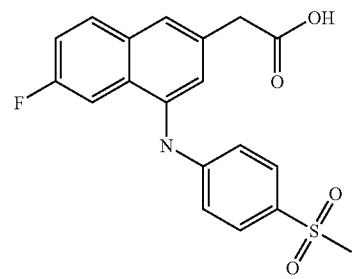

(6-fluoro-4-trifluoromethanesulfonyloxy-naphthalen-2-yl)-acetic acid methyl ester

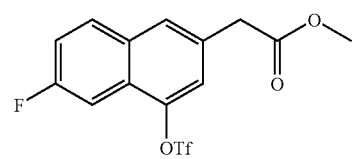 [SMILES: COC(=O)Cc1cc(OS(=O)(=O)C(F)(F)F)c2cc(F)ccc2c1]

To a mixture of (6-fluoro-4-hydroxy-naphthalen-2-yl)-acetic acid methyl ester (350 mg, 1.5 mmol) and trifluoromethanesulfonic anhydride (506 mg, 1.8 mmol) in dichloromethane (20 mL), which was cooled to 0° C. in an ice bath, pyridine (0.6 mL) was added dropwise. The reaction mixture was stirred at 0° C. for 2 hours and then concentrated in vacuo. The residue was dissolved in ethyl acetate (50 mL). The resulting solution was washed with water, 1 N aqueous hydrochloric acid, water, and brine, then dried over sodium sulfate, filtered, and concentrated in vacuo. The residue was purified by column chromatography (0-30% ethyl acetate in hexanes) to afford (6-fluoro-4-trifluoromethanesulfonyloxy-naphthalen-2-yl)-acetic acid methyl ester (450 mg, 82%) as a light yellow solid.

[6-fluoro-4-(4-methanesulfonyl-phenylamino)-naphthalen-2-yl]-acetic acid methyl ester

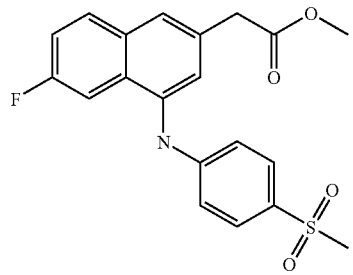 [SMILES: COC(=O)Cc1cc(Nc2ccc(S(C)(=O)=O)cc2)c2cc(F)ccc2c1]

To a solution of (6-fluoro-4-trifluoromethanesulfonyloxy-naphthalen-2-yl)-acetic acid methyl ester (115 mg, 0.31 mmol) and 4-methanesulfonyl-phenylamine (59 mg, 0.35 mmol) in N,N-dimethylformamide (3 mL), was added (R)-(+)-2,2'-bis(diphenylphosphino)-1,1'-binaphthyl (39 mg, 0.063 mmol), tris(dibenzylideneacetone)dipalladium(0) (14 mg, 0.016 mmol), and cesium carbonate (102 mg, 0.31 mmol). After being heated under microwave conditions (160° C., 15 minutes), the resulting mixture was diluted with water (10 mL) and extracted with ethyl acetate (15 mL×3). The organic layer was washed with brine, then dried over sodium sulfate, and concentrated in vacuo. The residue was purified by column chromatography (gradient elution with 0-50% ethyl acetate in hexanes) to afford [6-fluoro-4-(4-methanesulfonyl-phenylamino)-naphthalen-2-yl]-acetic acid methyl ester (84.0 mg, 69% yield) as a yellow solid.

[6-fluoro-4-(4-methanesulfonyl-phenylamino)-naphthalen-2-yl]-acetic acid

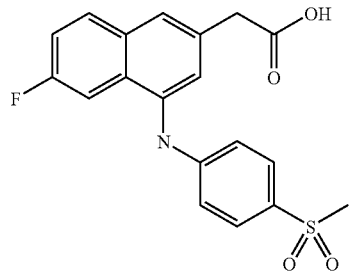 [SMILES: CS(=O)(=O)c1ccc(Nc2cc(CC(=O)O)cc3ccc(F)cc23)cc1]

Starting with [6-fluoro-4-(4-methanesulfonyl-phenylamino)-naphthalen-2-yl]-acetic acid methyl ester (30 mg), using a method analogous to the one described for example 1-1, final step, [6-fluoro-4-(4-methanesulfonyl-phenylamino)-naphthalen-2-yl]-acetic acid (17 mg) was obtained as a white solid. $^1$H NMR (400 MHz, CD$_3$OD) δ ppm (dd, J=9.09, 5.56 Hz, 1H), 7.67-7.72 (m, 2H), 7.66 (br. s., 1H), 7.61 (dd, J=10.99, 2.65 Hz, 1H), 7.49 (s, 1H), 7.30-7.36 (m, 1H), 6.95-7.00 (m, 2H), 3.77 (s, 2H), 3.06 (s, 3H); MS cald. for C$_{19}$H$_{16}$FNO$_4$S 373, obsd. (ESI$^+$) [(M+H)$^+$] 374.

Example 8-2

[6-fluoro-4-(4-methanesulfonyl-phenylamino)-3-methyl-naphthalen-2-yl]-acetic acid

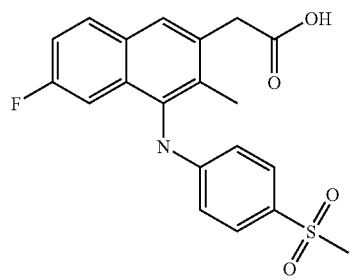

Starting with 6-fluoro-4-hydroxy-3-methyl-naphthalene-2-carboxylic acid methyl ester (36 mg), using a method analogous to the one described for example 8-1, [6-fluoro-4-(4-methanesulfonyl-phenylamino)-3-methyl-naphthalen-2-yl]-acetic acid (20 mg) was obtained as a white solid. $^1$H NMR (400 MHz, CDCl$_3$) δ ppm 7.85 (dd, J=8.97, 5.68 Hz, 1H), 7.76 (s, 1H), 7.70 (d, J=8.84 Hz, 2H), 7.47 (dd, J=10.36, 2.27 Hz, 1H), 6.56 (s, 2H), 5.97 (s, 1H), 3.92 (s, 2H), 3.02 (s, 3H), 2.36 (s, 3H); MS cald. for C$_{20}$H$_{18}$FNO$_4$S 387, obsd. (ESI$^+$) [(M+H)$^+$] 388.

Example 9-1

[6-fluoro-4-(4-methanesulfonyl-phenylsulfanyl)-naphthalen-2-yl]-acetic acid

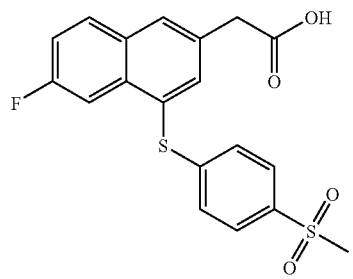

(4-dimethylthiocarbamoyloxy-6-fluoro-naphthalen-2-yl)-acetic acid methyl ester

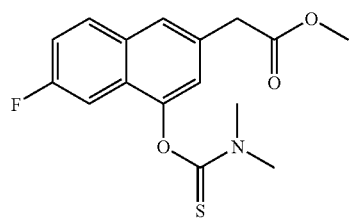 [SMILES: COC(=O)Cc1cc(OC(=S)N(C)C)c2cc(F)ccc2c1]

A mixture of (6-fluoro-4-hydroxy-naphthalen-2-yl)-acetic acid methyl ester (500 mg, 2.14 mmol), finely ground potassium carbonate (591 mg, 4.28 mmol), and N,N-dimethylformamide (10 mL) was stirred at room temperature for 20 minutes. Dimethylthiocarbamoyl chloride (290 mg, 2.35 mmol) was added in one portion. After being stirred for 2 hours, the resulting mixture was diluted with water (20 mL) and extracted with ethyl acetate (20 mL×2). The combined organic layers were washed with water (15 mL) and brine (20 mL), then dried over sodium sulfate, and concentrated in vacuo. The residue was purified by column chromatography (gradient elution with 0-30% ethyl acetate in hexanes) to afford (4-dimethylthiocarbamoyloxy-6-fluoro-naphthalen-2-yl)-acetic acid methyl ester (491 mg, 71.5%) as a yellow oil.

(4-dimethylcarbamoylsulfanyl-6-fluoro-naphthalen-2-yl)-acetic acid methyl ester

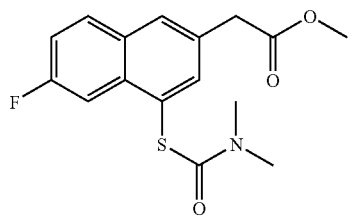 [SMILES: COC(=O)Cc1cc(SC(=O)N(C)C)c2cc(F)ccc2c1]

Neat (4-dimethylthiocarbamoyloxy-6-fluoro-naphthalen-2-yl)-acetic acid methyl ester (100 mg, 0.31 mmol) was heated at 240° C. for 1 hour with rigorous exclusion of air. The resulting brown oil was then purified by flash column chromatography (gradient elution with 20-30% ethyl ester in hexanes) to afford (4-dimethylcarbamoylsulfanyl-6-fluoro-naphthalen-2-yl)-acetic acid methyl ester (40 mg, 40%) as a yellow oil.

(6-fluoro-4-mercapto-naphthalen-2-yl)-acetic acid

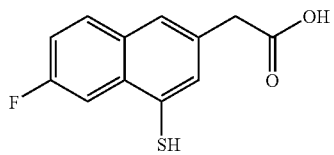 [SMILES: O=C(O)Cc1cc(S)c2cc(F)ccc2c1]

A solution of (4-dimethylcarbamoylsulfanyl-6-fluoro-naphthalen-2-yl)-acetic acid methyl ester (40 mg, 0.13 mmol) and potassium hydroxide (72 mg, 1.3 mmol) in methanol (10 mL) was heated at reflux for 3 hours. The resulting mixture was cooled to room temperature, diluted with water (10 mL), acidified with 2 N hydrochloric acid, and extracted with ethyl acetate (10 mL×2). The combined organic layers were washed with water and brine, then dried over sodium sulfate and concentrated in vacuo to afford crude (6-fluoro-4-mercapto-naphthalen-2-yl)-acetic acid (30 mg) as a yellow solid.

[6-fluoro-4-(4-methanesulfonyl-phenylsulfanyl)-naphthalen-2-yl]-acetic acid

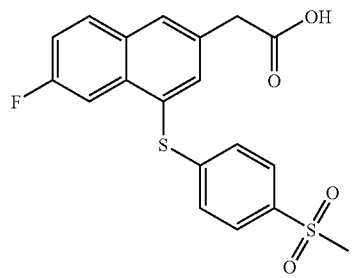

To a solution of (6-fluoro-4-mercapto-naphthalen-2-yl)-acetic acid (30 mg, 0.127 mmol) in N,N-dimethylformamide (2 mL), was added 1-fluoro-4-methanesulfonyl-benzene (43.4 mg, 0.25 mmol) and potassium carbonate (35 mg, 0.25 mmol) under a nitrogen atmosphere. After being heated under microwave conditions (100° C., 30 minutes), the resulting mixture was diluted with water (10 mL) and extracted with ethyl acetate (10 mL×3). The organic layer was washed with brine, dried over sodium sulfate and concentrated in vacuo. The residue was purified by column chromatography (0-20% methanol in dichloromethane) to afford [6-fluoro-4-(4-methanesulfonyl-phenylsulfanyl)-naphthalen-2-yl]-acetic acid (37.0 mg, 74.6%) as an off-white powder. $^1$H NMR (400 MHz, CDCl$_3$) δ ppm 7.86-7.93 (m, 4H), 7.69-7.74 (m, 2H), 7.34 (td, J=8.53, 2.65 Hz, 1H), 7.08-7.15 (m, 2H), 3.85 (s, 2H), 3.01 (s, 3H); MS cald. for C$_{19}$H$_{15}$FO$_4$S$_2$ 390, obsd. (ESI$^+$) [(M+H)$^+$] 391.

Example 10-1

[6-fluoro-4-(4-methanesulfonyl-benzenesulfinyl)-naphthalen-2-yl]-acetic acid

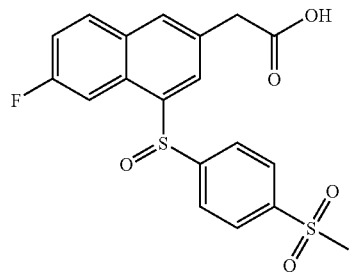 [SMILES: CS(=O)(=O)c1ccc(S(=O)c2cc(CC(=O)O)cc3ccc(F)cc23)cc1]

To a solution of 6-fluoro-4-(4-methanesulfonyl-phenylsulfanyl)-naphthalen-2-yl]-acetic acid (25 mg, 0.064 mmol) in dichloromethane was added m-chloroperoxybenzoic acid (12.1 mg, 0.07 mmol, 80% purity) at 0° C. After being stirred at room temperature for 2 hours, the resulting mixture was concentrated in vacuo. The residue was purified by preparative HPLC (gradient elution with 30-50% 0.1% trifluoroacetic acid in water in acetonitrile, 8 minutes) to afford [6-fluoro-4-(4-methanesulfonyl-benzenesulfinyl)-naphthalen-2-yl]-acetic acid (12.0 mg, 46%) as a white solid. $^1$H NMR (400 MHz, DMSO-d$_6$) δ ppm 12.59 (br. s, 1H), 8.21 (d, J=1.26 Hz, 1H), 8.09-8.15 (m, 2H), 8.07 (s, 1H), 8.03 (s, 4H), 7.55 (td, J=8.84, 2.53 Hz, 1H), 3.89 (s, 2H), 3.21 (s, 3H); MS cald. For C$_{19}$H$_{15}$FO$_5$S$_2$ 406, obsd. (ESI$^+$) [(M+H)$^+$] 407.

Example 11-1

[6-fluoro-4-(4-methanesulfonyl-benzenesulfonyl)-naphthalen-2-yl]-acetic acid

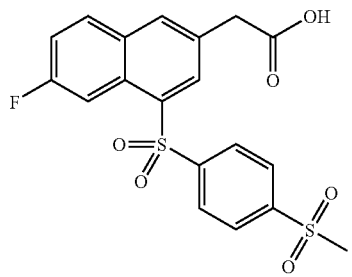 [SMILES: CS(=O)(=O)c1ccc(S(=O)(=O)c2cc(CC(=O)O)cc3ccc(F)cc23)cc1]

To a solution of 6-fluoro-4-(4-methanesulfonyl-phenylsulfanyl)-naphthalen-2-yl]-acetic acid (25 mg, 0.064 mmol) in dichloromethane was added m-chloroperoxybenzoic acid (41.4 mg, 0.192 mmol, 80% solution in water) at 0° C. After being stirred at reflux for 3 hours, the resulting mixture was concentrated in vacuo. The residue was purified by preparative HPLC (gradient elution with 30-50% 0.1% trifluoroacetic acid in water in acetonitrile, 8 minutes) to afford [6-fluoro-4-(4-methanesulfonyl-benzenesulfonyl)-naphthalen-2-yl]-acetic acid (18 mg, 66.7%) as a white solid. $^1$H NMR (400 MHz, DMSO-d$_6$) δ ppm 12.65 (s, 1H), 8.58 (d, J=1.52 Hz, 1H), 8.24-8.31 (m, 3H), 8.11-8.23 (m, 4H), 7.61 (dd, J=10.23, 7.45 Hz, 1H), 3.97 (s, 2H), 3.26 (s, 3H); MS cald. for C$_{19}$H$_{15}$FO$_6$S$_2$ 422, obsd. (ESI$^+$) [(M+H)$^+$] 423.

Example 12-1

[6-Bromo-4-(5-ethanesulfonyl-pyridin-2-yloxy)-naphthalen-2-yl]-acetic acid

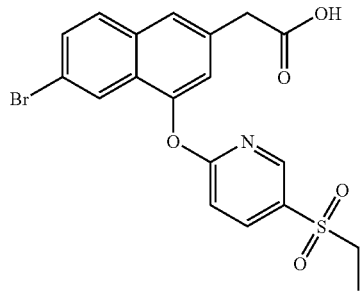 [SMILES: CCS(=O)(=O)c1ccc(Oc2cc(CC(=O)O)cc3ccc(Br)cc23)nc1]

6-Bromo-4-(5-ethanesulfonyl-pyridin-2-yloxy)-naphthalene-2-carboxylic acid methyl ester

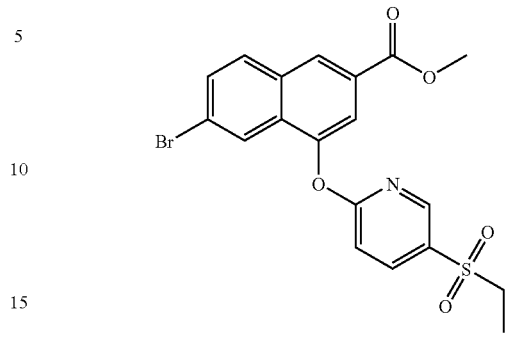

A mixture of 6-bromo-4-hydroxy-naphthalene-2-carboxylic acid methyl ester (423 mg, 1.5 mmol), potassium carbonate (414 mg, 3 mmol), 2,5-bis-ethanesulfonyl-pyridine (420 mg, 1.6 mmol) and N,N-dimethylformamide (4 mL) was vigorously stirred and heated at 100° C. overnight under an argon atmosphere, then cooled to room temperature, and diluted with ethyl acetate (10 mL). The resulting mixture was washed with water (10 mL×3). The combined aqueous layers were extracted with ethyl acetate (10 mL). The organic layers were combined, dried over sodium sulfate, and concentrated in vacuo. The residue was purified by silica gel chromatography (silica gel, 100-200 mesh, 30% ethyl acetate in petroleum ether) to give 6-bromo-4-(5-ethanesulfonyl-pyridin-2-yloxy)-naphthalene-2-carboxylic acid methyl ester (280 mg, 41%, crude yield) as a yellow solid.

[6-Bromo-4-(5-ethanesulfonyl-pyridin-2-yloxy)-naphthalen-2-yl]-methanol

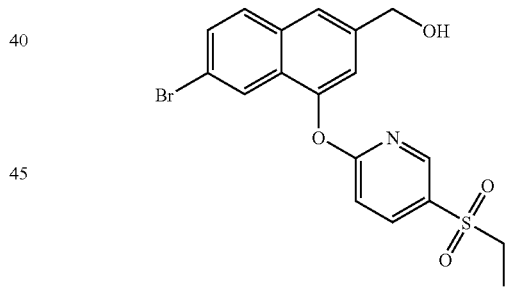

To a solution of 6-bromo-4-(5-ethanesulfonyl-pyridin-2-yloxy)-naphthalene-2-carboxylic acid methyl ester (280 mg, 0.63 mmol) in tetrahydrofuran (5 mL) was added a solution of diisobutylaluminum hydride (1 M in toluene, 1.3 mL, 1.3 mmol) dropwise at −78° C. under a nitrogen atmosphere. The resulting mixture was warmed to room temperature and stirred at room temperature (the total stirring time between −78° C. and room temperature was 3 hours). The reaction mixture was treated with an aqueous solution of potassium sodium tartrate tetrahydrate at 0° C., warmed to room temperature, and stirred at room temperature for 30 min. The resulting mixture was extracted with ethyl acetate (20 mL×3). The combined organic layers were washed with brine, dried over sodium sulfate, and concentrated in vacuo. The residue was purified by silica gel chromatography (silica gel, 100-200 mesh, 30% ethyl acetate in petroleum ether) to give

[6-bromo-4-(5-ethanesulfonyl-pyridin-2-yloxy)-naphthalen-2-yl]-methanol (263 mg, 99%) as a colorless oil.

2-(7-Bromo-3-chloromethyl-naphthalen-1-yloxy)-5-ethanesulfonyl-pyridine

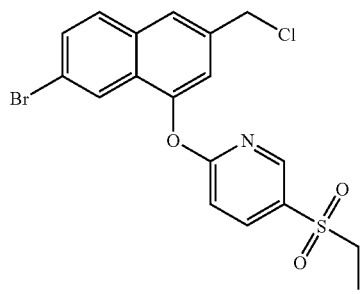 [SMILES: CCS(=O)(=O)c1ccc(Oc2cc(CCl)cc3ccc(Br)cc23)nc1]

After a solution of triphenylphosphine (330 mg, 1.26 mmol) and carbon tetrachloride (2 mL) in anhydrous tetrahydrofuran (6 mL) was stirred at room temperature for 10 minutes under a nitrogen atmosphere, [6-bromo-4-(5-ethanesulfonyl-pyridin-2-yloxy)-naphthalen-2-yl]-methanol (265 mg, 0.63 mmol) was introduced as a solid. The resulting mixture was heated at reflux for 4 hours, cooled to room temperature, then diluted with water (10 mL), and extracted with ethyl acetate (30 mL×2). The combined organic layers were dried over sodium sulfate and concentrated in vacuo. The residue was purified by silica gel chromatography (silica gel, 100-200 mesh, 5% ethyl acetate in petroleum ether) to afford 2-(7-bromo-3-chloromethyl-naphthalen-1-yloxy)-5-ethanesulfonyl-pyridine (210 mg, 76%) as a yellow oil.

[6-Bromo-4-(5-ethanesulfonyl-pyridin-2-yloxy)-naphthalen-2-yl]-acetic acid methyl ester

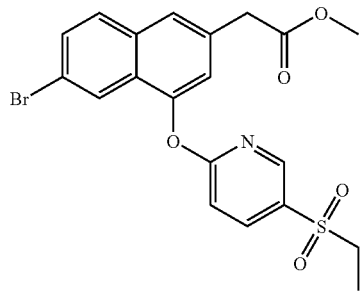 [SMILES: CCS(=O)(=O)c1ccc(Oc2cc(CC(=O)OC)cc3ccc(Br)cc23)nc1]

To a flask containing 2-(7-bromo-3-chloromethyl-naphthalen-1-yloxy)-5-ethanesulfonyl-pyridine (210 mg, 0.46 mmol), bis(triphenylphosphine)dichloropalladium(II) (16 mg, 0.023 mmol) and potassium carbonate (67 mg, 0.48 mmol), which was evacuated and then filled with carbon monoxide (balloon), were added methanol (2 mL) and tetrahydrofuran (4 mL) by means of a syringe. After being stirred at room temperature under a carbon monoxide atmosphere for 3 hours, the reaction mixture was diluted with water (5 mL), and extracted with ethyl acetate (20 mL). The organic layer was washed with water (10 mL×2). The combined aqueous layers were extracted with ethyl acetate (20 mL), and the combined organic layers were dried over sodium sulfate and concentrated in vacuo. The residue was purified by column chromatography (silica gel, 100-200 mesh, 20% ethyl acetate in petroleum ether) to afford [6-bromo-4-(5-ethanesulfonyl-pyridin-2-yloxy)-naphthalen-2-yl]-acetic acid methyl ester (245 mg, 99%) as a yellow solid.

[6-Bromo-4-(5-ethanesulfonyl-pyridin-2-yloxy)-naphthalen-2-yl]-acetic acid

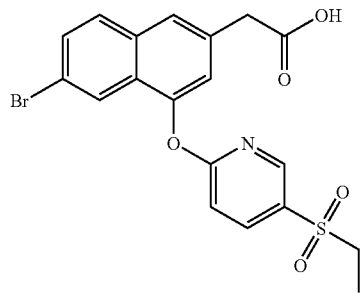 [SMILES: CCS(=O)(=O)c1ccc(Oc2cc(CC(=O)O)cc3ccc(Br)cc23)nc1]

Starting with [6-bromo-4-(5-ethanesulfonyl-pyridin-2-yloxy)-naphthalen-2-yl]-acetic acid methyl ester (23 mg, 0.05 mmol), using a method analogous to the one described for example 1-1, final step, [6-bromo-4-(5-ethanesulfonyl-pyridin-2-yloxy)-naphthalen-2-yl]-acetic acid (10.2 mg, 45%) was obtained as a white solid. $^1$H NMR (400 MHz, CDCl$_3$) δ ppm 8.63 (d, J=2.53 Hz, 1H), 8.23 (dd, J=8.84, 2.53 Hz, 1H), 8.03 (d, J=1.26 Hz, 1H), 7.77 (d, J=8.84 Hz, 1H), 7.69 (s, 1H), 7.62 (dd, J=8.72, 1.89 Hz, 1H), 7.31 (d, J=1.01 Hz, 1H), 7.23 (d, J=8.84 Hz, 1H), 3.85 (s, 2H), 3.17 (q, J=7.33 Hz, 2H), 1.35 (t, J=7.45 Hz, 3H); MS cald. for C$_{19}$H$_{16}$BrNO$_5$S 449, obsd. (ESI$^+$) [(M+H)$^+$] 450.

Example 13-1

[4-(5-Ethanesulfonyl-pyridin-2-yloxy)-6-methyl-naphthalen-2-yl]-acetic acid

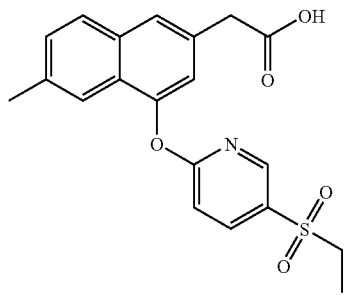 [SMILES: CCS(=O)(=O)c1ccc(Oc2cc(CC(=O)O)cc3ccc(C)cc23)nc1]

[4-(5-Ethanesulfonyl-pyridin-2-yloxy)-6-methyl-naphthalen-2-yl]-acetic acid methyl ester

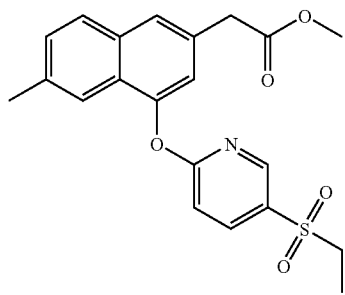

A mixture of [6-bromo-4-(5-ethanesulfonyl-pyridin-2-yloxy)-naphthalen-2-yl]-acetic acid methyl ester (30 mg, 0.07 mmol, methyl ester of example 12-1), methylboronic acid (7 mg, 0.11 mmol), tetrakis(triphenylphosphine)palladium(0) (8 mg, 0.007 mmol), potassium phosphate (45 mg, 0.21 mmol) and toluene (0.5 mL) was stirred at 115 overnight under an argon atmosphere. The resulting mixture was diluted with water (5 mL), and then extracted with ethyl acetate (20 mL×2). The combined organic layers were washed with brine (20 mL), dried over sodium sulfate and concentrated in vacuo. The residue was purified by preparative TLC (20% ethyl acetate in petroleum ether) to give [4-(5-ethanesulfonyl-pyridin-2-yloxy)-6-methyl-naphthalen-2-yl]-acetic acid methyl ester (20 mg) as a colorless oil.

[4-(5-Ethanesulfonyl-pyridin-2-yloxy)-6-methyl-naphthalen-2-yl]-acetic acid

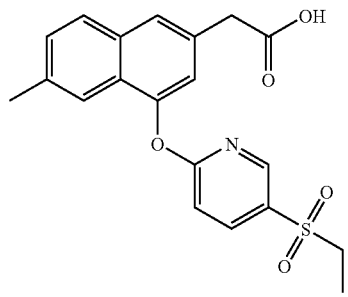 [SMILES: CCS(=O)(=O)c1ccc(Oc2cc(CC(=O)O)cc3ccc(C)cc23)nc1]

Starting with [4-(5-ethanesulfonyl-pyridin-2-yloxy)-6-methyl-naphthalen-2-yl]-acetic acid methyl ester (20 mg, 0.05 mmol), using a method analogous to the one described for example 1-1, final step, [4-(5-ethanesulfonyl-pyridin-2-yloxy)-6-methyl-naphthalen-2-yl]-acetic acid (4.5 mg, 17%, two steps) was obtained as a white powder. $^1$H NMR (400 MHz, CDCl$_3$) δ ppm 8.66 (d, J=2.53 Hz, 1H), 8.18 (dd, J=8.72, 2.40 Hz, 1H), 7.79 (d, J=8.34 Hz, 1H), 7.68 (s, 1H), 7.59 (s, 1H), 7.38 (d, J=8.34 Hz, 1H), 7.24 (s, 1H), 7.15 (d, J=8.59 Hz, 1H), 3.84 (s, 2H), 3.16 (q, J=7.16 Hz, 2H), 2.47 (s, 3H), 1.34 (t, J=7.45 Hz, 3H); MS calcd. for C$_{20}$H$_{19}$NO$_5$S 385, obsd. (ESI$^+$) [(M+H)$^+$] 386.

Example 14-1

[6-Cyano-4-(5-ethanesulfonyl-pyridin-2-yloxy)-naphthalen-2-yl]-acetic acid

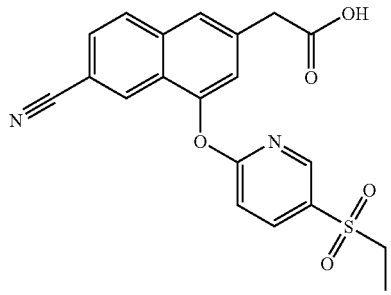 [SMILES: CCS(=O)(=O)c1ccc(Oc2cc(CC(=O)O)cc3ccc(C#N)cc23)nc1]

[6-Cyano-4-(5-ethanesulfonyl-pyridin-2-yloxy)-naphthalen-2-yl]-acetic acid methyl ester

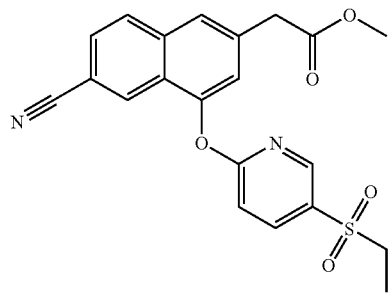 [SMILES: CCS(=O)(=O)c1ccc(Oc2cc(CC(=O)OC)cc3ccc(C#N)cc23)nc1]

A mixture of [6-bromo-4-(5-ethanesulfonyl-pyridin-2-yloxy)-naphthalen-2-yl]-acetic acid methyl ester (29 mg, 0.07 mmol, methyl ester of example 12-1), zinc cyanide (10 mg, 0.084 mmol), tetrakis(triphenylphosphine)palladium(0) (18 mg, 0.014 mmol) and N,N-dimethylacetamide (0.2 mL) was stirred at 150° C. for 24 hours under an argon atmosphere. The reaction mixture was diluted with water (5 mL), and extracted with ethyl acetate (20 mL×2). The combined organic layers were washed with brine (20 mL), dried over sodium sulfate and concentrated in vacuo. The residue was purified by preparative TLC (30% ethyl acetate in petroleum ether) to give [6-cyano-4-(5-ethanesulfonyl-pyridin-2-yloxy)-naphthalen-2-yl]-acetic acid methyl ester (17 mg) as a white solid.

[6-Cyano-4-(5-ethanesulfonyl-pyridin-2-yloxy)-naphthalen-2-yl]-acetic acid

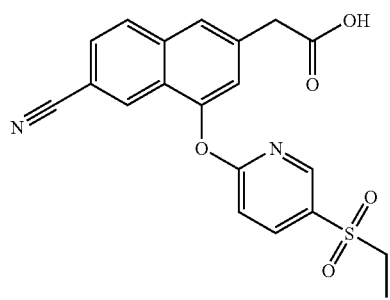 [SMILES: CCS(=O)(=O)c1ccc(Oc2cc(CC(=O)O)cc3ccc(C#N)cc23)nc1]

Starting with [6-cyano-4-(5-ethanesulfonyl-pyridin-2-yloxy)-naphthalen-2-yl]-acetic acid methyl ester (17 mg, 0.04 mmol), using a method analogous to the one described for example 1-1, final step, [6-cyano-4-(5-ethanesulfonyl-pyridin-2-yloxy)-naphthalen-2-yl]-acetic acid (1.1 mg) was obtained as a white solid. $^1$H NMR (400 MHz, CDCl$_3$) δ ppm 8.61 (d, J=2.27 Hz, 1H), 8.25-8.30 (m, 2H), 7.99 (d, J=8.59 Hz, 1H), 7.78 (s, 1H), 7.68 (dd, J=8.59, 1.26 Hz, 1H), 7.42 (d, J=1.01 Hz, 5H), 7.31 (d, J=8.84 Hz, 5H), 3.90 (s, 2H), 3.19 (q, J=7.24 Hz, 2H), 1.37 (t, J=7.45 Hz, 3H); MS cald. for $C_{20}H_{16}N_2O_5S$ 396, obsd. (ESI$^+$) [(M+H)$^+$] 397.

Example 15-1

[6-Bromo-4-(4-ethanesulfonyl-phenoxy)-naphthalen-2-yl]-acetic acid

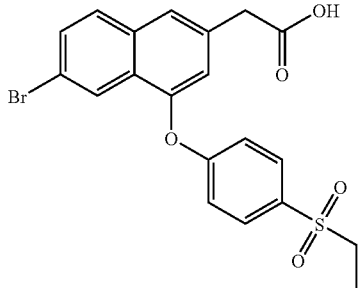 [SMILES: CCS(=O)(=O)c1ccc(Oc2cc(CC(=O)O)cc3ccc(Br)cc23)cc1]

Starting with 6-bromo-4-hydroxy-naphthalene-2-carboxylic acid methyl ester and 1-ethanesulfonyl-4-fluoro-benzene, using a method analogous to the one described for example 14-1, [6-bromo-4-(4-ethanesulfonyl-phenoxy)-naphthalen-2-yl]-acetic acid (10.4 mg, 63%) was obtained as a yellow solid. $^1$H NMR (400 MHz, CDCl$_3$) δ ppm 8.18 (s, 1H), 7.89 (d, J=8.84 Hz, 2H), 7.76 (d, J=8.59 Hz, 1H), 7.57-7.68 (m, 2H), 7.10-7.17 (m, 3H), 3.80 (s, 2H), 3.15 (q, J=7.58 Hz, 2H), 1.33 (t, J=7.45 Hz, 3H); MS cald. for $C_{20}H_{17}BrO_5S$ 448, obsd. (ESI$^+$) [(M+H)$^+$] 449.

Example 16-1

[4-(4-Ethanesulfonyl-phenoxy)-6-methanesulfonyl-naphthalen-2-yl]-acetic acid

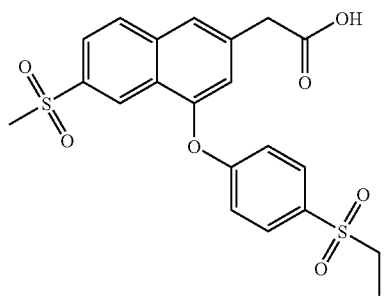 [SMILES: CCS(=O)(=O)c1ccc(Oc2cc(CC(=O)O)cc3ccc(S(C)(=O)=O)cc23)cc1]

[4-(4-Ethanesulfonyl-phenoxy)-6-methanesulfonyl-naphthalen-2-yl]-acetic acid methyl ester

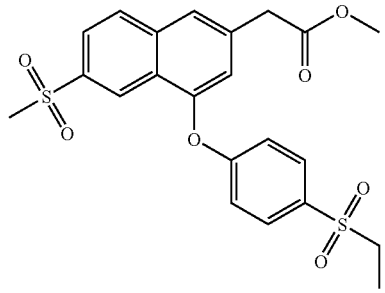 [SMILES: CCS(=O)(=O)c1ccc(Oc2cc(CC(=O)OC)cc3ccc(S(C)(=O)=O)cc23)cc1]

A mixture of [6-bromo-4-(4-ethanesulfonyl-phenoxy)-naphthalen-2-yl]-acetic acid methyl ester (32 mg, 0.07 mmol, methyl ester of example 15-1), sodium methanesulfinate (10 mg, 0.09 mmol), L-proline (4 mg, 0.028 mmol), copper(I) iodide (3 mg, 0.014 mmol) and dimethyl sulfoxide (0.3 mL) was stirred at 115° C. overnight under an argon atmosphere. The resulting mixture was diluted with water (5 mL), and extracted with ethyl acetate (20 mL×2). The combined organic layers were washed with brine (20 mL), dried over sodium sulfate and concentrated in vacuo. The residue was purified by preparative TLC (30% ethyl acetate in petroleum ether) to give [4-(4-ethanesulfonyl-phenoxy)-6-methanesulfonyl-naphthalen-2-yl]-acetic acid methyl ester (11 mg) as a yellow solid.

[4-(4-Ethanesulfonyl-phenoxy)-6-methanesulfonyl-naphthalen-2-yl]-acetic acid

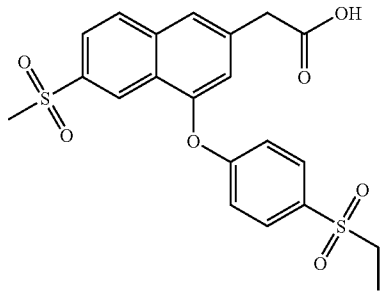 [SMILES: CCS(=O)(=O)c1ccc(Oc2cc(CC(=O)O)cc3ccc(S(C)(=O)=O)cc23)cc1]

Starting with [4-(4-ethanesulfonyl-phenoxy)-6-methanesulfonyl-naphthalen-2-yl]-acetic acid methyl ester (11 mg, 0.024 mmol), using a method analogous to the one described for example 1-1, final step, [4-(5-ethanesulfonyl-pyridin-2-yloxy)-6-methyl-naphthalen-2-yl]-acetic acid (8 mg, 26%, two steps) was obtained as a yellow solid. $^1$H NMR (400 MHz, CDCl$_3$) δ ppm 8.80 (s, 1H), 8.05-8.09 (m, 1H), 7.99-8.04 (m, 1H), 7.94 (d, J=8.59 Hz, 2H), 7.72 (s, 1H), 7.23 (d, J=8.59 Hz, 2H), 7.14 (s, 1H), 3.85 (s, 2H), 3.17 (q, J=7.58 Hz, 2H), 3.13 (s, 3H), 1.34 (t, J=7.45 Hz, 3H); MS cald. for $O_{21}H_{20}O_7S_2$ 448, obsd. (ESI$^+$) [(M+H)$^+$] 449.

Example 17-1

[4-(5-Ethanesulfonyl-pyridin-2-yloxy)-6-fluoro-3-vinyl-naphthalen-2-yl]-acetic acid

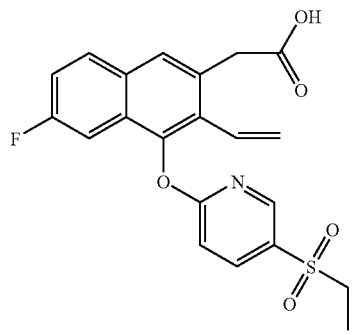 [SMILES: C=Cc1c(CC(=O)O)cc2ccc(F)cc2c1Oc1ccc(S(=O)(=O)CC)cn1]

(6-Fluoro-4-hydroxy-3-iodo-naphthalen-2-yl)-acetic acid methyl ester

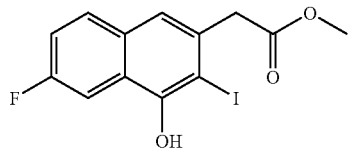

To a solution of (6-fluoro-4-hydroxy-naphthalen-2-yl)-acetic acid methyl ester (600 mg, 2.56 mmol, the product of 8$^{th}$ step for example 1-1) in chloroform (260 mL) was added N-iodosuccinimide (577 mg, 2.56 mmol) at 0° C. The mixture was allowed to warm to room temperature and stirred at room temperature for 2 hours. The resulting mixture was diluted with 10% aqueous solution of sodium bisulfate (100 mL). The organic layer was separated, washed with brine (100 mL), dried over sodium sulfate, and concentrated in vacuo. The residue was purified by flash column (elution with 15% ethyl acetate in petroleum ether) to afford (6-fluoro-4-hydroxy-3-iodo-naphthalen-2-yl)-acetic acid methyl ester (500 mg, 54%) as a white solid.

(4-Acetoxy-6-fluoro-3-iodo-naphthalen-2-yl)-acetic acid methyl ester

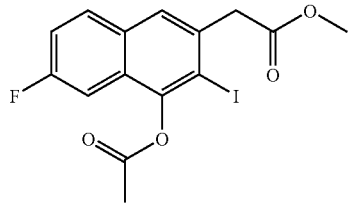 [SMILES: COC(=O)Cc1cc2ccc(F)cc2c(OC(C)=O)c1I]

To a stirred solution of (6-fluoro-4-hydroxy-3-iodo-naphthalen-2-yl)-acetic acid methyl ester (500 mg, 1.4 mmol) and 4-dimethylaminopyridine (34 mg, 0.28 mmol) in pyridine (3 mL) was added acetic anhydride (160 µL, 1.7 mmol). After being stirred at room temperature overnight, the resulting mixture was diluted with 10% hydrochloric acid (20 mL), and extracted with ethyl acetate (30 mL×2). The combined organic layers were washed with brine (30 mL×2), dried over sodium sulfate, and concentrated in vacuo. The residue was purified by flash column (elution with 20% ethyl acetate in petroleum ether) to afford (4-acetoxy-6-fluoro-3-iodo-naphthalen-2-yl)acetic acid methyl ester (300 mg, 53%) as a white solid.

(4-Acetoxy-6-fluoro-3-trimethylsilanylethynyl-naphthalen-2-yl)-acetic acid methyl ester

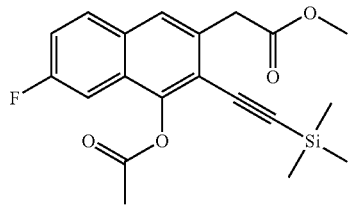 [SMILES: COC(=O)Cc1cc2ccc(F)cc2c(OC(C)=O)c1C#C[Si](C)(C)C]

To a solution of (4-acetoxy-6-fluoro-3-iodo-naphthalen-2-yl)acetic acid methyl ester (300 mg, 0.75 mmol) and triethylamine (3 mL) in N,N-dimethylformamide (3 mL), was added bis(triphenylphosphine)dichloropalladium(II) (53 mg, 0.075 mmol), copper iodide (42 mg, 0.229 mmol) and trimethylsilanylacetylene (108 mg, 1.12 mmol) under an argon atmosphere. After being heated at 150° C. for 6 minutes with microwave irradiation, the resulting mixture was cooled, diluted with ethyl acetate (20 mL), and washed with brine (15 mL×2). The organic layer was dried over sodium sulfate and concentrated in vacuo. The residue was purified by flash column (elution with 10% ethyl acetate in petroleum ether) to afford (4-acetoxy-6-fluoro-3-trimethylsilanylethynyl-naphthalen-2-yl)-acetic acid methyl ester (208 mg, 75%) as a light yellow solid.

(4-Acetoxy-3-ethynyl-6-fluoro-naphthalen-2-yl)-acetic acid methyl ester

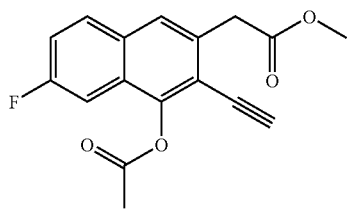 [SMILES: C#Cc1c(CC(=O)OC)cc2ccc(F)cc2c1OC(C)=O]

To a solution of (4-acetoxy-6-fluoro-3-trimethylsilanylethynyl-naphthalen-2-yl)-acetic acid methyl ester (200 mg, 0.538 mmol) in N,N-dimethylformamide and water (6 mL, v/v=150:1), was added potassium fluoride (156 mg, 2.7 mmol). The resulting mixture was stirred at room temperature for 4 hours, then poured into water (10 mL), and extracted with ethyl acetate (10 mL×3). The organic layers were combined, washed with brine, dried over sodium sulfate and concentrated in vacuo. The residue was purified by flash column (elution with 10% ethyl acetate in petroleum ether) to afford (4-acetoxy-3-ethynyl-6-fluoro-naphthalen-2-yl)-acetic acid methyl ester (153 mg, 95%) as a light yellow solid.

(4-Acetoxy-6-fluoro-3-vinyl-naphthalen-2-yl)-acetic acid methyl ester

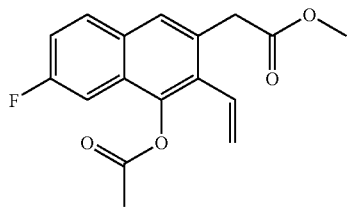

A round-bottom flask (5 mL) charged with indium trichloride (88 mg, 0.40 mmol) was heated at 100° C. under reduced pressure for 1 h, and filled with nitrogen. A solution of triethylsilane (46 mg, 0.4 mmol) in acetonitrile (4 mL), which was cooled to 0° C., was added by means of syringe. After the mixture was stirred at 0° C. for 5 minutes, (4-acetoxy-3-ethynyl-6-fluoro-naphthalen-2-yl)-acetic acid methyl ester (60 mg, 0.20 mmol) and a solution of triethylborane (1M solution in tetrahydrofuran, 20 µL, 0.02 mmol) were added. The resulting mixture was stirred at 0° C. for 3 hours, then poured into water (10 mL), and extracted with ethyl acetate (10 mL×3). The organic layers were combined, dried over sodium sulfate and concentrated in vacuo. The residue was purified by flash column (elution with 10% ethyl acetate in

(6-Fluoro-4-hydroxy-3-vinyl-naphthalen-2-yl)-acetic acid methyl ester

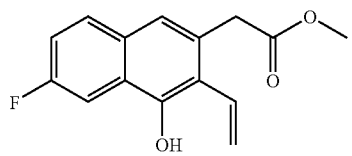

A mixture of (4-acetoxy-6-fluoro-3-vinyl-naphthalen-2-yl)acetic acid methyl ester (38 mg, 0.126 mmol), sodium methoxide (10.1 mg, 0.189 mmol), and methanol (4 mL) was stirred at room temperature for 2 hours. After the reaction mixture was acidified with concentrated hydrochloric acid to pH 5, a precipitate formed, which was collected by filtration, and dissolved in ethyl acetate (20 mL). The organic solution was dried over sodium sulfate, and concentrated in vacuo to afford the crude product (6-fluoro-4-hydroxy-3-vinyl-naphthalen-2-yl)-acetic acid methyl ester (32 mg, 97.7%) as a light yellow solid.

[4-(5-Ethanesulfonyl-pyridin-2-yloxy)-6-fluoro-3-vinyl-naphthalen-2-yl]-acetic acid methyl ester

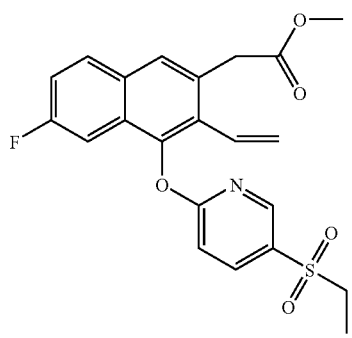 [SMILES: C=Cc1c(CC(=O)OC)cc2ccc(F)cc2c1Oc1ccc(S(=O)(=O)CC)cn1]

A mixture of (6-fluoro-4-hydroxy-3-vinyl-naphthalen-2-yl)-acetic acid methyl ester (22 mg, 0.084 mmol), 2,5-bis-ethanesulfonyl-pyridine (33 mg, 0.126 mmol), potassium iodide (5 mg), and cesium carbonate (68 mg, 0.21 mmol), N,N-dimethylformamide (0.5 mL) and acetone (1.5 mL) was heated at 100° C. for 30 minutes with microwave irradiation. The mixture was then concentrated in vacuo. The residue was purified by flash column (gradient elution with 0-50% ethyl acetate in petroleum ether) to afford [4-(5-ethanesulfonyl-pyridin-2-yloxy)-6-fluoro-3-vinyl-naphthalen-2-yl]-acetic acid methyl ester (13 mg, 36.1%) as a yellow solid.

[4-(5-Ethanesulfonyl-pyridin-2-yloxy)-6-fluoro-3-vinyl-naphthalen-2-yl]-acetic acid

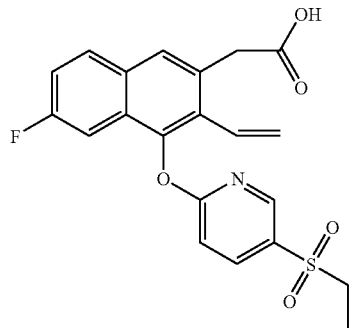 [SMILES: C=Cc1c(CC(=O)O)cc2ccc(F)cc2c1Oc1ccc(S(=O)(=O)CC)cn1]

Starting with [4-(5-ethanesulfonyl-pyridin-2-yloxy)-6-fluoro-3-vinyl-naphthalen-2-yl]-acetic acid methyl ester (8.6 mg, 0.02 mmol), using a method analogous to the one described for example 1-1, final step, [4-(5-ethanesulfonyl-pyridin-2-yloxy)-6-fluoro-3-vinyl-naphthalen-2-yl]-acetic acid (1.4 mg) was obtained as an off-white viscous oil. $^1$H NMR (400 MHz, CD$_3$OD) δ ppm 8.51 (d, J=2.53 Hz, 1H), 8.29 (dd, J=8.84, 2.53 Hz, 1H), 7.95-8.01 (m, 1H), 7.83 (s, 1H), 7.31-7.39 (m, 2H), 7.25 (d, J=8.84 Hz, 1H), 6.68 (dd, J=17.94, 11.62 Hz, 1H), 5.47-5.58 (m, 2H), 3.91 (s, 2H), 3.27 (q, J=7.33 Hz, 2H), 1.26 (t, J=7.45 Hz, 3H); MS cald. for C$_{21}$H$_{18}$FNO$_5$S 415, obsd. (ESI$^+$) [(M+H)$^+$] 416.

Example 18-1

[3-Cyclopropyl-4-(5-ethanesulfonyl-pyridin-2-yloxy)-6-fluoro-naphthalen-2-yl]-acetic acid

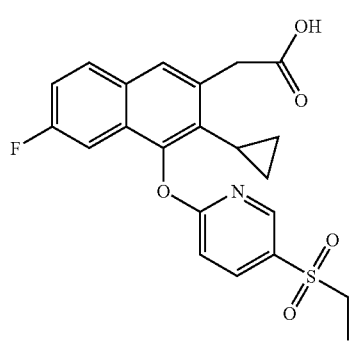 [SMILES: CCS(=O)(=O)c1ccc(Oc2c(C3CC3)c(CC(=O)O)cc3ccc(F)cc23)nc1]

[3-Cyclopropyl-4-(5-ethanesulfonyl-pyridin-2-yloxy)-6-fluoro-naphthalen-2-yl]-acetic acid methyl ester

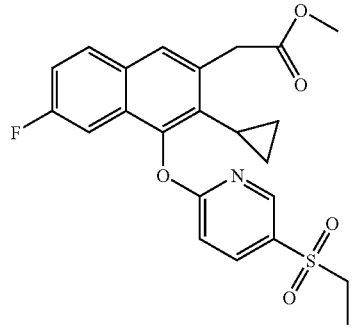 [SMILES: CCS(=O)(=O)c1ccc(Oc2c(C3CC3)c(CC(=O)OC)cc3ccc(F)cc23)nc1]

To a cooled solution of [4-(5-ethanesulfonyl-pyridin-2-yloxy)-6-fluoro-3-vinyl-naphthalen-2-yl]-acetic acid methyl ester (6.0 mg, 0.014 mmol, methyl ester of example 17-1) in tetrahydrofuran, was added a solution of diazomethane (0.1 M, 5 mL) in diethyl ether at 0° C. under an argon atmosphere, followed by palladium acetate (1 mg) in two portions. After being stirred at 0° C. for 2 hours, the reaction mixture was treated with acetic acid (0.2 mL) to quench the reaction, and then filtered. The filtrate was concentrated in vacuo to afford the crude product of [3-cyclopropyl-4-(5-ethanesulfonyl-pyridin-2-yloxy)-6-fluoro-naphthalen-2-yl]-acetic acid methyl ester as a yellow oil.

[3-Cyclopropyl-4-(5-ethanesulfonyl-pyridin-2-yloxy)-6-fluoro-naphthalen-2-yl]-acetic acid

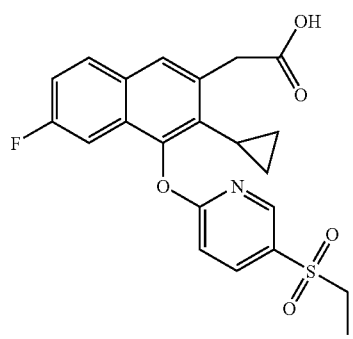 [SMILES: CCS(=O)(=O)c1ccc(Oc2c(C3CC3)c(CC(=O)O)cc3ccc(F)cc23)nc1]

Starting with [3-cyclopropyl-4-(5-ethanesulfonyl-pyridin-2-yloxy)-6-fluoro-naphthalen-2-yl]-acetic acid methyl ester, using a method analogous to the one described for example 1-1, final step, [3-cyclopropyl-4-(5-ethanesulfonyl-pyridin-2-yloxy)-6-fluoro-naphthalen-2-yl]-acetic acid (3.3 mg, 66%, two steps) was obtained as a white powder. $^1$H NMR (400 MHz, CD$_3$OD) δ ppm 9.31 (d, J=2.53 Hz, 1H), 9.15 (dd, J=8.84, 2.53 Hz, 1H), 8.85 (dd, J=9.60, 5.56 Hz, 1H), 8.62 (s, 1H), 8.19-8.29 (m, 3H), 4.80 (s, 2H), 4.17 (q, J=7.33 Hz, 2H), 2.25-2.34 (m, 1H), 1.94 (t, J=7.33 Hz, 3H), 1.55-1.64 (m, 2H), 1.37-1.52 (m, 2H); MS cald. for C$_{22}$H$_{20}$FNO$_5$S 429, obsd. (ESI$^+$) [(M+H)$^+$] 430.

Example 19-1

4-(5-Ethanesulfonyl-pyridin-2-yloxy)-3-ethyl-6-fluoro-naphthalen-2-yl]-acetic acid

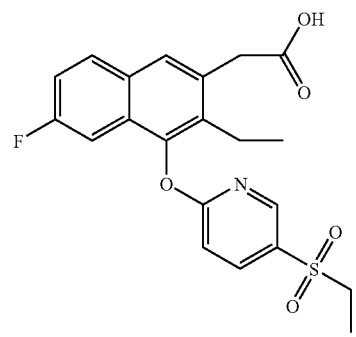 [SMILES: CCc1c(CC(=O)O)cc2ccc(F)cc2c1Oc1ccc(S(=O)(=O)CC)cn1]

(4-Acetoxy-3-ethyl-6-fluoro-naphthalen-2-yl)-acetic acid methyl ester

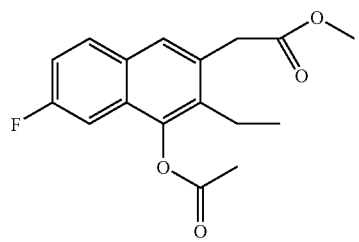 [SMILES: CCc1c(CC(=O)OC)cc2ccc(F)cc2c1OC(C)=O]

To a solution of (4-acetoxy-3-ethynyl-6-fluoro-naphthalen-2-yl)-acetic acid methyl ester (50 mg) in methanol was added 10% palladium on carbon (10 mg). The resulting mixture was hydrogenated under 40 psi of hydrogen for 2 hours and filtered. The filtrate was concentrated in vacuo to afford (4-acetoxy-3-ethyl-6-fluoro-naphthalen-2-yl)acetic acid methyl ester (50 mg) as a colorless oil.

(3-Ethyl-6-fluoro-4-hydroxy-naphthalen-2-yl)-acetic acid methyl ester

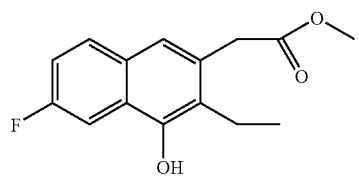 [SMILES: CCc1c(CC(=O)OC)cc2ccc(F)cc2c1O]

A mixture of (4-acetoxy-3-ethyl-6-fluoro-naphthalen-2-yl)-acetic acid methyl ester (50 mg, 0.164 mmol), sodium methoxide (13 mg, 0.247 mmol), and methanol (4 mL) was stirred at room temperature for 2 hours. After the reaction mixture was acidified with concentrated hydrochloric acid to pH 5, a precipitate formed, which was then collected by filtration, and dissolved in ethyl acetate (20 mL). The organic solution was dried over sodium sulfate, and concentrated in vacuo to afford the crude product of (3-ethyl-6-fluoro-4-hydroxy-naphthalen-2-yl)-acetic acid methyl ester (42 mg, 97.7%) as a light yellow solid.

[4-(5-Ethanesulfonyl-pyridin-2-yloxy)-3-ethyl-6-fluoro-naphthalen-2-yl]-acetic acid methyl ester

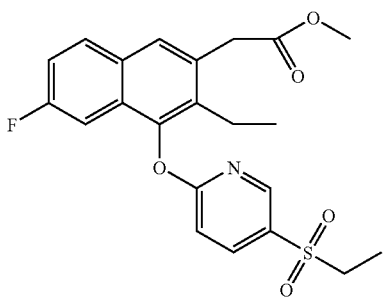 [SMILES: CCc1c(CC(=O)OC)cc2ccc(F)cc2c1Oc1ccc(S(=O)(=O)CC)cn1]

Starting with (3-ethyl-6-fluoro-4-hydroxy-naphthalen-2-yl)-acetic acid methyl ester (15 mg, 0.057 mmol) and 2,5-bis-ethanesulfonyl-pyridine (30 mg, 0.115 mmol), using a method analogous to the described for the methyl ester of example 17-1), [4-(5-ethanesulfonyl-pyridin-2-yloxy)-3-ethyl-6-fluoro-naphthalen-2-yl]-acetic acid methyl ester (15 mg, 61.1%) was obtained as a light yellow solid.

[4-(5-Ethanesulfonyl-pyridin-2-yloxy)-3-ethyl-6-fluoro-naphthalen-2-yl]-acetic acid

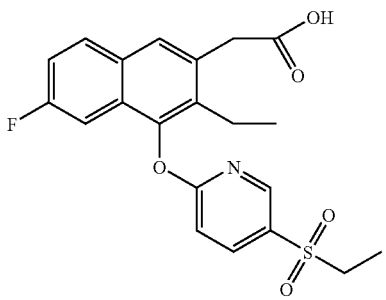 [SMILES: CCc1c(CC(=O)O)cc2ccc(F)cc2c1Oc1ccc(S(=O)(=O)CC)cn1]

Starting with [4-(5-ethanesulfonyl-pyridin-2-yloxy)-3-ethyl-6-fluoro-naphthalen-2-yl]-acetic acid methyl ester (15 mg), using a method analogous to the one described for example 1-1, final step, [4-(5-ethanesulfonyl-pyridin-2-yloxy)-3-ethyl-6-fluoro-naphthalen-2-yl]-acetic acid (6.0 mg) was obtained as an white semisolid. $^1$H NMR (400 MHz, CD$_3$OD) δ ppm 8.51 (d, J=2.53 Hz, 1H), 8.31 (dd, J=8.84, 2.53 Hz, 1H), 7.93 (dd, J=9.09, 5.56 Hz, 1H), 7.79 (s, 1H), 7.24-7.32 (m, 2H), 7.19 (dd, J=10.23, 2.40 Hz, 1H), 3.89 (s, 2H), 3.26 (q, J=7.49 Hz, 2H), 2.71 (q, J=7.58 Hz, 2H), 1.25 (t, J=7.45 Hz, 3H), 1.11 (t, J=7.45 Hz, 3H); MS cald. for O$_{21}$H$_{20}$FNO$_5$S 417, obsd. (ESI$^+$) [(M+H)$^+$] 418.

Example 20-1

[4-(5-Ethanesulfonyl-3-ethyl-pyridin-2-yloxy)-6-fluoro-3-methyl-naphthalen-2-yl]-acetic acid

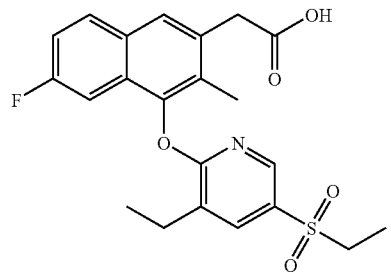 [SMILES: CCc1cc(S(=O)(=O)CC)cnc1Oc1c(C)c(CC(=O)O)cc2ccc(F)cc12]

[4-(3-Bromo-5-ethanesulfonyl-pyridin-2-yloxy)-6-fluoro-3-methyl-naphthalen-2-yl]-acetic acid methyl ester

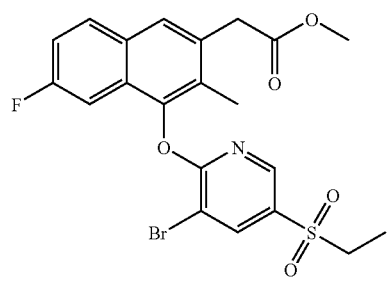 [SMILES: CCS(=O)(=O)c1cnc(Oc2c(C)c(CC(=O)OC)cc3ccc(F)cc23)c(Br)c1]

Starting with 6-fluoro-4-hydroxy-3-methyl-naphthalen-2-yl)-acetic acid methyl ester (124 mg, 0.50 mmol) and 3-bromo-2-chloro-5-ethanesulfonyl-pyridine (157 mg, 0.55 mmol), using a method analogous to the one described for the methyl ester of example 2-1, [4-(3-bromo-5-ethanesulfonyl-pyridin-2-yloxy)-6-fluoro-3-methyl-naphthalen-2-yl]-acetic acid methyl ester (183 mg, 73.9%) was obtained as a white solid.

[4-(5-Ethanesulfonyl-3-ethyl-pyridin-2-yloxy)-6-fluoro-3-methyl-naphthalen-2-yl]-acetic acid methyl ester

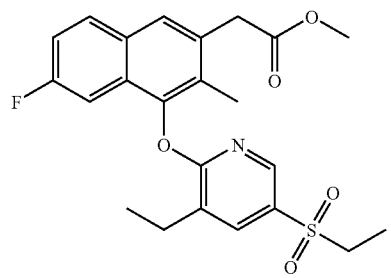 [SMILES: CCc1cc(S(=O)(=O)CC)cnc1Oc1c(C)c(CC(=O)OC)cc2ccc(F)cc12]

A mixture of [4-(3-bromo-5-ethanesulfonyl-pyridin-2-yloxy)-6-fluoro-3-methyl-naphthalen-2-yl]-acetic acid methyl ester (42 mg, 0.085 mmol), ethylboronic acid (15 mg, 0.20 mmol), bis(triphenylphosphine)dichloropalladium(II) (7.0 mg, 0.01 mmol), potassium phosphate (64 mg, 0.30 mmol), triphenylphosphine (15.2 mg, 0.05 mmol) and toluene (1 mL) was stirred at 100° C. overnight under an argon atmosphere. The resulting mixture was filtered. The filtrate was concentrated in vacuo. The residue was purified by preparative TLC (20% ethyl acetate in petroleum ether) to afford [4-(5-ethanesulfonyl-3-ethyl-pyridin-2-yloxy)-6-fluoro-3-methyl-naphthalen-2-yl]-acetic acid methyl ester (18 mg, 47.6%) as a white solid.

[4-(5-Ethanesulfonyl-3-ethyl-pyridin-2-yloxy)-6-fluoro-3-methyl-naphthalen-2-yl]-acetic acid

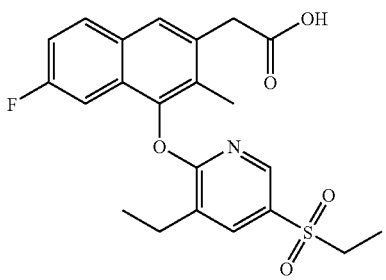 [SMILES: CCc1cc(S(=O)(=O)CC)cnc1Oc1c(C)c(CC(=O)O)cc2ccc(F)cc12]

Starting with [4-(5-ethanesulfonyl-3-ethyl-pyridin-2-yloxy)-6-fluoro-3-methyl-naphthalen-2-yl]-acetic acid methyl ester (18 mg), using a method analogous to the one described for example 1-1, final step, [4-(5-ethanesulfonyl-3-ethyl-pyridin-2-yloxy)-6-fluoro-3-methyl-naphthalen-2-yl]-acetic acid (2.9 mg) was obtained as a white powder. $^1$H NMR (400 MHz, CDCl$_3$) δ ppm 8.34 (d, J=2.53 Hz, 1H), 8.08 (d, J=2.53 Hz, 1H), 7.85 (dd, J=8.97, 5.43 Hz, 1H), 7.72 (s, 1H), 7.17-7.28 (m, 2H), 3.92 (s, 2H), 3.15 (q, J=7.41 Hz, 2H), 3.04 (q, J=7.58 Hz, 2H), 2.20-2.24 (m, 3H), 1.50 (t, J=7.45 Hz, 3H), 1.34 (t, J=7.45 Hz, 3H); MS calcd. for C$_{22}$H$_{22}$FNO$_5$S 431, obsd. (ESI$^+$) [(M+H)$^+$] 432.

Example 21-1

[4-(3-Cyclopropyl-5-ethanesulfonyl-pyridin-2-yloxy)-6-fluoro-3-methyl-naphthalen-2-yl]-acetic acid

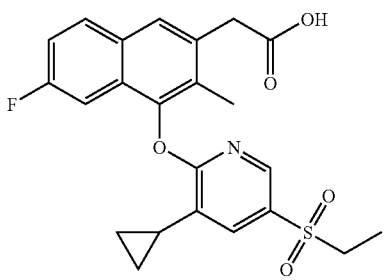 [SMILES: CCS(=O)(=O)c1cnc(Oc2c(C)c(CC(=O)O)cc3ccc(F)cc23)c(C2CC2)c1]

[4-(3-Cyclopropyl-5-ethanesulfonyl-pyridin-2-yloxy)-6-fluoro-3-methyl-naphthalen-2-yl]-acetic acid methyl ester

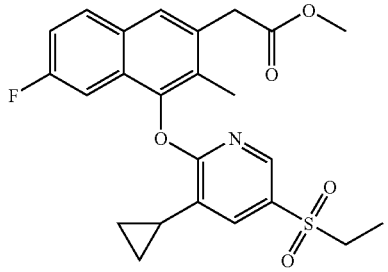 [SMILES: CCS(=O)(=O)c1cnc(Oc2c(C)c(CC(=O)OC)cc3ccc(F)cc23)c(C2CC2)c1]

Starting with 4-(3-bromo-5-ethanesulfonyl-pyridin-2-yloxy)-6-fluoro-3-methyl-naphthalen-2-yl]-acetic acid methyl ester (49 mg, 0.10 mmol), and cyclopropylboronic acid (17 mg, 0.20 mmol), using a method analogous to the one described for the methyl ester of example 20-1, [4-(3-cyclopropyl-5-ethanesulfonyl-pyridin-2-yloxy)-6-fluoro-3-methyl-naphthalen-2-yl]-acetic acid methyl ester (25 mg, 54.7%) as a white solid.

[4-(3-Cyclopropyl-5-ethanesulfonyl-pyridin-2-yloxy)-6-fluoro-3-methyl-naphthalen-2-yl]-acetic acid Starting with [4-(3-cyclopropyl-5-ethanesulfonyl-pyridin-2-yloxy)-6-fluoro-3-methyl-naphthalen-2-yl]-acetic acid methyl ester (25 mg), using a method analogous to the one described for example 1-1, final step, [4-(3-cyclopropyl-5-ethanesulfonyl-pyridin-2-yloxy)-6-fluoro-3-methyl-naphthalen-2-yl]-acetic acid (2.4 mg) was obtained as a white powder. $^1$H NMR (400 MHz, CDCl$_3$) δ ppm 8.28 (d, J=2.53 Hz, 1H), 7.85 (dd, J=8.97, 5.43 Hz, 1H), 7.77 (d, J=2.02 Hz, 1H), 7.72 (s, 1H), 7.21-7.28 (m, 2H), 3.92 (s, 2H), 3.13 (q, J=7.33 Hz, 2H), 2.42-2.52 (m, 1H), 2.25 (s, 3H), 1.32 (t, J=7.33 Hz, 3H), 1.22-1.26 (m, 2H), 0.91-1.04 (m, 2H); MS cald. for $C_{23}H_{22}FNO_5S$ 443, obsd. (ESI$^+$) [(M+H)$^+$] 444.

Example 22-1

2-[4-(5-Ethanesulfonyl-pyridin-2-yloxy)-6-fluoro-3-methyl-naphthalen-2-yl]-propionic acid

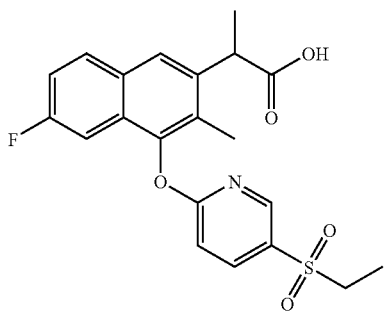 [SMILES: CCS(=O)(=O)c1ccc(Oc2c(C)c(C(C)C(=O)O)cc3ccc(F)cc23)nc1]

2-[4-(5-Ethanesulfonyl-pyridin-2-yloxy)-6-fluoro-3-methyl-naphthalen-2-yl]-propionic acid methyl ester

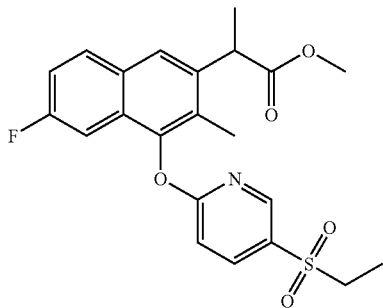 [SMILES: CCS(=O)(=O)c1ccc(Oc2c(C)c(C(C)C(=O)OC)cc3ccc(F)cc23)nc1]

To a solution of [4-(5-ethanesulfonyl-pyridin-2-yloxy)-6-fluoro-3-methyl-naphthalen-2-yl]-acetic acid (226.5 mg, 0.56 mmol, example 2-33) in anhydrous N,N-dimethylformamide (10 mL), which was cooled to −30° C., was added sodium hydride (50 mg, 1.12 mol, 60% in mineral oil). The mixture was stirred at −30° C. for 30 minutes, then treated with a solution of iodomethane (76 µL) in N,N-dimethylformamide (2 mL) dropwise at the same temperature. The mixture was allowed to warm to 0° C. and stirred at the same temperature for 2 hours. The resulting mixture was diluted with ethyl acetate (230 mL), washed with a saturated aqueous solution of ammonium chloride (10 mL×2), dried over sodium sulfate, and concentrated in vacuo. The residue was purified by flash column to afford 2-[4-(5-ethanesulfonyl-pyridin-2-yloxy)-6-fluoro-3-methyl-naphthalen-2-yl]-propionic acid methyl ester (220 mg, 85.1%) as a white solid.

2-[4-(5-Ethanesulfonyl-pyridin-2-yloxy)-6-fluoro-3-methyl-naphthalen-2-yl]-propionic acid

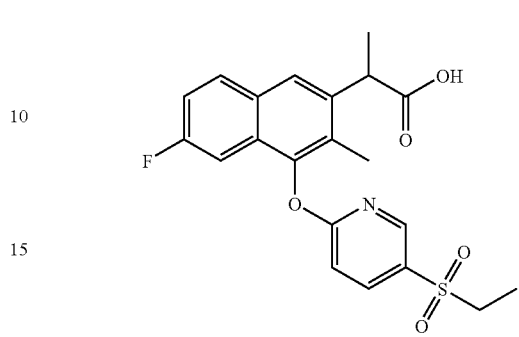

Starting with 2-[4-(5-ethanesulfonyl-pyridin-2-yloxy)-6-fluoro-3-methyl-naphthalen-2-yl]-propionic acid methyl ester (220 mg, 0.510 mmol), using a method analogous to the one described for example 1-1, final step, 2-[4-(5-ethanesulfonyl-pyridin-2-yloxy)-6-fluoro-3-methyl-naphthalen-2-yl]-propionic acid (205 mg, 96.4%) as a white solid. $^1$H NMR (400 MHz, CD$_3$OD) δ ppm 8.51 (d, J=2.27 Hz, 1H), 8.31 (dd, J=6.06, 2.78 Hz, 1H), 7.92-7.97 (m, J=5.31, 3.54 Hz, 1H), 7.81 (s, 1H), 7.23-7.32 (m, 3H), 4.14 (d, J=7.33 Hz, 1H), 3.26 (q, J=7.33 Hz, 2H), 2.29 (s, 3H), 1.61 (d, J=7.07 Hz, 3H), 1.26 (t, J=7.45 Hz, 3H); MS cald. for $O_{21}H_{20}FNO_5S$ 417, obsd. (ESI$^+$) [(M+H)$^+$] 418.

Activity and Use of the Compounds

The compounds of formula I possess valuable pharmacological properties. It has been found that said compounds are antagonists or partial agonists at the CRTH2 receptor and may be useful in treating diseases and disorders associated with that receptor such as asthma. The activity of the present compounds as CRTH2 receptor antagonists or partial agonists is demonstrated by the following biological assays.

Human CRTH2 Receptor Binding Assay

A whole cell receptor binding assay using [$^3$H]ramatroban as the competing radioactive ligand was employed to evaluate the compound binding activity to human CRTH2. The radioactive ligand [$^3$H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 µg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from Lonza Inc.), and suspended in PBS containing 10 mM $MgCl_2$ and 0.06% BSA (bovine serum albumin) at $1.5 \times 10^6$ cells/mL.

The binding reactions (0.2 mL) were performed in 96-well plates at room temperature in PBS containing $1.5 \times 10^5$ cells, 10 mM $MgCl_2$, 0.06% BSA, 20 nM [$^3$H]ramatroban, and test compound at various concentrations. After 1 hour of binding reactions, the cells were harvested on GF™/B filter microplates (microtiter plates with embedded glass fiber from PerkinElmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 μL of Microscint™ 20 scintillation fluid (from PerkinElmer, Inc.) to each well of the filter plates. The radioactivity from non-specific binding was determined by replacing compound with 10 μM of 15(R)-15-methyl $PGD_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The $IC_{50}$ value is defined as the concentration of the tested compound that is required for 50% inhibition of total specific binding. In order to calculate the $IC_{50}$ value, the percent inhibition data were determined for 7 concentrations for each compound. The percent inhibition for a compound at each concentration was calculated according to the following formula, [1−(specific binding in the presence of compound)/(total specific binding)]×100. The $IC_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B−A)/(1+((C/x)^D)))$].

Compounds of the foregoing examples were tested using the above Human CRTH2 Receptor Binding Assay. The results of the assay showed that all of the compounds tested have binding activity exhibiting $IC_{50}$ values ranging from less than 0.0010 μM to 0.3785 μM as shown below:

| Example No. | Human CRTH2 Binding $IC_{50}$ (μM) |
|---|---|
| Example 1-1 | 0.0023 |
| Example 1-2 | 0.0031 |
| Example 1-3 | 0.0085 |
| Example 1-4 | 0.0067 |
| Example 1-5 | 0.0093 |
| Example 1-6 | 0.0071 |
| Example 1-7 | 0.0035 |
| Example 1-8 | 0.0033 |
| Example 1-9 | 0.0037 |
| Example 1-10 | 0.0033 |
| Example 1-11 | 0.0056 |
| Example 1-12 | 0.0025 |
| Example 1-13 | 0.0023 |
| Example 1-14 | 0.0191 |
| Example 1-15 | 0.0053 |
| Example 1-16 | 0.0191 |
| Example 1-17 | 0.0105 |
| Example 1-18 | 0.0026 |
| Example 1-19 | 0.0026 |
| Example 1-20 | 0.0181 |
| Example 1-21 | 0.0047 |
| Example 1-22 | 0.0054 |
| Example 1-23 | 0.09729 |
| Example 2-1 | 0.0032 |

-continued

| Example No. | Human CRTH2 Binding $IC_{50}$ (μM) |
|---|---|
| Example 2-2 | 0.0023 |
| Example 2-3 | 0.0075 |
| Example 2-4 | 0.0028 |
| Example 2-5 | 0.0035 |
| Example 2-6 | 0.0027 |
| Example 2-7 | 0.0022 |
| Example 2-8 | 0.0045 |
| Example 2-9 | 0.0027 |
| Example 2-10 | 0.0073 |
| Example 2-11 | 0.0030 |
| Example 2-12 | 0.0018 |
| Example 2-13 | 0.0024 |
| Example 2-14 | 0.0016 |
| Example 2-15 | 0.0026 |
| Example 2-16 | 0.0034 |
| Example 2-17 | 0.0037 |
| Example 2-18 | 0.0017 |
| Example 2-19 | 0.0124 |
| Example 2-20 | 0.0025 |
| Example 2-21 | 0.0024 |
| Example 2-22 | 0.0024 |
| Example 2-23 | 0.0021 |
| Example 2-24 | 0.0082 |
| Example 2-25 | 0.0024 |
| Example 2-26 | 0.0023 |
| Example 2-27 | 0.0029 |
| Example 2-28 | 0.0050 |
| Example 2-29 | 0.0028 |
| Example 2-30 | 0.0027 |
| Example 2-31 | 0.0036 |
| Example 2-32 | 0.0009 |
| Example 2-33 | 0.0027 |
| Example 2-34 | 0.0031 |
| Example 2-35 | 0.0029 |
| Example 2-36 | 0.00002 |
| Example 2-37 | 0.0019 |
| Example 2-38 | 0.0022 |
| Example 2-39 | 0.0020 |
| Example 2-40 | 0.0063 |
| Example 2-41 | 0.0017 |
| Example 2-42 | 0.0029 |
| Example 2-43 | 0.0018 |
| Example 2-44 | 0.0100 |
| Example 2-45 | 0.1344 |
| Example 3-1 | 0.0129 |
| Example 3-2 | 0.0047 |
| Example 4-1 | 0.0079 |
| Example 4-2 | 0.0213 |
| Example 5-1 | 0.0031 |
| Example 6-1 | 0.0321 |
| Example 7-1 | 0.1302 |
| Example 8-1 | 0.0033 |
| Example 8-2 | 0.0026 |
| Example 9-1 | 0.0075 |
| Example 10-1 | 0.0103 |
| Example 11-1 | 0.0077 |
| Example 12-1 | 0.0053 |
| Example 13-1 | 0.0737 |
| Example 14-1 | 0.0033 |
| Example 15-1 | 0.0054 |
| Example 16-1 | 0.0915 |
| Example 17-1 | 0.01245 |
| Example 18-1 | 0.0067 |
| Example 19-1 | 0.0175 |
| Example 20-1 | 0.0029 |
| Example 21-1 | 0.0028 |
| Example 22-1 | 0.3785 |

Calcium Flux Assay Using Fluorometric Imaging Plate Reader

Cell Culture Conditions:

CHO-K1 cells previously transfected with G-alpha 16 were subsequently transfected with the human CRTH2 receptor and the neomycin resistance gene. Following selection in 800 μg/mL G418 (geneticin), individual clones were assayed for their receptor expression based on staining with an anti human CRTH2 IgG, followed by assaying for their response to 13,14-dihydro-15-keto Prostaglandin $D_2$ (DK-PDG$_2$) (ligand) in the $Ca^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 μg/mL streptomycin, 200 μg/mL hygromycin B, and 800 μg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to $2.5 \times 10^5$ cells/mL with complete growth media. Aliquots of 50 μL were dispensed into BD Falcon™ 384 well black/clear microplates (from BD Biosciences, a division of Becton, Dickinson and Company) and the microplates were placed in a 37° C. $CO_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Specific representative compounds tested in the binding assay were tested using the above FLIPR® assay (examples 1-1 to 2-5, 2-7 to 2-18, 2-20, 2-23 to 2-26, 2-28 to 2-35, 2-37 to 11-1, 15-1 and 16-1). The results of the FLIPR® assay showed that, with the exception of examples 1-1 and 7-1 (which exhibited $IC_{50}$ values of 5 and 4.198 μM respectively), these compounds exhibited $IC_{50}$ values ranging from less than 0.0001 μM to 1.4078 μM.

DK-PGD$_2$-Induced IL-13 Production Assay in Th2 Cells

Inhibition of 13,14-dihydro-15-keto Prostaglandin $D_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by $CD4^+$ cell purification using a $CD4^+$ T Cell Isolation Kit II (from Miltenyi Biotec Inc.). The $CD4^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM DK-PGD$_2$ for 4 hrs at 37° C. in 200 μL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^{\wedge}D)))$].

Representative compounds tested in the binding assay were tested using the foregoing DK-PGD$_2$-induced IL-13 production assay (examples 1-2 to 1-13, 2-1 to 2-8, 2-10 to 2-30, 2-32 to 5-1, 8-1, and 9-1 to 11-1). The results of the DK-PGD$_2$-induced IL-13 production assay showed that these compounds exhibited activity in inhibiting IL-13 production, with IC$_{50}$ values ranging from 0.0007 µM to 1.7419 µM.

Thus, the compounds of the present invention are useful since the compounds tested show some activity in at least one of the above three assays (i.e., binding at the CRTH2 receptor), and therefore may be useful as antagonists or partial agonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic rhinitis, allergic inflammation, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phosphodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

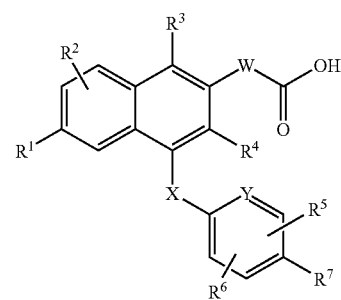

or a pharmaceutically acceptable salt or ester thereof, wherein:
W is C(H)$_2$, C(H)$_2$—C(H)$_2$, C(H)(CH$_3$), CH$_2$—C(H)(CH$_3$), or C(H)(CH$_3$)—CH$_2$;
X is selected from the group consisting of:
  (1) O,
  (2) N(H),
  (3) N(CH$_3$),
  (4) S,
  (5) S(O), and
  (6) S(O)$_2$;
Y is carbon or nitrogen;
R$^1$ is selected from the group consisting of:
  (1) hydrogen,
  (2) halogen,
  (3) methyl optionally substituted by fluoro,
  (4) lower alkoxy optionally substituted by fluoro,
  (5) cyano, and
  (6) lower alkylsulfonyl;
R$^2$ is hydrogen, fluoro, chloro, lower alkyl, or lower alkoxy;
R$^3$ is hydrogen, fluoro, chloro, bromo, or methyl;
R$^4$ is selected from the group consisting of:
  (1) hydrogen,
  (2) halogen,
  (3) lower alkyl optionally substituted by fluoro,
  (4) lower cycloalkyl, and
  (5) ethenyl;
R$^5$ and R$^6$, independently of each other, are selected from the group consisting of:
  (1) hydrogen,
  (2) halogen,
  (3) lower alkyl,
  (4) cyano, and
  (5) lower cycloalkyl;
R$^7$ is cyano or S(O)$_2$—R$^8$, wherein R$^8$ is selected from the group consisting of:
  (1) lower alkyl,
  (2) lower cycloalkyl,
  (3) phenyl optionally substituted by (a) halogen, (b) lower alkyl optionally substituted by fluoro, or (c) lower alkoxy,
  (4) lower alkylamino,
  (5) lower dialkylamino,
  (6) lower heterocycloalkyl optionally substituted by halogen, lower alkyl, or lower alkoxycarbonyl, and
  (7) 2-oxa-6-aza-spiro[3.3]hept-6-yl.
2. A compound of claim 1 wherein W is C(H)$_2$.
3. A compound of claim 1 wherein X is O.

4. A compound of claim 1 wherein X is N(H).

5. A compound of claim 1 wherein X is S, S(O), or $S(O)_2$.

6. A compound of claim 1 wherein W is $C(H)_2$, X is O, Y is carbon, and $R^7$ is $S(O)_2$—$R^8$.

7. A compound of claim 1 wherein W is $C(H)_2$, X is O, Y is nitrogen, and $R^7$ is $S(O)_2$—$R^8$.

8. A compound of claim 1 wherein $R^2$ is hydrogen.

9. A compound of claim 1 wherein $R^1$ is fluoro and $R^2$ is hydrogen.

10. A compound of claim 1 wherein $R^3$ is hydrogen, fluoro, or methyl.

11. A compound of claim 1 wherein $R^3$ is hydrogen.

12. A compound of claim 1 wherein $R^4$ is hydrogen, fluoro, or methyl.

13. A compound of claim 1 wherein $R^4$ is methyl.

14. A compound of claim 1 wherein $R^5$ and $R^6$, independently of each other, are selected from the group consisting of: (1) hydrogen, (2) fluoro, (3) chloro, (4) methyl, and (5) cyano.

15. A compound of claim 1 wherein at least one of $R^5$ or $R^6$ is hydrogen.

16. A compound of claim 1 wherein $R^5$ and $R^6$ are both hydrogen.

17. A compound of claim 1 wherein $R^7$ is $S(O)_2$—$R^8$ and $R^8$ is selected from the group consisting of:
   (1) methyl,
   (2) ethyl,
   (3) propyl,
   (4) isopropyl,
   (5) butyl,
   (6) cyclopropyl,
   (7) cyclobutyl,
   (8) cyclopentyl,
   (9) dimethylamino,
   (10) diethylamino,
   (11) pyrrolidin-1-yl,
   (12) morpholin-4-yl,
   (13) 4,4-difluoro-piperidin-1-yl,
   (14) 4-methyl-piperazin-1-yl, and
   (15) 2-oxa-6-aza-spiro[3.3]hept-6-yl.

18. A compound of claim 1 wherein $R^7$ is $S(O)_2$—$R^8$ and $R^8$ is selected from the group consisting of:
   (1) ethyl,
   (2) propyl,
   (3) isopropyl,
   (4) cyclopropyl,
   (5) butyl, and
   (6) cyclopentyl.

19. A compound of claim 1 wherein $R^7$ is $S(O)_2$—$R^8$ and $R^8$ is ethyl.

20. A compound of claim 1 selected from the group consisting of:
   [4-(4-ethanesulfonyl-phenoxy)-6-fluoro-naphthalen-2-yl]-acetic acid;
   [6-fluoro-4-(4-methanesulfonyl-phenoxy)-naphthalen-2-yl]-acetic acid;
   [6-chloro-4-(4-methanesulfonyl-phenoxy)-naphthalen-2-yl]-acetic acid;
   {6-fluoro-4-[4-(propane-2-sulfonyl)-phenoxy]-naphthalen-2-yl}-acetic acid;
   [4-(4-cyclopropanesulfonyl-phenoxy)-6-fluoro-naphthalen-2-yl]-acetic acid;
   [6-fluoro-4-(4-methanesulfonyl-2-methyl-phenoxy)-naphthalen-2-yl]-acetic acid;
   [6-fluoro-4-(4-methanesulfonyl-3-methyl-phenoxy)-naphthalen-2-yl]-acetic acid;
   [4-(4-ethanesulfonyl-2-methyl-phenoxy)-6-fluoro-naphthalen-2-yl]-acetic acid;
   [6-fluoro-4-(5-methanesulfonyl-pyridin-2-yloxy)-naphthalen-2-yl]-acetic acid;
   [6-fluoro-4-(5-methanesulfonyl-3-methyl-pyridin-2-yloxy)-naphthalen-2-yl]-acetic acid;
   or a pharmaceutically acceptable salt or ester thereof.

21. A compound of claim 1 selected from the group consisting of:
   [4-(5-ethanesulfonyl-pyridin-2-yloxy)-6-fluoro-naphthalen-2-yl]-acetic acid;
   [4-(5-ethanesulfonyl-3-methyl-pyridin-2-yloxy)-6-fluoro-naphthalen-2-yl]-acetic acid;
   [4-(3-bromo-5-ethanesulfonyl-pyridin-2-yloxy)-6-fluoro-naphthalen-2-yl]-acetic acid;
   [4-(3-bromo-5-methanesulfonyl-pyridin-2-yloxy)-6-fluoro-naphthalen-2-yl]-acetic acid;
   [4-(4-ethanesulfonyl-phenoxy)-6-methoxy-naphthalen-2-yl]-acetic acid;
   [4-(5-ethanesulfonyl-pyridin-2-yloxy)-6-trifluoromethyl-naphthalen-2-yl]-acetic acid;
   [4-(4-ethanesulfonyl-phenoxy)-6-trifluoromethyl-naphthalen-2-yl]-acetic acid;
   [4-(5-ethanesulfonyl-pyridin-2-yloxy)-6-trifluoromethoxy-naphthalen-2-yl]-acetic acid;
   [4-(4-ethanesulfonyl-phenoxy)-6-trifluoromethoxy-naphthalen-2-yl]-acetic acid;
   and [4-(4-ethanesulfonyl-phenoxy)-7-fluoro-naphthalen-2-yl]-acetic acid;
   or a pharmaceutically acceptable salt or ester thereof.

22. A compound of claim 1 selected from the group consisting of:
   [4-(5-Ethanesulfonyl-pyridin-2-yloxy)-6-methoxy-naphthalen-2-yl]-acetic acid;
   [4-(4-Ethanesulfonyl-phenoxy)-5-fluoro-naphthalen-2-yl]-acetic acid;
   [4-(4-Ethanesulfonyl-phenoxy)-6,7-dimethoxy-naphthalen-2-yl]-acetic acid;
   [4-(4-ethanesulfonyl-phenoxy)-6-fluoro-3-methyl-naphthalen-2-yl]-acetic acid;
   [6-fluoro-4-(4-methanesulfonyl-phenoxy)-3-methyl-naphthalen-2-yl]-acetic acid;
   [6-fluoro-4-(4-methanesulfonyl-2-methyl-phenoxy)-3-methyl-naphthalen-2-yl]-acetic acid;
   {6-fluoro-3-methyl-4-[4-(propane-2-sulfonyl)-phenoxy]-naphthalen-2-yl}-acetic acid;
   [4-(4-cyclopropanesulfonyl-phenoxy)-6-fluoro-3-methyl-naphthalen-2-yl]-acetic acid;
   [6-fluoro-4-(4-methanesulfonyl-3-methyl-phenoxy)-3-methyl-naphthalen-2-yl]-acetic acid; and
   [6-chloro-4-(4-methanesulfonyl-phenoxy)-3-methyl-naphthalen-2-yl]-acetic acid;
   or a pharmaceutically acceptable salt or ester thereof.

23. A compound of claim 1 selected from the group consisting of:
   [6-chloro-4-(4-methanesulfonyl-3-methyl-phenoxy)-3-methyl-naphthalen-2-yl]-acetic acid;
   [6-chloro-4-(4-methanesulfonyl-2-methyl-phenoxy)-3-methyl-naphthalen-2-yl]-acetic acid;
   [4-(4-ethanesulfonyl-2-methyl-phenoxy)-6-fluoro-3-methyl-naphthalen-2-yl]-acetic acid;
   [4-(3-chloro-4-methanesulfonyl-phenoxy)-6-fluoro-3-methyl-naphthalen-2-yl]-acetic acid;
   [6-fluoro-4-(2-fluoro-4-methanesulfonyl-phenoxy)-3-methyl-naphthalen-2-yl]-acetic acid;
   [4-(4-ethanesulfonyl-2-fluoro-phenoxy)-6-fluoro-3-methyl-naphthalen-2-yl]-acetic acid;

[4-(4-ethanesulfonyl-3-methyl-phenoxy)-6-fluoro-3-methyl-naphthalen-2-yl]-acetic acid;
[4-(2,5-difluoro-4-methanesulfonyl-phenoxy)-6-fluoro-3-methyl-naphthalen-2-yl]-acetic acid;
[6-fluoro-4-(3-fluoro-4-methanesulfonyl-phenoxy)-3-methyl-naphthalen-2-yl]-acetic acid; and
[4-(4-ethanesulfonyl-3-fluoro-phenoxy)-6-fluoro-3-methyl-naphthalen-2-yl]-acetic acid;
or a pharmaceutically acceptable salt or ester thereof.

24. A compound of claim 1 selected from the group consisting of:
[4-(2-cyano-4-ethanesulfonyl-phenoxy)-6-fluoro-3-methyl-naphthalen-2-yl]-acetic acid;
[4-(3-chloro-4-ethanesulfonyl-phenoxy)-6-fluoro-3-methyl-naphthalen-2-yl]-acetic acid;
[4-(2-chloro-4-methanesulfonyl-phenoxy)-6-fluoro-3-methyl-naphthalen-2-yl]-acetic acid;
[4-(2-chloro-4-ethanesulfonyl-phenoxy)-6-fluoro-3-methyl-naphthalen-2-yl]-acetic acid;
{6-fluoro-3-methyl-4-[4-(propane-1-sulfonyl)-phenoxy]-naphthalen-2-yl}-acetic acid;
{4-[4-(butane-1-sulfonyl)-phenoxy]-6-fluoro-3-methyl-naphthalen-2-yl}-acetic acid;
[4-(5-chloro-4-ethanesulfonyl-2-fluoro-phenoxy)-6-fluoro-3-methyl-naphthalen-2-yl]-acetic acid;
[4-(2-chloro-4-ethanesulfonyl-5-fluoro-phenoxy)-6-fluoro-3-methyl-naphthalen-2-yl]-acetic acid;
[4-(4-cyclopentanesulfonyl-phenoxy)-6-fluoro-3-methyl-naphthalen-2-yl]-acetic acid; and
{6-fluoro-4-[4-(4-fluoro-benzenesulfonyl)-phenoxy]-3-methyl-naphthalen-2-yl}-acetic acid;
or a pharmaceutically acceptable salt or ester thereof.

25. A compound of claim 1 selected from the group consisting of:
[4-(4-benzenesulfonyl-phenoxy)-6-fluoro-3-methyl-naphthalen-2-yl]-acetic acid;
{6-fluoro-3-methyl-4-[4-(toluene-4-sulfonyl)-phenoxy]-naphthalen-2-yl}-acetic acid;
{6-fluoro-4-[4-(4-methoxy-benzenesulfonyl)-phenoxy]-3-methyl-naphthalen-2-yl}-acetic acid;
{4-[4-(4-chloro-benzenesulfonyl)-phenoxy]-6-fluoro-3-methyl-naphthalen-2-yl}-acetic acid;
[6-fluoro-4-(5-methanesulfonyl-pyridin-2-yloxy)-3-methyl-naphthalen-2-yl]-acetic acid;
[4-(5-ethanesulfonyl-pyridin-2-yloxy)-6-fluoro-3-methyl-naphthalen-2-yl]-acetic acid;
[6-fluoro-4-(5-methanesulfonyl-3-methyl-pyridin-2-yloxy)-3-methyl-naphthalen-2-yl]-acetic acid;
[4-(5-ethanesulfonyl-3-methyl-pyridin-2-yloxy)-6-fluoro-3-methyl-naphthalen-2-yl]-acetic acid;
[4-(3-bromo-5-methanesulfonyl-pyridin-2-yloxy)-6-fluoro-3-methyl-naphthalen-2-yl]-acetic acid; and
[4-(4-dimethylsulfamoyl-phenoxy)-6-fluoro-3-methyl-naphthalen-2-yl]-acetic acid;
or a pharmaceutically acceptable salt or ester thereof.

26. A compound of claim 1 selected from the group consisting of:
{6-fluoro-3-methyl-4-[4-(pyrrolidine-1-sulfonyl)-phenoxy]-naphthalen-2-yl}-acetic acid;
[4-(4-diethylsulfamoyl-phenoxy)-6-fluoro-3-methyl-naphthalen-2-yl]-acetic acid;
{6-fluoro-3-methyl-4-[4-(morpholine-4-sulfonyl)-phenoxy]-naphthalen-2-yl}-acetic acid;
{6-fluoro-3-methyl-4-[4-(4-methyl-piperazine-1-sulfonyl)-phenoxy]-naphthalen-2-yl}-acetic acid;
{4-[4-(4,4-difluoro-piperidine-1-sulfonyl)-phenoxy]-6-fluoro-3-methyl-naphthalen-2-yl}-acetic acid;
{6-fluoro-3-methyl-4-[4-(2-oxa-6-aza-spiro[3.3]heptane-6-sulfonyl)-phenoxy]-naphthalen-2-yl}-acetic acid;
[4-(4-cyano-phenoxy)-6-fluoro-3-methyl-naphthalen-2-yl]-acetic acid;
[6-chloro-4-(4-cyano-phenoxy)-3-methyl-naphthalen-2-yl]-acetic acid;
[4-(4-methanesulfonyl-phenoxy)-naphthalen-2-yl]-acetic acid; and
[4-(4-methanesulfonyl-phenoxy)-3-methyl-naphthalen-2-yl]-acetic acid;
or a pharmaceutically acceptable salt or ester thereof.

27. A compound of claim 1 selected from the group consisting of:
[1,6-difluoro-4-(5-methanesulfonyl-pyridin-2-yloxy)-naphthalen-2-yl]-acetic acid;
[1,6-difluoro-4-(5-ethanesulfonyl-pyridin-2-yloxy)-naphthalen-2-yl]-acetic acid;
[4-(5-ethanesulfonyl-pyridin-2-yloxy)-3,6-difluoro-naphthalen-2-yl]-acetic acid;
[4-(5-ethanesulfonyl-pyridin-2-yloxy)-6-fluoro-1-methyl-naphthalen-2-yl]-acetic acid;
3-[4-(4-ethanesulfonyl-phenoxy)-6-fluoro-3-methyl-naphthalen-2-yl]-propionic acid;
[6-fluoro-4-(4-methanesulfonyl-phenylamino)-naphthalen-2-yl]-acetic acid;
[6-fluoro-4-(4-methanesulfonyl-phenylamino)-3-methyl-naphthalen-2-yl]-acetic acid;
[6-fluoro-4-(4-methanesulfonyl-phenylsulfanyl)-naphthalen-2-yl]-acetic acid;
[6-fluoro-4-(4-methanesulfonyl-benzenesulfinyl)-naphthalen-2-yl]-acetic acid; and
[6-fluoro-4-(4-methanesulfonyl-benzenesulfonyl)-naphthalen-2-yl]-acetic acid;
or a pharmaceutically acceptable salt or ester thereof.

28. A compound of claim 1 selected from the group consisting of:
[6-bromo-4-(5-ethanesulfonyl-pyridin-2-yloxy)-naphthalen-2-yl]-acetic acid;
[4-(5-ethanesulfonyl-pyridin-2-yloxy)-6-methyl-naphthalen-2-yl]-acetic acid;
[6-cyano-4-(5-ethanesulfonyl-pyridin-2-yloxy)-naphthalen-2-yl]-acetic acid;
[6-bromo-4-(4-ethanesulfonyl-phenoxy)-naphthalen-2-yl]-acetic acid;
[4-(5-ethanesulfonyl-pyridin-2-yloxy)-6-methyl-naphthalen-2-yl]-acetic acid;
[4-(5-ethanesulfonyl-pyridin-2-yloxy)-6-fluoro-3-vinyl-naphthalen-2-yl]-acetic acid;
[3-cyclopropyl-4-(5-ethanesulfonyl-pyridin-2-yloxy)-6-fluoro-naphthalen-2-yl]- acetic acid;
[4-(5-ethanesulfonyl-pyridin-2-yloxy)-3-ethyl-6-fluoro-naphthalen-2-yl]-acetic acid;
[4-(5-ethanesulfonyl-3-ethyl-pyridin-2-yloxy)-6-fluoro-3-methyl-naphthalen-2-yl]-acetic acid; and
[4-(3-cyclopropyl-5-ethanesulfonyl-pyridin-2-yloxy)-6-fluoro-3-methyl-naphthalen -2-yl]-acetic acid;
or a pharmaceutically acceptable salt or ester thereof.

29. A compound of claim 1 which is [4-(4-ethanesulfonyl-phenoxy)-6-fluoro -naphthalen-2-yl]-acetic acid.

30. A compound of claim 1 which is [4-(4-ethanesulfonyl-phenoxy)-6-fluoro-3-methyl-naphthalen-2-yl]-acetic acid.

31. A compound of claim 1 which is [6-Chloro-4-(4-methanesulfonyl-phenoxy)-3-methyl-naphthalen-2-yl]-acetic acid.

32. A compound of claim 1 which is [6-fluoro-4-(2-fluoro-4-methanesulfonyl -phenoxy)-3-methyl-naphthalen-2-yl]-acetic acid.

33. A compound of claim 1 which is [4-(4-ethanesulfonyl-3-methyl-phenoxy)-6-fluoro-3-methyl-naphthalen-2-yl]-acetic acid.

34. A compound of claim 1 which is [4-(2-cyano-4-ethanesulfonyl-phenoxy)-6-fluoro-3-methyl-naphthalen-2-yl]-acetic acid.

35. A compound of claim 1 which is {4-[4-(butane-1-sulfonyl)-phenoxy]-6-fluoro-3-methyl-naphthalen-2-yl}-acetic acid.

36. A compound of claim 1 which is [6-fluoro-4-(5-methanesulfonyl-pyridin-2-yloxy)-3-methyl-naphthalen-2-yl]-acetic acid.

37. A compound of claim 1 which is [4-(3-bromo-5-methanesulfonyl-pyridin-2-yloxy)-6-fluoro-3-methyl-naphthalen-2-yl]-acetic acid.

38. A compound of claim 1 which is [4-(4-dimethylsulfamoyl-phenoxy)-6-fluoro-3-methyl-naphthalen-2-yl]-acetic acid.

39. A compound of claim 1 which is {6-fluoro-3-methyl-4-[4-(pyrrolidine-1-sulfonyl)-phenoxy]-naphthalen-2-yl}-acetic acid.

40. A compound of claim 1 which is [4-(4-diethylsulfamoyl-phenoxy)-6-fluoro-3-methyl-naphthalen-2-yl]-acetic acid.

41. A compound of claim 1 which is {6-fluoro-3-methyl-4-[4-(4-methyl-piperazine-1-sulfonyl)-phenoxy]-naphthalen-2-yl}-acetic acid.

42. A compound of claim 1 which is {6-fluoro-3-methyl-4-4-[4-(2-oxa-6-aza-spiro[3.3]heptane-6-sulfonyl)-phenoxy]-naphthalen-2-yl}l-acetic acid.

43. [4-(5-ethanesulfonyl-pyridin-2-yloxy)-6-fluoro-3-methyl-naphthalen-2-yl]-acetic acid.

44. A pharmaceutically acceptable salt of the compound of claim 42.

45. A pharmaceutically acceptable ester of the compound of claim 42.

46. A pharmaceutical composition comprising a therapeutically effective amount of the compound according to claim 42 and a pharmaceutically acceptable carrier.

47. A pharmaceutical composition comprising a therapeutically effective amount of a compound according to claim 1 and a pharmaceutically acceptable carrier.

* * * * *